US010981918B2

(12) United States Patent
Jakob et al.

(10) Patent No.: US 10,981,918 B2
(45) Date of Patent: Apr. 20, 2021

(54) FURTHER SUBSTITUTED TRIAZOLO QUINOXALINE DERIVATIVES

(71) Applicant: Grünenthal GmbH, Aachen (DE)

(72) Inventors: Florian Jakob, Aachen (DE); Jo Alen, Vliermaal (BE); Simon Lucas, Bad König (DE); Tobias Craan, Niedernberg (DE); Ingo Konetzki, Monschau (DE); Achim Kless, Aachen (DE); Stefan Schunk, Aachen (DE); Paul Ratcliffe, Aachen (DE); Sebastian Wachten, Aachen (DE); Simon Cruwys, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 16/517,080

(22) Filed: Jul. 19, 2019

(65) Prior Publication Data

US 2020/0024281 A1    Jan. 23, 2020

(30) Foreign Application Priority Data

Jul. 20, 2018   (EP) ..................................... 18184607

(51) Int. Cl.
C07D 487/04    (2006.01)

(52) U.S. Cl.
CPC .................. C07D 487/04 (2013.01)

(58) Field of Classification Search
CPC ............................ A61P 37/00; C07D 487/04
See application file for complete search history.

(56) References Cited

U.S. PATENT DOCUMENTS

| | | | |
|---|---|---|---|
| 10,189,796 B2 | 1/2019 | Kawashima et al. | |
| 2013/0303537 A1 | 11/2013 | Matsuda et al. | |

FOREIGN PATENT DOCUMENTS

| | | | | |
|---|---|---|---|---|
| WO | 2009/035067 A1 | 3/2009 | | |
| WO | 2017/034006 A1 | 3/2017 | | |
| WO | WO 2020/016453 | * | 1/2020 | ......... C07D 4857/04 |

OTHER PUBLICATIONS

Buttgereit F. et al., "Polymyalgia Rheumatica and Giant Cell Arteritis a Systematic Review", JAMA. 2016;315 (22):2442-2458).
Buttgereit F. et al., "Novel Glucocorticoids: Where are we now and where do we want to go?", Clin. Exp. Rheumatol. 2015, vol. 33, pp. S29-S33.
De Bosscher K. et al., "Activation of the Glucocorticoid Receptor in Acute Inflammation: The SEDIGRAM Concept", Trends Pharmacol. Sci. Jan. 2016;37(1):4-16.
Cui et al., "Synthesis and Anticonvulsant Activity of 1-Substituted-7-Benzyloxy-4,5dihydro-[1,2,4]triazolo[4,3-a] quinoline", Biological and Pharmaceutical Bulletin, 2005, vol. 28, pp. 1216-1220.
Hapgood J.P. et al., "Glucocorticoid-independent Modulation of GR activity: Implications for Immunotherapy", Pharmacol. Ther. Sep. 2016; 165: 93-113.
Hartmann K. et al., "Molecular Actions of Glucocorticoids in Cartilage and Bone During Health, Disease, and Steroid Therapy", Physiol. Rev. vol. 96, No. 2, pp. 409-447, 2016.
Liu D. et al., "A Practical guide to the monitoring and management of the complications of systemic corticosteriod therapy", Allergy Asthma Clin. Immunol. Aug. 15, 2013;9(1):30, pp. 1-25.
"Metal-Catalyzed Cross-Coupling Reactions and More", de Meijere et al., Eds., Wiley, 2014.
Nicolaou K.C. et al., "Palladiumkatalysierte Kreuzkupplungen in der Totalsynthese", Angew. Chem., 2005, 117, 4516-4563.
Reiter L.A. et al., "The Synthesis of Spirocyclic [1,2,4]Triazolo[4,3-a]Quinolines as Potential Ligands for the Benzodiazepine Receptor", Heterocycles, 1992, 34, 771-780.
Johansson Seechurn C.C.C. et al., "Palladium-Catalyzed Cross-Coupling: A Historical Contextual Perspective to the 2010 Nobel Prize", Angew. Chem. Int. Ed., 2012, 51, 5062-5085.
"Science of Synthesis: Compounds with One Saturated Carbon-Heteroatom Bond", vol. 35, Houben-Weyl, 2007 (Schaumann E., vol. Ed.).
Tanimori S. et al., "A General and Practical Access to Chiral Quinoxalinones with Low Copper-Catalyst Loading", Adv. Synth. Catal., 2010, 352, 2531-2537.
U.S. Appl. No. 17/152,930, filed Jan. 20, 2021 (Florian Jakob et al.).

* cited by examiner

*Primary Examiner* — Erich A Leeser
(74) *Attorney, Agent, or Firm* — Norris McLaughlin, P.A.

(57) ABSTRACT

The present invention relates to compounds according to general formula (I)

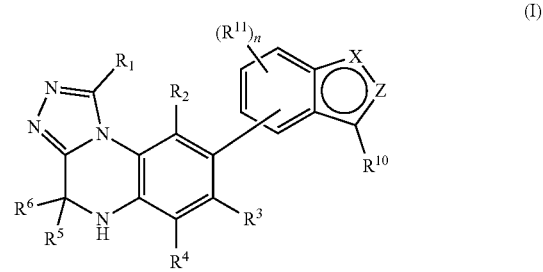

which act as modulators of the glucocorticoid receptor and can be used in the treatment and/or prophylaxis of disorders which are at least partially mediated by the glucocorticoid receptor.

15 Claims, No Drawings

FURTHER SUBSTITUTED TRIAZOLO QUINOXALINE DERIVATIVES

This application claims foreign priority benefit under 35 U.S.C. § 119 of European Patent Application No. 18184607.2, filed Jul. 20, 2018, the disclosures of which are incorporated herein by reference.

The present invention relates to compounds according to general formula (I)

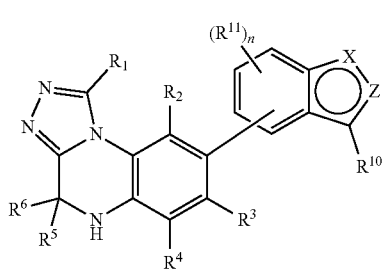

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. et al, Clin Exp Rheumatol. 2015 July-August; 33(4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., *JAMA*. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known from WO 2009/035067 and WO 2017/034006.

It was an object of the present invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter disclosed herein.

It was surprisingly found that the compounds according to the present invention are highly potent modulators of the glucocorticoid receptor.

The present invention relates to a compound according to general formula (I),

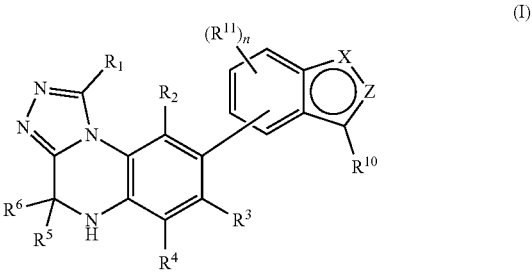

wherein $R^1$ represents H; $C_{1-10}$-alkyl; $C_{3-10}$-Cycloalkyl; 3 to 7 membered heterocycloalkyl; aryl; or 5 or 6-membered heteroaryl;
wherein $C_{3-10}$-cycloalkyl, 3 to 7 membered heterocycloalkyl, aryl and 5 or 6-membered heteroaryl can optionally be bridged via $C_{1-6}$-alkylene;

$R^2$ represents H; F; Cl; Br; I; CN; $C_{1-10}$-alkyl; $C_{3-10}$-Cycloalkyl; O—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-Cycloalkyl), N($C_{1-10}$-alkyl)($C_{3-10}$-Cycloalkyl); C(O)—$C_{3-10}$-Cycloalkyl; C(O)—O—$C_{3-10}$-cycloalkyl; C(O)—N(H)($C_{3-10}$-Cycloalkyl) or C(O)—N($C_{1-10}$-alkyl)($C_{3-10}$-Cycloalkyl);
wherein $C_{3-10}$-Cycloalkyl can optionally be bridged via $C_{1-6}$-alkylene;

$R^3$ represents H; F; Cl; Br; I; CN; $C_{1-10}$-alkyl; $C_{3-10}$-Cycloalkyl; O—$C_{1-10}$-alkyl; N(H)($C_{1-10}$-alkyl); N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-Cycloalkyl), N($C_{1-10}$-alkyl)($C_{3-10}$-Cycloalkyl); C(O)—$C_{3-10}$-Cycloalkyl; C(O)—O—$C_{3-10}$-cycloalkyl; C(O)—N(H)($C_{3-10}$-Cycloalkyl) or C(O)—N($C_{1-10}$-alkyl)($C_{3-10}$-Cycloalkyl);
wherein $C_{3-10}$-cycloalkyl can optionally be bridged via $C_{1-6}$-alkylene;

R⁴ represents F or Cl;

R⁵ and R⁶ represent independently from one another H or unsubstituted $C_{1-4}$-alkyl;

X represents N or NR⁷;

Z represents N, NR⁷ or CR⁹;
with the proviso that
when X represents NR⁷, Z represents N or CR⁹;
when X represents N, Z represents NR⁷;

R⁷ represents H or L-R⁸; wherein
L represents bond; S(O); S(O)₂; $C_{1-6}$-alkylene; C(O); $C_{1-6}$-alkylene-C(O); C(O)—O; $C_{1-6}$-alkylene-C(O)—O; $C_{1-6}$-alkylene-N(H)—C(O); $C_{1-6}$-alkylene-N($C_{1-10}$-alkyl)-C(O); $C_{1-6}$-alkylene-N(H)—C(O)—O; $C_{1-6}$-alkylene-N($C_{1-10}$-alkyl)-C(O)—O; O; NH or N($C_{1-10}$-alkyl);
R⁸ represents $C_{1-10}$-alkyl; $C_{3-10}$-cycloalkyl or 3 to 7 membered heterocycloalkyl;
wherein $C_{3-10}$-cycloalkyl and 3 to 7 membered heterocycloalkyl can optionally be bridged via $C_{1-6}$-alkylene;

R⁹ and R¹⁰ represent independently from one another H; F; Cl; Br; I; CN; $C_{1-10}$-alkyl; $C_{3-10}$-cycloalkyl; 3 to 7 membered heterocycloalkyl; S(O)—($C_{1-10}$-alkyl); S(O)—($C_{3-10}$-cycloalkyl); S(O)-(3 to 7-membered heterocycloalkyl); S(O)₂—($C_{1-10}$-alkyl); S(O)₂—($C_{3-10}$-cycloalkyl); S(O)₂-(3 to 7-membered heterocycloalkyl); P(O)—($C_{1-10}$-alkyl)₂; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)₂; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; S—$C_{1-10}$-alkyl; N(H)($C_{1-10}$-alkyl), N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);
wherein $C_{3-10}$-cycloalkyl and 3 to 7 membered heterocycloalkyl can optionally be bridged via $C_{1-6}$-alkylene;

R¹¹ represents F; Cl; Br; I; CN; $C_{1-10}$-alkyl; O—$C_{1-10}$-alkyl; NO₂; OH, NH₂; $C_{3-10}$-cycloalkyl; 3 to 7-membered heterocycloalkyl; S(O)—($C_{1-10}$-alkyl); S(O)—($C_{3-10}$-cycloalkyl); S(O)-(3 to 7-membered heterocycloalkyl); S(O)₂—($C_{1-10}$-alkyl); S(O)₂—($C_{3-10}$-cycloalkyl); S(O)₂-(3 to 7-membered heterocycloalkyl); P(O)—($C_{1-10}$-alkyl)₂; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)₂; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; N(H)($C_{1-10}$-alkyl), N($C_{1-10}$-alkyl)₂; C(O)—$C_{1-10}$-alkyl; C(O)—O—$C_{1-10}$-alkyl; C(O)—NH₂; C(O)—N(H)($C_{1-10}$-alkyl); C(O)—N($C_{1-10}$-alkyl)₂; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl);
wherein $C_{3-10}$-cycloalkyl and 3 to 7 membered heterocycloalkyl can optionally be bridged via $C_{1-6}$-alkylene;

n represents 0, 1, 2 or 3;

wherein $C_{1-10}$-alkyl, $C_{1-4}$-alkyl and $C_{1-6}$-alkylene in each case independently from one another is linear or branched, saturated or unsaturated;

wherein $C_{1-10}$-alkyl, $C_{1-4}$-alkyl, $C_{1-6}$-alkylene, $C_{3-10}$-cycloalkyl and 3 to 7 membered heterocycloalkyl in each case independently from one another are unsubstituted or mono- or polysubstituted with one or more substituents selected from F; Cl; Br; I; CN; $C_{1-6}$-alkyl; CF₃; CF₂H; CFH₂; CF₂Cl; CFCl₂; C(O)—$C_{1-6}$-alkyl; C(O)—OH; C(O)—O$C_{1-6}$-alkyl; C(O)—NH₂; C(O)—N(H)($C_{1-6}$-alkyl); C(O)—N($C_{1-6}$-alkyl)₂; OH; =O; OCF₃; OCF₂H; OCFH₂; OCF₂Cl; OCFCl₂; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)₂; O—S(O)₂—NH₂; O—S(O)₂—N(H)($C_{1-6}$-alkyl); O—S(O)₂—N($C_{1-6}$-alkyl)₂; NH₂; N(H)($C_{1-6}$-alkyl); N($C_{1-6}$-alkyl)₂; N(H)—C(O)—$C_{1-6}$-alkyl; N(H)—C(O)—O—$C_{1-6}$-alkyl; N(H)—C(O)—NH₂; N(H)—C(O)—N(H)($C_{1-6}$-alkyl); N(H)—C(O)—N($C_{1-6}$-alkyl)₂; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—NH₂; N($C_{1-6}$-alkyl)-C(O)—N(H)($C_{1-6}$-alkyl); N($C_{1-6}$-alkyl)-C(O)—N($C_{1-6}$-alkyl)₂; N(H)—S(O)₂OH; N(H)—S(O)₂—$C_{1-6}$-alkyl; N(H)—S(O)₂—O—$C_{1-6}$-alkyl; N(H)—S(O)₂—NH₂; N(H)—S(O)₂—N(H)($C_{1-6}$-alkyl); N(H)—S(O)₂N($C_{1-6}$-alkyl)₂; N($C_{1-6}$-alkyl)-S(O)₂—OH; N($C_{1-6}$-alkyl)-S(O)₂—$C_{1-6}$-alkyl; N($C_{1-6}$-alkyl)-S(O)₂—O—$C_{1-6}$-alkyl; N($C_{1-6}$-alkyl)-S(O)₂—NH₂; N($C_{1-6}$-alkyl)-S(O)₂—N(H)($C_{1-6}$-alkyl); N($C_{1-6}$-alkyl)-S(O)₂—N($C_{1-6}$-alkyl)₂; SCF₃; SCF₂H; SCFH₂; S—$C_{1-6}$-alkyl; S(O)—$C_{1-6}$-alkyl; S(O)₂—$C_{1-6}$-alkyl; S(O)₂—OH; S(O)₂—O—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)₂—($C_{3-6}$-cycloalkyl); S(O)₂-(3 to 6-membered heterocycloalkyl); S(O)₂-phenyl or S(O)₂-(5 or 6-membered heteroaryl);

wherein aryl and 5 or 6-membered heteroaryl in each case independently from one another are unsubstituted or mono- or polysubstituted with one or more substituents selected from F; Cl; Br; I; CN; $C_{1-6}$-alkyl; CF₃; CF₂H; CFH₂; CF₂Cl; CFCl₂; $C_{1-4}$-alkylene-CF₃; $C_{1-4}$-alkylene-CF₂H; $C_{1-4}$-alkylene-CFH₂; C(O)—$C_{1-6}$-alkyl; C(O)—OH; C(O)—OC$_{1-6}$-alkyl; C(O)—N(H)(OH); C(O)—NH₂; C(O)—N(H)($C_{1-6}$-alkyl); C(O)—N($C_{1-6}$-alkyl)₂; OH; OCF₃; OCF₂H; OCFH₂; OCF₂Cl; OCFCl₂; O—$C_{1-6}$-alkyl; O—$C_{3-6}$-cycloalkyl; O-(3 to 6-membered heterocycloalkyl); NH₂; N(H)($C_{1-6}$-alkyl); N($C_{1-6}$-alkyl)₂; N(H)—C(O)—$C_{1-6}$-alkyl; N($C_{1-6}$-alkyl)-C(O)—$C_{1-6}$-alkyl; N(H)—C(O)—NH₂; N(H)—C(O)—N(H)($C_{1-6}$-alkyl); N(H)—C(O)—N($C_{1-6}$-alkyl)₂; N($C_{1-6}$-alkyl)-C(O)—C(O)—N(H)($C_{1-6}$-alkyl); N($C_{1-6}$-alkyl)-C(O)—N($C_{1-6}$-alkyl)₂; N(H)—S(O)₂—$C_{1-6}$-alkyl; SCF₃; S—$C_{1-6}$-alkyl; S(O)—$C_{1-6}$-alkyl; S(O)₂—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl;

in the form of the free compound or a physiologically acceptable salt thereof.

In a preferred embodiment, the compound according to the present invention is present in form of the free compound. For the purpose of specification, "free compound" preferably means that the compound according to the present invention is not present in form of a salt. Methods to determine whether a chemical substance is present as the free compound or as a salt are known to the skilled artisan such as $^{14}$N or $^{15}$N solid state NMR, x-ray diffraction, x-ray powder diffraction, IR, Raman, XPS. $^{1}$H-NMR recorded in solution may also be used to consider the presence of protonation.

In another preferred embodiment, the compound according to the present invention is present in form of a physiologically acceptable salt. For the purposes of this specification, the term "physiologically acceptable salt" preferably refers to a salt obtained from a compound according to the present invention and a physiologically acceptable acid or base.

According to the present invention, the compound according to the present invention may be present in any possible form including solvates, cocrystals and polymorphs. For the purposes of this specification, the term "solvate" preferably refers to an adduct of (i) a compound according to the present invention and/or a physiologically acceptable salt thereof with (ii) distinct molecular equivalents of one or more solvents.

Further, the compound according to the present invention may be present in form of the racemate, enantiomers, diastereomers, tautomers or any mixtures thereof.

The present invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^{2}$H (deuterium), $^{3}$H (tritium), $^{13}$C and $^{14}$C. Isotopic isomers of a compound of the invention can generally be prepared by conventional procedures known to a person skilled in the art.

According to the present invention, the terms "$C_{1-10}$-alkyl", "$C_{1-8}$-alkyl", "$C_{1-6}$-alkyl" and "$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, $C_{1-10}$-alkyl, $C_{1-8}$-alkyl, $C_{1-6}$-alkyl and $C_{1-4}$-alkyl are saturated. In another preferred embodiment, $C_{1-10}$-alkyl, $C_{1-8}$-alkyl, $C_{1-6}$-alkyl and $C_{1-4}$-alkyl are not saturated. According to this embodiment, $C_{1-10}$-alkyl, $C_{1-8}$-alkyl, $C_{1-6}$-alkyl and $C_{1-4}$-alkyl comprise at least one C—C double bond (a C=C-bond) or at least one C—C triple bond (a C≡C-bond). In still another preferred embodiment, $C_{1-10}$-alkyl, $C_{1-8}$-alkyl, $C_{1-6}$-alkyl and $C_{1-4}$-alkyl are (i) saturated or (ii) not saturated, wherein $C_{1-10}$-alkyl, $C_{1-8}$-alkyl, $C_{1-6}$-alkyl and $C_{1-4}$-alkyl comprise at least one, preferably one, C—C triple bond (a C≡C-bond). Preferred $C_{1-10}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl. Preferred $C_{1-8}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl. Preferred $C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred $C_{1-6}$-alkyl groups are selected from $C_{1-4}$-alkyl groups. Preferred $C_{1-4}$-alkyl groups are selected from methyl, ethyl, ethenyl (vinyl), n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, isobutyl, sec-butyl, tert-butyl and 3-methylbut-1-ynyl.

Further according to the present invention, the terms "$C_{1-6}$-alkylene"; "$C_{1-4}$-alkylene" and "$C_{1-2}$-alkylene" relate to a linear or branched, preferably linear, and preferably saturated aliphatic residues which are preferably selected from the group consisting of methylene (—CH$_2$—), ethylene (—CH$_2$CH$_2$—), propylene (—CH$_2$CH$_2$CH$_2$— or —C(CH$_3$)$_2$—), butylene (—CH$_2$CH$_2$CH$_2$CH$_2$—), pentylene (—CH$_2$CH$_2$CH$_2$CH$_2$CH$_2$—) and hexylene (—CH$_2$CH$_2$CH$_2$CH$_2$CH$_2$CH$_2$—); more preferably methylene (—CH$_2$—) and ethylene (—CH$_2$CH$_2$—) and most preferably methylene (—CH$_2$—). Preferably, $C_{1-6}$-alkylene is selected from $C_{1-4}$-alkylene, more preferably from $C_{1-2}$-alkylene.

Still further according to the present invention, the terms "$C_{3-10}$-Cycloalkyl" and "$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted. Preferably, $C_{3-10}$-Cycloalkyl and $C_{3-6}$-cycloalkyl are saturated. The $C_{3-10}$-Cycloalkyl and $C_{3-6}$-cycloalkyl can be bound to the respective superordinate general structure via any desired and possible ring member of the cycloalkyl group. The $C_{3-10}$-Cycloalkyl and $C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, $C_{3-10}$-Cycloalkyl and $C_{3-6}$-cycloalkyl can be singly or multiply bridged such as, for example, in the case of adamantyl, bicyclo[2.2.1]heptyl or bicyclo[2.2.2]octyl. However, preferably, $C_{3-10}$-Cycloalkyl and $C_{3-6}$-cycloalkyl are neither condensed with further ring systems nor bridged. More preferably, $C_{3-10}$-Cycloalkyl and $C_{3-6}$-cycloalkyl are neither condensed with further ring systems nor bridged and are saturated. Preferred $C_{3-10}$-Cycloalkyl groups are selected from the group consisting of cyclopropyl, cyclobutyl, cyclopentyl, cyclohexyl, cyclopentenyl, cyclohexenyl, cycloheptyl, cyclooctyl, cyclononyl, cyclodecyl, adamantly, cyclopentenyl, cyclohexenyl, cycloheptenyl, cyclooctenyl, bicyclo[2.2.1]heptyl and bicyclo[2.2.2]octyl. Particularly preferred $C_{3-10}$-cycloalkyl groups are selected from $C_{3-6}$-cycloalkyl groups. Preferred $C_{3-6}$-cycloalkyl groups are selected from the group consisting of cyclopropyl, cyclobutyl, cyclopentyl, cyclohexyl, cyclopentenyl and cyclohexenyl. Particularly preferred $C_{3-6}$-cycloalkyl groups are selected from the group consisting of cyclopropyl, cyclobutyl, cyclopentyl and cyclohexyl, most preferably cyclopropyl.

According to the present invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{1-4}$-alkyl) such as N(CH$_3$), wherein the carbon atoms of the ring can be unsubstituted or mono- or polysubstituted. Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, tetrahydrofuranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups. Preferred 3 to 6-membered heterocycloalkyl groups are selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. Particularly preferred 3 to 6-membered heterocycloalkyl groups are selected from the group consisting of tetrahydropyranyl, oxetanyl, oxiranyl, and tetrahydrofuranyl.

According to the present invention, the term "aryl" preferably means aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further saturated or (partially) unsaturated cycloalkyl or heterocycloalkyl, aromatic or heteroaromatic ring systems, which can in turn be unsubstituted or mono- or polysubstituted. In a preferred embodiment, aryl is condensed with a further ring system. Examples of condensed aryl residues are 2H-benzo[b][1,4]oxazin-3 (4H)-onyl, 1H-benzo[d]imidazolyl, 2,3-dihydro-1H-indenyl, tetrahydronaphthalenyl, isochroman, 1,3-dihydroisobenzofuranyl, benzodioxolanyl and benzodioxanyl. Preferably, aryl is selected from the group consisting of phenyl, 1H-benzo[d]imidazolyl, 2H-benzo[b][1,4]oxazin-3(4H)-onyl, 2,3-dihydro-1H-indenyl, tetrahydronaphthalenyl, isochroman, 1,3-dihydroisobenzofuranyl, 1-naphthyl, 2-naphthyl, fluorenyl and anthracenyl, each of which can be respectively unsubstituted or mono- or polysubstituted. In another preferred embodiment, aryl is not condensed with any further ring system. A particularly preferred aryl is phenyl, unsubstituted or mono- or polysubstituted.

According to the present invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system. Preferably, the 5- to 6-membered heteroaryl is selected from the group consisting of pyridyl (i.e. 2-pyridyl, 3-pyridyl, 4-pyridyl), pyrimidinyl, pyridazinyl, pyrazinyl, pyrrolyl, imidazolyl, pyrazolyl, oxazolyl, isoxazolyl, thiazolyl, isothiazolyl, furanyl, thienyl (thiophenyl), triazolyl, thiadiazolyl, 4,5,6,7-tetrahydro-2H-indazolyl, 2,4,5,6-tetrahydrocyclopenta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, oxadiazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl).

The compounds according to the present invention are defined by substituents, for example by $R^1$, $R^2$ and $R^3$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R^1$=a $C_{1-10}$-alkyl ($1^{st}$ generation substituent), then the $C_{1-10}$-alkyl can for its part be substituted, for example with a $N(H)(C_{1-6}$-alkyl) ($2^{nd}$ generation substituent). This produces the functional group $R^1$=($C_{1-10}$-alkyl-NH—$C_{1-6}$-alkyl). The NH—$C_{1-6}$-alkyl can then for its part be resubstituted, for example with Cl ($3^{rd}$ generation substituent). Overall, this produces the functional group $R^1$=$C_{1-10}$-alkyl-NH—$C_{1-6}$-alkyl, wherein the $C_{1-6}$-alkyl of the NH—$C_{1-6}$-alkyl is substituted by Cl. However, in a preferred embodiment, the $3^{rd}$ generation substituents may not be resubstituted, i.e. there are then no $4^{th}$ generation substituents. More preferably, the $2^{nd}$ generation substituents may not be resubstituted, i.e. there are no $3^{rd}$ generation substituents.

If a residue occurs multiply within a molecule, then this residue can have respectively different meanings for various substituents: if, for example, both $R^2$ and $R^3$ denote $C_{1-6}$-alkyl, then $C_{1-6}$-alkyl can e.g. represent ethyl for $R^2$ and can represent methyl for $R^3$.

In connection with the terms "$C_{1-10}$-alkyl", "$C_{1-6}$-alkyl", "$C_{1-4}$-alkyl", "$C_{3-10}$-Cycloalkyl", "$C_{3-6}$-cycloalkyl", "3 to 7 membered heterocycloalkyl", "3 to 6-membered heterocycloalkyl", "$C_{1-6}$-alkylene", "$C_{1-4}$-alkylene" and "$C_{1-2}$-alkylene", the term "substituted" refers in the sense of the present invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of $CF_3$, $CH_2CF_3$ or disubstituted as in the case of 1,1-difluorocyclohexyl, or at various points, as in the case of CH(OH)—CH=CH—$CHCl_2$ or 1-chloro-3-fluorocyclohexyl. The multiple substitution can be carried out using the same or using different substituents.

In relation to the terms "aryl", "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the present invention, preferably $C_{1-10}$-alkyl, $C_{1-6}$-alkyl, $C_{1-4}$-alkyl, $C_{3-10}$-Cycloalkyl, $C_{3-6}$-cycloalkyl, 3 to 7 membered heterocycloalkyl, 3 to 6-membered heterocycloalkyl, $C_{1-6}$-alkylene, $C_{1-4}$-alkylene and $C_{1-2}$-alkylene in each case independently from one another are unsubstituted or mono- or polysubstituted with one or more substituents selected from F; Cl; Br; I; CN; $C_{1-6}$-alkyl; $CF_3$; $CF_2H$; $CFH_2$; $CF_2Cl$; $CFCl_2$; C(O)—$C_{1-6}$-alkyl; C(O)—OH; C(O)—O$C_{1-6}$-alkyl; C(O)—$NH_2$; C(O)—N(H)($C_{1-6}$-alkyl); C(O)—N($C_{1-6}$-alkyl)$_2$; OH; =O; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—$NH_2$; O—S(O)$_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—$NH_2$; N(H)—C(O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)— O—$C_{1-6}$-alkyl; N($C_{1-6}$-alkyl)-C(O)—$NH_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—$NH_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—$NH_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)$_2$—($C_{3-6}$-cycloalkyl); S(O)$_2$-(3 to 6-membered heterocycloalkyl); S(O)$_2$-phenyl and S(O)$_2$-(5 or 6-membered heteroaryl).

Preferred substituents of $C_{1-10}$-alkyl, $C_{1-6}$-alkyl, $C_{1-4}$-alkyl, $C_{3-10}$-Cycloalkyl, $C_{3-6}$-cycloalkyl, 3 to 7 membered heterocycloalkyl, 3 to 6-membered heterocycloalkyl, $C_{1-6}$-alkylene and $C_{1-4}$-alkylene are selected from the group consisting of F; Cl; Br; I; CN; $C_{1-6}$-alkyl; $CF_3$; $CF_2H$; $CFH_2$; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; $C_{3-6}$-cycloalkyl; 3 to 6-membered heterocycloalkyl; phenyl and 5 or 6-membered heteroaryl; and particularly preferably F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, SCH₃, S(O)₂(CH₃), S(O)(CH₃), N(CH₃)₂, cyclopropyl and oxetanyl. According to this embodiment, $C_{1-10}$-alkyl, $C_{1-6}$-alkyl, $C_{1-4}$-alkyl, $C_{3-10}$-Cycloalkyl, $C_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or monosubstituted or disubstituted with a substituent selected from the group consisting of F; Cl; Br; I; CN; $C_{1-6}$-alkyl; CF₃; CF₂H; CFH₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; NH₂; N(H)($C_{1-6}$-alkyl); N($C_{1-6}$-alkyl)₂; SCF₃; SCF₂H; SCFH₂; S—$C_{1-6}$-alkyl; S(O)—$C_{1-6}$-alkyl; S(O)₂—$C_{1-6}$-alkyl; $C_{3-6}$-cycloalkyl; 3 to 6-membered heterocycloalkyl; phenyl and 5 or 6-membered heteroaryl. Preferably, $C_{1-6}$-alkylene groups and $C_{1-4}$-alkylene groups are unsubstituted.

According to the present invention, preferably aryl, phenyl and 5 or 6-membered heteroaryl in each case independently from one another are unsubstituted or mono- or polysubstituted with one or more substituents selected from F; Cl; Br; I; CN; $C_{1-6}$-alkyl; CF₃; CF₂H; CFH₂; CF₂Cl; CFCl₂; $C_{1-4}$-alkylene-CF₃; $C_{1-4}$-alkylene-CF₂H; $C_{1-4}$-alkylene-CFH₂; C(O)—$C_{1-6}$-alkyl; C(O)—OH; C(O)—O$C_{1-6}$-alkyl; C(O)—N(H)(OH); C(O)—NH₂; C(O)—N(H)($C_{1-6}$-alkyl); C(O)—N($C_{1-6}$-alkyl)₂; OH; OCF₃; OCF₂H; OCFH₂; OCF₂Cl; OCFCl₂; O—$C_{1-6}$-alkyl; O—$C_{3-6}$-cycloalkyl; O-(3 to 6-membered heterocycloalkyl); NH₂; N(H)($C_{1-6}$-alkyl); N($C_{1-6}$-alkyl)₂; N(H)—C(O)—$C_{1-6}$-alkyl; N($C_{1-6}$-alkyl)-C(O)—$C_{1-6}$-alkyl; N(H)—C(O)—NH₂; N(H)—C(O)—N(H)($C_{1-6}$-alkyl); N(H)—C(O)—N($C_{1-6}$-alkyl)₂; N($C_{1-6}$-alkyl)-C(O)—N(H)($C_{1-6}$-alkyl); N($C_{1-6}$-alkyl)-C(O)—N($C_{1-6}$-alkyl)₂; N(H)—S(O)₂—$C_{1-6}$-alkyl; SCF₃; S—$C_{1-6}$-alkyl; S(O)—$C_{1-6}$-alkyl; S(O)₂—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl. Preferred substituents of aryl, phenyl and 5 or 6-membered heteroaryl are selected from the group consisting of F; Cl; Br; I; CN; $C_{1-6}$-alkyl; CF₃; CF₂H; CFH₂; $C_{1-4}$-alkylene-CF₃; $C_{1-4}$-alkylene-CF₂H; $C_{1-4}$-alkylene-CFH₂; OH; OCF₃; OCF₂H; OCFH₂; O—$C_{1-6}$-alkyl; O—$C_{3-6}$-cycloalkyl and $C_{3-6}$-cycloalkyl; and particularly preferably of F; Cl; Br; CN; CH₃; CH₂CH₃; CF₃; CF₂H; CFH₂; CH₂—CF₃; OH; OCF₃; OCF₂H; OCFH₂; O—CH₃; O-cyclopropyl and cyclopropyl. According to this embodiment, aryl, phenyl and 5 or 6-membered heteroaryl are preferably each independently from one another unsubstituted, mono- di- or trisubstituted, more preferably unsubstituted or monosubstituted or disubstituted with a substituent selected from the group consisting of F; Cl; Br; I; CN; $C_{1-6}$-alkyl; CF₃; CF₂H; CFH₂; $C_{1-4}$-alkylene-CF₃; $C_{1-4}$-alkylene-CF₂H; $C_{1-4}$-alkylene-CFH₂; OH; OCF₃; OCF₂H; OCFH₂; O—$C_{1-6}$-alkyl; O—$C_{3-6}$-cycloalkyl and $C_{3-6}$-cycloalkyl.

In a preferred embodiment, the compound according to the present invention is according to general formula (II) or (III)

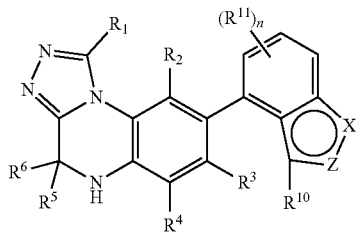

(II)

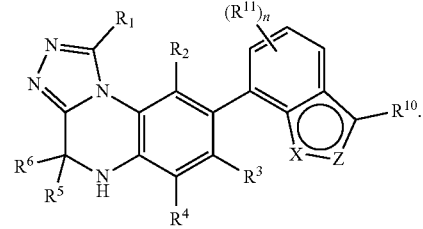

(III)

In a preferred embodiment, X represents NR⁷ and Z represents N or CR⁹. More preferably, X represents NR⁷ and Z represents CR⁹. In another preferred embodiment, X represents N and Z represents NR⁷.

More preferably, the compound according to the present invention is according to general formula (II) or (III), wherein X represents NR⁷ and Z represents N or CR⁹, more preferably CR⁹.

In a preferred embodiment, R¹ represents H; $C_{1-6}$-alkyl; $C_{3-6}$-cycloalkyl; 3 to 6-membered heterocycloalkyl; phenyl; or 5 or 6-membered heteroaryl; wherein $C_{3-6}$-cycloalkyl, 3 to 6-membered heterocycloalkyl, phenyl and 5 or 6-membered heteroaryl can optionally be bridged via $C_{1-4}$-alkylene. According to this embodiment, preferably $C_{1-6}$-alkyl; $C_{3-6}$-cycloalkyl; $C_{1-4}$-alkylene and 3 to 6-membered heterocycloalkyl in each case independently from one another are unsubstituted or mono-; di- or trisubstituted with one or more substituents selected from F; Cl; Br; I; CN; $C_{1-6}$-alkyl; CF₃; CF₂H; CFH₂; CF₂Cl; CFCl₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; O—C(O)—$C_{1-6}$-alkyl; NH₂; N(H)($C_{1-6}$-alkyl); N($C_{1-6}$-alkyl)₂; N(H)—C(O)—$C_{1-6}$-alkyl; N(H)—C(O)—O—$C_{1-6}$-alkyl; SCF₃; SCF₂H; SCFH₂; S—$C_{1-6}$-alkyl; S(O)—$C_{1-6}$-alkyl; S(O)₂—$C_{1-6}$-alkyl; S(O)₂—O—$C_{1-6}$-alkyl; S(O)₂—NH₂; S(O)₂—N(H)($C_{1-6}$-alkyl); S(O)₂—N($C_{1-6}$-alkyl)₂; $C_{3-6}$-cycloalkyl; 3 to 6-membered heterocycloalkyl; phenyl; 5 or 6-membered heteroaryl; O—$C_{3-6}$-cycloalkyl; O-(3 to 6-membered heterocycloalkyl); O-phenyl; O-(5 or 6-membered heteroaryl); C(O)—$C_{3-6}$-cycloalkyl; C(O)-(3 to 6-membered heterocycloalkyl); C(O)-phenyl; C(O)-(5 or 6-membered heteroaryl); S(O)₂—($C_{3-6}$-cycloalkyl); S(O)₂-(3 to 6-membered heterocycloalkyl); S(O)₂-phenyl or S(O)₂-(5 or 6-membered heteroaryl); more preferably F; Cl; Br; I; CN; $C_{1-6}$-alkyl; CF₃; CF₂H; CFH₂; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; NH₂; N(H)($C_{1-6}$-alkyl); N($C_{1-6}$-alkyl)₂; SCF₃; SCF₂H; SCFH₂; S—$C_{1-6}$-alkyl; S(O)—$C_{1-6}$-alkyl; S(O)₂—$C_{1-6}$-alkyl; $C_{3-6}$-cycloalkyl; 3 to 6-membered heterocycloalkyl; phenyl and 5 or 6-membered heteroaryl; and particularly preferably F, CN, CH₃, CH₂CH₃, CF₃; CF₂H; CFH₂; C(O)—NH₂; C(O)—N(H)(CH₃); C(O)—N(CH₃)₂; OH, NH₂, OCH₃, SCH₃, S(O)₂(CH₃), S(O)(CH₃), N(CH₃)₂, cyclopropyl and oxetanyl;

and preferably phenyl and 5 or 6-membered heteroaryl in each case independently from one another are unsubstituted or mono-; di- or trisubstituted with one or more substituents selected from F; Cl; Br; I; CN; $C_{1-6}$-alkyl; CF₃; CF₂H; CFH₂; $C_{1-4}$-alkylene-CF₃; $C_{1-4}$-alkylene-CF₂H; $C_{1-4}$-alkylene-CFH₂; C(O)—$C_{1-6}$-alkyl; C(O)—O$C_{1-6}$-alkyl; C(O)—; C(O)—NH₂; C(O)—N(H)($C_{1-6}$-alkyl); C(O)—N($C_{1-6}$-alkyl)₂; OH; OCF₃; OCF₂H; OCFH₂; O—$C_{1-6}$-alkyl; O—$C_{3-6}$-cycloalkyl; O-(3 to 6-membered heterocycloalkyl); NH₂; N(H)($C_{1-6}$-alkyl); N($C_{1-6}$-alkyl)₂; SCF₃; S—$C_{1-6}$-alkyl; S(O)—$C_{1-6}$-alkyl; S(O)$_2$—$C_{1-6}$-alkyl; $C_{3-6}$-cycloalkyl; $C_{1-4}$-alkylene-$C_{3-6}$-cycloalkyl; 3 to 6-membered heterocycloalkyl; $C_{1-4}$-alkylene-(3 to 6-membered heterocycloalkyl); phenyl or 5 or 6-membered heteroaryl; more preferably F; Cl; Br; I; CN; $C_{1-6}$-alkyl; $CF_3$; $CF_2H$; $CFH_2$; $C_{1-4}$-alkylene-$CF_3$; $C_{1-4}$-alkylene-$CF_2H$; $C_{1-4}$-alkylene-$CFH_2$; OH; $OCF_3$; $OCF_2H$; $OCFH_2$; O—$C_{1-6}$-alkyl; O—$C_{3-6}$-cycloalkyl and $C_{3-6}$-cycloalkyl; and particularly preferably F; Cl; Br; CN; $CH_3$; $CH_2CH_3$; $CF_3$; $CF_2H$; $CFH_2$; $CH_2$—$CF_3$; OH; $OCF_3$; $OCF_2H$; $OCFH_2$; O—$CH_3$; O-cyclopropyl and cyclopropyl.

In another preferred embodiment, $R^1$ represents H; $C_{1-4}$-alkyl; $C_{3-6}$-cycloalkyl, optionally bridged via $C_{1-2}$-alkylene; 3 to 6-membered heterocycloalkyl, optionally bridged via $C_{1-2}$-alkylene; phenyl, optionally bridged via $C_{1-2}$-alkylene; or 5 or 6-membered heteroaryl, optionally bridged via $C_{1-2}$-alkylene;

preferably wherein $C_{1-4}$-alkyl, $C_{3-6}$-cycloalkyl and 3 to 6-membered heterocycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-2}$-alkylene is unsubstituted; and phenyl and 5 or 6-membered heteroaryl in each case independently from one another is unsubstituted, mono-, di- or trisubstituted with one or more substituents selected from the group consisting of F; Cl; Br; CN; $CH_3$; $CH_2CH_3$; $CF_3$; $CF_2H$; $CFH_2$; $CH_2$—$CF_3$; OH; $OCF_3$; $OCF_2H$; $OCFH_2$; O—$CH_3$; O-cyclopropyl and cyclopropyl.

In still another preferred embodiment, $R^1$ represents H; $CH_3$, $CF_3$, $CF_2H$; $CFH_2$; ethyl, n-propyl, 2-propyl, 1-propynyl, 2-propynyl, propenyl (—$CH_2CH$=$CH_2$, —CH=CH—$CH_3$, —C(=$CH_2$)—$CH_3$), n-butyl, 1-butynyl, 2-butynyl, 1-butenyl, 2-butenyl, isobutyl, sec-butyl; tert-butyl; $(CH_2)_{1-2}OCH_3$; $(CH_2)_{1-2}OH$; $(CH_2)_{0-2}C(H)(OH)$—$(CH_2)_{0-2}CH_3$; $(CH_2)_{1-2}SCH_3$; $(CH_2)_{1-2}N(CH_3)_2$; $(CH_2)_{1-2}S(O)CH_3$; $(CH_2)_{1-2}S(O)_2CH_3$; $(CH_2)_{1-2}CN$; $(CH_2)_{0-2}C(H)(CN)$—$(CH_2)_{0-2}CH_3$; $(CH_2)_{0-2}$-cyclopropyl, $(CH_2)_{0-2}$-cyclobutyl, $(CH_2)_{0-2}$-cyclopentyl and $(CH_2)_{0-2}$-cyclohexyl; $(CH_2)_{0-2}$-tetrahydropyranyl, $(CH_2)_{0-2}$-oxetanyl, $(CH_2)_{0-2}$-oxiranyl, $(CH_2)_{0-2}$-tetrahydrofuranyl; $(CH_2)_{0-2}$-phenyl; $(CH_2)_{0-2}$-pyridyl, $(CH_2)_{0-2}$-pyrimidinyl, $(CH_2)_{0-2}$-pyridazinyl, $(CH_2)_{0-2}$-thienyl, $(CH_2)_{0-2}$-oxazolyl or $(CH_2)_{0-2}$-thiazolyl.

Preferably, $R^2$ represents H; F; Cl; Br; CN; $C_{1-6}$-alkyl; $C_{3-6}$-cycloalkyl; O—$C_{1-6}$-alkyl; N(H)($C_{1-6}$-alkyl), N($C_{1-6}$-alkyl)$_2$; C(O)—$C_{1-6}$-alkyl; C(O)—O—$C_{1-6}$-alkyl; C(O)—$NH_2$; C(O)—N(H)($C_{1-6}$-alkyl); C(O)—N($C_{1-6}$-alkyl)$_2$; O—$C_{3-6}$-cycloalkyl; N(H)($C_{3-6}$-cycloalkyl), N($C_{1-6}$-alkyl)($C_{3-6}$-cycloalkyl); C(O)—$C_{3-6}$-cycloalkyl; C(O)—O—$C_{3-6}$-cycloalkyl; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene.

In a preferred embodiment, $R^2$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene;

preferably wherein $C_{1-6}$-alkyl and $C_{3-6}$-cycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-4}$-alkylene is unsubstituted.

In a particularly preferred embodiment, $R^2$ represents H; F; Cl; Br; CN; methyl; ethyl; ethenyl (vinyl); n-propyl; 2-propyl; 1-propynyl; 2-propynyl; propenyl (—$CH_2CH$=$CH_2$; —CH=CH—$CH_3$; —C(=$CH_2$)—$CH_3$); n-butyl; isobutyl; sec-butyl; tert-butyl; $CF_3$; $CH_2CF_3$; $CHF_2$; $CH_2CHF_2$; $CH_2F$; $CH_2CH_2F$; $OCH_3$; $OCH_2CH_3$; OC(H)($CH_3$)$_2$; $OCH_2CH_2CH_3$; O—C($CH_3$)$_3$; $OCF_3$; $OCH_2CF_3$; $OCHF_2$; $OCH_2CHF_2$; $OCH_2F$; $OCH_2CH_2F$; $CH_2OH$; $CH_2CH_2OH$; $CH_2C(H)(OH)CH_3$; $CH_2CH_2CH_2OH$; $CH_2CH_2CH_2CH_2OH$; C($CH_3$)$_2CH_2OH$; C(O)—$CH_3$; C(O)—$CH_2CH_3$; C(O)—C(H)($CH_3$)$_2$C(O)—$CH_2CH_2CH_3$; C(O)—C($CH_3$)$_3$; cyclopropyl; cyclobutyl; cycopentyl; cyclohexyl; $CH_2$-cyclopropyl; $CH_2$-cyclobutyl; $CH_2$-cycopentyl; $CH_2$-cyclohexyl; O-cyclopropyl; O-cyclobutyl; O-cycopentyl; O-cyclohexyl; C(O)-cyclopropyl; C(O)-cyclobutyl; C(O)-cycopentyl; C(O)-cyclohexyl or C(O)—$NH_2$.

Preferably, $R^3$ represents H; F; Cl; Br; CN; $C_{1-6}$-alkyl; $C_{3-6}$-cycloalkyl; O—$C_{1-6}$-alkyl; N(H)($C_{1-6}$-alkyl), N($C_{1-6}$-alkyl)$_2$; C(O)—$C_{1-6}$-alkyl; C(O)—O—$C_{1-6}$-alkyl; C(O)—$NH_2$; C(O)—N(H)($C_{1-6}$-alkyl); C(O)—N($C_{1-6}$-alkyl)$_2$; O—$C_{3-6}$-cycloalkyl; N(H)($C_{3-6}$-cycloalkyl), N($C_{1-6}$-alkyl)($C_{3-6}$-cycloalkyl); C(O)—$C_{3-6}$-cycloalkyl; C(O)—O—$C_{3-6}$-cycloalkyl; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene.

In a preferred embodiment, $R^3$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl); wherein $C_{3-6}$-cycloalkyl can optionally be bridged via $C_{1-4}$-alkylene;

preferably wherein $C_{1-6}$-alkyl and $C_{3-6}$-cycloalkyl in each case independently from one another is unsubstituted, mono-, di- or trisubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl; and $C_{1-4}$-alkylene is unsubstituted.

In a particularly preferred embodiment, $R^3$ represents H; F; Cl; Br; CN; methyl; ethyl; ethenyl (vinyl); n-propyl; 2-propyl; 1-propynyl; 2-propynyl; propenyl (—$CH_2CH$=$CH_2$; —CH=CH—$CH_3$; —C(=$CH_2$)—$CH_3$); n-butyl; isobutyl; sec-butyl; tert-butyl; $CF_3$; $CH_2CF_3$; $CHF_2$; $CH_2CHF_2$; $CH_2F$; $CH_2CH_2F$; $OCH_3$; $OCH_2CH_3$; OC(H)($CH_3$)$_2$; $OCH_2CH_2CH_3$; O—C($CH_3$)$_3$; $OCF_3$; $OCH_2CF_3$; $OCHF_2$; $OCH_2CHF_2$; $OCH_2F$; $OCH_2CH_2F$; $CH_2OH$; $CH_2CH_2OH$; $CH_2C(H)(OH)CH_3$; $CH_2CH_2CH_2OH$; $CH_2CH_2CH_2CH_2OH$; C($CH_3$)$_2CH_2OH$; C(O)—$CH_3$; C(O)—$CH_2CH_3$; C(O)—C(H)($CH_3$)$_2$C(O)—$CH_2CH_2CH_3$; C(O)—C($CH_3$)$_3$; cyclopropyl; cyclobutyl; cycopentyl; cyclohexyl; $CH_2$-cyclopropyl; $CH_2$-cyclobutyl; $CH_2$-cycopentyl; $CH_2$-cyclohexyl; O-cyclopropyl; O-cyclobutyl; O-cycopentyl; O-cyclohexyl; C(O)-cyclopropyl; C(O)-cyclobutyl; C(O)-cycopentyl; C(O)-cyclohexyl; C(O)—$NH_2$.

In a preferred embodiment, $R^2$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl);
wherein $C_{3-6}$-cycloalkyl can optionally be bridged via $C_{1-4}$-alkylene; and/or $R^3$ represents H; F; Cl; Br; CN; $C_{1-6}$-alkyl; $C_{3-6}$-cycloalkyl; O—$C_{1-6}$-alkyl; C(O)—$NH_2$; C(O)—N(H)($C_{1-6}$-alkyl); C(O)—N($C_{1-6}$-alkyl)$_2$; C(O)—N(H)($C_{3-6}$-cycloalkyl) or C(O)—N($C_{1-6}$-alkyl)($C_{3-6}$-cycloalkyl);
wherein $C_{3-6}$-cycloalkyl can optionally be bridged via $C_{1-4}$-alkylene.

According to the present invention, $R^4$ represents F or Cl.

According to the present invention, $R^5$ and $R^6$ represent independently from one another H or unsubstituted $C_{1-4}$-alkyl. Preferably, $R^5$ and $R^6$ represent independently from one another H, $CH_3$, $CH_2CH_3$; $CH_2CH_2CH_3$, $CH(CH_3)_2$ or $CH_2CH_2CH_2CH_3$, more preferably H, $CH_3$, $CH_2CH_3$ or $CH_2CH_2CH_3$; still more preferably H, $CH_3$ or $CH_2CH_3$; most preferably H or $CH_3$. In a particularly preferred embodiment, $R^5$ and $R^6$ both represent $CH_3$.

In a particularly preferred embodiment, the compound according to the present invention is according to general formula (II) or (III), wherein X represents $NR^7$ and Z represents N or $CR^9$, more preferably $CR^9$, and wherein $R^5$ and $R^6$ both represent $CH_3$.

In a preferred embodiment, at least one of $R^1$, $R^2$, $R^3$, $R^5$ and $R^6$ is not H. More preferably, both $R^5$ and $R^6$ are not H and at least one of $R^1$, $R^2$, and $R^3$ is not H. In a preferred embodiment, both $R^5$ and $R^6$ are not H and one of $R^1$, $R^2$, and $R^3$ is not H. In another preferred embodiment, both $R^5$ and $R^6$ are not H and two of $R^1$, $R^2$, and $R^3$ are not H. In yet another preferred embodiment, $R^1$, $R^2$, $R^3$, $R^5$ and $R^6$ are not H.

In a particularly preferred embodiment,
the compound according to the present invention is according to general formula (II) or (III); and/or
X represents $NR^7$ and Z represents N or $CR^9$; and/or
$R^5$ and $R^6$ both represent methyl; and/or
at least one of $R^1$, $R^2$, and $R^3$ is not H.

According to the present invention, $R^7$ represents H or L-$R^8$.

In a preferred embodiment, $R^7$ represents H. According to this embodiment, preferably X represents NH and Z represents N or $CR^9$; or X represents N and Z represents NH. More preferably, X represents NH and Z represents $CR^9$.

Still further according to this embodiment, preferably the compound according to the present invention is according to general formula (II) or (III), wherein X represents NH and Z represents N or $CR^9$, more preferably $CR^9$.

In another preferred embodiment, $R^7$ is not H. According to this preferred embodiment, $R^7$ represents L-$R^8$.

In a preferred embodiment, L represents bond; S(O); S(O)$_2$; $C_{1-4}$-alkylene; C(O); $C_{1-4}$-alkylene-C(O); C(O)—O; $C_{1-4}$-alkylene-C(O)—O; $C_{1-4}$-alkylene-N(H)—C(O); $C_{1-4}$-alkylene-N($C_{1-6}$-alkyl)-C(O); $C_{1-4}$-alkylene-N(H)—C(O)—O or $C_{1-4}$-alkylene-N($C_{1-6}$-alkyl)-C(O)—O. According to this embodiment, $C_{1-4}$-alkylene and $C_{1-6}$-alkyl are preferably unsubstituted.

More preferably, L represents bond; S(O); S(O)$_2$; $C_{1-4}$-alkylene; C(O); $C_{1-4}$-alkylene-C(O); C(O)—O; $C_{1-4}$-alkylene-C(O)—O; $C_{1-4}$-alkylene-N(H)—C(O) or $C_{1-4}$-alkylene-N(H)—C(O)—O; still more preferably bond; S(O); S(O)$_2$; $CH_2$; $CH_2CH_2$; C(CH$_3$)$_2$; $CH_2CH_2CH_2$; C(O); $CH_2$—C(O); $CH_2CH_2$—C(O); $CH_2CH_2CH_2$—C(O); C(CH$_3$)$_2$—C(O); C(O)—O; $CH_2$—C(O)—O; $CH_2CH_2$—C(O)—O; $CH_2CH_2CH_2$—C(O)—O; C(CH$_3$)$_2$—C(O)—O; $CH_2$—N(H)—C(O); $CH_2CH_2$—N(H)—C(O); C(CH$_3$)$_2$—N(H)—C(O); $CH_2CH_2CH_2$—N(H)—C(O); $CH_2$—N(H)—C(O)—O; $CH_2CH_2$—N(H)—C(O)—O; C(CH$_3$)$_2$—N(H)—C(O)—O or $CH_2CH_2CH_2$—N(H)—C(O)—O; most preferably bond; S(O)$_2$; $CH_2$; C(O); C(O)—O; $CH_2$—C(O)—O; $CH_2CH_2$—C(O)—O; $CH_2CH_2$—N(H)—C(O) or $CH_2CH_2$—N(H)—C(O)—O.

In a preferred embodiment, $R^8$ represents $C_{1-6}$-alkyl; $C_{3-6}$-cycloalkyl or 3 to 6-membered heterocycloalkyl;
wherein $C_{3-6}$-cycloalkyl and 3 to 6-membered heterocycloalkyl can optionally be bridged via $C_{1-4}$-alkylene; and preferably wherein $C_{1-6}$-alkyl; $C_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; $C_{1-6}$-alkyl; $CF_3$; $CF_2H$; $CFH_2$; C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; O—$C_{1-6}$-alkyl; $NH_2$; N(H)($C_{1-6}$-alkyl); N($C_{1-6}$-alkyl)$_2$; $SCF_3$; $SCF_2H$; $SCFH_2$; S—$C_{1-6}$-alkyl; S(O)—$C_{1-6}$-alkyl; S(O)$_2$—$C_{1-6}$-alkyl; $C_{3-6}$-cycloalkyl; 3 to 6-membered heterocycloalkyl; phenyl and 5 or 6-membered heteroaryl.

More preferably $R^8$ represents
$C_{1-6}$-alkyl, which is selected from the group consisting of methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; preferably methyl, ethyl, ethenyl (vinyl), n-propyl, 2-propyl, 1-propynyl, 2-propynyl, propenyl (—$CH_2CH=CH_2$, —CH=CH—$CH_3$, —C(=$CH_2$)—$CH_3$), n-butyl, 1-butynyl, 2-butynyl, 1-butenyl, 2-butenyl, isobutyl, sec-butyl and tert-butyl;

$C_{3-6}$-cycloalkyl, which is selected from the group consisting of cyclopropyl, cyclobutyl, cyclopentyl, cyclohexyl, cyclopentenyl and cyclohexenyl; preferably cyclopropyl, cyclobutyl, cyclopentyl and cyclohexyl;
or
3 to 6-membered heterocycloalkyl, which is selected from the group consisting of tetrahydropyranyl, oxetanyl, oxiranyl, tetrahydrofuranyl, thiazolidinyl, tetrahydrothiophenyl, tetrahydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl; preferably tetrahydropyranyl, oxetanyl, oxiranyl and tetrahydrofuranyl;

wherein $C_{3-6}$-cycloalkyl and 3 to 6-membered heterocycloalkyl can optionally be bridged via $C_{1-4}$-alkylene; and
wherein $C_{1-6}$-alkyl, $C_{3-6}$-cycloalkyl and 3 to 6-membered heterocycloalkyl in each case independently from one another are unsubstituted or mono- or polysubstituted with one or more substituents selected from the group consisting of F, CN, $CH_3$, $CH_2CH_3$, $CF_3$; $CF_2H$; $CFH_2$; C(O)—$NH_2$; C(O)—N(H)($CH_3$); C(O)—N($CH_3$)$_2$; OH, $NH_2$, $OCH_3$, $SCH_3$, S(O)$_2$($CH_3$), S(O)($CH_3$), N($CH_3$)$_2$, cyclopropyl and oxetanyl.

Most preferably $R^8$ represents methyl, ethyl, n-propyl, 2-propyl, n-butyl, isobutyl, sec-butyl, tert-butyl, $CF_3$, $CHF_2$, $CH_2F$, $CH_2CF_3$, $CH_2CHF_2$, $CH_2CH_2F$, $CHFCH_3$, CHFCH$_2$F, CHFCHF$_2$, CHFCF$_3$, CF$_2$CH$_3$, CF$_2$CH$_2$F, CF$_2$CHF$_2$, CF$_2$CF$_3$, CH$_2$CH$_2$CF$_3$, CH$_2$CH$_2$CHF$_2$, CH$_2$CH$_2$CH$_2$F, CH$_2$CHFCH$_3$, CH$_2$CHFCH$_2$F, CH$_2$CHFCHF$_2$, CH$_2$CHFCF$_3$, CH$_2$CF$_2$CH$_3$, CH$_2$CF$_2$CH$_2$F, CH$_2$CF$_2$CHF$_2$, CH$_2$CF$_2$CF$_3$, CH$_2$OH, CH$_2$CH$_2$OH, C(H)(OH)CH$_3$, CH$_2$CH$_2$CH$_2$OH, C(CH$_3$)$_2$OH, C(H)(OH)CH$_2$CH$_3$, C(H)(CH$_3$)—CH$_2$OH, CH$_2$C(H)(OH)—CH$_3$, CH$_2$CH$_2$CH$_2$CH$_2$OH, CH$_2$CH$_2$C(H)(OH)CH$_3$, CH$_2$C(H)(OH)CH$_2$CH$_3$, C(H)(OH)CH$_2$CH$_2$CH$_3$, CH$_2$—C(CH$_3$)$_2$—OH, C(CH$_3$)$_2$CH$_2$OH, C(H)(OH)CH$_2$CF$_3$, C(H)(OH)CH$_2$CHF$_2$, C(H)(OH)CH$_2$CH$_2$F, CH$_2$C(H)(OH)—CF$_3$, CH$_2$C(H)(OH)—CHF$_2$, CH$_2$C(H)(OH)—CH$_2$F, CH$_2$OCH$_3$, CH$_2$CH$_2$OCH$_3$, C(H)(CH$_3$)—OCH$_3$, CH$_2$CH$_2$CH$_2$OCH$_3$, C(CH$_3$)$_2$OCH$_3$, C(H)(OCH$_3$)CH$_2$CH$_3$, C(H)(CH$_3$)—CH$_2$OCH$_3$, CH$_2$C(H)(OCH$_3$)—CH$_3$, CH$_2$CH$_2$CH$_2$CH$_2$OCH$_3$, CH$_2$CH$_2$C(H)(OCH$_3$)CH$_3$, CH$_2$C(H)(OCH$_3$)CH$_2$CH$_3$, C(H)(OCH$_3$)CH$_2$CH$_2$CH$_3$, CH$_2$—C(CH$_3$)$_2$—OCH$_3$, C(CH$_3$)$_2$CH$_2$OCH$_3$, CH$_2$NH$_2$, CH$_2$CH$_2$NH$_2$, CH$_2$CH$_2$CH$_2$NH$_2$, C(CH$_3$)$_2$NH$_2$, C(H)(NH$_2$)CH$_2$CH$_3$, C(H)(CH$_3$)—CH$_2$NH$_2$, CH$_2$C(H)(NH$_2$)—CH$_3$, CH$_2$CH$_2$CH$_2$CH$_2$NH$_2$, CH$_2$CH$_2$C(H)(NH$_2$)CH$_3$, CH$_2$C(H)(NH$_2$)CH$_2$CH$_3$, C(H)(NH$_2$)CH$_2$CH$_2$CH$_3$, CH$_2$—C(CH$_3$)$_2$—NH$_2$, C(CH$_3$)$_2$CH$_2$NH$_2$, CH$_2$N(CH$_3$)$_2$, CH$_2$CH$_2$N(CH$_3$)$_2$, CH$_2$CH$_2$CH$_2$N(CH$_3$)$_2$, C(CH$_3$)$_2$N(CH$_3$)$_2$, C(H)(N(CH$_3$)$_2$)CH$_2$CH$_3$, C(H)(CH$_3$)—CH$_2$N(CH$_3$)$_2$, CH$_2$C(H)(N(CH$_3$)$_2$)—CH$_3$, CH$_2$CH$_2$CH$_2$CH$_2$N(CH$_3$)$_2$, CH$_2$CH$_2$C(H)(N(CH$_3$)$_2$)CH$_3$, CH$_2$C(H)(N(CH$_3$)$_2$)CH$_2$CH$_3$, C(H)(N(CH$_3$)$_2$)CH$_2$CH$_2$CH$_3$, CH$_2$—C(CH$_3$)$_2$—N(CH$_3$)$_2$, C(CH$_3$)$_2$CH$_2$N(CH$_3$)$_2$, CH$_2$—C(O)N(CH$_3$)$_2$, CH$_2$CH$_2$—C(O)N(CH$_3$)$_2$, CH$_2$CH$_2$CH$_2$—C(O)N(CH$_3$)$_2$, C(CH$_3$)$_2$—C(O)N(CH$_3$)$_2$, C(H)(C(O)N(CH$_3$)$_2$)CH$_2$CH$_3$, C(H)(CH$_3$)—CH$_2$—C(O)N(CH$_3$)$_2$, CH$_2$C(H)(C(O)N(CH$_3$)$_2$)—CH$_3$, CH$_2$CH$_2$CH$_2$CH$_2$—C(O)N(CH$_3$)$_2$, CH$_2$CH$_2$C(H)(C(O)N(CH$_3$)$_2$)CH$_3$, CH$_2$C(H)(C(O)N(CH$_3$)$_2$)CH$_2$CH$_3$, C(H)(C(O)N(CH$_3$)$_2$)CH$_2$CH$_2$CH$_3$, CH$_2$—C(CH$_3$)$_2$—C(O)N(CH$_3$)$_2$, C(CH$_3$)$_2$CH$_2$—C(O)N(CH$_3$)$_2$, (CH$_2$)$_{0-2}$-cyclopropyl, (CH$_2$)$_{0-2}$-cyclobutyl, (CH$_2$)$_{0-2}$-cyclopentyl, (CH$_2$)$_{0-2}$-cyclohexyl, (CH$_2$)$_{0-2}$-tetrahydropyranyl, (CH$_2$)$_{0-2}$-oxetanyl, (CH$_2$)$_{0-2}$-oxiranyl or (CH$_2$)$_{0-2}$-tetrahydrofuranyl.

Preferred embodiments (E1 to E45) encompass those wherein L and R$^8$ have the meaning as given in the table below:

|  | L | R$^8$ |
| --- | --- | --- |
| E1 | bond | (CH$_2$)$_{0-6}$—C$_{1-10}$-alkyl |
| E2 | bond | (CH$_2$)$_{0-6}$—C$_{3-10}$-cycloalkyl |
| E3 | bond | (CH$_2$)$_{0-6}$-3 to 7 membered heterocycloalkyl |
| E4 | S(O) | (CH$_2$)$_{0-6}$—C$_{1-10}$-alkyl |
| E5 | S(O) | (CH$_2$)$_{0-6}$—C$_{3-10}$-cycloalkyl |
| E6 | S(O) | (CH$_2$)$_{0-6}$-3 to 7 membered heterocycloalkyl |
| E7 | S(O)$_2$ | (CH$_2$)$_{0-6}$—C$_{1-10}$-alkyl |
| E8 | S(O)$_2$ | (CH$_2$)$_{0-6}$—C$_{3-10}$-cycloalkyl |
| E9 | S(O)$_2$ | (CH$_2$)$_{0-6}$-3 to 7 membered heterocycloalkyl |
| E10 | C$_{1-6}$-alkylene | (CH$_2$)$_{0-6}$—C$_{1-10}$-alkyl |
| E11 | C$_{1-6}$-alkylene | (CH$_2$)$_{0-6}$—C$_{3-10}$-cycloalkyl |
| E12 | C$_{1-6}$-alkylene | (CH$_2$)$_{0-6}$-3 to 7 membered heterocycloalkyl |
| E13 | C(O) | (CH$_2$)$_{0-6}$—C$_{1-10}$-alkyl |
| E14 | C(O) | (CH$_2$)$_{0-6}$—C$_{3-10}$-cycloalkyl |
| E15 | C(O) | (CH$_2$)$_{0-6}$-3 to 7 membered heterocycloalkyl |
| E16 | C$_{1-6}$-alkylene-C(O) | (CH$_2$)$_{0-6}$—C$_{1-10}$-alkyl |
| E17 | C$_{1-6}$-alkylene-C(O) | (CH$_2$)$_{0-6}$—C$_{3-10}$-cycloalkyl |
| E18 | C$_{1-6}$-alkylene-C(O) | (CH$_2$)$_{0-6}$-3 to 7 membered heterocycloalkyl |
| E19 | C(O)—O | (CH$_2$)$_{0-6}$—C$_{1-10}$-alkyl |
| E20 | C(O)—O | (CH$_2$)$_{0-6}$—C$_{3-10}$-cycloalkyl |
| E21 | C(O)—O | (CH$_2$)$_{0-6}$-3 to 7 membered heterocycloalkyl |
| E22 | C$_{1-6}$-alkylene-C(O)—O | (CH$_2$)$_{0-6}$—C$_{1-10}$-alkyl |
| E23 | C$_{1-6}$-alkylene-C(O)—O | (CH$_2$)$_{0-6}$—C$_{3-10}$-cycloalkyl |
| E24 | C$_{1-6}$-alkylene-C(O)—O | (CH$_2$)$_{0-6}$-3 to 7 membered heterocycloalkyl |
| E25 | C$_{1-6}$-alkylene-N(H)—C(O) | (CH$_2$)$_{0-6}$—C$_{1-10}$-alkyl |
| E26 | C$_{1-6}$-alkylene-N(H)—C(O) | (CH$_2$)$_{0-6}$—C$_{3-10}$-cycloalkyl |
| E27 | C$_{1-6}$-alkylene-N(H)—C(O) | (CH$_2$)$_{0-6}$-3 to 7 membered heterocycloalkyl |
| E28 | C$_{1-6}$-alkylene-N(C$_{1-10}$-alkyl)-C(O) | (CH$_2$)$_{0-6}$—C$_{1-10}$-alkyl |
| E29 | C$_{1-6}$-alkylene-N(C$_{1-10}$-alkyl)-C(O) | (CH$_2$)$_{0-6}$—C$_{3-10}$-cycloalkyl |
| E30 | C$_{1-6}$-alkylene-N(C$_{1-10}$-alkyl)-C(O) | (CH$_2$)$_{0-6}$-3 to 7 membered heterocycloalkyl |
| E31 | C$_{1-6}$-alkylene-N(H)—C(O)—O | (CH$_2$)$_{0-6}$—C$_{1-10}$-alkyl |
| E32 | C$_{1-6}$-alkylene-N(H)—C(O)—O | (CH$_2$)$_{0-6}$—C$_{3-10}$-cycloalkyl |
| E33 | C$_{1-6}$-alkylene-N(H)—C(O)—O | (CH$_2$)$_{0-6}$-3 to 7 membered heterocycloalkyl |
| E34 | C$_{1-6}$-alkylene-N(C$_{1-10}$-alkyl)-C(O)—O | (CH$_2$)$_{0-6}$—C$_{1-10}$-alkyl |
| E35 | C$_{1-6}$-alkylene-N(C$_{1-10}$-alkyl)-C(O)—O | (CH$_2$)$_{0-6}$—C$_{3-10}$-cycloalkyl |
| E36 | C$_{1-6}$-alkylene-N(C$_{1-10}$-alkyl)-C(O)—O | (CH$_2$)$_{0-6}$-3 to 7 membered heterocycloalkyl |
| E37 | O | (CH$_2$)$_{0-6}$—C$_{1-10}$-alkyl |
| E38 | O | (CH$_2$)$_{0-6}$—C$_{3-10}$-cycloalkyl |
| E39 | O | (CH$_2$)$_{0-6}$-3 to 7 membered heterocycloalkyl |
| E40 | NH | (CH$_2$)$_{0-6}$—C$_{1-10}$-alkyl |
| E41 | NH | (CH$_2$)$_{0-6}$—C$_{3-10}$-cycloalkyl |
| E42 | NH | (CH$_2$)$_{0-6}$-3 to 7 membered heterocycloalkyl |
| E43 | N(C$_{1-10}$-alkyl) | (CH$_2$)$_{0-6}$—C$_{1-10}$-alkyl |
| E44 | N(C$_{1-10}$-alkyl) | (CH$_2$)$_{0-6}$—C$_{3-10}$-cycloalkyl |
| E45 | N(C$_{1-10}$-alkyl) | (CH$_2$)$_{0-6}$-3 to 7 membered heterocycloalkyl |

Preferably,

L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O); C$_{1-4}$-alkylene-N(C$_{1-6}$-alkyl)-C(O); C$_{1-4}$-alkylene-N(H)—C(O)—O or C$_{1-4}$-alkylene-N(C$_{1-6}$-alkyl)-C(O)—O; and R$^8$ represents C$_{1-6}$-alkyl; C$_{3-6}$-cycloalkyl or 3 to 6-membered heterocycloalkyl;

wherein C$_{3-6}$-cycloalkyl and 3 to 6-membered heterocycloalkyl can optionally be bridged via C$_{1-4}$-alkylene.

In a particularly preferred embodiment,

L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O;

R$^8$ represents C$_{1-6}$-alkyl; C$_{3-6}$-cycloalkyl or 3 to 6-membered heterocycloalkyl;

wherein C$_{3-6}$-cycloalkyl and 3 to 6-membered heterocycloalkyl can optionally be bridged via C$_{1-4}$-alkylene.

More preferably,

L represents bond; S(O); S(O)$_2$; C$_{1-4}$-alkylene; C(O); C$_{1-4}$-alkylene-C(O); C(O)—O; C$_{1-4}$-alkylene-C(O)—O; C$_{1-4}$-alkylene-N(H)—C(O) or C$_{1-4}$-alkylene-N(H)—C(O)—O; still more preferably bond; S(O); S(O)$_2$; CH$_2$; CH$_2$CH$_2$; C(CH$_3$)$_2$; CH$_2$CH$_2$CH$_2$; C(O); CH$_2$—C(O); CH$_2$CH$_2$—C(O); CH$_2$CH$_2$CH$_2$—C(O); C(CH$_3$)$_2$—C(O); C(O)—O; CH$_2$—C(O)—O; CH$_2$CH$_2$—C(O)—O; CH$_2$CH$_2$CH$_2$—C(O)—O; C(CH$_3$)$_2$—C(O)—O; CH$_2$—N(H)—C(O); CH$_2$CH$_2$—N(H)—C(O); C(CH$_3$)$_2$—N(H)—C(O); CH$_2$CH$_2$CH$_2$—N(H)—C(O); CH$_2$—N(H)—C(O)—O; CH$_2$CH$_2$—N(H)—C(O)—O; C(CH$_3$)$_2$—N(H)—C(O)—O or CH$_2$CH$_2$CH$_2$—N(H)—C(O)—O; most preferably bond; S(O)$_2$; CH$_2$; C(O); C(O)—O; CH$_2$—C(O)—O; CH$_2$CH$_2$—C(O)—O; CH$_2$CH$_2$—N(H)—C(O) or CH$_2$CH$_2$—N(H)—C(O)—O; and R$^8$ represents C$_{1-6}$-alkyl; C$_{3-6}$-cycloalkyl or 3 to 6-membered heterocycloalkyl;

wherein C$_{3-6}$-cycloalkyl and 3 to 6-membered heterocycloalkyl can optionally be bridged via C$_{1-4}$-alkylene; and preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-6}$-alkyl; CF$_3$; CF$_2$H; CFH$_2$; C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; O—C$_{1-6}$-alkyl; NH$_2$; N(H)(C$_{1-6}$-alkyl); N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; C$_{3-6}$-cycloalkyl; 3 to 6-membered heterocycloalkyl; phenyl and 5 or 6-membered heteroaryl.

Preferably, R$^9$ represents H; F; Cl; Br; I; CN; C$_{1-6}$-alkyl; C$_{3-6}$-cycloalkyl, 3 to 6-membered heterocycloalkyl; S(O)—(C$_{1-6}$-alkyl); S(O)—(C$_{3-6}$-cycloalkyl); S(O)-(3 to 6-membered heterocycloalkyl); S(O)$_2$—(C$_{1-6}$-alkyl); S(O)$_2$—(C$_{3-6}$-cycloalkyl); S(O)$_2$-(3 to 6-membered heterocycloalkyl); P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl); P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl)); O—C$_{1-6}$-alkyl; S—C$_{1-6}$-alkyl; N(H)(C$_{1-6}$-alkyl), N(C$_{1-6}$-alkyl)$_2$; C(O)—C$_{1-6}$-alkyl; C(O)—O—C$_{1-6}$-alkyl; C(O)—NH$_2$; C(O)—N(H)(C$_{1-6}$-alkyl); C(O)—N(C$_{1-6}$-alkyl)$_2$; O—C$_{3-6}$-cycloalkyl; N(H)(C$_{3-6}$-cycloalkyl), N(C$_{1-6}$-alkyl)(C$_{3-6}$-cycloalkyl); C(O)—C$_{3-6}$-cycloalkyl; C(O)—O—C$_{3-6}$-cycloalkyl; C(O)—N(H)(C$_{3-6}$-cycloalkyl); C(O)—N(C$_{1-6}$-alkyl)(C$_{3-6}$-cycloalkyl); O-(3 to 6-membered heterocycloalkyl); N(H)(3 to 6-membered heterocycloalkyl), N(C$_{1-6}$-alkyl)(3 to 6-membered heterocycloalkyl); C(O)-3 to 6-membered heterocycloalkyl; C(O)—O-(3 to 6-membered heterocycloalkyl); C(O)—N(H)(3 to 6-membered heterocycloalkyl) or C(O)—N(C$_{1-6}$-alkyl)(3 to 6-membered heterocycloalkyl);

wherein C$_{3-6}$-cycloalkyl and 3 to 6-membered heterocycloalkyl can optionally be bridged via C$_{1-4}$-alkylene; preferably wherein C$_{1-6}$-alkyl, C$_{3-6}$-cycloalkyl and 3 to 6-membered heterocycloalkyl is in each case unsubstituted.

More preferably, R$^9$ represents H; F; Cl; Br; I; CN; methyl, ethyl, n-propyl, 2-propyl, n-butyl, isobutyl, sec-butyl, tert-butyl, CF$_3$, CHF$_2$, CH$_2$F, CH$_2$CF$_3$, CH$_2$CHF$_2$, CH$_2$CH$_2$F, cyclopropyl, cyclobutyl, tetrahydropyranyl, oxetanyl, oxiranyl, tetrahydrofuranyl, S(O)—(CH$_3$); S(O)—(CH$_2$CH$_3$); S(O)—((CH$_2$)$_{0-2}$-cyclopropyl); S(O)—((CH$_2$)$_{0-2}$-cyclobutyl); S(O)—((CH$_2$)$_{0-2}$-cyclopentyl); S(O)—((CH$_2$)$_{0-2}$-cyclohexyl); S(O)—((CH$_2$)$_{0-2}$-tetrahydropyranyl), S(O)—((CH$_2$)$_{0-2}$-oxetanyl), S(O)—((CH$_2$)$_{0-2}$-oxiranyl), S(O)—((CH$_2$)$_{0-2}$-tetrahydrofuranyl), S(O)$_2$—(CH$_3$); S(O)$_2$—(CH$_2$CH$_3$); S(O)$_2$—((CH$_2$)$_{0-2}$-cyclopropyl); S(O)$_2$—((CH$_2$)$_{0-2}$-cyclobutyl); S(O)$_2$—((CH$_2$)$_{0-2}$-cyclopentyl); S(O)$_2$—((CH$_2$)$_{0-2}$-cyclohexyl); S(O)$_2$—((CH$_2$)$_{0-2}$-tetrahydropyranyl), S(O)$_2$—((CH$_2$)$_{0-2}$-oxetanyl), S(O)$_2$—((CH$_2$)$_{0-2}$-oxiranyl), S(O)$_2$—((CH$_2$)$_{0-2}$-tetrahydrofuranyl), O—CH$_3$, O—CH$_2$CH$_3$, O—CH$_2$CH$_2$CH$_3$, O—C(H)(CH$_3$)$_2$, N(H)(CH$_3$), N(H)(CH$_2$CH$_3$), N(CH$_3$)$_2$ or N(CH$_3$)(CH$_2$CH$_3$).

In a particularly preferred embodiment, R$^9$ represents H; F; CN; methyl; ethyl; n-propyl; 2-propyl; CF$_3$; CH$_2$CF$_3$; CHF$_2$; CH$_2$CHF$_2$; CH$_2$F; CH$_2$CH$_2$F; S(O)—CH$_3$; S(O)—CH$_2$CH$_3$; S(O)—CH$_2$CH$_2$CH$_3$; S(O)—CH(CH$_3$)$_2$; S(O)$_2$—CH$_3$; S(O)$_2$—CH$_2$CH$_3$; S(O)$_2$—CH$_2$CH$_2$CH$_3$ or S(O)$_2$—CH(CH$_3$)$_2$.

Preferably, R$^{10}$ represents H; F; Cl; Br; I; CN; C$_{1-6}$-alkyl; C$_{3-6}$-cycloalkyl, 3 to 6-membered heterocycloalkyl; S(O)—(C$_{1-6}$-alkyl); S(O)—(C$_{3-6}$-cycloalkyl); S(O)-(3 to 6-membered heterocycloalkyl); S(O)$_2$—(C$_{1-6}$-alkyl); S(O)$_2$—(C$_{3-6}$-cycloalkyl); S(O)$_2$-(3 to 6-membered heterocycloalkyl); P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl); P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl)); O—C$_{1-6}$-alkyl; S—C$_{1-6}$-alkyl; N(H)(C$_{1-6}$-alkyl), N(C$_{1-6}$-alkyl)$_2$; C(O)—C$_{1-6}$-alkyl; C(O)—O—C$_{1-6}$-alkyl; C(O)—NH$_2$; C(O)—N(H)(C$_{1-6}$-alkyl); C(O)—N(C$_{1-6}$-alkyl)$_2$; O—C$_{3-6}$-cycloalkyl; N(H)(C$_{3-6}$-cycloalkyl), N(C$_{1-6}$-alkyl)(C$_{3-6}$-cycloalkyl); C(O)—C$_{3-6}$-cycloalkyl; C(O)—O—C$_{3-6}$-cycloalkyl; C(O)—N(H)(C$_{3-6}$-cycloalkyl); C(O)—N(C$_{1-6}$-alkyl)(C$_{3-6}$-cycloalkyl); O-(3 to 6-membered heterocycloalkyl); N(H)(3 to 6-membered heterocycloalkyl), N(C$_{1-6}$-alkyl)(3 to 6-membered heterocycloalkyl); C(O)-3 to 6-membered heterocycloalkyl; C(O)—O-(3 to 6-membered heterocycloalkyl); C(O)—N(H)(3 to 6-membered heterocycloalkyl) or C(O)—N(C$_{1-6}$-alkyl)(3 to 6-membered heterocycloalkyl);

wherein C$_{3-6}$-cycloalkyl and 3 to 6-membered heterocycloalkyl can optionally be bridged via C$_{1-4}$-alkylene; and preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-6}$-alkyl; CF$_3$; CF$_2$H; CFH$_2$; C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; O—C$_{1-6}$-alkyl; NH$_2$; N(H)(C$_{1-6}$-alkyl); N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; C$_{3-6}$-cycloalkyl; 3 to 6-membered heterocycloalkyl; phenyl and 5 or 6-membered heteroaryl.

In another preferred embodiment, R$^{10}$ represents H; F; Cl; Br; CN; C$_{1-6}$-alkyl; C$_{3-6}$-cycloalkyl; 3 to 6-membered heterocycloalkyl; P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl) P(O)—(O—C$_{1-6}$-alkyl)$_2$; P(O)(O—C$_{1-6}$-alkyl)(O—C$_{3-6}$-cycloalkyl); P(O)(O—C$_{1-6}$-alkyl)(O-(3 to 6-membered heterocycloalkyl));

preferably wherein C$_{1-6}$-alkyl; C$_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; C$_{1-4}$-alkyl; CF$_3$; CF$_2$H; CFH$_2$; OH; OCF$_3$; OCF$_2$H; OCFH$_2$; O—C$_{1-4}$-alkyl; NH$_2$; N(H)(C$_{1-4}$-alkyl); N(C$_{1-4}$-alkyl)$_2$; S—C$_{1-4}$-alkyl; S(O)—C$_{1-4}$-alkyl and S(O)$_2$—C$_{1-4}$-alkyl; more preferably F, Cl, Br, CF$_3$, OCH$_3$, OCF$_3$, OCHF$_2$, OCH$_2$F, OH and NH$_2$.

More preferably, $R^{10}$ represents H; F; Cl; Br; I; CN; methyl, ethyl, n-propyl, 2-propyl, 1-propynyl, 2-propynyl, propenyl (—CH$_2$CH=CH$_2$, —CH=CH—CH$_3$, —C(=CH$_2$)—CH$_3$), n-butyl, 1-butynyl, 2-butynyl, 1-butenyl, 2-butenyl, 3-methyl-1-butynyl, n-butyl, isobutyl, sec-butyl, tert-butyl, CF$_3$, CHF$_2$, CH$_2$F, CH$_2$CF$_3$, CH$_2$CHF$_2$, CH$_2$CH$_2$F, CH$_2$CHFCH$_3$, CH$_2$CHFCH$_2$F, CH$_2$CHFCHF$_2$, CH$_2$CHFCF$_3$, CH$_2$CF$_2$CH$_3$, CH$_2$CF$_2$CH$_2$F, CH$_2$CF$_2$CHF$_2$, CH$_2$CF$_2$CF$_3$, CH$_2$OH, CH$_2$CH$_2$OH, C(H)(OH)CH$_3$, CH$_2$CH$_2$CH$_2$OH, C(CH$_3$)$_2$OH, C(H)(OH)CH$_2$CH$_3$, C(H)(CH$_3$)—CH$_2$OH, CH$_2$C(H)(OH)—CH$_3$, CH$_2$CH$_2$CH$_2$CH$_2$OH, CH$_2$CH$_2$C(H)(OH)CH$_3$, CH$_2$C(H)(OH)CH$_2$CH$_3$, C(H)(OH)CH$_2$CH$_2$CH$_3$, CH$_2$—C(CH$_3$)$_2$—OH, C(CH$_3$)$_2$CH$_2$OH, C≡C—C(H)(OH)CH$_3$, C(H)(OH)—C≡C—CH$_3$, C≡C—C(CH$_3$)(OH)CH$_3$, C(CH$_3$)(OH)—C≡C—CH$_3$, C(H)(OH)CH$_2$CF$_3$, C(H)(OH)CH$_2$CHF$_2$, C(H)(OH)CH$_2$CH$_2$F, CH$_2$C(H)(OH)—CF$_3$, CH$_2$C(H)(OH)—CHF$_2$, CH$_2$C(H)(OH)—CH$_2$F, CH$_2$OCH$_3$, CH$_2$CH$_2$OCH$_3$, C(H)(CH$_3$)—OCH$_3$, CH$_2$CH$_2$CH$_2$OCH$_3$, C(CH$_3$)$_2$OCH$_3$, C(H)(OCH$_3$)CH$_2$CH$_3$, C(H)(CH$_3$)—CH$_2$OCH$_3$, CH$_2$C(H)(OCH$_3$)—CH$_3$, CH$_2$CH$_2$CH$_2$CH$_2$OCH$_3$, CH$_2$CH$_2$C(H)(OCH$_3$)CH$_3$, CH$_2$C(H)(OCH$_3$)CH$_2$CH$_3$, C(H)(OCH$_3$)CH$_2$CH$_2$CH$_3$, CH$_2$—C(CH$_3$)$_2$—OCH$_3$, C(CH$_3$)$_2$CH$_2$OCH$_3$, CH$_2$NH$_2$, CH$_2$CH$_2$NH$_2$, CH$_2$CH$_2$CH$_2$NH$_2$, C(CH$_3$)$_2$NH$_2$, C(H)(NH$_2$)CH$_2$CH$_3$, C(H)(CH$_3$)—CH$_2$NH$_2$, CH$_2$C(H)(NH$_2$)—CH$_3$, CH$_2$CH$_2$CH$_2$CH$_2$NH$_2$, CH$_2$CH$_2$C(H)(NH$_2$)CH$_3$, CH$_2$C(H)(NH$_2$)CH$_2$CH$_3$, C(H)(NH$_2$)CH$_2$CH$_2$CH$_3$, CH$_2$—C(CH$_3$)$_2$—NH$_2$, C(CH$_3$)$_2$CH$_2$NH$_2$, C≡C—C(H)(NH$_2$)CH$_3$, C(H)(NH$_2$)—C≡C—CH$_3$, C≡C—C(CH$_3$)(NH$_2$)CH$_3$, C(CH$_3$)(NH$_2$)—C≡C—CH$_3$, CH$_2$N(CH$_3$)$_2$, CH$_2$CH$_2$N(CH$_3$)$_2$, CH$_2$CH$_2$CH$_2$N(CH$_3$)$_2$, C(CH$_3$)$_2$N(CH$_3$)$_2$, C(H)(N(CH$_3$)$_2$)CH$_2$CH$_3$, C(H)(CH$_3$)—CH$_2$N(CH$_3$)$_2$, CH$_2$C(H)(N(CH$_3$)$_2$)—CH$_3$, CH$_2$CH$_2$CH$_2$CH$_2$N(CH$_3$)$_2$, CH$_2$CH$_2$C(H)(N(CH$_3$)$_2$)CH$_3$, CH$_2$C(H)(N(CH$_3$)$_2$)CH$_2$CH$_3$, C(H)(N(CH$_3$)$_2$)CH$_2$CH$_2$CH$_3$, CH$_2$—C(CH$_3$)$_2$—N(CH$_3$)$_2$, C(CH$_3$)$_2$CH$_2$N(CH$_3$)$_2$, S(O)—CH$_3$, S(O)—CH$_2$CH$_3$, S(O)—((CH$_2$)$_{0-2}$-cyclopropyl), S(O)—((CH$_2$)$_{0-2}$-cyclobutyl), S(O)—((CH$_2$)$_{0-2}$-cyclopentyl), S(O)—((CH$_2$)$_{0-2}$-cyclohexyl), S(O)$_2$—CH$_3$, S(O)$_2$—CH$_2$CH$_3$, S(O)$_2$—((CH$_2$)$_{0-2}$-cyclopropyl), S(O)$_2$—((CH$_2$)$_{0-2}$-cyclobutyl), S(O)$_2$—((CH$_2$)$_{0-2}$-cyclopentyl), S(O)$_2$—((CH$_2$)$_{0-2}$-cyclohexyl), P(O)—(CH$_3$)$_2$, P(O)—(CH$_3$)(CH$_2$CH$_3$), P(O)—(CH$_3$)((CH$_2$)$_{0-2}$-cyclopropyl), P(O)—(CH$_3$)((CH$_2$)$_{0-2}$-cyclobutyl), P(O)—(CH$_3$)((CH$_2$)$_{0-2}$-cyclopentyl), P(O)—(CH$_3$)((CH$_2$)$_{0-2}$-cyclohexyl), (CH$_2$)$_{0-2}$-cyclopropyl, (CH$_2$)$_{0-2}$-cyclobutyl, (CH$_2$)$_{0-2}$-tetrahydropyranyl, (CH$_2$)$_{0-2}$-oxetanyl, (CH$_2$)$_{0-2}$-oxiranyl, (CH$_2$)$_{0-2}$-tetrahydrofuranyl, O—CH$_3$, O—CH$_2$CH$_3$, O—CH$_2$CH$_2$CH$_3$, O—C(H)(CH$_3$)$_2$, N(H)(CH$_3$), N(H)(CH$_2$CH$_3$), N(CH$_3$)$_2$ or N(CH$_3$)(CH$_2$CH$_3$).

In a preferred embodiment, at least one of $R^9$ and $R^{10}$ is H.

According to the present invention, n represents 0, 1, 2 or 3. In a preferred embodiment, n represents 0. In another preferred embodiment, n represents 1. In yet another preferred embodiment, n represents 2. In still another preferred embodiment, n represents 3. More preferably, n represents 1 or 2, most preferably 1.

Preferably, $R^{11}$ represents F; Cl; Br; I; CN; $C_{1-6}$-alkyl; O—$C_{1-6}$-alkyl; NO$_2$; OH; NH$_2$; $C_{3-6}$-cycloalkyl; 3 to 6-membered heterocycloalkyl; S(O)—($C_{1-6}$-alkyl); S(O)$_2$—($C_{1-6}$-alkyl); P(O)—($C_{1-6}$-alkyl)$_2$; O—$C_{1-6}$-alkyl; N(H)($C_{1-6}$-alkyl), N($C_{1-6}$-alkyl)$_2$;

preferably wherein $C_{1-6}$-alkyl; $C_{3-6}$-cycloalkyl and 3 to 6-membered heterocycloalkyl in each case independently from one another are unsubstituted or mono- or polysubstituted with one or more substituents selected from the group consisting of F; Cl; Br; I; CN; $C_{1-4}$-alkyl; CF$_3$; CF$_2$H; CFH$_2$; OH; OCF$_3$; OCF$_2$H; OCFH$_2$; O—$C_{1-4}$-alkyl; NH$_2$; N(H)($C_{1-4}$-alkyl); N($C_{1-4}$-alkyl)$_2$; S—$C_{1-4}$-alkyl; S(O)—$C_{1-4}$-alkyl and S(O)$_2$—$C_{1-4}$-alkyl; more preferably F, Cl, Br, CF$_3$, OCH$_3$, OCF$_3$, OCHF$_2$, OCH$_2$F, OH and NH$_2$.

In a particularly preferred embodiment, $R^{11}$ represents F; Cl; Br; I; CN; $C_{1-6}$-alkyl or O—$C_{1-6}$-alkyl; preferably wherein $C_{1-6}$-alkyl in each case independently from one another is unsubstituted or mono- or polysubstituted with one or more substituents selected from the group consisting of F and CF$_3$.

More preferably, $R^{11}$ represents F; Cl; Br; I; CN; CH$_3$, CH$_2$CH$_3$, O—CH$_3$ or O—CH$_2$CH$_3$.

In a particularly preferred embodiment, $R^{11}$ represents F; Cl; Br; I; CN; $C_{1-6}$-alkyl or O—$C_{1-6}$-alkyl; and/or n represents 0, 1 or 2.

In a preferred embodiment, the compound according to the present invention is selected from the group consisting of

| | |
|---|---|
| 38 | 8-(3-Cyclopropyl-5-fluoro-1H-indol-7-yl)-6-fluoro-1,4,4,9-tetramethyl-5H-[1,2,4]triazolo[4,3-a]quinoxaline |
| 48 | 9-Ethyl-6-fluoro-8-(6-fluoro-1-methylsulfonyl-1H-indol-4-yl)-1,4,4-trimethyl-5H-[1,2,4]triazolo[4,3-a]quinoxaline |
| 49 | 9-Ethyl-6-fluoro-1,4,4-trimethyl-8-(1-methylsulfonyl-1H-indol-4-yl)-5H-[1,2,4]triazolo[4,3-a]quinoxaline |
| 53 | 9-Ethyl-6-fluoro-8-(6-fluoro-1-methylsulfonyl-1H-indazol-4-yl)-1,4,4-trimethyl-5H-[1,2,4]triazolo[4,3-a]quinoxaline |
| 54 | 6-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline |
| 55 | 2-[6-Fluoro-4-(6-fluoro-9-methoxy-1,4,4-trimethyl-5H-[1,2,4]triazolo[4,3-a]quinoxalin-8-yl)-1H-indol-1-yl]-EtOH |
| 56 | 6-Fluoro-8-(6-fluoro-1-methylsulfonyl-1H-indol-4-yl)-9-methoxy-1,4,4-trimethyl-5H-[1,2,4]triazolo[4,3-a]quinoxaline |
| 57 | 6-Fluoro-9-methoxy-1,4,4-trimethyl-8-(1-methylsulfonyl-1H-indol-4-yl)-5H-[1,2,4]triazolo[4,3-a]quinoxaline |
| 58 | 8-[1-(2,2-Difluoro-ethyl)-6-fluoro-1H-indol-4-yl]-6-fluoro-9-methoxy-1,4,4-trimethyl-5H-[1,2,4]triazolo[4,3-a]quinoxaline |
| 59 | 1-Cyclopropyl-6-fluoro-8-(6-fluoro-1-methylsulfonyl-1H-indol-4-yl)-9-methoxy-4,4-dimethyl-5H-[1,2,4]triazolo[4,3-a]quinoxaline |
| 60 | 1-Cyclopropyl-6-fluoro-9-methoxy-4,4-dimethyl-8-(1-methylsulfonyl-1H-indol-4-yl)-5H-[1,2,4]triazolo[4,3-a]quinoxaline |
| 61 | 2-[4-(1-Cyclopropyl-6-fluoro-9-methoxy-4,4-dimethyl-5H-[1,2,4]triazolo[4,3-a]quinoxalin-8-yl)-6-fluoro-1H-indol-1-yl]-EtOH |
| 62 | 1-Cyclopropyl-6-fluoro-8-(5-fluoro-3-methyl-1H-indol-7-yl)-9-methoxy-4,4-dimethyl-5H-[1,2,4]triazolo[4,3-a]quinoxaline |

-continued

| | |
|---|---|
| 63 | 1-Cyclopropyl-6-fluoro-8-(6-fluoro-1-methylsulfonyl-1H-indol-4-yl)-4,4,9-trimethyl-5H-[1,2,4]triazolo[4,3-a]quinoxaline |
| 64 | 1-Cyclopropyl-6-fluoro-4,4,9-trimethyl-8-(1-methylsulfonyl-1H-indol-4-yl)-5H-[1,2,4]triazolo[4,3-a]quinoxaline |
| 65 | 2-[4-(1-Cyclopropyl-6-fluoro-4,4,9-trimethyl-5H-[1,2,4]triazolo[4,3-a]quinoxalin-8-yl)-6-fluoro-1H-indol-1-yl]-EtOH |
| 66 | 1-Cyclopropyl-6-fluoro-8-(5-fluoro-3-methyl-1H-indol-7-yl)-4,4,9-trimethyl-5H-[1,2,4]triazolo[4,3-a]quinoxaline |
| 300 | 6-Fluoro-8-[1-(2-methoxy-ethyl)-1H-indol-4-yl]-1,4,4,9-tetramethyl-5H-[1,2,4]triazolo[4,3-a]quinoxaline |
| 301 | 2-[4-(6-Fluoro-1,4,4,9-tetramethyl-5H-[1,2,4]triazolo[4,3-a]quinoxalin-8-yl)-1H-indol-1-yl]-EtOH |
| 304 | 6-Fluoro-1,4,4,9-tetramethyl-8-(1-methyl-1H-indazol-4-yl)-5H-[1,2,4]triazolo[4,3-a]quinoxaline |
| 305 | 8-(1-Cyclopropyl-1H-indol-4-yl)-6-fluoro-1,4,4,9-tetramethyl-5H-[1,2,4]triazolo[4,3-a]quinoxaline |
| 308 | 1-Ethyl-6-fluoro-4,4,9-trimethyl-8-(1-methylsulfonyl-1H-indol-4-yl)-5H-[1,2,4]triazolo[4,3-a]quinoxaline |
| 316 | 1-Ethyl-6-fluoro-8-(5-fluoro-3-methyl-1H-indol-7-yl)-4,4,9-trimethyl-5H-[1,2,4]triazolo[4,3-a]quinoxaline |
| 322 | 1-Ethyl-6-fluoro-8-[1-(2-methoxy-ethyl)-1H-indol-4-yl]-4,4,9-trimethyl-5H-[1,2,4]triazolo[4,3-a]quinoxaline |
| 323 | 1-Ethyl-6-fluoro-8-(6-fluoro-1-methylsulfonyl-1H-indol-4-yl)-4,4,9-trimethyl-5H-[1,2,4]triazolo[4,3-a]quinoxaline |
| 326 | 8-[1-(2,2-Difluoro-ethyl)-1H-indol-4-yl]-6-fluoro-1,4,4,9-tetramethyl-5H-[1,2,4]triazolo[4,3-a]quinoxaline |
| 340 | 6-Fluoro-8-(6-fluoro-1-methylsulfonyl-1H-indazol-4-yl)-1,4,4,9-tetramethyl-5H-[1,2,4]triazolo[4,3-a]quinoxaline |
| 349 | 6-Fluoro-8-[1-(fluoro-methylsulfonyl)-1H-indol-4-yl]-1,4,4,9-tetramethyl-5H-[1,2,4]triazolo[4,3-a]quinoxaline |
| 350 | 8-[1-(Ethylsulfonyl)-1H-indol-4-yl]-6-fluoro-1,4,4,9-tetramethyl-5H-[1,2,4]triazolo[4,3-a]quinoxaline |
| 352 | 6-Fluoro-1,4,4,9-tetramethyl-8-(3-methyl-1H-indazol-7-yl)-5H-[1,2,4]triazolo[4,3-a]quinoxaline |
| 355 | 1-Ethyl-6-fluoro-4,4,9-trimethyl-8-(3-methyl-1H-indol-7-yl)-5H-[1,2,4]triazolo[4,3-a]quinoxaline |
| 366 | 6-Fluoro-8-[1-(isopropylsulfonyl)-1H-indol-4-yl]-1,4,4,9-tetramethyl-5H-[1,2,4]triazolo[4,3-a]quinoxaline |
| 374 | 1-Ethyl-6-fluoro-8-(6-fluoro-1-methylsulfonyl-1H-indazol-4-yl)-4,4,9-trimethyl-5H-[1,2,4]triazolo[4,3-a]quinoxaline |
| 375 | [2-[4-(6-Fluoro-1,4,4,9-tetramethyl-5H-[1,2,4]triazolo[4,3-a]quinoxalin-8-yl)-1H-indol-1-yl]-ethyl]-dimethyl-amine |
| 378 | 6-Fluoro-1,4,4,9-tetramethyl-8-(1-methylsulfonyl-1H-indazol-4-yl)-5H-[1,2,4]triazolo[4,3-a]quinoxaline |
| 389 | 1-Ethyl-6-fluoro-4,4,9-trimethyl-8-(1-methylsulfonyl-1H-indazol-4-yl)-5H-[1,2,4]triazolo[4,3-a]quinoxaline |
| 391 | 8-[1-(Cyclopropylsulfonyl)-1H-indol-4-yl]-6-fluoro-1,4,4,9-tetramethyl-5H-[1,2,4]triazolo[4,3-a]quinoxaline |
| 446 | 8-[1-(Ethylsulfonyl)-6-fluoro-1H-indol-4-yl]-6,7-difluoro-1,4,4,9-tetramethyl-5H-[1,2,4]triazolo[4,3-a]quinoxaline |
| 447 | 6,7-Difluoro-8-(6-fluoro-1-methylsulfonyl-1H-indol-4-yl)-1,4,4,9-tetramethyl-5H-[1,2,4]triazolo[4,3-a]quinoxaline |
| 448 | 6,7-Difluoro-1,4,4,9-tetramethyl-8-(1-methylsulfonyl-1H-indol-4-yl)-5H-[1,2,4]triazolo[4,3-a]quinoxaline |
| 449 | 2-[4-(6,7-Difluoro-1,4,4,9-tetramethyl-5H-[1,2,4]triazolo[4,3-a]quinoxalin-8-yl)-6-fluoro-1H-indol-1-yl]-EtOH |
| 450 | 8-(1-Cyclopropyl-1H-indol-4-yl)-6-fluoro-1,4,4-trimethyl-5H-[1,2,4]triazolo[4,3-a]quinoxaline-9-carbonitrile |
| 451 | 6,7-Difluoro-1,4,4,9-tetramethyl-8-(1-methylsulfonyl-1H-indazol-4-yl)-5H-[1,2,4]triazolo[4,3-a]quinoxaline |
| 452 | 6,7-Difluoro-8-(6-fluoro-1-methylsulfonyl-1H-indazol-4-yl)-1,4,4,9-tetramethyl-5H-[1,2,4]triazolo[4,3-a]quinoxaline |
| 453 | [6-Fluoro-8-(6-fluoro-1-methylsulfonyl-1H-indol-4-yl)-1,4,4-trimethyl-5H-[1,2,4]triazolo[4,3-a]quinoxalin-9-yl]-MeOH |
| 454 | 6-Chloro-8-(5-fluoro-3-methyl-1H-indol-7-yl)-1,4,4,9-tetramethyl-5H-[1,2,4]triazolo[4,3-a]quinoxaline |
| 455 | 9-(Difluoro-methyl)-6-fluoro-8-(6-fluoro-1-methylsulfonyl-1H-indol-4-yl)-1,4,4-trimethyl-5H-[1,2,4]triazolo[4,3-a]quinoxaline |
| 456 | 6-Chloro-1,4,4,9-tetramethyl-8-(1-methylsulfonyl-1H-indol-4-yl)-5H-[1,2,4]triazolo[4,3-a]quinoxaline |
| 457 | 6-Chloro-8-(6-fluoro-1-methylsulfonyl-1H-indol-4-yl)-1,4,4,9-tetramethyl-5H-[1,2,4]triazolo[4,3-a]quinoxaline |
| 458 | 6-Chloro-1,4,4,9-tetramethyl-8-(1-methylsulfonyl-1H-indazol-4-yl)-5H-[1,2,4]triazolo[4,3-a]quinoxaline |
| 459 | 9-(Difluoro-methyl)-6-fluoro-1,4,4-trimethyl-8-(1-methylsulfonyl-1H-indol-4-yl)-5H-[1,2,4]triazolo[4,3-a]quinoxaline |
| 460 | 9-(Difluoro-methyl)-8-[1-(ethylsulfonyl)-6-fluoro-1H-indol-4-yl]-6-fluoro-1,4,4-trimethyl-5H-[1,2,4]triazolo[4,3-a]quinoxaline |
| 461 | 9-(Difluoro-methyl)-8-[1-(ethylsulfonyl)-1H-indol-4-yl]-6-fluoro-1,4,4-trimethyl-5H-[1,2,4]triazolo[4,3-a]quinoxaline |
| 462 | 9-(Difluoro-methyl)-6-fluoro-8-(5-fluoro-3-methyl-1H-indol-7-yl)-1,4,4-trimethyl-5H-[1,2,4]triazolo[4,3-a]quinoxaline |
| 463 | 2-[4-(6-Chloro-1,4,4,9-tetramethyl-5H-[1,2,4]triazolo[4,3-a]quinoxalin-8-yl)-6-fluoro-1H-indol-1-yl]-EtOH |

-continued

| | |
|---|---|
| 464 | 2-[4-(9-Ethyl-6-fluoro-1,4,4-trimethyl-5H-[1,2,4]triazolo[4,3-a]quinoxalin-8-yl)-6-fluoro-1H-indol-1-yl]-EtOH |
| 465 | 6-Fluoro-8-(6-fluoro-1H-indol-4-yl)-1,4,4,9-tetramethyl-5H-[1,2,4]triazolo[4,3-a]quinoxaline |
| 466 | 9-(Difluoro-methyl)-6-fluoro-1,4,4-trimethyl-8-(3-methyl-1H-indazol-7-yl)-5H-[1,2,4]triazolo[4,3-a]quinoxaline |
| 467 | 9-Cyclopropyl-6-fluoro-8-(6-fluoro-1-methylsulfonyl-1H-indazol-4-yl)-1,4,4-trimethyl-5H-[1,2,4]triazolo[4,3-a]quinoxaline |
| 468 | 6-Fluoro-8-(1H-indol-4-yl)-1,4,4,9-tetramethyl-5H-[1,2,4]triazolo[4,3-a]quinoxaline |
| 469 | 6-Fluoro-8-(1H-indol-4-yl)-9-methoxy-1,4,4-trimethyl-5H-[1,2,4]triazolo[4,3-a]quinoxaline |
| 470 | 6-Fluoro-8-(6-fluoro-1H-indol-4-yl)-9-methoxy-1,4,4-trimethyl-5H-[1,2,4]triazolo[4,3-a]quinoxaline |
| 471 | 9-Cyclopropyl-6-fluoro-8-(6-fluoro-1-methylsulfonyl-1H-indol-4-yl)-1,4,4-trimethyl-5H-[1,2,4]triazolo[4,3-a]quinoxaline |
| 472 | 9-Cyclopropyl-6-fluoro-1,4,4-trimethyl-8-(3-methyl-1H-indol-7-yl)-5H-[1,2,4]triazolo[4,3-a]quinoxaline |
| 473 | 6-Fluoro-9-methoxy-1,4,4-trimethyl-8-[6-(trifluoromethyl)-1H-indol-4-yl]-5H-[1,2,4]triazolo[4,3-a]quinoxaline |
| 474 | 9-Cyclopropyl-6-fluoro-1,4,4-trimethyl-8-(1-methylsulfonyl-1H-indol-4-yl)-5H-[1,2,4]triazolo[4,3-a]quinoxaline |
| 475 | 6-Fluoro-1,4,4,9-tetramethyl-8-(6-methyl-1-methylsulfonyl-1H-indol-4-yl)-5H-[1,2,4]triazolo[4,3-a]quinoxaline |
| 476 | 6-Fluoro-9-methoxy-1,4,4-trimethyl-8-(6-methyl-1-methylsulfonyl-1H-indol-4-yl)-5H-[1,2,4]triazolo[4,3-a]quinoxaline |
| 477 | 4-(6-Fluoro-1,4,4,9-tetramethyl-5H-[1,2,4]triazolo[4,3-a]quinoxalin-8-yl)-1H-indole-6-carbonitrile |
| 478 | 8-(3-Cyclopropyl-5-fluoro-1H-indol-7-yl)-6-fluoro-9-methoxy-1,4,4-trimethyl-5H-[1,2,4]triazolo[4,3-a]quinoxaline |
| 479 | [8-[1-(Ethylsulfonyl)-6-fluoro-1H-indol-4-yl]-6-fluoro-1,4,4-trimethyl-5H-[1,2,4]triazolo[4,3-a]quinoxalin-9-yl]-methyl-amine |
| 480 | 2-[6-Fluoro-4-(6-fluoro-1,4,4-trimethyl-9-methylamino-5H-[1,2,4]triazolo[4,3-a]quinoxalin-8-yl)-1H-indol-1-yl]-EtOH |
| 481 | [8-(1-Cyclopropyl-1H-indol-4-yl)-6-fluoro-1,4,4-trimethyl-5H-[1,2,4]triazolo[4,3-a]quinoxalin-9-yl]-methyl-amine |
| 482 | 6-Chloro-9-methoxy-1,4,4-trimethyl-8-(1-methylsulfonyl-1H-indol-4-yl)-5H-[1,2,4]triazolo[4,3-a]quinoxaline |
| 483 | 6-Chloro-8-(6-fluoro-1-methylsulfonyl-1H-indol-4-yl)-9-methoxy-1,4,4-trimethyl-5H-[1,2,4]triazolo[4,3-a]quinoxaline |
| 484 | 6-Fluoro-1,4,4,9-tetramethyl-8-(1-methyl-1H-indol-4-yl)-5H-[1,2,4]triazolo[4,3-a]quinoxaline |
| 485 | 6-Fluoro-9-methoxy-1,4,4-trimethyl-8-(1-methyl-1H-indol-4-yl)-5H-[1,2,4]triazolo[4,3-a]quinoxaline |
| 486 | [6-Fluoro-8-(6-fluoro-1-methylsulfonyl-1H-indol-4-yl)-1,4,4-trimethyl-5H-[1,2,4]triazolo[4,3-a]quinoxalin-9-yl]-methyl-amine |
| 487 | [6-Fluoro-8-(5-fluoro-3-methyl-1H-indol-7-yl)-1,4,4-trimethyl-5H-[1,2,4]triazolo[4,3-a]quinoxalin-9-yl]-methyl-amine |
| 488 | 6-Chloro-8-(6-fluoro-1H-indol-4-yl)-9-methoxy-1,4,4-trimethyl-5H-[1,2,4]triazolo[4,3-a]quinoxaline |
| 489 | 6-Fluoro-8-(7-fluoro-1H-indazol-4-yl)-9-methoxy-1,4,4-trimethyl-5H-[1,2,4]triazolo[4,3-a]quinoxaline |
| 490 | 6-Fluoro-8-(7-fluoro-1H-indol-4-yl)-1,4,4,9-tetramethyl-5H-[1,2,4]triazolo[4,3-a]quinoxaline |
| 491 | 8-[1-(Cyclopropyl-methylsulfonyl)-1H-indol-4-yl]-6-fluoro-1,4,4,9-tetramethyl-5H-[1,2,4]triazolo[4,3-a]quinoxaline |
| 492 | 6-Fluoro-9-methoxy-1,4,4-trimethyl-8-[1-methylsulfonyl-6-(trifluoromethyl)-1H-indol-4-yl]-5H-[1,2,4]triazolo[4,3-a]quinoxaline |
| 493 | 6-Chloro-8-(6-fluoro-1-methylsulfonyl-1H-indazol-4-yl)-9-methoxy-1,4,4-trimethyl-5H-[1,2,4]triazolo[4,3-a]quinoxaline |
| 494 | 6-Fluoro-8-(7-fluoro-1H-indol-4-yl)-9-methoxy-1,4,4-trimethyl-5H-[1,2,4]triazolo[4,3-a]quinoxaline |
| 495 | 6-Fluoro-8-(6-fluoro-1H-indazol-4-yl)-9-methoxy-1,4,4-trimethyl-5H-[1,2,4]triazolo[4,3-a]quinoxaline |
| 496 | 6-Fluoro-8-(6-fluoro-1H-indazol-4-yl)-1,4,4,9-tetramethyl-5H-[1,2,4]triazolo[4,3-a]quinoxaline |
| 497 | 8-[1-(Cyclopropyl-methylsulfonyl)-6-fluoro-1H-indol-4-yl]-6-fluoro-1,4,4,9-tetramethyl-5H-[1,2,4]triazolo[4,3-a]quinoxaline |
| 498 | 6,7-Difluoro-8-(6-fluoro-1-methylsulfonyl-1H-indol-4-yl)-9-methoxy-1,4,4-trimethyl-5H-[1,2,4]triazolo[4,3-a]quinoxaline |
| 499 | 6,7-Difluoro-9-methoxy-1,4,4-trimethyl-8-(1-methylsulfonyl-1H-indol-4-yl)-5H-[1,2,4]triazolo[4,3-a]quinoxaline |
| 500 | 6,7-Difluoro-1,4,4-trimethyl-8-(1-methylsulfonyl-1H-indol-4-yl)-9-(trifluoromethyl)-5H-[1,2,4]triazolo[4,3-a]quinoxaline |
| 501 | 6,7-Difluoro-8-(6-fluoro-1-methylsulfonyl-1H-indazol-4-yl)-9-methoxy-1,4,4-trimethyl-5H-[1,2,4]triazolo[4,3-a]quinoxaline |
| 502 | 6-Chloro-7-fluoro-1,4,4,9-tetramethyl-8-(1-methylsulfonyl-1H-indol-4-yl)-5H-[1,2,4]triazolo[4,3-a]quinoxaline |
| 503 | 6-Chloro-7-fluoro-8-(6-fluoro-1-methylsulfonyl-1H-indol-4-yl)-1,4,4,9-tetramethyl-5H-[1,2,4]triazolo[4,3-a]quinoxaline |
| 504 | 6-Fluoro-8-(1H-indazol-4-yl)-1,4,4,9-tetramethyl-5H-[1,2,4]triazolo[4,3-a]quinoxaline |
| 505 | 8-[1-(Cyclopropylsulfonyl)-1H-indol-4-yl]-6-fluoro-9-methoxy-1,4,4-trimethyl-5H-[1,2,4]triazolo[4,3-a]quinoxaline |
| 506 | 8-(6-Chloro-1H-indol-4-yl)-6-fluoro-1,4,4,9-tetramethyl-5H-[1,2,4]triazolo[4,3-a]quinoxaline |
| 507 | 6-Fluoro-1,4,4,9-tetramethyl-8-[6-(trifluoromethyl)-1H-indazol-4-yl]-5H-[1,2,4]triazolo[4,3-a]quinoxaline |
| 508 | 6-Chloro-7-fluoro-8-(5-fluoro-3-methyl-1H-indol-7-yl)-1,4,4,9-tetramethyl-5H-[1,2,4]triazolo[4,3-a]quinoxaline |
| 509 | 6-Chloro-7-fluoro-1,4,4,9-tetramethyl-8-(1-methylsulfonyl-1H-indazol-4-yl)-5H-[1,2,4]triazolo[4,3-a]quinoxaline |

-continued

| | |
|---|---|
| 510 | 6-Chloro-7-fluoro-8-(6-fluoro-1-methylsulfonyl-1H-indazol-4-yl)-1,4,4,9-tetramethyl-5H-[1,2,4]triazolo[4,3-a]quinoxaline |
| 511 | 8-(1-Cyclopropyl-1H-indol-4-yl)-6-fluoro-9-methoxy-1,4,4-trimethyl-5H-[1,2,4]triazolo[4,3-a]quinoxaline |
| 512 | 6,7-Difluoro-8-(1H-indol-4-yl)-1,4,4,9-tetramethyl-5H-[1,2,4]triazolo[4,3-a]quinoxaline |
| 513 | 6,7-Difluoro-1,4,4,9-tetramethyl-8-(3-methyl-1H-indol-7-yl)-5H-[1,2,4]triazolo[4,3-a]quinoxaline |
| 514 | 6,7-Difluoro-8-(5-fluoro-3-methyl-1H-indol-7-yl)-1,4,4,9-tetramethyl-5H-[1,2,4]triazolo[4,3-a]quinoxaline |
| 515 | 6-Fluoro-8-(5-fluoro-1H-indol-7-yl)-9-methoxy-1,4,4-trimethyl-5H-[1,2,4]triazolo[4,3-a]quinoxaline |
| 516 | 6,7-Difluoro-8-(6-fluoro-1H-indol-4-yl)-1,4,4-trimethyl-9-(trifluoromethyl)-5H-[1,2,4]triazolo[4,3-a]quinoxaline |
| 517 | 6-Fluoro-8-(7-fluoro-1H-indazol-4-yl)-1,4,4,9-tetramethyl-5H-[1,2,4]triazolo[4,3-a]quinoxaline |
| 518 | 6,7-Difluoro-8-(6-fluoro-1-methylsulfonyl-1H-indol-4-yl)-1,4,4-trimethyl-9-(trifluoromethyl)-5H-[1,2,4]triazolo[4,3-a]quinoxaline |
| 519 | 6,7-Difluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline |
| 520 | 4-(6,7-Difluoro-1,4,4,9-tetramethyl-5H-[1,2,4]triazolo[4,3-a]quinoxalin-8-yl)-1H-indole-7-carbonitrile |
| 521 | 6,7-Difluoro-8-(6-fluoro-1-methyl-1H-indol-4-yl)-1,4,4,9-tetramethyl-5H-[1,2,4]triazolo[4,3-a]quinoxaline |
| 522 | 6,7-Difluoro-8-(6-methoxy-1-methylsulfonyl-1H-indol-4-yl)-1,4,4,9-tetramethyl-5H-[1,2,4]triazolo[4,3-a]quinoxaline |
| 523 | 6-Fluoro-8-(6-methoxy-1-methylsulfonyl-1H-indol-4-yl)-1,4,4,9-tetramethyl-5H-[1,2,4]triazolo[4,3-a]quinoxaline |
| 524 | 6-Fluoro-9-methoxy-8-(6-methoxy-1-methylsulfonyl-1H-indol-4-yl)-1,4,4-trimethyl-5H-[1,2,4]triazolo[4,3-a]quinoxaline |
| 525 | 7-Chloro-6-fluoro-8-(6-fluoro-1-methylsulfonyl-1H-indazol-4-yl)-1,4,4,9-tetramethyl-5H-[1,2,4]triazolo[4,3-a]quinoxaline |
| 526 | 7-Chloro-6-fluoro-8-(5-fluoro-3-methyl-1H-indol-7-yl)-1,4,4,9-tetramethyl-5H-[1,2,4]triazolo[4,3-a]quinoxaline |
| 527 | 7-Chloro-6-fluoro-1,4,4,9-tetramethyl-8-(1-methylsulfonyl-1H-indazol-4-yl)-5H-[1,2,4]triazolo[4,3-a]quinoxaline | in the form of the free compound or a physiologically acceptable salt thereof.

The compounds according to the present invention can be synthesized by standard reactions in the field of organic chemistry known to the person skilled in the art or in a manner as described herein (cf Reaction Scheme 1 below) or analogously. The reaction conditions in the synthesis routes described herein are known to the skilled person and are for some cases also exemplified in the Examples described herein.

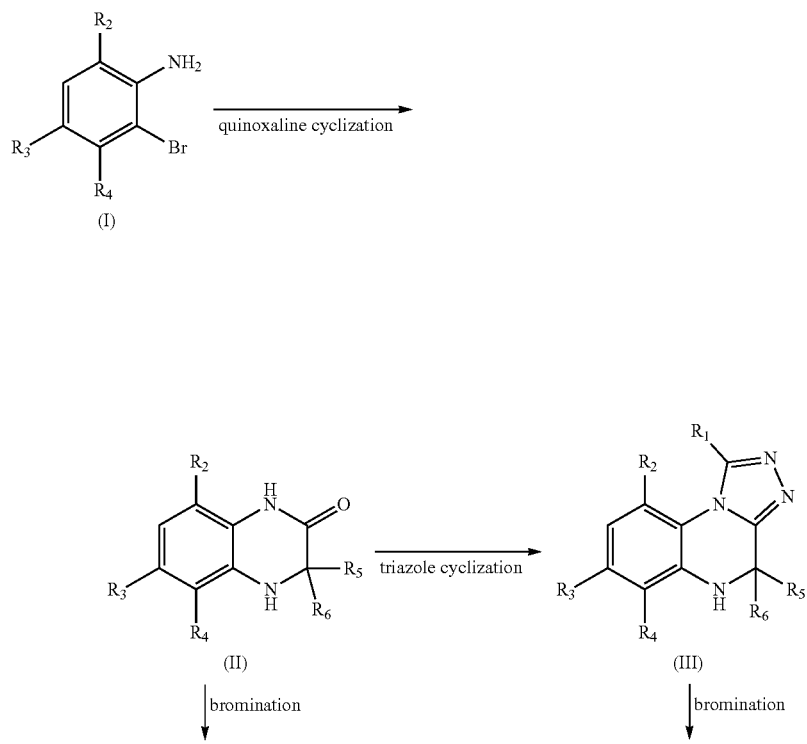

-continued

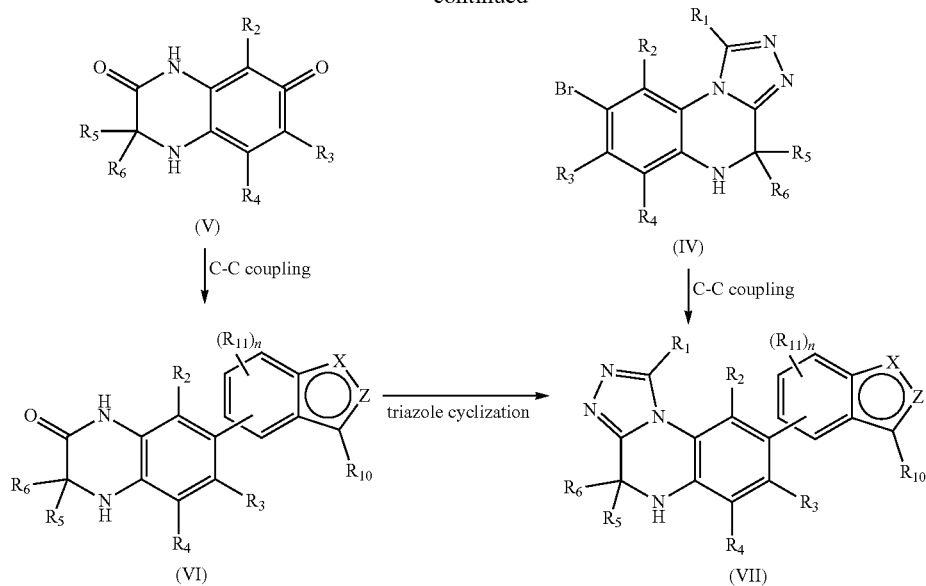

Substituted indole/indazole moiety in compounds of formula (VII) can be introduced by subjecting a compound of formula (IV) in a metal catalyzed C—C coupling reaction. Metal catalyzed C—C coupling reactions are known in the art (cf *Metal Catalyzed Cross-Coupling Reactions and More*, 3 Volume Set Wiley, 2014; *Angew. Chem. Int. Ed.*, 2012, 51, 5062-5085). Favorable C—C coupling reactions are palladium catalyzed cross coupling reactions (cf. *Angew. Chem.*, 2005, 117, 4516-4563). Triazole cyclization of compound (II) gives access to compounds of general formula (III). Triazole formation on quinoxalines is known in the art (cf. *Heterocycles*, 1992, 34, 771-780; *Biological and Pharmaceutical Bulletin*, 2005, 28, 1216-1220). Electrophilic aromatic bromination of compound (III) gives compound (IV). Bromination reactions of aromatic compounds are generally known (cf. *Science of Synthesis*, Compounds with One Saturated Carbon-Heteroatom Bond, Volume 35, Houben-Weyl, 2007). If desired, compound of formula (II) can be brominated to compound (V) which can undergo a metal catalyzed cross-coupling reaction to give compound (VI). Triazole formation leads to an alternate route to compounds of general formula (VII). Copper mediated quinoxaline cyclization of compound (I) to compound (II) is known in the art (cf. *Adv. Synth. Catal.*, 2010, 352, 2531-2537). Compounds of formula (I) are commercially available or can be prepared according to methods known in the art.

The compounds according to the present invention can be produced in the manner described here or in an analogous manner.

In a preferred embodiment, the compounds according to the present invention are modulators of the glucocorticoid receptor. In the sense of the present invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 µM ($10 \cdot 10^{-6}$ mol/L) or at most 10 µM; more preferably at most 1 µM; still more preferably at most 500 nM ($10^{-9}$ mol/L); yet more preferably at most 300 nM; even more preferably at most 100 nM; most preferably at most 10 nM; and in particular at most 1 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor fragments used are capable of binding the ligand (e.g. beclomethasone) to identify molecules that compete for binding with glucocorticoid receptor ligands. In more detail, the glucocorticoid receptor ligand binding domain is fused to the DNA binding domain (DBD) of the transcriptionfactor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calculated. Engagement of molecules which induce gene expression via glucocorticoid receptor binding to the DNA leads to expression of the luciferase gene under the control of the fusion protein GAL4 DBD-GR and therefore to a dose-dependent increase of the luminescence signal. Binding of molecules which repress beclomethasone-induced gene expression of the luciferase gene under the control of the fusion protein GAL4 DBD-GR leads to a dose-dependent reduction of the luminescence signal.

In a preferred embodiment, the compound according to the present invention exhibits in a cellular target engagement assay for agonistic or antagonistic potency on the glucocorticoid receptor an EC50 or IC50 value on the glucocorticoid receptor of at most 1 µM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the present invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Preferably, the compounds according to the present invention are useful as selective modulators of the glucocorticoid receptor.

Therefore, the compounds according to the present invention are preferably useful for the in vivo treatment or prevention of diseases in which participation of the glucocorticoid receptor is implicated.

The present invention therefore further relates to a compound according to the present invention for use in the modulation of glucocorticoid receptor activity.

Therefore, another aspect of the present invention relates to a compound according to the present invention for use in the treatment and/or prophylaxis of a disorder which is mediated at least in part by the glucocorticoid receptor. Still another aspect of the present invention relates to a method of treatment of a disorder which is mediated at least in part by the glucocorticoid receptor comprising the administration of a therapeutically effective amount of a compound according to the present invention to a subject in need thereof, preferably a human.

A further aspect of the invention relates to the use of a compound according to the present invention as medicament.

Another aspect of the present invention relates to a pharmaceutical dosage form comprising a compound according to the present invention. Preferably, the pharmaceutical dosage form comprises a compound according to the present invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik und angrenzende Gebiete, Editio Cantor Aulendoff).

The pharmaceutical dosage form according to the present invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the present invention is preferably prepared with the aid of conventional means, devices, methods and processes known in the art. The amount of the compound according to the present invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the present invention are administered per kg of the patient's body weight.

The glucocorticoid receptor is believed to have potential to modify a variety of diseases or disorders in mammals such as humans. These include in particular inflammatory diseases.

Another aspect of the present invention relates to a compound according to the present invention for use in the treatment and/or prophylaxis of pain and/or inflammation; more preferably inflammatory pain.

A further aspect of the present invention relates to a method of treatment of pain and/or inflammation; more preferably inflammatory pain.

EXAMPLES

The following abbreviations are used in the descriptions of the experiments:

AcOH=acetic acid; Ac=acetyl group; Attaphos=bis(di-tert-butyl(4 dimethylaminophenyl)phosphine)dichloropalladium(II); Ar=argon; BISPIN (or Bis-Pin)=bis(pinacolato)diborane; dba=dibenzylideneacetone; DAST=(diethylamino)sulfur trifluoride; DCM=DCM; DIPEA=N,N-diisopropylethylamine; DIBAL-H=diisobutylaluminium hydride; DMA=dimethylacetamide; DMADMF=N,N-dimethylformamide dimethylacetal; DMAP=4-(dimethylamino)-pyridine; DMF=N,N-dimethylformamid; DMSO=dimethylsulfoxid; dppf=1,1'; bis(diphenylphosphanyl)ferrocene; EtOAc=EtOAc; EtOH=EtOH; h=hour; LAH=lithium aluminium hydride; LDA=lithiumdiisopropylamide; LiHMDS=lithium bis(trimethylsilyl)amide; $m_c$=multiplet centered; MeOH=MeOH; min=minute; MTBE=methyl tert-butyl ether; n-BuLi=n-butyllithium; RT=room temperature; Rt=retention time; tert=tertiary; TEA=triethylamine; THF=tetrahydrofuran; p-TSA=para-toluene sulfonic acid; TMSCl=trimethylsilyl chloride; X-Phos=2-Dicyclohexylphosphino-2',4',6'-triisopropylbiphenyl; XANTphos=4,5-bis(diphenylphosphino)-9,9-dimethylxanthene.

Synthesis of 6-fluoro-4-(4,4,5,5-tetramethyl-1,3,2-dioxaborolan-2-yl)-1H-indole (Intermediate A-1)

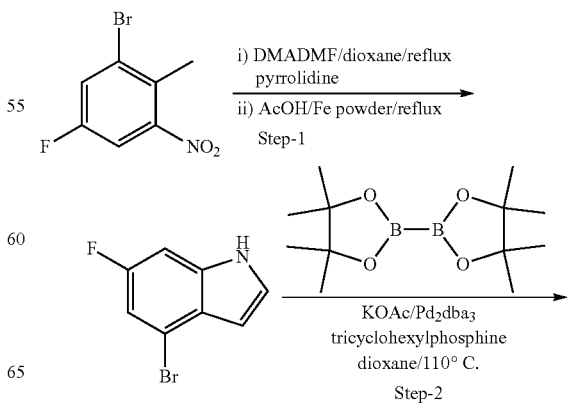

-continued

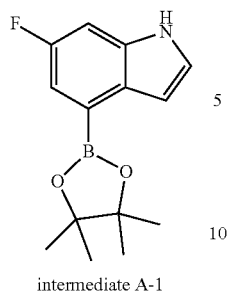

intermediate A-1

Step 1:

To a stirring solution of 2-bromo-4-fluoro-6-nitrotoluene (4.69 g, 20 mmol, 1 eq) in 1,4-dioxane (25 ml) was slowly added N,N-dimethylformamide dimethylacetal (13.3 mL, 100 mmol, 5 eq) and pyrrolidine (1.47 mL, 20 mmol, 1 eq). The reaction mixture was then stirred for 18 h at 100° C. The reaction mixture was concentrated to a dark residue. To this residue were added AcOH (30 mL) and iron powder (11 g, 200 mmol, 10 eq) and then the reaction mixture was refluxed for 1 h. The reaction mixture was then cooled to RT and then filtered through a celite bed. The filtrate was neutralised by 50% sodium hydroxide solution and then extracted with EtOAc (2×100 mL). Combined organic layers was washed with water (100 mL), brine (100 mL), dried over anhydrous Na$_2$SO$_4$ and evaporated to get the crude which was purified by column chromatography to afford 4-bromo-6-fluoro-1H-indole (1.3 g, 30%) as brown liquid.

Step 2:

To a stirring suspension of 4-bromo-6-fluoro-1H-indole (1.1 g, 5.1 mmol, 1 eq), bis(pinacolato)diborane (2.6 g, 10.2 mmol, 2 eq) and potassium acetate (2.0 g, 20.4 mmol, 4 eq) in 1,4-dioxan (20 mL) was deoxygenated by Ar for 10 min. Pd$_2$(dba)$_3$ (0.07 g, 0.07 mmol. 0.015 eq) and tricyclohexylphosphine (0.102 g, 0.36 mmol, 0.07 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 6-fluoro-4-(4,4,5,5-tetramethyl-1,3,2-dioxaborolan-2-yl)-1H-indole (1.1 g, 82%) as light yellow solid.

Synthesis of 6-fluoro-1-(methylsulfonyl)-4-(4,4,5,5-tetramethyl-1,3,2-dioxaborolan-2-yl)-1H-indole (Intermediate A-2)

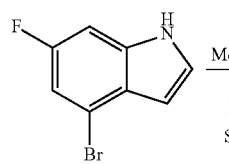

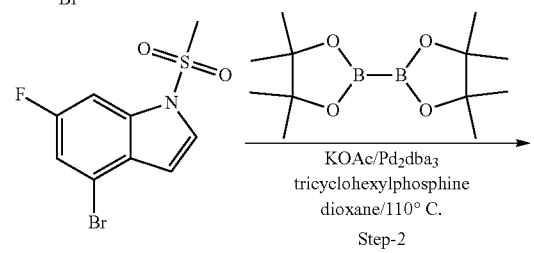

-continued

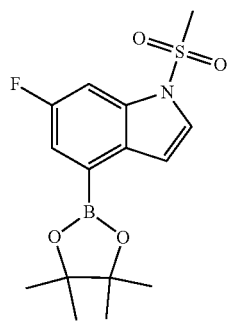

intermediate A-2

Step 1:

To a stirring solution of 4-bromo-6-fluoro-1H-indole (0.18 g, 0.841 mmol, 1 eq) in DMF (5 mL) was portion wise added sodium hydride (60%, 0.07 g, 1.68 mmol, 2 eq) at 0° C. The reaction mixture was then stirred for 30 min at RT. Methanesulfonylchloride (0.114 ml, 1.26 mmol, 1.5 eq) then added to the reaction mixture at 0° C. The reaction mixture then stirred for 2 h at RT. Reaction mixture was diluted with EtOAc (50 mL). Combined organic layers was washed with water (5×10 mL), brine (10 mL), dried over anhydrous Na$_2$SO$_4$ and evaporated under reduced pressure. Crude product was purified by column chromatography to afford 4-bromo-6-fluoro-1-(methylsulfonyl)-1H-indole (0.1 g, 41%) as off-white solid.

Step 2:

To a stirring suspension of 4-bromo-6-fluoro-1-(methylsulfonyl)-1H-indole (1.2 g, 3.53 mmol, 1 eq), bis-pinacolatodiborane (1.79 g, 7.06 mmol, 2 eq) and potassium acetate (1.39 g, 10.62 mmol, 4 eq) in 1,4-dioxan (20 mL) was deoxygenated by Ar for 10 min. Pd$_2$(dba)$_3$ (0.048 g, 0.052 mmol. 0.015 eq) and triclyclohexylphosphine (0.071 g, 0.25 mmol, 0.07 eq) was then added to the reaction mixture and again deoxygenated by Ar for 10 min. The reaction mixture then stirred for 14 h at 110° C. The reaction mixture then cooled to RT and then filtered through celite bed. Filtrate was concentrated under reduced pressure to get the crude product which was purified by column chromatography to afford 6-fluoro-1-(methylsulfonyl)-4-(4,4,5,5-tetramethyl-1,3,2-dioxaborolan-2-yl)-1H-indole (1.0 g, 80%) as light yellow solid.

Synthesis of 1-(ethylsulfonyl)-6-fluoro-4-(4,4,5,5-tetramethyl-1,3,2-dioxaborolan-2-yl)-1H-indole (Intermediate A-8)

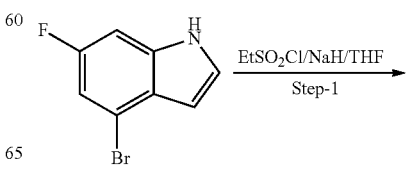

Synthesis of 1-(4-(4,4,5,5-tetramethyl-1,3,2-dioxaborolan-2-yl)-1H-indol-1-yl)ethanone (Intermediate A-10)

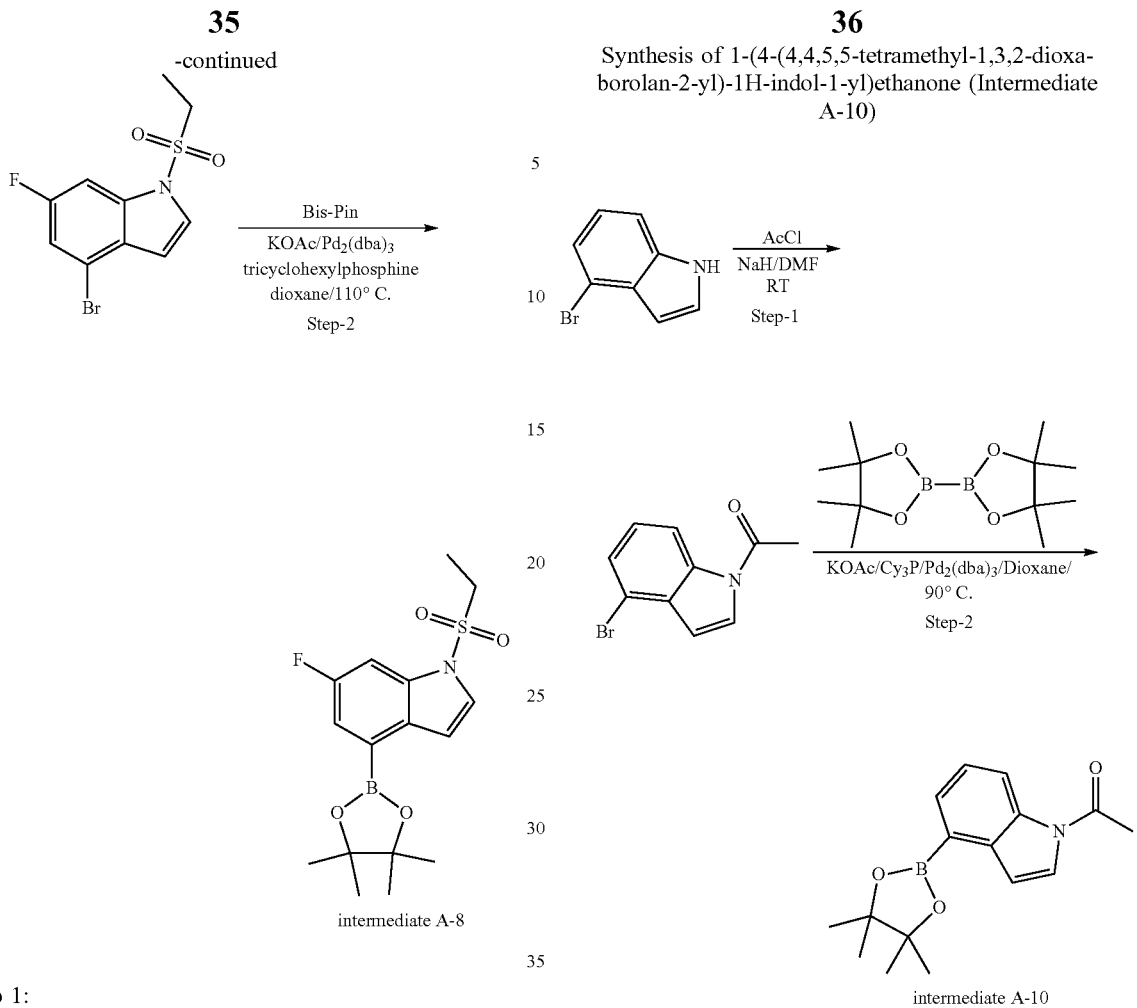

intermediate A-8 intermediate A-10

Step 1:

To a stirring solution of 4-bromo-6-fluoro-1H-indole (1.0 g, 4.67 mmol, 1 eq) in DMF (24 mL) was portion wise added sodium hydride (60%, 0.224 g, 9.34 mmol, 2 eq) at 0° C. The reaction mixture was then stirred for 30 min at RT. Ethanesulfonylchloride (0.604 mL, 7 mmol, 1.5 eq) then added to the reaction mixture at 0° C. The reaction mixture then stirred for 2 h at RT. Reaction mixture was diluted with EtOAc (200 mL). Combined organic layers was washed with water (5×30 mL), brine (30 mL), dried over anhydrous $Na_2SO_4$ and evaporated under reduced pressure. Crude product was purified by column chromatography to afford 4-bromo-1-(ethylsulfonyl)-6-fluoro-1H-indole (0.513 g, 36%) as off white solid.

Step 2:

To a stirring suspension of 4-bromo-1-(ethylsulfonyl)-6-fluoro-1H-indole (0.51 g, 1.6 mmol, 1 eq), bis(pinacolato)diborane (0.843 g, 3.2 mmol, 2 eq) and potassium acetate (0.653 g, 6.4 mmol, 4 eq) in 1,4-dioxan (15 mL) was deoxygenated by Ar for 10 min. $Pd_2(dba)_3$ (0.023 g, 0.025 mmol. 0.015 eq) and tricyclohexylphosphine (0.036 g, 0.12 mmol, 0.072 eq) was then added to the reaction mixture and again deoxygenated by Ar for 10 min. The reaction mixture was then stirred for 14 h at 110° C. The reaction mixture cooled to RT and then filtered through celite bed. Filtrate was concentrated under reduced pressure to get the crude material which was purified by column chromatography to afford 1-(ethylsulfonyl)-6-fluoro-4-(4,4,5,5-tetramethyl-1,3,2-dioxaborolan-2-yl)-1H-indole (0.212 g, 38%) as off white solid.

Step 1:

To a stirred solution of 4-bromo-1H-indole (0.5 g, 2.55 mmol, 1 eq) in THF (25 mL) was added sodium hydride (60%) (0.122 g, 3.06 mmol, 1.2 eq) at 0° C. and continued stirred at RT for 30 min. Acetyl chloride (0.02 mL, 3.06 mmol, 1.2 eq) was then added to the reaction mixture and again stirred for another 2 h. The reaction mixture was quenched with water and extracted with EtOAc (2×100 mL). Combined organic layers were washed with water (100 mL), brine (100 mL), dried over anhydrous $Na_2SO_4$ and the solvent was evaporated to get the crude product which was purified by column chromatography to afford 1-(4-bromo-1H-indol-1-yl)ethanone (0.55 g, 91%) as brown liquid.

Step 2:

To a stirred solution of 1-(4-bromo-1H-indol-1-yl)ethanone (0.55 g, 2.31 mmol, 1 eq), bis(pinacolato)diborane (0.707 g, 4.62 mmol, 2 eq) and potassium acetate (0.680 g, 6.93 mmol, 3 eq) in 1,4-dioxan (20 mL) was deoxygenated by Ar for 10 min. $Pd_2(dba)_3$ (0.106 g, 0.1155 mmol, 0.08 eq) and $Cy_3P$ (0.052 g, 0.1848 mmol. 0.08 eq) was then added to the reaction mixture and reflux at 90° C. for another 16 h. The reaction mixture was cooled to RT and filtered through celite bed. Filtrate was concentrated under reduced pressure to get the crude material which was purified by column chromatography to afford 1-(4-(4,4,5,5-tetramethyl-1,3,2-dioxaborolan-2-yl)-1H-indol-1-yl)ethanone (0.600 g, 92%) as brown liquid.

Synthesis of 6-fluoro-4-(4,4,5,5-tetramethyl-1,3,2-dioxaborolan-2-yl)-1-(2,2,2-trifluoroethyl)-1H-indole (Intermediate A-11)

Synthesis of 1-(methylsulfonyl)-4-(4,4,5,5-tetramethyl-1,3,2-dioxaborolan-2-yl)-1H-indole (Intermediate A-12)

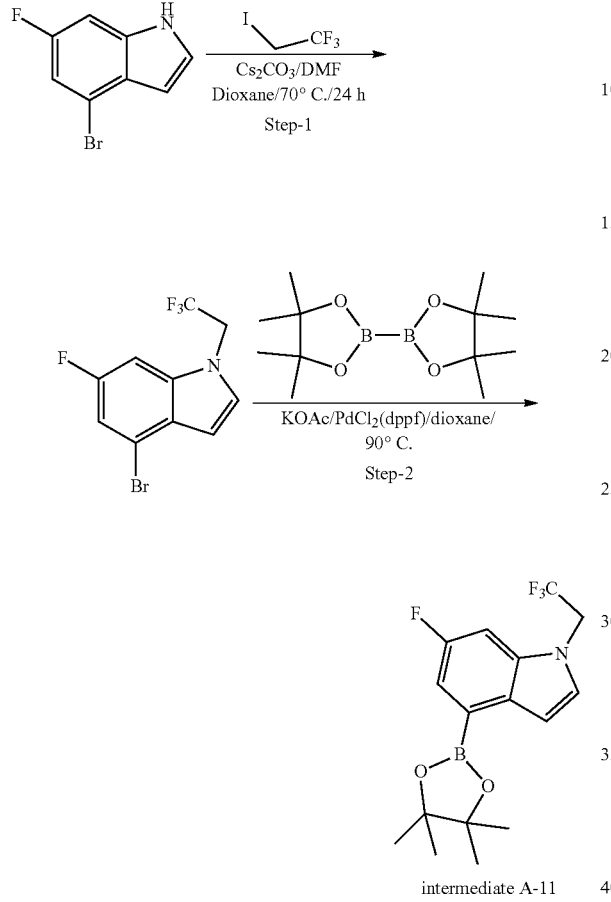

intermediate A-11

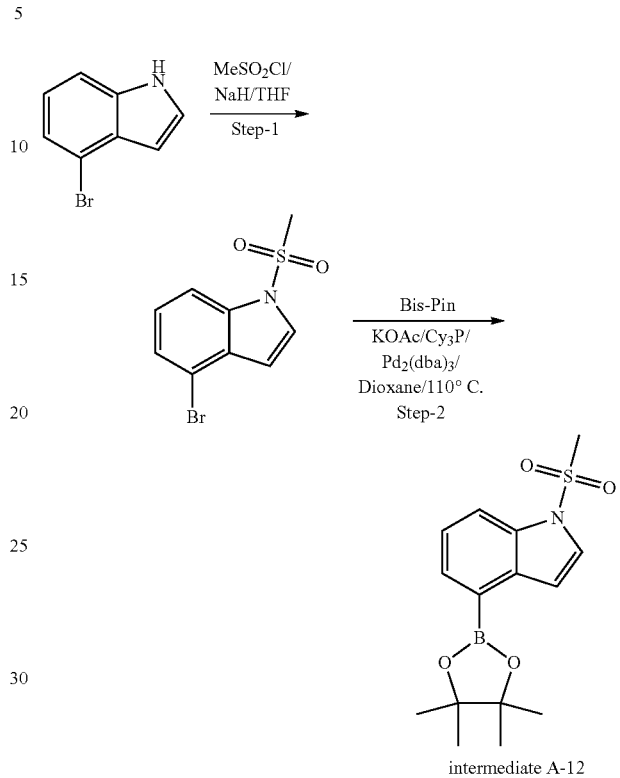

intermediate A-12

Step 1:

To a solution of 4-bromo-6-fluoro-1H-indole (2.0 g, 9.345 mmol, 1 eq.) in DMF (25 mL) was added Cs₂CO₃ (15.18 g, 46.72 mmol, 5 eq.) and 1,1,1-trifluoro-2-iodoethane (5.8 g, 28.037 mmol, 3.0 eq) in a sealed tube. The reaction mixture was refluxed at 50° C. for 24 h. The reaction mixture was filtered through sintered and the filtrate was diluted with EtOAc (100 mL). Organic layer was washed with cold water (3×50 mL), brine (25 mL), dried over anhydrous Na₂SO₄ and the solvent was evaporated to get the crude product, which was purified by flash column chromatography to afford mixture which further purified by Prep HPLC to afford 4-bromo-6-fluoro-1-(2,2,2-trifluoroethyl)-1H-indole (0.400 g, 14%) as off white solid.

Step 2:

To a stirred solution of 4-bromo-6-fluoro-1-(2,2,2-trifluoroethyl)-1H-indole (0.450 g, 1.52 mmol, 1 eq), bis(pinacolato)diborane (0.461 g, 1.824 mmol, 1.2 eq) and potassium acetate (0.446 g, 4.56 mmol, 3 eq) in 1,4-dioxan (20 mL) was deoxygenated by Ar for 10 min. PdCl₂(dppf).DCM (0.124 g, 0.152 mmol. 0.1 eq) was then added to the reaction mixture and stirred at 90° C. for another 16 h. The reaction mixture was filtered through celite bed. Filtrate was concentrated under reduced pressure to get the crude material which was used in next step without further purification.

Step 1:

To a stirring solution of 4-bromo-1H-indole (1.0 g, 5.1 mmol, 1 eq) in DMF (20 ml) was portion wise added sodium hydride (60%, 0.245 g, 10.2 mmol, 2 eq) at 0° C. The reaction mixture was then stirred for 30 min at RT. Methanesulfonylchloride (0.584 ml, 7.6 mmol, 1.5 eq) then added to the reaction mixture at 0° C. The reaction mixture was stirred for 2 h at RT. Reaction mixture was diluted with EtOAc (100 mL). Combined organic layers was washed with water (5×20 mL), brine (20 mL), dried over anhydrous Na₂SO₄ and the solvent was evaporated under reduced pressure. The crude product was purified by column chromatography to afford 4-bromo-1-(methylsulfonyl)-1H-indole (0.532 g, 38%) as off white solid.

Step 2:

To a stirring suspension of 1-(methylsulfonyl)-4-(4,4,5,5-tetramethyl-1,3,2-dioxaborolan-2-yl)-1H-indole (0.36 g, 1.31 mmol, 1 eq), bis(pinacolato)diborane (0.66 g, 2.62 mmol, 2 eq) and potassium acetate (0.57 g, 5.25 mmol, 4 eq) in 1,4-dioxan (10 Ll) was deoxygenated by Ar for 10 min. Pd₂(dba)₃ (0.018 g, 0.019 mmol, 0.015 eq) and tricyclohexylphosphine (0.027 g, 0.094 mmol, 0.072 eq) was then added to the reaction mixture and again deoxygenated by Ar for 10 min. The reaction mixture was then stirred for 14 h at 110° C. The reaction mixture then cooled to RT and then filtered through celite bed. Filtrate was concentrated under reduced pressure to get the crude material which was purified by column chromatography to afford 1-(methylsulfonyl)-4-(4,4,5,5-tetramethyl-1,3,2-dioxaborolan-2-yl)-1H-indole (0.31 g, 73%) as off white solid.

Synthesis of 5-fluoro-3-methyl-7-(4,4,5,5-tetramethyl-1,3,2-dioxaborolan-2-yl)-1H-indole (Intermediate A-15)

Synthesis of 3-cyclopropyl-5-fluoro-7-(4,4,5,5-tetramethyl-1,3,2-dioxaborolan-2-yl)-1H-indole (Intermediate A-16)

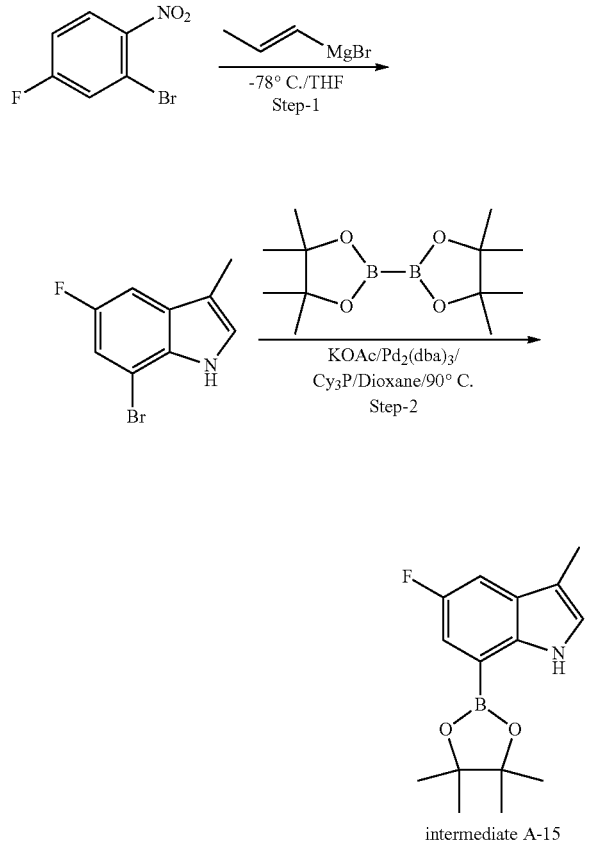

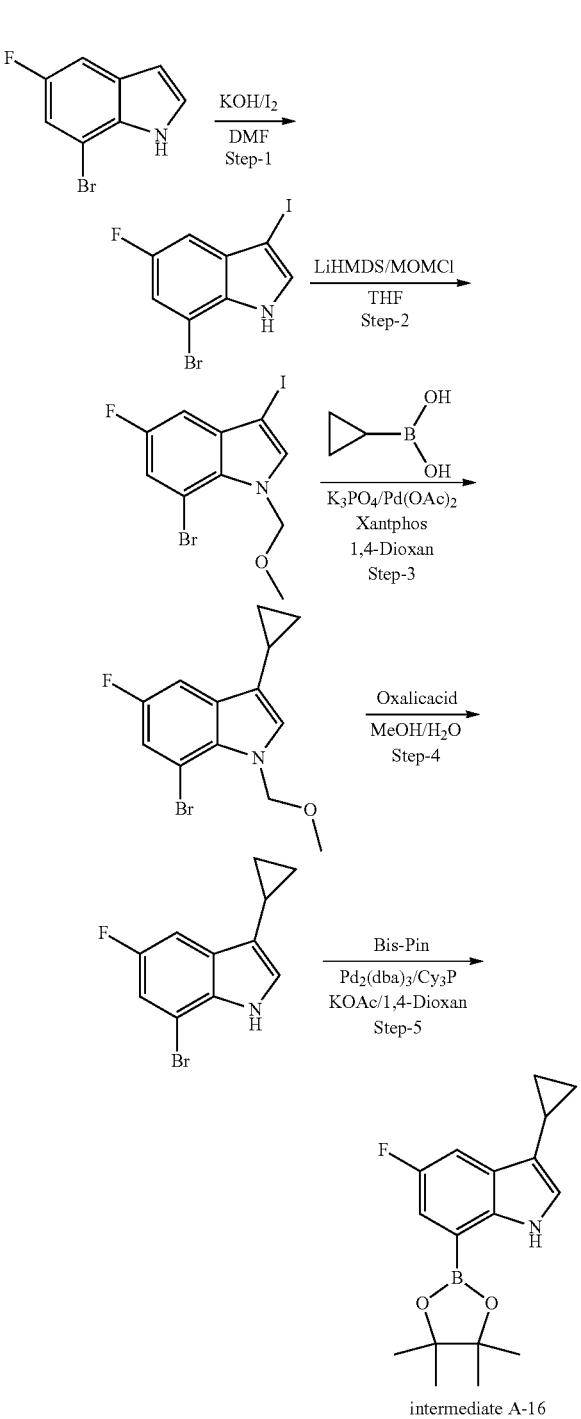

intermediate A-15 intermediate A-16

Step 1:
To a solution of 2-bromo-4-fluoro-1-nitrobenzene (0.5 g, 2.27 mmol, 1 eq.) in THF (20 mL) was added (E)-prop-1-en-1-ylmagnesium bromide (0.5 M in THF) (13.6 mL, 6.818 mmol, 3 eq) at −60° C. under nitrogen atmosphere. Then the reaction mixture was stirred at the same temperature for 4 h. The reaction was quenched with saturated ammonium chloride solution at −60° C. Then the resulting mixture was extracted with EtOAc (2×100 mL), washed with brine solution and concentrated under reduced pressure to give the crude product which was purified by flash column chromatography to afford 7-bromo-5-fluoro-3-methyl-1H-indole (0.3 g, 58%) as dense yellow liquid.

Step 2:
To a solution of 7-bromo-5-fluoro-3-methyl-1H-indole (0.8 g, 3.669 mmol, 1 eq) in 1,4-dioxane (15.0 mL) were added KOAC (1.43 g, 14.67 mmol, 4 eq) and bispincolatediborane (1.12 g, 7.33 mmol, 2 eq). The solution was degassed with Ar for 20 min followed by addition of Pd$_2$(dba)$_3$ (0.16 g, 0.183 mmol, 0.05 eq) and Cy$_3$P (0.082 g, 0.293 mmol, 0.08 eq). The reaction mixture was refluxed for 16 h. After completion of reaction (monitored by TLC), solvent was evaporated under reduced pressure to get the crude product which was purified by column chromatography to afford 5-fluoro-3-methyl-7-(4,4,5,5-tetramethyl-1,3,2-dioxaborolan-2-yl)-1H-indole (0.7 g, 70%), as brown solid.

Step 1:
To a stirring solution of 7-bromo-5-fluoroindole (7.0 g, 32.7 mmol, 1 eq) in DMF (175 mL) was added powdered potassium hydroxide (4.56 g, 81.77 mmol, 2.5 eq). The reaction mixture was then stirred for 30 min at RT. Iodine (12.46 g, 49.06 mmol, 1.5 eq) was then added to the reaction mixture and finally stirred for 2 h at RT. The reaction mixture was diluted with EtOAc (1000 mL) and washed with water (5×100 mL) followed brine (100 mL). The organic layer was dried over anhydrous Na$_2$SO$_4$ and the solvent was evaporated to get the crude product, which was purified by column chromatography to afford 7-bromo-5-fluoro-3-iodo-1H-indole (6.2, 56%) as brown solid.

Step 2:

To a stirring solution of 7-bromo-5-fluoro-3-iodo-1H-indole (6.2 g, 18.23 mmol, 1 eq) in THF (109 mL) was added drop wise LiHMDS (1M) (91.15 mL, 91.15 mmol, 5 eq) at −78° C. under inert atmosphere. The reaction mixture was stirred for 30 min at same condition. MOMCl (5.83 g, 72.94 mmol, 4 eq) was then added to the reaction mixture at −78° C. The reaction mixture was allowed to warm up to RT and then stirred for 16 h. The reaction mixture was quenched by addition of saturated solution of ammonium chloride (100 mL). Organic layer was separated and the aqueous layer was extracted with EtOAc (100 mL). The combined organic layers were washed with brine (100 mL). The organic layer was dried over anhydrous Na$_2$SO$_4$ and the solvent was evaporated to get the crude product, which was purified by column chromatography to afford 7-bromo-5-fluoro-3-iodo-1-(methoxymethyl)-1H-indole (5.4 g, 57%) as off white solid.

Step 3:

To a stirred suspension of 7-bromo-5-fluoro-3-iodo-1-(methoxymethyl)-1H-indole (2.7 g, 7.03 mmol, 1 eq), cyclopropylbronic acid (1.84 g, 2.03 mmol, 3 eq) and K$_3$PO$_4$ (4.5 g, 21.05 mmol, 3 eq) in 1,4-dioxan (45 mL) was deoxygenated by Ar for 10 min. Pd(OAc)$_2$ (0.08 g, 0.3525 mmol, 0.05 eq) and xantphos (0.407 g, 0.713 mmol, 0.1 eq) were then added to the reaction mixture and again deoxygenated for 10 min. Finally the reaction mixture was stirred at 100° C. for 16 h. The reaction mixture was cooled to RT and then filtered through celit bed. The filtrate was concentrated under reduced pressure to get the crude material which was purified by column chromatography to afford 7-bromo-3-cyclopropyl-5-fluoro-1-(methoxymethyl)-1H-indole (0.65 g, 31%) as off white solid.

Step 4:

To a stirring solution of 7-bromo-3-cyclopropyl-5-fluoro-1-(methoxymethyl)-1H-indole (1.25 g, 4.19 mmol, 1 eq) in mixture of MeOH and water (3:1) (66 mL) was added oxalic acid (1.13 g, 12.58 mmol, 3 eq). The reaction mixture was then stirred at 90° C. for 18 h. The reaction mixture was cooled to RT and concentrated under reduced pressure to get the residue. The residue was diluted with EtOAc (100 mL) and washed with water (2×40 mL) and brine (40 mL). The organic layer was dried over anhydrous Na$_2$SO$_4$ and the solvent was evaporated to get the crude product, which was purified by column chromatography to afford 7-bromo-3-cyclopropyl-5-fluoro-1H-indole (0.57 g, 54%) as color less liquid.

Step 5:

To a stirring suspension of 7-bromo-3-cyclopropyl-5-fluoro-1H-indole (0.57 g, 2.24 mmol, 1 eq), bis-pinacolatodiborane (1.7 g, 6.73 mmol, 3 eq) and potassium acetate (0.66 g, 6.73 mmol, 3 eq) in 1,4-dioxan (20 mL) was deoxygenated by Ar for 10 min. Pd$_2$(dba)$_3$ (0.031 g, 0.033 mmol. 0.015 eq) and triclyclohexylphosphine (0.047 g, 0.168 mmol, 0.075 eq) was then added to the reaction mixture and again deoxygenated by Ar for 10 min. The reaction mixture was then stirred for 14 h at 110° C. The reaction mixture was then cooled to RT and then filtered through celite bed. Filtrate was concentrated under reduced pressure to get the crude material which was purified by column chromatography to afford 3-cyclopropyl-5-fluoro-7-(4,4,5,5-tetramethyl-1,3,2-dioxaborolan-2-yl)-1H-indole (0.35 g, 52%) as off white solid.

Synthesis of 2-(6-fluoro-4-(4,4,5,5-tetramethyl-1,3, 2-dioxaborolan-2-yl)-1H-indol-1-yl)ethan-1-ol (Intermediate A-20)

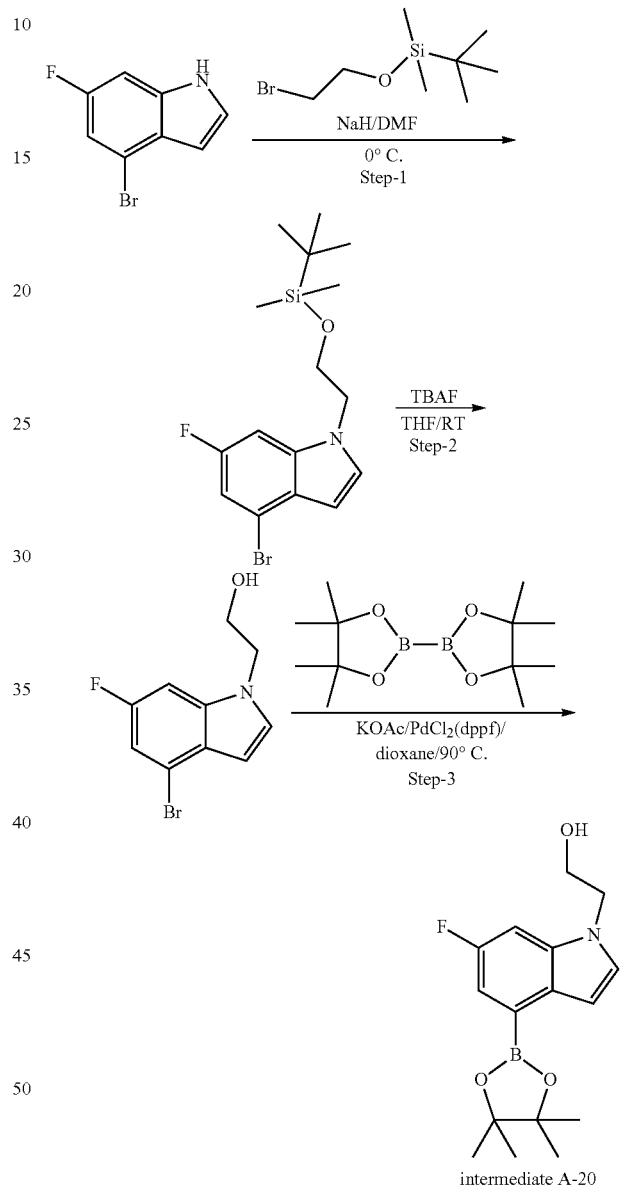

intermediate A-20

Step 1:

To a solution of 4-bromo-6-fluoro-1H-indole (0.5 g, 2.34 mmol, 1 eq.) in DMF (5 mL) was added sodium hydride (0.130 g, 2.80 mmol, 1.2 eq) at 0° C. The solution was stirred at RT for 30 min followed by addition of (2-bromoethoxy)(tert-butyl)dimethylsilane (1.17 g, 4.67 mmol, 2.0 eq) and reaction mixture was stirred at RT for 2 h. After completion of reaction (monitored by LCMS), reaction mixture was diluted with EtOAc (20 mL) and organic layer was washed with cold water (5×10 mL), brine (10 mL), dried over anhydrous Na$_2$SO$_4$ and the solvent was evaporated under reduced pressure. Crude product was purified by column chromatography to afford 4-bromo-1-(2-((tert-butyldimethylsilyl)oxy)ethyl)-6-fluoro-1H-indole (0.85 g, 98%) as brown liquid having (2-bromoethoxy)(tert-butyl)dimethylsilane as impurity.

Step 2:

To a stirred solution of 4-bromo-1-(2-((tert-butyldimethylsilyl)oxy)ethyl)-6-fluoro-1H-indole (1.3 g, 3.49 mmol, 1 eq.) in THF (15 mL) was added TBAF (3.49 mL) (1M) at RT and the mixture was stirred for 16 h. After completion of reaction (monitored by LCMS & TLC), reaction mixture was diluted with EtOAc (20 mL) and organic layer was washed with cold water (5×10 mL), brine (10 mL), dried over anhydrous $Na_2SO_4$ and the solvent was evaporated under reduced pressure. Crude product was purified by column chromatography to afford 2-(4-bromo-6-fluoro-1H-indol-1-yl)ethan-1-ol (0.55 g, 61%) as brown liquid.

Step 3:

To a stirred solution of 2-(4-bromo-6-fluoro-1H-indol-1-yl)ethan-1-ol (0.55 g, 2.13 mmol, 1 eq), bis(pinacolato)diborane (0.647 g, 2.55 mmol, 1.2 eq) and potassium acetate (0.626 g, 6.393 mmol, 3 eq) in 1,4-dioxan (20 mL) was deoxygenated by Ar for 10 min. $PdCl_2(dppf)\cdot DCM$ (0.173 g, 0.213 mmol. 0.1 eq) was then added to the reaction mixture and the mixture was stirred at 90° C. for 16 h. After completion of reaction (monitored by TLC), reaction mixture was filtered through celite bed. Filtrate was concentrated under reduced pressure to get the crude 2-(6-fluoro-4-(4,4,5,5-tetramethyl-1,3,2-dioxaborolan-2-yl)-1H-indol-1-yl)ethan-1-ol which was used in next step without further purification.

Synthesis of 2-(6-fluoro-4-(4,4,5,5-tetramethyl-1,3,2-dioxaborolan-2-yl)-1H-indazol-1-yl)ethan-1-ol (Intermediate A-21)

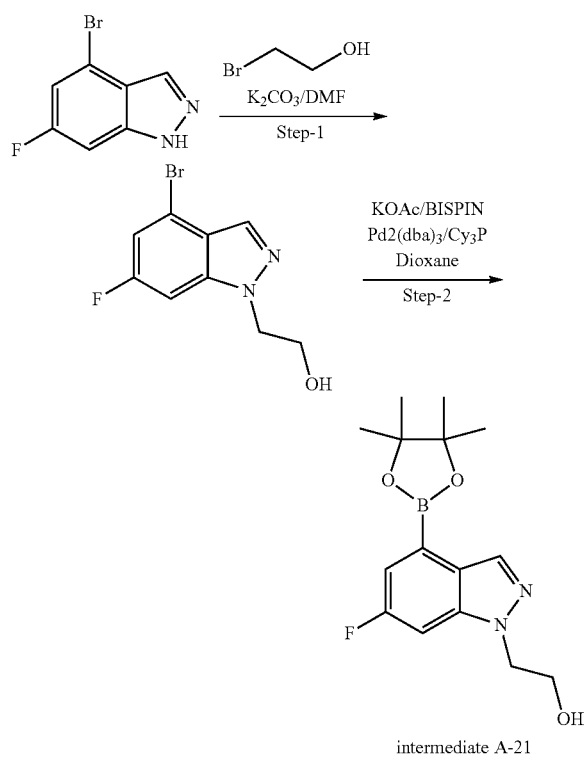

intermediate A-21

Step 1:

To a stirred solution of 4-bromo-6-fluoro-1H-indazole (0.2 g, 0.93 mmol, 1 eq) in DMF (5 mL) was added $K_2CO_3$ (0.38 g, 2.79 mmol, 3.0 eq) at RT and the mixture was stirred for 20 min. Then bromoethan-1-ol (0.07 mL, 0.93 mmol, 1 eq) was added and the mixture was stirred for 16 h at 50° C. After completion of the reaction (monitored by TLC), the reaction mass quenched with ice cold water and extracted with EtOAc (3×20 mL), washed with $H_2O$ (3×20 mL), brine (25 mL), dried over $Na_2SO_4$ and concentrated. The crude product was purified by column chromatography to afford 2-(4-bromo-6-fluoro-1H-indazol-1-yl)ethan-1-ol (0.12 g, 50%) as white solid.

Step 2:

To a solution of 2-(4-bromo-6-fluoro-1H-indazol-1-yl)ethan-1-ol (0.9 g, 3.473 mmol, 1 eq) in 1,4-dioxane (60.0 mL) were added KOAc (1.02 g, 10.419 mmol, 3 eq) and bispincolatediborane (1.76 g, 6.947 mmol, 2.0 eq). The solution was degassed with Ar for 20 min followed by addition of $Pd_2(dba)_3$ (0.17 g, 0.173 mmol, 0.05 eq) and $Cy_3P$ (0.077 g, 0.277 mmol, 0.08 eq). The reaction mixture was refluxed for 16 h. After completion of reaction (monitored by TLC), solvent was evaporated under reduced pressure to get the crude product which was purified by column chromatography to afford 2-(6-fluoro-4-(4,4,5,5-tetramethyl-1,3,2-dioxaborolan-2-yl)-1H-indazol-1-yl)ethan-1-ol (0.95 g, 89%) as brown solid.

Synthesis of 1-(methylsulfonyl)-4-(4,4,5,5-tetramethyl-1,3,2-dioxaborolan-2-yl)-1H-indazole (Intermediate A-22)

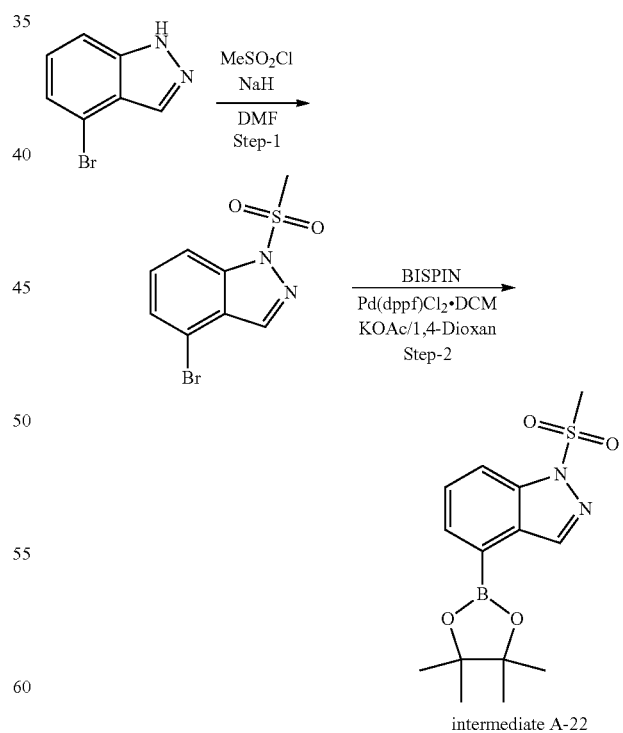

intermediate A-22

Step 1:

To a stirring solution of 4-bromo-1H-indazole (1.0 g, 5.07 mmol, 1 eq) in DMF (25 ml) was portion wise added sodium hydride (60%, 0.406 g, 10.152 mmol, 2 eq) at 0° C. The reaction mixture was stirred for 30 min at RT. Methanesulfonylchloride (0.59 mL, 7.6 mmol, 1.5 eq) was added to the reaction mixture at 0° C. The reaction mixture was stirred for 2 h at RT. Reaction mixture was diluted with EtOAc (150 mL). Combined organic layers were washed with water (5×30 mL), brine (30 mL), dried over anhydrous $Na_2SO_4$ and the solvent was evaporated under reduced pressure. Crude product was purified by column chromatography (230-400 mesh silica gel 10% EtOAc/hexane; $R_f$-value-0.5) to afford 4-bromo-1-(methylsulfonyl)-1H-indazole (0.95 g, 69%) as light yellow solid.

Step 2:

To a stirring suspension of 4-bromo-1-(methylsulfonyl)-1H-indazole (0.95, 3.45 mmol, 1 eq), bis(pinacolato)diborane (1.75 g, 6.91 mmol, 2 eq) and potassium acetate (1.01 g, 10.36 mmol, 3 eq) in 1,4-dioxane (35 mL) was deoxygenated by Ar for 10 min. Pd(dppf)$Cl_2$.DCM (0.141 g, 0.1727 mmol. 0.05 eq) was added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 10% EtOAc/hexane; $R_f$-value-0.45) to afford 1-(methylsulfonyl)-4-(4,4,5,5-tetramethyl-1,3,2-dioxaborolan-2-yl)-1H-indazole (0.9 g, 85.4%) as off white solid.

Synthesis of 6-fluoro-1-(methylsulfonyl)-4-(4,4,5,5-tetramethyl-1,3,2-dioxaborolan-2-yl)-1H-indazole (Intermediate A-23)

0° C. The reaction mixture was then stirred for 30 min at RT. Methanesulfonylchloride (0.65 ml, 8.37 mmol, 1.5 eq) was added to the reaction mixture at 0° C. The reaction mixture was stirred for 2 h at RT. Reaction mixture was diluted with EtOAc (150 mL). Combined organic layers were washed with water (5×30 mL), brine (30 mL), dried over anhydrous $Na_2SO_4$ and evaporated under reduced pressure. Crude product was purified by column chromatography (230-400 mesh silica gel 10% EtOAc/hexane; $R_f$-value-0.5) to afford 4-bromo-6-fluoro-1-(methylsulfonyl)-1H-indazole (1.3 g, 80%) as light yellow solid.

Step 2:

To a stirring suspension of 4-bromo-6-fluoro-1-(methylsulfonyl)-1H-indazole (1.3, 4.43 mmol, 1 eq), bis(pinacolato)diborane (2.25 g, 8.87 mmol, 2 eq) and potassium acetate (1.3 g, 13.3 mmol, 3 eq) in 1,4-dioxane (45 mL) was deoxygenated by Ar for 10 min. Pd(dppf)$Cl_2$.DCM (0.18 g, 0.22 mmol. 0.05 eq) and was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 10% EtOAc/hexane; $R_f$-value-0.45) to afford 6-fluoro-1-(methylsulfonyl)-4-(4,4,5,5-tetramethyl-1,3,2-dioxaborolan-2-yl)-1H-indazole (1.1 g, 73%) as off white solid.

Synthesis of 6-fluoro-1-(2-methoxyethyl)-4-(4,4,5,5-tetramethyl-1,3,2-dioxaborolan-2-yl)-1H-indole (Intermediate A-24)

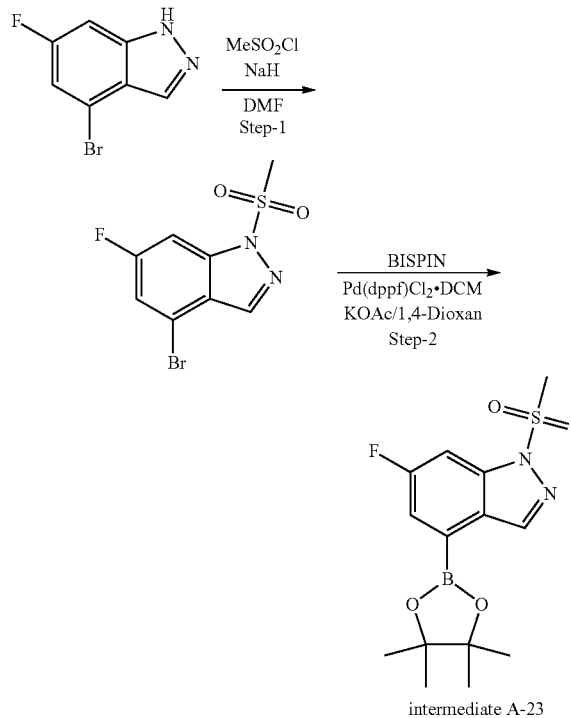

intermediate A-23

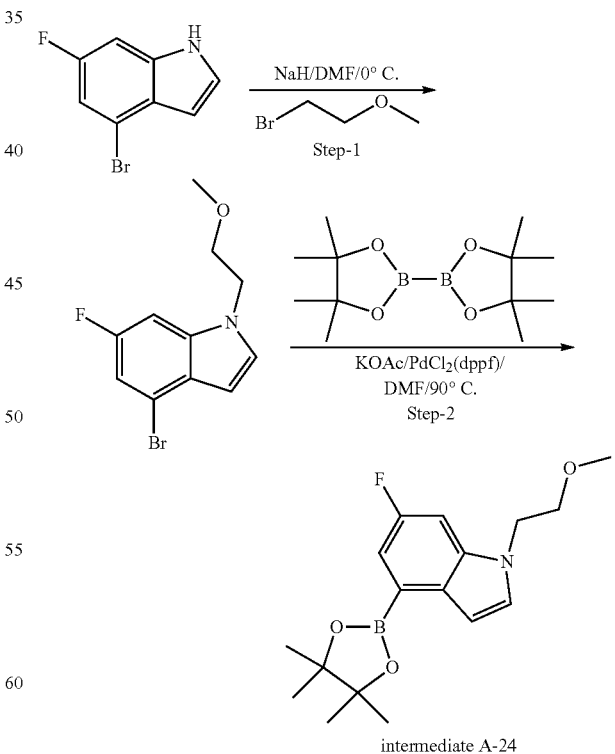

intermediate A-24

Step 1:

To a stirring solution of 4-bromo-6-fluoro-1H-indazole (1.2 g, 5.58 mmol, 1 eq) in DMF (30 mL) was portion wise added sodium hydride (60%, 0.446 g, 11.16 mmol, 2 eq) at Step 1:

To a stirring solution of 4-bromo-6-fluoro-1H-indole (0.5 g, 2.34 mmol, 1 eq) in DMF (5 mL) was portion wise added sodium hydride (0.112 g, 2.8 mmol, 1.2 eq.) at 0° C. The reaction mixture was then stirred for 30 min at RT. 1-Bromo-2-methoxyethane (0.812 mL, 5.84 mmol, 2.5 eq) was then added to the reaction mixture at 0° C. The reaction mixture was stirred for 2 h at RT. Reaction mixture was diluted with EtOAc (50 mL). Combined organic layers were washed with water (5×10 mL), brine (10 mL), dried over anhydrous Na$_2$SO$_4$ and the solvent was evaporated under reduced pressure. Crude product was purified by column chromatography (230-400 mesh silica gel 20% EtOAc/hexane; R$_f$-value-0.6) to afford 4-bromo-6-fluoro-1-(2-methoxyethyl)-1H-indole (0.63 g, 99%) as brown gum.

Step 2:

To a stirring suspension of 4-bromo-6-fluoro-1-(2-methoxyethyl)-1H-indole (0.8 g, 2.94 mmol, 1 eq), bis-pinacolatodiborane (1.2 g, 4.4 mmol, 1.5 eq.) and potassium acetate (0.865 g, 8.823 mmol, 3 eq.) in 1,4-dioxan (20 mL) was deoxygenated by Ar for 10 min. PdCl$_2$(dppf).DCM (0.239 g, 0.29 mmol. 0.01 eq.) q) was then added and the reaction mixture was stirred for 14 h at 90° C. The reaction mixture was cooled to RT and then filtered through celite bed. Filtrate was concentrated under reduced pressure to get the crude product which was purified by column chromatography (230-400 mesh silica gel 5% EtOAc/hexane; R$_f$-value-0.6) to afford 6-fluoro-1-(2-methoxyethyl)-4-(4,4,5,5-tetramethyl-1,3,2-dioxaborolan-2-yl)-1H-indole (0.93 g, 99%) as light brown gummy solid.

Synthesis of 1-(2,2-difluoroethyl)-6-fluoro-4-(4,4,5,5-tetramethyl-1,3,2-dioxaborolan-2-yl)-1H-indole (Intermediate A-25)

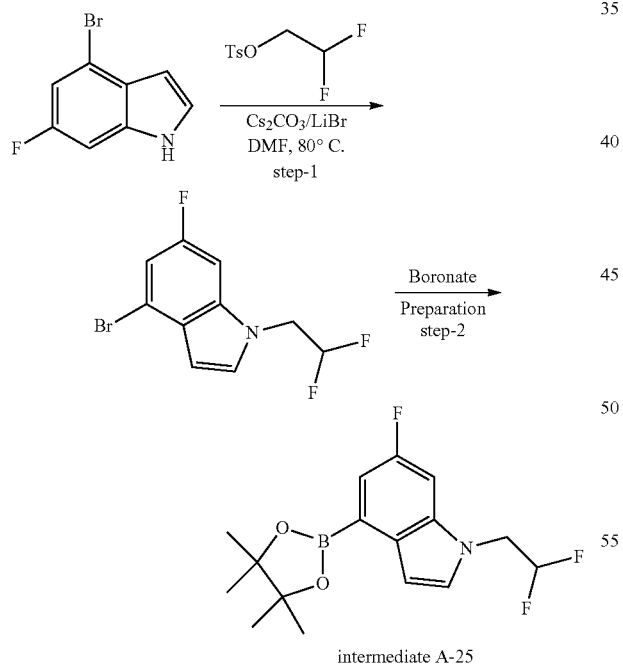

intermediate A-25

Step 1:

To a stirred solution of 4-bromo-6-fluoro-1H-indole (0.1 g, 0.469 mmol, 1 eq) in DMF (25 ml) was added Cs$_2$CO$_3$ (0.457 g, 1.407 mmol, 3 eq) followed by LiBr (86.84 g, 0.469 mmol, 1 eq) and the mixture was stirred at RT for 10 minutes. Then 2,2-difluoroethyl 4-methylbenzenesulfonate (0.133 g, 0.563 mmol, 1.2 eq) was added to the reaction mixture and heated at 80° C. for 3 h (TLC). Reaction mixture was then diluted with water (10 mL) and EtOAc (15 mL). The organic layer was washed with cold water (3×10 mL) brine (10 mL), dried over anhydrous Na$_2$SO$_4$ and concentrated under reduced pressure to get crude product which was purified by column chromatography (100-200 mesh silica gel; TLC system: EtOAc/Hexane (3:7); R$_f$-value-0.5) to afford 4-bromo-1-(2,2-difluoroethyl)-6-fluoro-1H-indole (0.75 g, 58%).

Step 2:

A suspension of 4-bromo-1-(2,2-difluoroethyl)-6-fluoro-1H-indole (0.2 g, 0.722 mmol, 1 eq), bis(pinacolato)diboron (0.275 g, 1.083 mmol, 1.5 eq) and potassium acetate (0.212 g, 2.166 mmol, 3 eq) in 1,4-dioxane (10 mL) was deoxygenated well by Ar for 10 min. 1,1'-Bis(diphenylphospino)ferrocene palladium(II)dichloride DCM complex (0.03 g, 0.0361 mmol, 0.05 eq) was then added to the reaction mixture and the reaction mixture heated at 100° C. for 16 h (LCMS). The reaction mixture was then cooled to RT, filtered through celite pad and the filtrate was concentrated under reduced pressure to get the crude 1-(2,2-difluoroethyl)-6-fluoro-4-(4,4,5,5-tetramethyl-1,3,2-dioxaborolan-2-yl)-1H-indole which was used in the next step without further purification (Yield ~49% in LCMS).

Synthesis of 1-cyclopropyl-6-fluoro-4-(4,4,5,5-tetramethyl-1,3,2-dioxaborolan-2-yl)-1H-indole (Intermediate A-27)

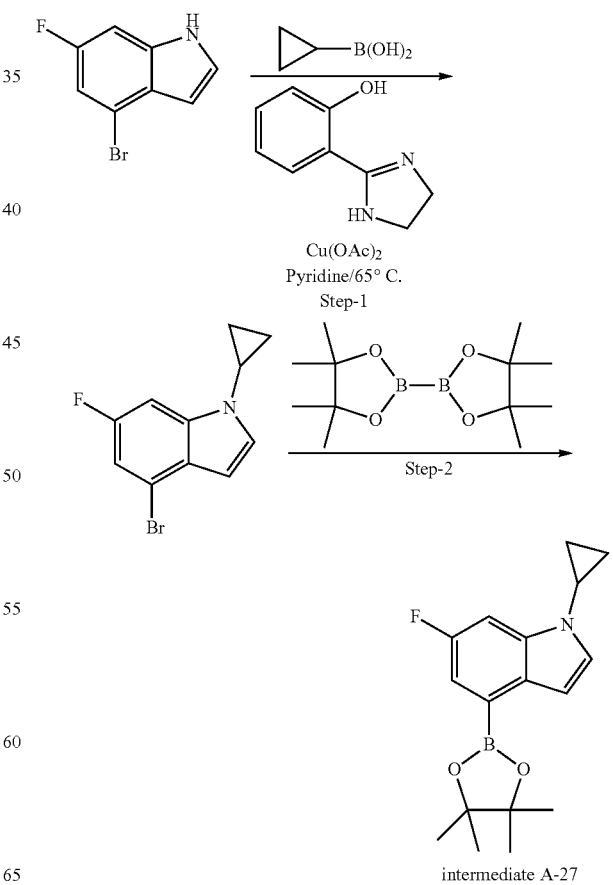

intermediate A-27

Step 1:
To a stirring solution of 4-bromo-6-fluoro-1H-indole (5.4 g, 25.23 mmol, 1 eq) in toluene (45 mL) were added cyclopropylboronic acid (4.33 g, 50.46 mmol, 2 eq), Cu(OAc)$_2$ (0.46 g, 2.52 mmol, 0.1 eq), 2-(4,5-dihydro-1H-imidazol-2-yl)phenol (0.41 g, 2.52 mmol, 0.1 eq) and pyridine (6.0 g, 75.7 mmol, 3 eq). The reaction mixture was stirred for 24 h at 65° C. Solvent was removed under reduced pressure and azitrope by MeOH twice. The residue was purified by column chromatography (230-400 mesh silica gel; 10% EtOAc/hexane; R$_f$-value-0.6) to afford 4-bromo-1-cyclopropyl-6-fluoro-1H-indole (0.85 g, 13%) as brown liquid.

Step 2:
To a stirring suspension of 4-bromo-1-cyclopropyl-6-fluoro-1H-indole (0.85 g, 3.35 mmol, 1 eq), bis(pinacolato) diborane (1.7 g, 6.7 mmol, 2 eq) and potassium acetate (1.31 g, 13.38 mmol, 4 eq) in 1,4-dioxan (20 mL) was deoxygenated by Ar for 10 min. Pd$_2$(dba)$_3$ (0.046 g, 0.05 mmol. 0.015 eq) and ommtricyclohexylphosphine (0.067 g, 0.24 mmol, 0.072 eq) was then added to the reaction mixture and again deoxygenated by Ar for 10 min. The reaction mixture was stirred for 14 h at 110° C. The reaction mixture was cooled to RT and then filtered through celite bed. Filtrate was concentrated under reduced pressure to get the crude material which was purified by column chromatography (230-400 mesh silica gel, 20% EtOAc/hexane; R$_f$-value-0.6) to afford 1-cyclopropyl-6-fluoro-4-(4,4,5,5-tetramethyl-1,3,2-dioxaborolan-2-yl)-1H-indole (0.61 g, 61%) as light yellow solid. 1H-NMR (400 MHz; DMSO-D$_6$, 20° C.): δ 7.45 (dd, 1H), 7.35 (d, 1H), 7.15 (dd, 1H), 6.67 (d, 1H), 3.41 (m, 1H), 1.32 (12H), 1.03-1.08 (2H), 0.82-0.92 (2H).

Synthesis of 5-fluoro-7-(4,4,5,5-tetramethyl-1,3,2-dioxaborolan-2-yl)-1H-indole (Intermediate A-71)

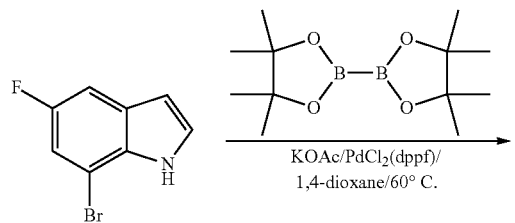

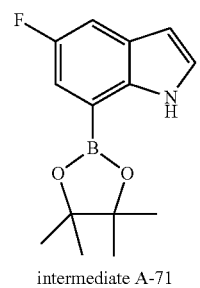

intermediate A-71

A mixture of 7-bromo-5-fluoro-1H-indole (1 g, 4.7 mmol, 1 eq), bis(pinacolato)diborane (2.02 g, 7.9 mmol, 1.7 eq), potassium acetate (917 mg, 9.4 mmol, 2 eq), 1,1'-Bis(diphenylphospino)ferrocene palladium(II)dichloride dichloromethane complex (382 mg, 0.467 mmol, 0.1 eq) in 1,4-dioxane (13 mL) was degassed with nitrogen, and the reaction mixture was stirred at 60° C. After completion of the reaction (monitored by LCMS), a sat. sodiumbicarbonate solution was added to the reaction mixture, which was then extracted with EtOAc (2×). The combined organic layers were washed with brine, dried over anhydrous MgSO$_4$ and evaporated under reduced pressure. The crude product was purified by column chromatography (silica gel; EtOAc/cyclo-Hexane as eluent) to afford 5-fluoro-7-(4,4,5,5-tetramethyl-1,3,2-dioxaborolan-2-yl)-1H-indole (940 mg, 77%).

The intermediates in Table 1 were synthesized in analogy to Intermediate A-1 to Intermediate A-27.

| Intermediate | Synthesized in analogy to | Structure |
|---|---|---|
| Int-A-30 | Int-A-2 | 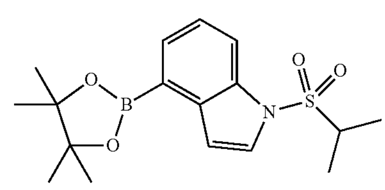 [SMILES: CC(C)S(=O)(=O)n1ccc2c(B3OC(C)(C)C(C)(C)O3)cccc21] |
| Int-A-42 | Int-A-11 | 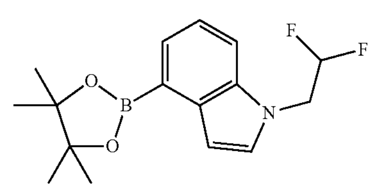 [SMILES: CC1(C)OB(c2cccc3c2ccn3CC(F)F)OC1(C)C] |

-continued
| Intermediate | Synthesized in analogy to | Structure |
|---|---|---|
| Int-A-43 | Int-A-11 | 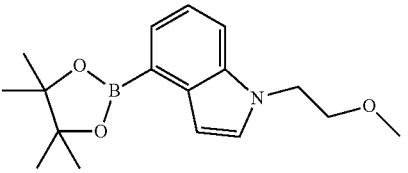 |
| Int-A-44 | Int-A-27 | 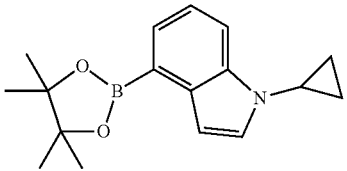 [SMILES: CC1(C)OB(c2cccc3c2ccn3C2CC2)OC1(C)C] |
| Int-A-45 | Int-A-2 | 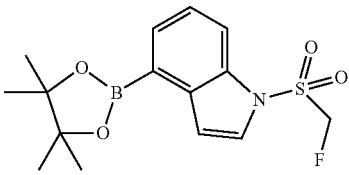 |
| Int-A-46 | Int-A-11 | 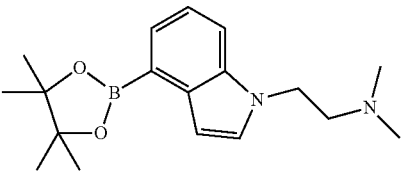 |
| Int-A-47 | Int-A-2 | 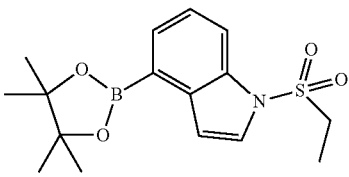 [SMILES: CCS(=O)(=O)n1ccc2c(B3OC(C)(C)C(C)(C)O3)cccc21] |
| Int-A-48 | Int-A-2 | 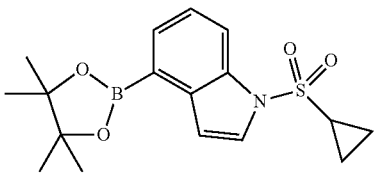 [SMILES: CC1(C)OB(c2cccc3c2ccn3S(=O)(=O)C2CC2)OC1(C)C] |
| Int-A-54 | Int-A-22 | 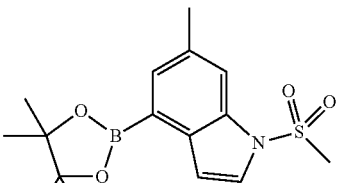 |
| Int-A-63 | Int-A-22 | 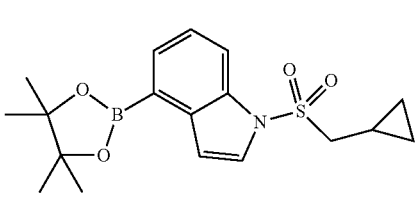 [SMILES: CC1(C)OB(c2cccc3c2ccn3S(=O)(=O)CC2CC2)OC1(C)C] |

-continued

| Intermediate | Synthesized in analogy to | Structure |
|---|---|---|
| Int-A-59 | Int-A-21 | 4-(4,4,5,5-tetramethyl-1,3,2-dioxaborolan-2-yl)-1-methyl-1H-indole |
| Int-A-66 | Int-A-22 | 6-(trifluoromethyl)-1-(methylsulfonyl)-4-(4,4,5,5-tetramethyl-1,3,2-dioxaborolan-2-yl)-1H-indole |
| Int-A-68 | Int-A-22 | 6-fluoro-1-(cyclopropylmethylsulfonyl)-4-(4,4,5,5-tetramethyl-1,3,2-dioxaborolan-2-yl)-1H-indole |
| Int-A-72 | Int-A-22 | 7-methyl-1-(methylsulfonyl)-4-(4,4,5,5-tetramethyl-1,3,2-dioxaborolan-2-yl)-1H-indole |
| Int-A-73 | Int-A-21 | 6-fluoro-1-methyl-4-(4,4,5,5-tetramethyl-1,3,2-dioxaborolan-2-yl)-1H-indole |
| Int-A-75 | Int-A-71 | 4-(4,4,5,5-tetramethyl-1,3,2-dioxaborolan-2-yl)-1H-indole-7-carbonitrile |
| Int-A-76 | Int-A-22 | 7-chloro-1-(methylsulfonyl)-4-(4,4,5,5-tetramethyl-1,3,2-dioxaborolan-2-yl)-1H-indole |

-continued

| Intermediate | Synthesized in analogy to | Structure |
|---|---|---|
| Int-A-77 | Int-A-22 | (6-methoxy-1-(methylsulfonyl)-1H-indol-4-yl) pinacol boronate structure |

The Intermediates in Table 2 are commercially available:

| Name | Structure |
|---|---|
| 4-(tetramethyl-1,3,2-dioxaborolan-2-yl)-6-(trifluoromethyl)-1H-indole | 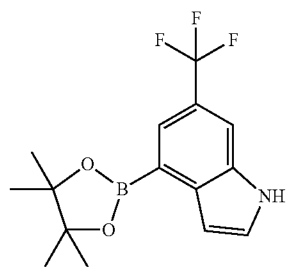 [SMILES: CC1(C)OB(c2cc(C(F)(F)F)cc3[nH]ccc23)OC1(C)C] |
| 5-fluoro-1H-indole-4-boronic acid pinacol ester | 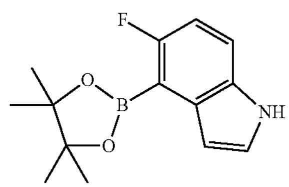 [SMILES: CC1(C)OB(c2c(F)ccc3[nH]ccc23)OC1(C)C] |
| 2-methyl-4-(4,4,5,5-tetramethyl-1,3,2-dioxaborolan-2-yl)-2H-indazole | 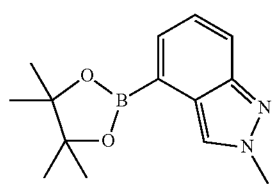 |
| 1-methyl-4-(4,4,5,5-tetramethyl-[1,3,2]dioxaborolan-2-yl)-1H-indazole | 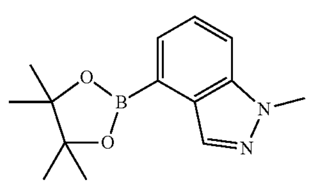 |
| 4-(tetramethyl-1,3,2-dioxaborolan-2-yl)-2-(trifluoromethyl)-1H-indole | 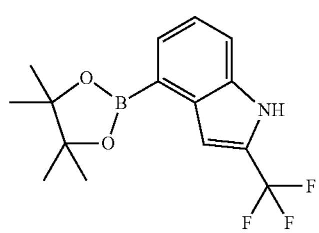 [SMILES: CC1(C)OB(c2cccc3[nH]c(C(F)(F)F)cc23)OC1(C)C] |

-continued

| Name | Structure |
|---|---|
| 4-(4,4,5,5-tetramethyl-1,3,2-dioxaborolan-2-yl)-1H-indazole | 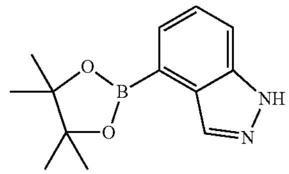 [SMILES: CC1(C)OB(c2cccc3[nH]ncc23)OC1(C)C] |
| tert-butyl 4-(4,4,5,5-tetramethyl-1,3,2-dioxaborolan-2-yl)-1H-indazole-1-carboxylate | 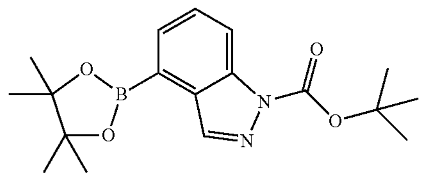 [SMILES: CC(C)(C)OC(=O)n1ncc2c(B3OC(C)(C)C(C)(C)O3)cccc21] |
| indole-4-boronic acid | 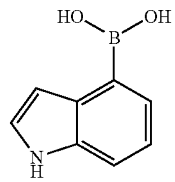 [SMILES: OB(O)c1cccc2[nH]ccc12] |
| 1,1-dimethylethyl 4-(4,4,5,5-tetramethyl-1,3,2-dioxaborolan-2-yl)-1H-indole-1-carboxylate | 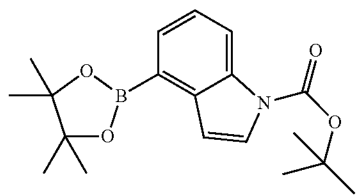 [SMILES: CC(C)(C)OC(=O)n1ccc2c(B3OC(C)(C)C(C)(C)O3)cccc21] |
| 3-methyl-7-(4,4,5,5-tetramethyl-1,3,2-dioxaborolan-2-yl)-1H-indole | 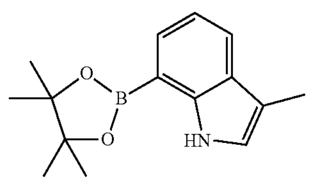 |
| (7-chloro-1H-indazol-4-yl)boronic acid | 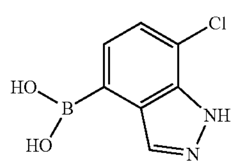 |
| 7-fluoro-4-(4,4,5,5-tetramethyl-1,3,2-dioxaborolan-2-yl)-1H-indazole | 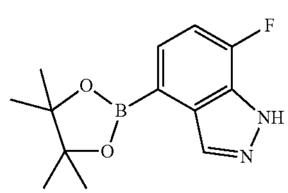 [SMILES: CC1(C)OB(c2ccc(F)c3[nH]ncc23)OC1(C)C] |
| 7-methoxy-4-(4,4,5,5-tetramethyl-1,3,2-dioxaborolan-2-yl)-1H-indazole | 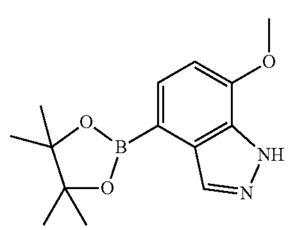 |

-continued

| Name | Structure |
|---|---|
| 4-(4,4,5,5-tetramethyl-1,3,2-dioxaborolan-2-yl)-7-(trifluoromethyl)-1H-indazole | 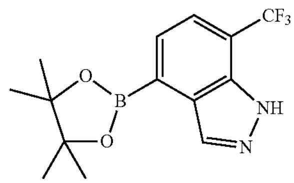 [SMILES: CC1(C)OB(c2ccc(C(F)(F)F)c3[nH]ncc23)OC1(C)C] |
| (6-(trifluoromethyl)-1H-indazol-4-yl)boronic acid | 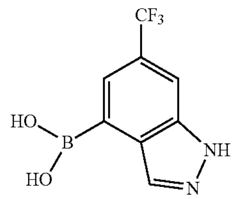 |
| (6-fluoro-1H-indazol-4-yl)boronic acid | 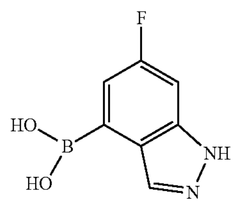 [SMILES: OB(O)c1cc(F)cc2[nH]ncc12] |
| 7-chloro-6-fluoro-4-(4,4,5,5-tetramethyl-1,3,2-dioxaborolan-2-yl)-1H-indazole | 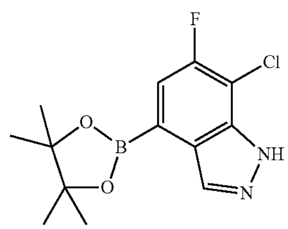 [SMILES: CC1(C)OB(c2cc(F)c(Cl)c3[nH]ncc23)OC1(C)C] |
| 7-fluoro-4-(4,4,5,5-tetramethyl-[1,3,2]dioxaborolan-2-yl)-1H-indole | 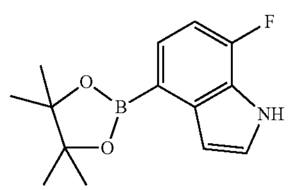 [SMILES: CC1(C)OB(c2ccc(F)c3[nH]ccc23)OC1(C)C] |
| 7-methyl-4-(4,4,5,5-tetramethyl-[1,3,2]dioxaborolan-2-yl)-1H-indole | 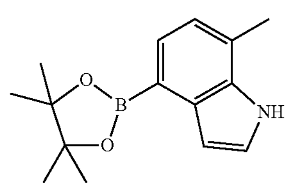 |
| 6-methoxy-4-(4,4,5,5-tetramethyl-[1,3,2]dioxaborolan-2-yl)-1H-indole | 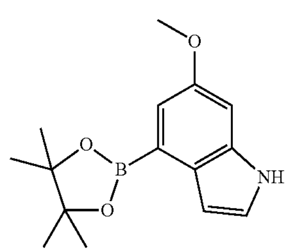 [SMILES: COc1cc(B2OC(C)(C)C(C)(C)O2)c2cc[nH]c2c1] |

-continued

| Name | Structure |
|------|-----------|
| (1H-indol-7-yl)boronic acid | 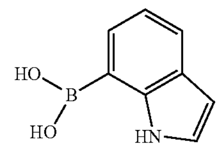 [SMILES: OB(O)c1cccc2cc[nH]c12] |
| 3-Methyl-1H-indazole-7-boronic acid | 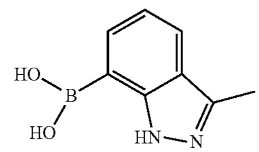 |
| 4-(4,4,5,5-Tetramethyl-1,3,2-dioxaborolan-2-yl)-1H-indole-6-carbonitrile | 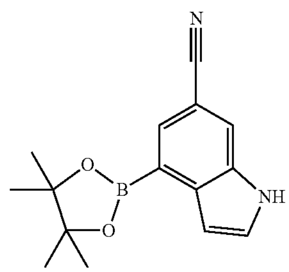 [SMILES: CC1(C)OB(c2cc(C#N)cc3[nH]ccc23)OC1(C)C] |
| 7-fluoro-4-(4,4,5,5-tetramethyl-1,3,2-dioxaborolan-2-yl)-1H-indazole | 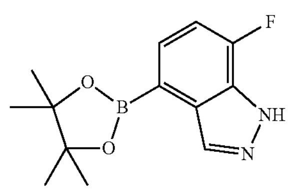 [SMILES: CC1(C)OB(c2ccc(F)c3[nH]ncc23)OC1(C)C] |
| 7-fluoro-4-(tetramethyl-1,3,2-dioxaborolan-2-yl)-1H-indole | 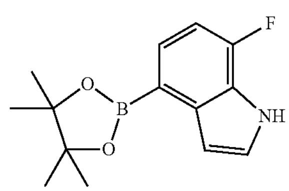 [SMILES: CC1(C)OB(c2ccc(F)c3[nH]ccc23)OC1(C)C] |
| 6-fluoro-4-(4,4,5,5-tetramethyl-1,3,2-dioxaborolan-2-yl)-1H-indazole | 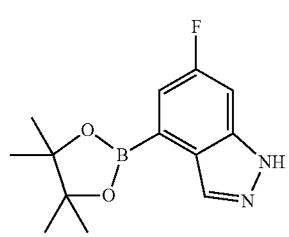 [SMILES: CC1(C)OB(c2cc(F)cc3[nH]ncc23)OC1(C)C] |
| 6-chloro-4-(4,4,5,5-tetramethyl-1,3,2-dioxaborolan-2-yl)-1H-indole | 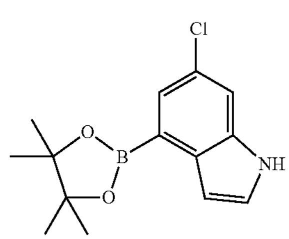 [SMILES: CC1(C)OB(c2cc(Cl)cc3[nH]ccc23)OC1(C)C] |

-continued
| Name | Structure |
|---|---|
| 7-chloro-4-(4,4,5,5-tetramethyl-1,3,2-dioxaborolan-2-yl)-1H-indole | 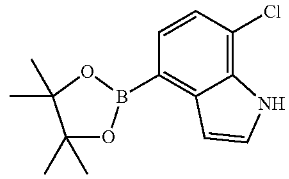 [SMILES: CC1(C)OB(c2ccc(Cl)c3[nH]ccc23)OC1(C)C] |
| 7-fluoro-4-(4,4,5,5-tetramethyl-1,3,2-dioxaborolan-2-yl)-1H-indole | 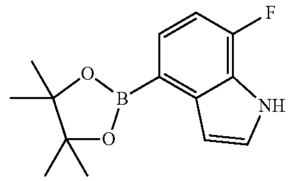 [SMILES: CC1(C)OB(c2ccc(F)c3[nH]ccc23)OC1(C)C] |
| 6-fluoro-4-(4,4,5,5-tetramethyl-1,3,2-dioxaborolan-2-yl)-1H-indazole | 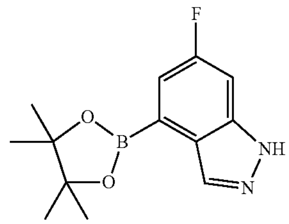 [SMILES: CC1(C)OB(c2cc(F)cc3[nH]ncc23)OC1(C)C] |
| 6-chloro-4-(4,4,5,5-tetramethyl-1,3,2-dioxaborolan-2-yl)-1H-indole | 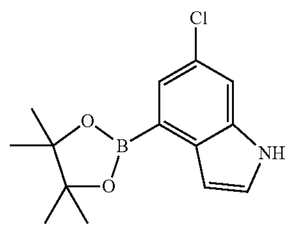 [SMILES: CC1(C)OB(c2cc(Cl)cc3[nH]ccc23)OC1(C)C] |
| 4-(4,4,5,5-tetramethyl-1,3,2-dioxaborolan-2-yl)-6-(trifluoromethyl)-1H-indazole | 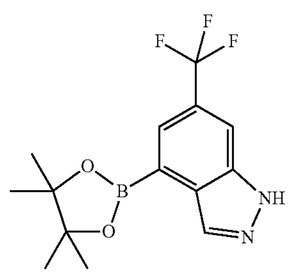 [SMILES: CC1(C)OB(c2cc(C(F)(F)F)cc3[nH]ncc23)OC1(C)C] |
Synthesis of 8-bromo-6-fluoro-1,4,4,9-tetramethyl-4,5-dihydro-[1,2,4]triazolo[4,3-a]quinoxaline (Intermediate B-7)
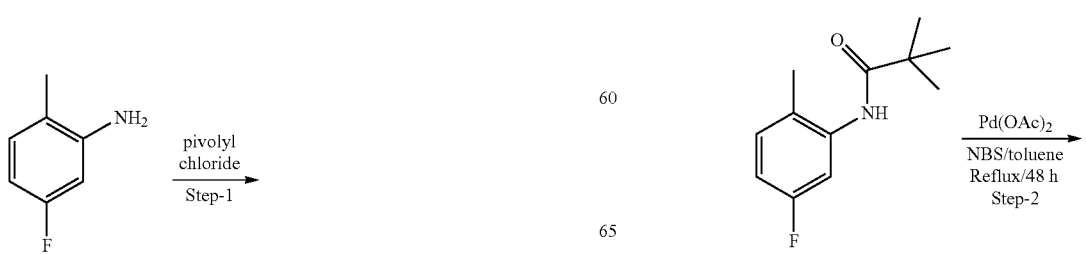

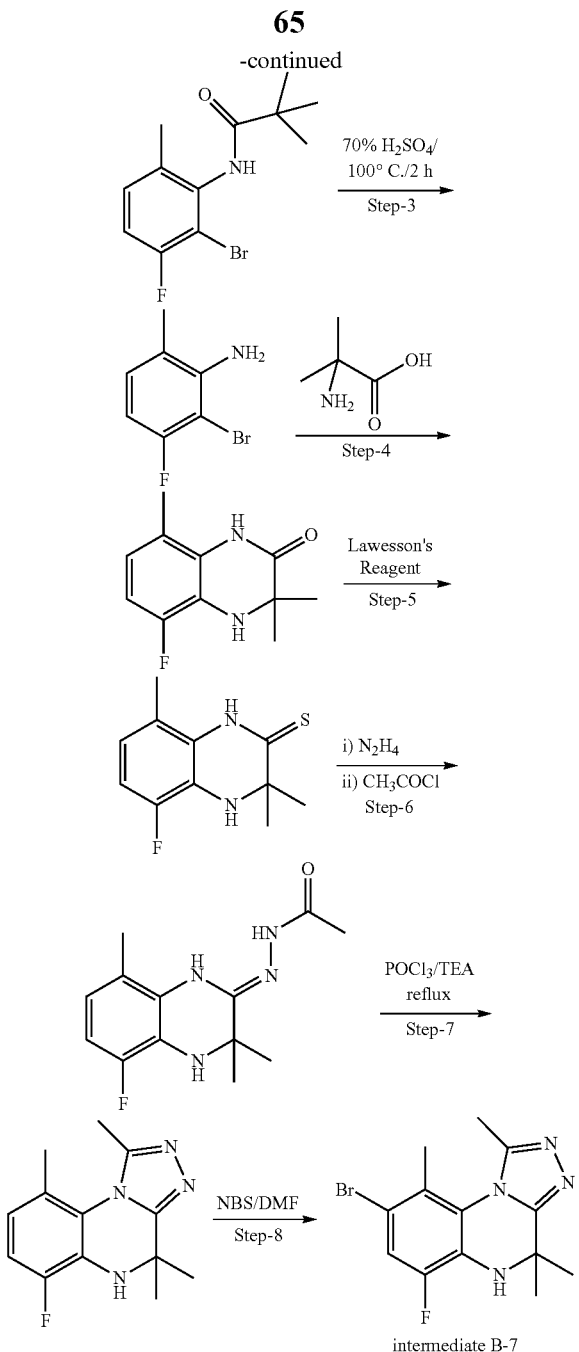

intermediate B-7

Step 1: To a stirred solution of 5-fluoro-2-methyl-phenylamine (100 g, 0.8 mol) in DCM (1500 mL) was added pyridine (129 mL, 1.6 mol) followed by DMAP (1 g, 0.008 mol) at RT. To this reaction mixture was added drop wise pivolyl chloride (109 mL, 0.88 mol) at 0° C. Resulting reaction mixture was stirred at 0° C. for 2 h. After completion of starting material reaction mixture was poured into ice cooled 1(N) HCl solution (1500 mL) and stirred for 30 min. The two layers were separated and the organic layer was washed with 1(N) HCl solution (1000 mL) followed by saturated NaHCO$_3$ solution (1000 mL) followed by brine (1000 mL) and then dried over anhydrous Na$_2$SO$_4$ and concentrated under reduced pressure to afford crude product. Crude product was triturated using hexane to afford N-(5-fluoro-2-methyl-phenyl)-2,2-dimethyl-propionamide (158 g, 95%) as white solid.

Step 2:
To a stirring solution N-(5-fluoro-2-methyl-phenyl)-2,2-dimethyl-propionamide (90 g, 0.43 mol) in toluene (2000 mL) was added para-toluene sulphonic acid monohydrate (82.0 g, 0.43 mol), Pd(OAC)$_2$ (9.66 g, 0.043 mol) followed by N-bromo succinimide (84.5 g, 0.473 mol) at RT. Resulting reaction mixture was stirred at RT for 48 h. Reaction monitoring TLC in 20% EA-Hex, showed formation of desired product (Rf=0.4) along with the ~60% un-reacted SM (Rf=0.5). Reaction mixture was then concentrated, obtained residue was diluted with EtOAc and washed with water (twice). Total organic layer was dried over anhydrous Na$_2$SO$_4$ and concentrated to afford crude product. Two combined batches of crude product (obtained from 90 g and 100 g reaction of N-(5-fluoro-2-methyl-phenyl)-2,2-dimethyl-propionamide) were purified by flash chromatography to afford N-(2-bromo-3-fluoro-6-methyl-phenyl)-2,2-dimethyl-propionamide (60 g, 23%) as white solid and recovered un-reacted N-(5-fluoro-2-methyl-phenyl)-2,2-dimethyl-propionamide (125 g).

Step 3:
To a pre cooled solution of 70% H$_2$SO$_4$ in water (430 mL) was added N-(2-bromo-3-fluoro-6-methyl-phenyl)-2,2-dimethyl-propionamide (60 g, 0.208 mol) portion wise at 0° C. Resulting reaction mixture was stirred at RT for 10 min and then heated to 100° C. for 2 h. After completion of starting material (monitored by TLC in 10% EA-Hex, Rf=0.8) reaction mixture was cooled to 0° C. and pH adjusted to ~10 with 10% NaOH solution. Resulting basic aqueous was extracted with EtOAc (3×500 mL). Total organic layers were washed with water followed by brine, dried over anhydrous Na$_2$SO$_4$ and concentrated to afford crude product. Crude product was purified by column chromatography to afford 2-bromo-3-fluoro-6-methyl-phenylamine (36 g, 85%) as pale yellow liquid.

Step 4:
To the stirred suspension of 2-bromo-3-fluoro-6-methyl-phenylamine (36 g, 0.1764 mol) in dry DMSO (540 mL) was added 2-amino-2-methyl-propionic acid (16.9 g, 0.164 mol) followed by K$_3$PO$_4$ (75 g, 0.353 mol) at RT. Resulting reaction mixture was degassed with nitrogen for 30 min, then CuCl (1.75 g, 0.0176 mol) was added and reaction mixture was heated at 140° C. for 5 h. After completion of the starting material (monitored by TLC, 20% EA-Hexane, Rf 0.4) reaction mixture was cooled to RT and filtered through celite. Celite bed was washed with EtOAc (500 mL). Resulting filtrate was poured into ice cold water (2500 mL). Resulting aqueous layer was extracted with EtOAc (2×750 mL). Total organic part was washed with water (2×750 mL), followed by brine (500 mL), dried over anhydrous Na$_2$SO$_4$ and evaporated under reduced pressure to afford crude product. Obtained crude product was triturated with hexane and filtered and dried to afford 5-fluoro-3,3,8-trimethyl-3,4-dihydro-1H-quinoxalin-2-one (19 g, 52%) as brown solid.

Step 5:
To a solution of 5-fluoro-3,3,8-trimethyl-3,4-dihydro-1H-quinoxalin-2-one (19 g, 91.2 mmol) in toluene (380 mL) was added Lawesson's reagent (55.5 g, 137 mmol) at RT and the reaction mixture was refluxed at 120° C. for 1 h. After completion of starting material (monitored by TLC in 20% EA-Hexane, Rf 0.7), the reaction mass was cooled to RT and quenched with sat. NaHCO$_3$ solution (250 mL) and resulting aqueous layer was extracted with EtOAc (3×250 mL). Combined organic layers were washed with water (250 mL), followed by brine (250 mL), dried over anhydrous Na$_2$SO$_4$ and the solvent was evaporated to afford crude product.

Obtained crude product was purified by column chromatography to afford 5-fluoro-3,3,8-trimethyl-3,4-dihydro-1H-quinoxaline-2-thione (19 g, 93%) as yellow solid.

Step 6:

To a stirred solution of 5-fluoro-3,3,8-trimethyl-3,4-dihydro-1H-quinoxaline-2-thione (20.5 g, 91.5 mmol) in THF (512 mL) was added drop wise hydrazine hydrate (13.5 mL, 274.5 mmol) at 0° C. The reaction mixture was stirred at RT for 16 h. TEA (64 mL, 457.5 mmol) followed acetyl chloride (21.5 mL, 274.5 mmol) were added to the reaction mixture drop-wise at 0° C. and stirred for 2 h at RT. After completion of starting material (monitored by LCMS) reaction mixture diluted with water (500 mL) and extracted by 10% MeOH-DCM (5×500 mL). The total organic part was washed by brine (250 mL), dried over Na$_2$SO$_4$ and concentrated under reduced pressure to afford acetic acid (5-fluoro-3,3,8-trimethyl-3,4-dihydro-1H-quinoxalin-2-ylidene)-hydrazide (21 g, 87%, crude) as pale yellow solid.

Step 7:

Acetic acid (5-fluoro-3,3,8-trimethyl-3,4-dihydro-1H-quinoxalin-2-ylidene)-hydrazide (10.5 g, 0.04 mol) was taken in round bottom flax (100 mL) and then cooled to −10° C. Then phosphorus oxalylchloride (18.5 ml, 0.2 mol) was added drop wise followed by drop wise addition of TEA (5.6 ml, 0.04 mol). After that the reaction mixture was stirred at −10° C. for 10 min and then 10 min at RT and finally at reflux condition for 1 h. After completion of starting material (monitored by LCMS) reaction mixture cooled to 0° C. and quenched with crushed ice water (100 mL). The aqueous part was then basified using cold aqueous ammonia solution (100 mL) drop-wise. Resulting basic aqueous was then extracted with EtOAc (3×150 mL). Total organic part was washed with brine (150 mL), dried over anhydrous Na$_2$SO$_4$ and concentrated under reduced pressure to afford crude compound. Crude product co-distillation with MTBE twice, then trituration with hexane and dried to afford 6-fluoro-1,4,4,9-tetramethyl-4,5-dihydro-[1,2,4]triazolo[4,3-a]quinoxaline (6 g, 61%) as pale yellow solid.

Step 8:

To a solution of 6-fluoro-1,4,4,9-tetramethyl-4,5-dihydro-[1,2,4]triazolo[4,3-a]quinoxaline (12 g, 0.048 mol) in DMF (360 mL) was added NBS (9.39 g, 0.0528 mol) portion wise at −10° C. Resulting reaction mixture was stirred at RT for 4 h. After completion of starting material (monitored by LCMS), reaction mixture was diluted with water (500 mL) and extracted with EtOAc (2×500 mL). Combined organic layers were washed with water (750 mL) followed by brine (400 mL), dried over anhydrous Na$_2$SO$_4$ and concentrated to afford crude compound. Obtained crude product was purified by column chromatography followed by trituration using MTBE to afford 8-bromo-6-fluoro-1,4,4,9-tetramethyl-4,5-dihydro-[1,2,4]triazolo[4,3-a]quinoxaline (9.1 g, 57%) as off white solid.

Synthesis of 8-bromo-9-ethyl-6-fluoro-1,4,4-trimethyl-4,5-dihydro-[1,2,4]triazolo[4,3-a]quinoxaline (Intermediate B-9)

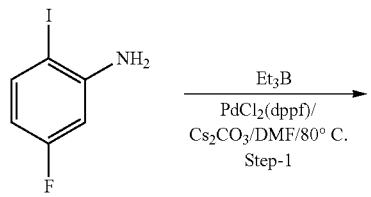

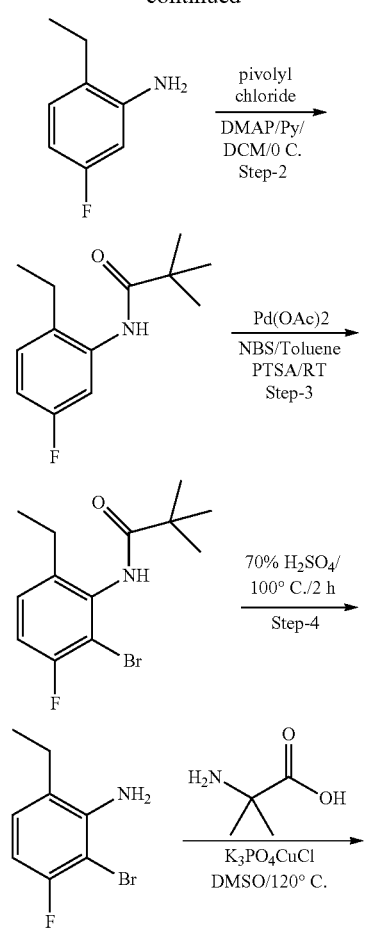

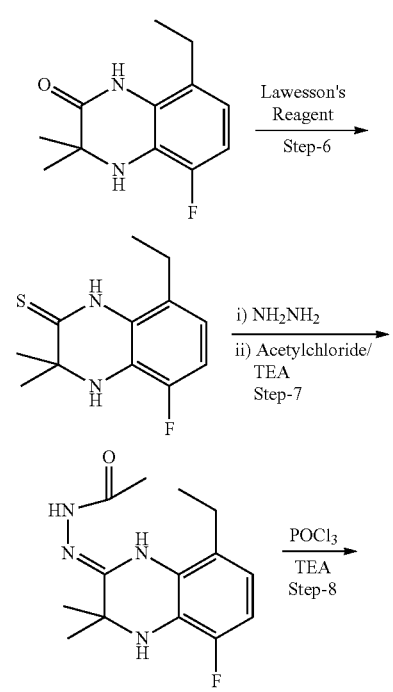

-continued

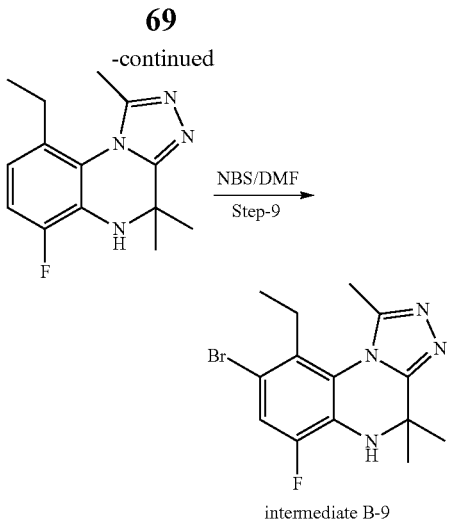

intermediate B-9

Step 1:
A stirring suspension of Pd(dppf)Cl$_2$.DCM (1.03 g, 1.27 mmol, 0.1 eq) and Cs$_2$CO3 (16.5 g, 50.63 mmol, 4 eq) in DMF (78 mL) was deoxygenated by Ar for 5 min. 5-Fluoro-2-iodoaniline (3.0 g, 12.65 mmol, 1 eq) and triethylborane (1M) (16.45 mL, 16.45 mmol, 1.5 eq) was added to the reaction mixture and again deoxygenated by Ar for 10 min. Finally the reaction mixture was stirred for 16 h at 70° C. The reaction mixture was cooled to RT and then diluted with EtOAc (100 mL). The organic layer was washed with water (5×20 mL) and brine (20 mL), dried over Na$_2$SO$_4$, concentrated under reduced pressure to get the crude product. Crude product was purified by column chromatography (230-400 mesh silica gel; 10% EtOAc/hexane; R$_f$-value-0.5) to afford 2-ethyl-5-fluoroaniline (1.20 g, 68%) as off white solid.

Step 2:
To a stirring solution of 2-ethyl-5-fluoroaniline (2.0 g, 14.38 mmol 1 eq), pyridine (2.31 mL, 28.77 mmol, 2 eq), and DMAP (0.018 g, 0.144 mmol, 0.01 eq) in DCM (50 mL) was drop wise added pivolyl chloride (1.91 g, 15.82 mmol, 1.1 eq) at 0° C. The reaction mixture was then stirred for another 1 h at 0° C. and then poured into ice cooled HCl (20 ml) (1M) solution. The organic layer was separated and the aqueous layer was extracted with Et$_2$O (2×20 mL). The combined organic layer was washed with water (2×20 mL) and brine (20 mL). The organic layer was dried over anhydrous Na$_2$SO$_4$, concentrated under reduced pressure to get the crude material. Crude product was purified by column chromatography (230-400 mesh silica gel; 10% EtOAc/hexane; R$_f$-value-0.5) to afford N-(2-ethyl-5-fluorophenyl)pivalamide (2.3 g, 72%) as off white solid.

Step 3:
To a stirring solution of N-(2-ethyl-5-fluorophenyl)pivalamide (25.0 g, 112.1 mmol, 1 eq), in toluene (500 mL) was added p-TSA (19.3 g, 112.1 mmol, 1 eq), Pd(OAc)$_2$ (2.52 g, 11.21 mmol, 0.1 eq) and NBS (21.5 g, 123.3 mmol, 1.1 eq) respectively at RT. The reaction mixture was stirred for 48 h at RT under air. Solvent was evaporated and the residue was dissolved in EtOAc (1000 mL) and washed with water (2×200 mL) followed by brine (200 mL). The organic layer was dried over anhydrous Na$_2$SO$_4$, concentrated under reduced pressure to get the crude material. Crude product was purified by column chromatography (230-400 mesh silica gel; 10% EtOAc/hexane; R$_f$-value-0.45) to afford N-(2-bromo-6-ethyl-3-fluorophenyl)pivalamide (5.0 g, 15%) as off white solid.

Step 4:
70% H$_2$SO$_4$ (70 mL) was added to N-(2-bromo-6-ethyl-3-fluorophenyl)pivalamide (9.2 g, 30.46 mmol, 1 eq) in a round bottom flask at 0° C. The reaction mixture was stirred for 20 min at 0° C. and for 2 h 110° C. The reaction mixture then cooled to 0° C. and basified by 20%-NaOH solution up to pH~14. The aqueous part was extracted with EtOAc (3×150 mL). The combined organic layers were washed with water (2×100 mL) and brine (100 mL). The organic layer was dried over anhydrous Na$_2$SO$_4$, concentrated under reduced pressure to get the crude material. Crude product was purified by column chromatography (230-400 mesh silica gel; 5% EtOAc/hexane; R$_f$-value-0.5) to afford 2-bromo-6-ethyl-3-fluoroaniline (5.9 g, 89%) as brown liquid.

Step 5:
A suspension of 2-bromo-6-ethyl-3-fluoroaniline (4.9 g, 22.47 mmol, 1 eq), 2-amino-2-methylpropanoic acid (4.63 g, 44.94 mmol, 2 eq), K$_3$PO$_4$ (9.54 g, 44.94 mmol, 2 eq) and cuprous chloride (0.22 g, 2.247 mmol, 0.1 eq) in dry DMSO (75 mL) in a sealed tube was deoxygenated with Ar for 20 min. Reaction mixture was then stirred at 140° C. for 2 h. After completion of the reaction, the reaction mixture cooled to RT and filtered through celite bed and washed with EtOAC (100 mL). The filtrate was diluted with EtOAc (500 mL) and washed with water (3×150 mL), brine (200 mL), dried over anhydrous Na$_2$SO$_4$ and the solvent was evaporated under reduced pressure. Crude product was purified by column chromatography (230-400 mesh silica gel; 20% EtOAc/hexane; R$_f$-value-0.4) to afford 8-ethyl-5-fluoro-3,3-dimethyl-3,4-dihydroquinoxalin-2(1H)-one (2.83 g, 57%) light brown solid.

Step 6:
To a solution of 8-ethyl-5-fluoro-3,3-dimethyl-3,4-dihydroquinoxalin-2(1H)-one (3.4 g, 15.3 mmol, 1 eq.) in toluene (110 mL) was added Lawesson's reagent (8.03 g, 19.89 mmol, 1.3 eq.) at RT and the reaction mixture was refluxed at 120° C. for 40 min. After completion of reaction (monitored by TLC), the reaction mixture was quenched with sat. NaHCO$_3$ solution (80 mL) followed by extraction with etOAc (2×70 mL). Combined organic layers were washed with water (80 mL), brine (80 mL), dried over anhydrous Na$_2$SO$_4$ and the solvent was evaporated to get the crude product which was purified by column chromatography (230-400 mesh silica gel; 20% EtOAc/hexane; R$_f$-value-0.6) to afford 8-ethyl-5-fluoro-3,3-dimethyl-3,4-dihydroquinoxaline-2(1H)-thione (3.0 g, 82%) as yellow solid.

Step 7:
To a stirring solution of 8-ethyl-5-fluoro-3,3-dimethyl-3,4-dihydroquinoxaline-2(1H)-thione (3.0 g, 12.58 mmol, 1 eq) in THF (50 mL) was drop wise added hydrazine hydrate (3.03 mL, 62.93 mmol, 5 eq) at 0° C. The reaction mixture was stirred for 16 h at RT. TEA (8.56 mL, 62.93 mmol, 5 eq) was added to the reaction mixture and stirred for another 10 min Acetyl chloride (2.7 ml, 37.74 mmol, 3 eq) was added to the reaction mixture very slowly at 0° C. and then stirred for 2 h at RT. The reaction mixture was diluted with water (100 mL) and extracted with DCM (3×100 mL). The combined organic layer was washed with brine (100 mL). The organic layer was dried over Na$_2$SO$_4$, concentrated under reduced pressure to get the crude material which purified by washing with diethyl ether to afford the N'-(8-ethyl-5-fluoro-3,3-dimethyl-3,4-dihydroquinoxalin-2(1H)-ylidene)acetohydrazide (3.4 g, 97%) as off white solid.

Step 8:
N'-(8-ethyl-5-fluoro-3,3-dimethyl-3,4-dihydroquinoxalin-2(1H)-ylidene)acetohydrazide (3.4 g, 12.23 mmol, 1 eq)

was taken in round bottom flax (100 mL) and cooled to −10° C. Phosphorus oxychloride (11.7 mL, 122.3 mmol, 10 eq) was then added drop wise to the compound followed by drop wise addition of TEA (1.66 mL, 12.23 mmol, 1 eq). The reaction mixture was stirred at −10° C. for 10 min and then for 10 min at RT and finally heated to reflux for 2 h. The reaction mixture was cooled to 0° C. and then drop wise added into crushed ice with constant stirring. To this aqueous part was slowly added cold ammonium solution up to pH~12. The aqueous part was extracted with DCM (3×100 mL). The combined organic layer was washed with brine (100 mL). The organic layer was dried over anhydrous Na$_2$SO$_4$, concentrated under reduced pressure to get the crude material. Crude product was purified by column chromatography (230-400 mesh silica gel; 5% MeOH/DCM; R$_f$-value-0.4) to afford 9-ethyl-6-fluoro-1,4,4-trimethyl-4,5-dihydro-[1,2,4]triazolo[4,3-a]quinoxaline (1.4 g, 44%) as light yellow solid.

Step 9:

A stirred solution of 9-ethyl-6-fluoro-1,4,4-trimethyl-4,5-dihydro-[1,2,4]triazolo[4,3-a]quinoxaline (1.4 g, 5.38 mmol, 1 eq) in DMF (30 mL) at −10° C. was treated portion wise over 10 min with solid N-bromosuccinimide (1.01 g, 5.65 mmol, 1.05 eq). Reaction mixture was allowed to warm to RT and stirred for 1.5 h. After completion of reaction (monitored by LCMS), reaction mixture was diluted with EtOAc (300 mL) and organic layers was washed with water (5×50 mL), brine (50 mL), dried over anhydrous Na$_2$SO$_4$ and evaporated under reduced pressure. Crude product was purified by silica gel (230-400) column chromatography (5% MeOH/DCM; R$_f$-value-0.4) to afford 8-bromo-9-ethyl-6-fluoro-1,4,4-trimethyl-4,5-dihydro-[1,2,4]triazolo[4,3-a]quinoxaline (1.45 g, 80%) as off white solid. 1H-NMR (400 MHz; DMSO-D$_6$, 20° C.): δ 7.54-7.56 (1H), 6.69 (s, 1H), 2.82-2.85 (2H), 2.38 (s, 3H), 1.46 (bs, 3H), 0.94-0.97 (3H)

Synthesis of 8-bromo-6-fluoro-9-methoxy-1,4,4-trimethyl-4,5-dihydro-[1,2,4]triazolo[4,3-a]quinoxaline (Intermediate B-10)

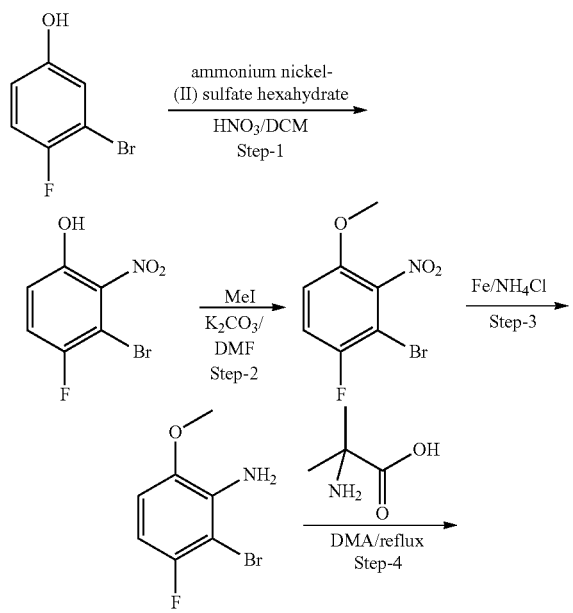

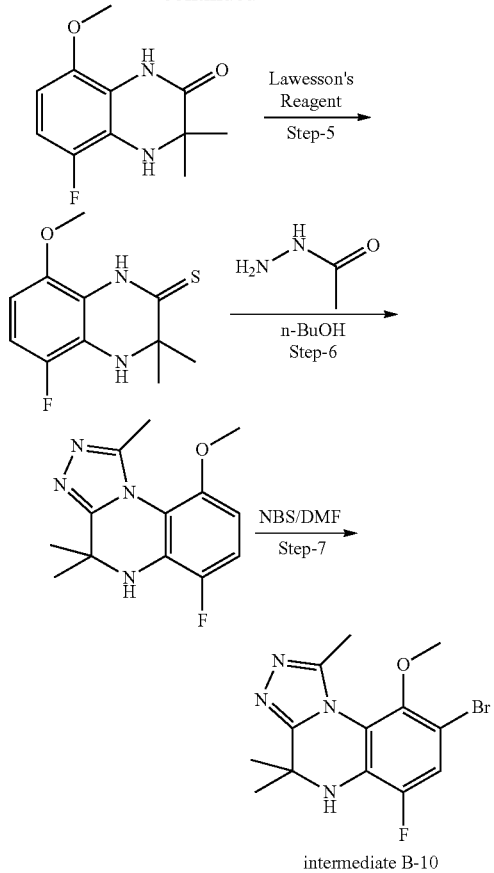

intermediate B-10

Step 1:

To an ice cold solution of 3-bromo-4-fluorophenol (100 g, 523.56 mmol, 1 eq) and ammonium nickel(II) sulfate hexahydrate (103.4 g, 261.77 mmol, 0.5 eq) in DCM (1000 mL) fuming nitric acid was added drop wise and the reaction mixture was stirred at same temperature for 3 h (TLC). Reaction mixture was poured into crushed ice and diluted with DCM. The extracted organic layer was washed with brine; the organic layer was dried over Na$_2$SO$_4$ and concentrated. The crude product was purified by column chromatography (230-400 mesh silica gel, TLC system: EtOAc/hexane (2:8); R$_f$=0.2) to give 3-bromo-4-fluoro-2-nitrophenol (35 g, 28%).

Step 2:

To a stirred solution of 3-bromo-4-fluoro-2-nitrophenol (35 g, 148.30 mmol, 1 eq) in ACN (40 mL) potassium carbonate (61.48 g, 444.91 mmol, 3 eq) and iodo methane (63.15 g, 444.91 mmol, 3 eq) were added and the reaction mixture was heated at 80° C. for 4 h. After completion (monitored by TLC) the reaction mixture was diluted with EtOAc and washed with water. The extracted organic layer was washed with brine, dried over anhydrous Na$_2$SO$_4$ and concentrated under reduced pressure. The crude product was purified by column chromatography (230-400 mesh silica gel, TLC system: EtOAc/hexane (2:8); R$_f$=0.6) to give 2-bromo-1-fluoro-4-methoxy-3-nitrobenzene (35 g, 94%).

Step 3:

To a stirred solution of 2-bromo-1-fluoro-4-methoxy-3-nitrobenzene (35 g, 140 mmol, 1 eq) in EtOH and water (300 mL, 1:1), iron powder (78.17 g, 1400 mmol, 10 eq) and ammonium chloride (74.886 g, 1400 mmol, 10 eq) were added. The reaction mixture was heated to reflux for 12 h. After completion (monitored by TLC) the reaction mixture was filtered through a pad of celite. The filtrate was concentrated under reduced pressure to get crude product. The crude product was purified by column chromatography (230-400 mesh silica gel, TLC system: EtOAc/hexane (2:8); $R_f$=0.6) to give 2-bromo-3-fluoro-6-methoxyaniline (30 g, 97%).

Step 4:

A suspension of 2-bromo-3-fluoro-6-methoxyaniline (30 g, 136.36 mmol, 1 eq), 2-aminoisobutaric acid (44.65 g, 340.83 mmol, 2.5 eq), DBU (49.70 g, 272.21 mmol, 2 eq) and copper iodide (2.59 g, 13.59 mmol, 0.1 eq.) in dry DMA (300 mL) in a round bottom flask was deoxygenated with Ar for 20 min. Reaction mixture was then stirred at 120° C. for 16 h. After completion of the reaction, (monitored by TLC), it was filtered through a pad of celite and washed with EtOAc (500 mL), washed with water (3×500 mL), brine (500 mL), dried over anhydrous $Na_2SO_4$ and evaporated under reduced pressure to get the crude product which was purified by column chromatography (230-400 mesh silica gel; TLC system: EtOAc/hexane (2:8); $R_f$=0.3) to give 5-fluoro-8-methoxy-3,3-dimethyl-3,4-dihydroquinoxalin-2 (1H)-one (14 g, 46%) as brown solid.

Step 5:

To a solution of 5-fluoro-8-methoxy-3,3-dimethyl-3,4-dihydroquinoxalin-2(1H)-one (14 g, 62.22 mmol, 1 eq) in toluene (150 mL) was added Lawesson's reagent (37.75 g, 93.33 mmol, 1.5 eq) at RT and the reaction mixture was refluxed at 120° C. for 1 h. After completion of reaction (monitored by TLC), the reaction mixture was quenched with sat. $NaHCO_3$ solution (200 mL) followed by extraction with EtOAc (2×200 mL). Combined organic layers were washed with water (300 mL), brine (100 mL), dried over anhydrous $Na_2SO_4$ and the solvent was evaporated to get the crude product which was purified by column chromatography using 230-400 mesh silica gel and 10% EtOAc in hexane as an eluting solvent to afford 5-fluoro-8-methoxy-3,3-dimethyl-3,4-dihydroquinoxaline-2(1H)-thione (10 g, 67%) as a yellow solid. TLC system: EtOAc/hexane (2:8); $R_f$=0.4).

Step 6:

To a solution of 5-fluoro-8-methoxy-3,3-dimethyl-3,4-dihydroquinoxaline-2(1H)-thione (10 g, 41.61 mmol, 1 eq) in n-BuOH (100 mL) was added acetic hydrazide (10.80 g, 145.93 mmol, 3.5 eq) followed by addition of acetic acid (10 mL) and then the reaction mixture was stirred at 140° C. for 16 h. After completion of reaction (monitored by TLC) reaction mixture was diluted with water (100 mL) and extracted with EtOAc (2×50 mL). Combined organic layers were washed with water (100 mL), brine (100 mL), dried over anhydrous $Na_2SO_4$ and evaporated to get the crude product which was purified by column chromatography using 5% MeOH in DCM as an eluting solvent and 230-400 silica gel to afford 6-fluoro-9-methoxy-1,4,4-trimethyl-4,5-dihydro-[1,2,4]triazolo[4,3-a]quinoxaline (3.5 g, 32%) as off white solid (TLC system, 5% MeOH in DCM, Rf-0.2).

Step 7:

A stirred solution of 6-fluoro-9-methoxy-1,4,4-trimethyl-4,5-dihydro-[1,2,4]triazolo[4,3-a]quinoxaline (3.5 g, 13.34 mmol, 1 eq) in DMF (30 mL) at 0° C. was treated portion wise over 10 min with solid N-bromosuccinamide (2.48 g, 13.93 mmol, 1.05 eq). Reaction mixture was allowed to warm to RT and stirred for 30 min. After completion of reaction (monitored by LCMS), reaction mixture was diluted with EtOAc (50 mL) and organic layers were washed with water (3×100 mL), brine (100 mL), dried over anhydrous $Na_2SO_4$ and the solvent was evaporated under reduced pressure. Crude product was purified by column chromatography using 1.5% MeOH in DCM as an eluting solvent and 230-400 silica gel to afford 8-bromo-6-fluoro-9-methoxy-1,4,4-trimethyl-4,5-dihydro-[1,2,4]triazolo[4,3-a]quinoxaline (1.9 g, 42%) as off white solid (TLC system, 5% MeOH in DCM, Rf-0.4). 1H-NMR (400 MHz; DMSO-$D_6$, 20° C.): δ 7.58 (d, 1H), 6.73 (s, 1H), 3.56 (s, 3H), 2.44 (s, 3H), 1.49 (s, 3H), 1.46 (s, 3H).

Synthesis of 8-bromo-1-cyclopropyl-6-fluoro-9-methoxy-4,4-dimethyl-4,5-dihydro-[1,2,4]triazolo[4,3-a]quinoxaline (Intermediate B-11)

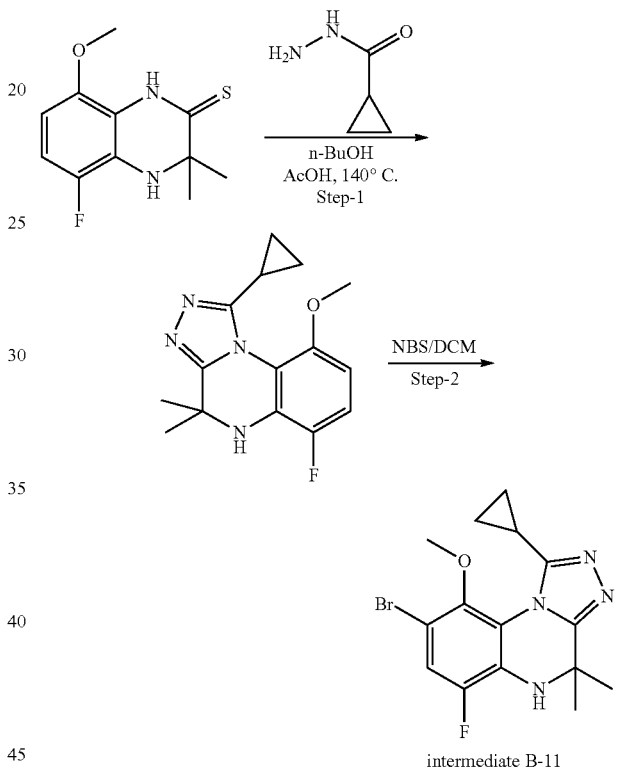

intermediate B-11

Step 1:

To a solution of 5-fluoro-8-methoxy-3,3-dimethyl-3,4-dihydroquinoxaline-2(1H)-thione (10 g, 41.61 mmol, 1 eq) inn-BuOH (100 mL) was added cyclopropanecarbohydrazide (14.58 g, 145.62 mmol, 3.5 eq) followed by addition of acetic acid (10 mL) and then the reaction mixture was stirred at 140° C. for 16 h. After completion of reaction (monitored by TLC) reaction mixture was diluted with water (100 mL) and extracted with EtOAc (2×50 mL). Combined organic layers washed with water (100 mL), brine (100 mL), dried over anhydrous $Na_2SO_4$ and the solvent was evaporated to get the crude product which was purified by column chromatography using 5% MeOH in DCM as an eluting solvent and 230-400 silica gel to afford 1-cyclopropyl-6-fluoro-9-methoxy-4,4-dimethyl-4,5-dihydro-[1,2,4]triazolo[4,3-a]quinoxaline (2.6 g, 32%) as off white solid.

Step 2:

A stirred solution of 1-cyclopropyl-6-fluoro-9-methoxy-4,4-dimethyl-4,5-dihydro-[1,2,4]triazolo[4,3-a]quinoxaline (2.6 g, 9.02 mmol, 1 eq) in DMF (30 mL) at 0° C. was treated portion wise over 10 min with solid N-bromosuccinamide (1.68 g, 9.43 mmol, 1.05 eq). Reaction mixture was allowed to warm up to RT and stirred for 30 min. After completion of reaction (monitored by LCMS), reaction mixture was diluted with EtOAc (50 mL) and organic layers were washed with water (3×100 mL), brine (100 mL), dried over anhydrous $Na_2SO_4$ and the solvent was evaporated under reduced pressure. Crude product was purified by column chromatography using 1.5% MeOH in DCM as an eluting solvent and 230-400 silica gel to afford 8-bromo-1-cyclopropyl-6-fluoro-9-methoxy-4,4-dimethyl-4,5-dihydro-[1,2,4]triazolo[4,3-a]quinoxaline (1.8 g, 55%) as off white solid.

Synthesis of 8-bromo-1-cyclopropyl-6-fluoro-4,4,9-trimethyl-4,5-dihydro-[1,2,4]triazolo[4,3-a]quinoxaline (Intermediate B-12)

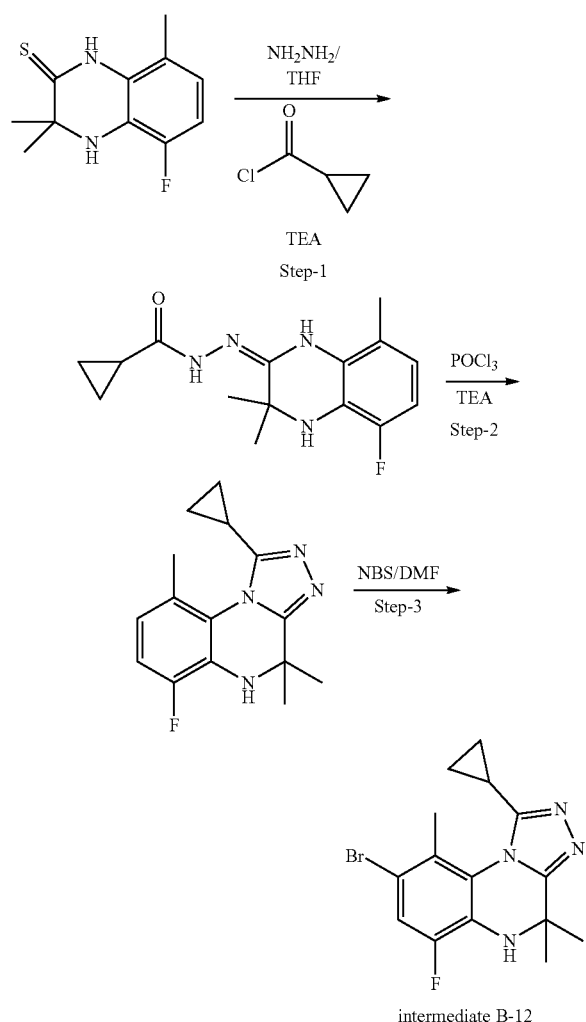

intermediate B-12

Step 1:
To a stirring solution of 5-fluoro-3,3,8-trimethyl-3,4-dihydroquinoxaline-2(1H)-thione (1.7 g, 7.58 mmol, 1 eq) in THF (40 mL) was drop wise added hydrazine hydrate (1.72 mL, 37.94 mmol, 5 eq) at 0° C. The reaction mixture was stirred for 16 h at RT. TEA (5.13 mL, 37.94 mmol, 5 eq) was added to the reaction mixture and stirred for another 10 min. Cyclopropanecarbonyl chloride (2.39 g, 22.76 mmol, 3 eq) was added to the reaction mixture very slowly at 0° C. and then stirred for 2 h at RT. The reaction mixture was diluted with water (100 mL) and extracted with DCM (3×100 mL). The combined organic layers were with brine (100 mL). The organic layer was dried over $Na_2SO_4$, concentrated under reduced pressure to get the crude product which was purified by washing with diethyl ether to afford N'-(5-fluoro-3,3,8-trimethyl-3,4-dihydroquinoxalin-2(1H)-ylidene)cyclopropanecarbohydrazide (2.1 g, 95%) as off white solid.

Step 2:
N'-(5-fluoro-3,3,8-trimethyl-3,4-dihydroquinoxalin-2(1H)-ylidene)cyclopropanecarbohydrazide (1.44 g, 4.96 mmol, 1 eq) was taken in a round bottom flax (50 mL) and then cooled to −10° C. Phosphorus oxychloride (4.7 mL, 49.65 mmol, 10 eq) was then added drop wise to the compound followed by drop wise addition of TEA (10.67 mL, 4.96 mmol, 1 eq). After that the reaction mixture was stirred at −10° C. for 10 min and then 10 min at RT and finally at reflux condition for 2 h. The reaction mixture was cooled to 0° C. and then it was drop wise added into crushed ice with constant stirring. To this aqueous part was slowly added cold ammonium solution up to pH~12. The aqueous part was extracted with DCM (3×50 mL). The combined organic layer were washed with brine (50 mL). The organic layer was dried over anhydrous $Na_2SO_4$, concentrated under reduced pressure to get the crude product. Crude product was purified by column chromatography (230-400 mesh silica gel; 5% MeOH/DCM; $R_f$-value-0.4) to afford 1-cyclopropyl-6-fluoro-4,4,9-trimethyl-4,5-dihydro-[1,2,4]triazolo[4,3-a]quinoxaline (0.24 g, 18%) as light yellow solid.

Step 3:
A stirred solution of 1-cyclopropyl-6-fluoro-4,4,9-trimethyl-4,5-dihydro-[1,2,4]triazolo[4,3-a]quinoxaline (0.55 g, 2.02 mmol, 1 eq) in DMF (15 mL) at −10° C. was treated portion wise over 10 min with solid N-bromosuccinimide (0.36 g, 2.02 mmol, 1 eq). Reaction mixture was allowed to warm to RT and stirred for 1.5 h. After completion of reaction (monitored by LCMS), reaction mixture was diluted with EtOAc (80 mL) and organic layers were washed with water (5×20 mL), brine (20 mL), dried over anhydrous $Na_2SO_4$ and solvent was evaporated under reduced pressure. Crude product was purified by silica gel (230-400) column chromatography (5% MeOH/DCM; $R_f$-value-0.4) to afford 8-bromo-1-cyclopropyl-6-fluoro-4,4,9-trimethyl-4,5-dihydro-[1,2,4]triazolo[4,3-a]quinoxaline (0.55 g, 78%) as off white solid. 1H-NMR (400 MHz; DMSO-$D_6$, 20° C.): δ 7.58 (d, 1H), 6.58 (s, 1H), 2.45 (s, 3H), 1.71-1.77 (1H), 1.44 (bs, 6H), 1.02-1.27 (4H).

Synthesis of 8-bromo-1-ethyl-6-fluoro-4,4,9-trimethyl-4,5-dihydro-[1,2,4]triazolo[4,3-a]quinoxaline (Intermediate B-30)

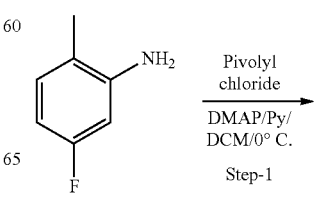

Step-1

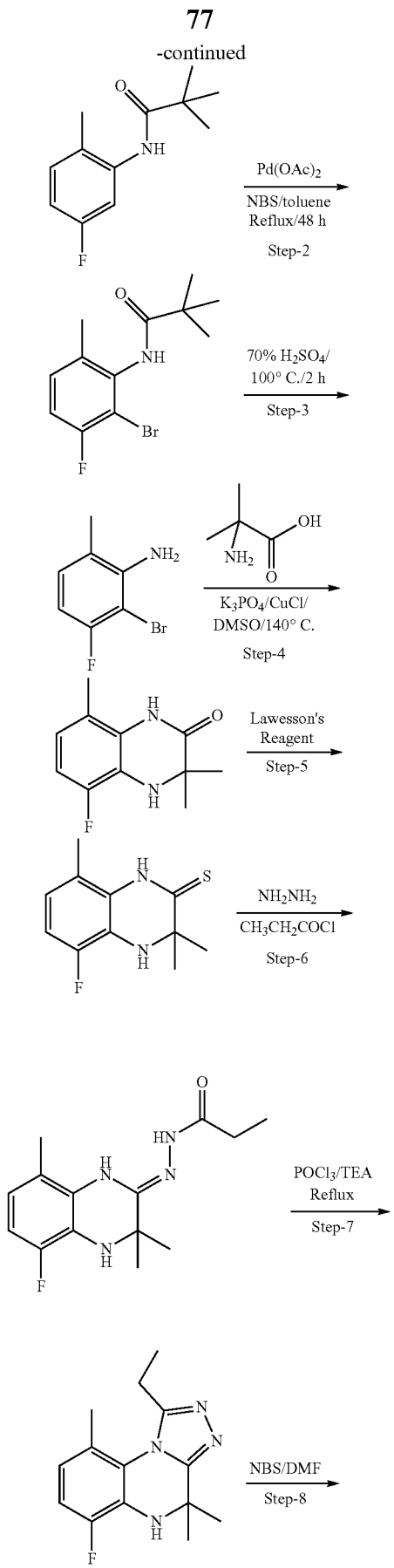

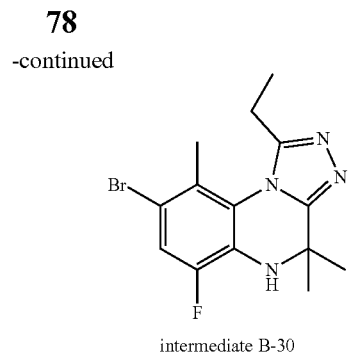

intermediate B-30

Step 1:

To a stirred solution of 5-fluoro-2-methyl-phenylamine (100 g, 0.8 mol, 1 eq) in DCM (1.5 L) was added pyridine (129 mL, 1.6 mol, 2 eq), followed by DMAP (1 g, 0.008 mol, 0.01 eq) at room temperature. To this reaction mixture was added dropwise pivolyl chloride (109 mL, 0.88 mol, 1.1 eq) at 0° C. and the resulting reaction mixture was stirred at 0° C. for 2 h. After complete consumption of starting material (monitored by TLC in 10% EtOAc-Hex, $R_f$ 0.7), the reaction mixture was poured into an ice-cooled 1N HCl solution (1.5 L) and stirred for 30 min. The two layers were separated and the organic layer was washed with an 1N HCl solution (1 L), followed by saturated $NaHCO_3$ solution (1 L) and brine (1 L), dried over anhydrous $Na_2SO_4$ and concentrated under reduced pressure. This crude residue was triturated using hexane to afford N-(5-fluoro-2-methyl-phenyl)-2,2-dimethyl-propionamide (158 g, 95%) as a white solid.

Step 2:

To a stirring solution of N-(5-fluoro-2-methyl-phenyl)-2,2-dimethyl-propionamide (90 g, 0.43 mol, 1 eq) in toluene (2 L) were added para-toluene sulfonic acid monohydrate (82.0 g, 0.43 mol, 1 eq) and $Pd(OAc)_2$ (9.66 g, 0.043 mol, 0.1 eq) followed by N-bromo succinimide (84.5 g, 0.473 mol, 1.1 eq) at room temperature and the resulting reaction mixture was stirred at room temperature for 48 h. Reaction monitoring by TLC (20% EtOAc in Hexane) showed formation of desired product (Rf 0.4) along with ~60% unreacted starting material (Rf 0.5). A second batch was then run starting from 100 g of N-(5-fluoro-2-methyl-phenyl)-2,2-dimethyl-propionamide, following the same procedure as described above The combined reaction mixtures of the two batches (190 g of starting material in total) were then concentrated and the obtained residue was diluted in EtOAc and washed with water (twice). The combined organic layers were then dried over anhydrous $Na_2SO_4$ and concentrated under reduced pressure. The crude residue was purified by column chromatography (100-200 mesh silica gel; 1-5% EtOAc/hexane as eluent) to afford N-(2-bromo-3-fluoro-6-methyl-phenyl)-2,2-dimethyl-propionamide (60 g, 22.9%) as a white solid along with recovered unreacted starting material (125 g).

Step 3:

To a pre-cooled solution of 70% $H_2SO_4$ in water (430 mL) was added N-(2-bromo-3-fluoro-6-methyl-phenyl)-2,2-dimethyl-propionamide (60 g, 0.208 mol, 1 eq) portion wise at 0° C. and the resulting reaction mixture was stirred at room temperature for 10 min and then heated at 100° C. for 2 h. After complete consumption of starting material (monitored by TLC in 10% EtOAc-Hexane, Rf 0.8), the reaction mixture was cooled to 0° C. and the pH adjusted to ~10 with 10% NaOH solution. The resulting basic aqueous fraction was extracted with EtOAc (3×500 mL), the combined organic layers were washed with water and brine subsequently, dried over anhydrous Na$_2$SO$_4$ and concentrated under reduced pressure to afford a crude residue. This was purified by column chromatography (silica 100-200 mesh; 1-3% EtOAc/hexane as eluent) to afford 2-bromo-3-fluoro-6-methyl-phenylamine (36 g, 85%) as a pale yellow liquid.

Step 4:

To a stirred suspension of 2-bromo-3-fluoro-6-methyl-phenylamine (36 g, 0.1764 mol, 1 eq) in dry DMSO (540 ml) was added 2-amino-2-methyl-propionic acid (16.9 g, 0.1636 mol, 0.93 eq), followed by K$_3$PO$_4$ (75 g, 0.3528 mol, 2 eq) at room temperature. The resulting reaction mixture was degassed with nitrogen for 30 minutes, then CuCl (1.75 g, 0.0176 mol, 0.1 eq) was added and the reaction mixture was heated at 140° C. for 5 h. After complete consumption of the starting material (monitored by TLC, 20% EtOAc-Hexane, Rf 0.4), the reaction mixture was cooled to room temperature and filtered over a bed of celite. After washing with EtOAc (500 mL), the resulting filtrate was poured into ice-cold water (2.5 L) and the resulting aqueous fraction was extracted with EtOAc (2×750 mL). The combined organic layers were washed with water (2×750 mL) and brine (500 ml), dried over anhydrous Na$_2$SO$_4$ and evaporated under reduced pressure to afford a crude residue. This was triturated with hexane, filtered and dried to afford 5-fluoro-3,3,8-trimethyl-3,4-dihydro-1H-quinoxalin-2-one (19 g, 52%) as a brown solid.

Step 5:

To a solution of 5-fluoro-3,3,8-trimethyl-3,4-dihydro-1H-quinoxalin-2-one (19, 91.2 mmol, 1 eq) in toluene (380 mL) was added Lawesson's reagent (55.5 g, 137 mmol, 1.5 eq) at RT and the reaction mixture was refluxed at 120° C. for 1 h. After complete consumption of starting material (monitored by TLC in 20% EtOAc-Hexane, Rf 0.7), the reaction mass was cooled to room temperature and quenched with sat. NaHCO$_3$ solution (250 mL) and the resulting aqueous fraction was extracted with EtOAc (3×250 mL). The combined organic layers were washed with water (250 mL) and brine (250 mL), dried over anhydrous Na$_2$SO$_4$ and evaporated under reduced pressure. The obtained crude residue was purified by column chromatography (silica 100-200 mesh; 3-5% EtOAc/hexane) to afford 5-fluoro-3,3,8-trimethyl-3,4-dihydro-1H-quinoxaline-2-thione (19 g, 93%) as a yellow solid.

Step 6:

To a stirring solution of 5-fluoro-3,3,8-trimethyl-3,4-dihydro-1H-quinoxaline-2-thione (9 g, 0.0401 mol, 1 eq) in tetrahydrofuran (225 mL) was added dropwise hydrazine hydrate (6.02 g, 0.1203 mol, 3 eq) at 0° C. and the reaction mixture was stirred at room temperature for 16 h. Triethyl amine (27.8 mL, 0.2006 mol, 5 eq) and propanyl chloride (10.5 mL, 0.1203 mol. 3 eq) were added to the reaction mixture dropwise at 0° C. and this was stirred for 2 h at room temperature. After complete consumption of starting material (monitored by LCMS), the reaction mixture was diluted with water (250 mL) and extracted with 10% MeOH-DCM (5×250 mL). The combined organic layers were washed with brine (250 mL), dried over Na$_2$SO$_4$ and concentrated under reduced pressure to afford propionic acid (5-fluoro-3,3,8-trimethyl-3,4-dihydro-1H-quinoxalin-2-ylidene)-hydrazide (12.5 g crude material) as an off-white solid.

Step 7:

Crude propionic acid (5-fluoro-3,3,8-trimethyl-3,4-dihydro-1H-quinoxalin-2-ylidene)-hydrazide (12.5 g, 0.0449 mol, 1 eq) was taken up in a round-bottom flask, that was then cooled to −10° C. Phosphorus oxalylchloride (20.9 mL, 0.2243 mol, 5 eq) was then added dropwise to the compound, followed by dropwise addition of triethyl amine (6.25 mL, 0.0449 mol, 1 eq). After that, the reaction mixture was stirred at −10° C. for 10 min followed by stirring at room temperature for 10 min and finally at reflux conditions for 4 h. After complete consumption of starting material (monitored by LCMS), the reaction mixture was cooled to 0° C. and quenched with crushed ice in water (250 mL). The aqueous part was then basified by dropwise addition of a cold ammonia solution (250 mL). The resulting basic aqueous fraction was extracted with EtOAc (3×500 mL) and the combined organic layers were washed with brine (250 mL), dried over anhydrous Na$_2$SO$_4$ and concentrated under reduced pressure. The obtained crude residue was purified by trituration using MTBE to afford 1-ethyl-6-fluoro-4,4,9-trimethyl-4,5-dihydro-[1,2,4]triazolo[4,3-a]quinoxaline (6.5 g, 56%) as an off-white solid.

Step 8:

To a solution of 1-ethyl-6-fluoro-4,4,9-trimethyl-4,5-dihydro-[1,2,4]triazolo[4,3-a]quinoxaline (10 g, 0.0384 mol, 1 eq) in DMF (250 mL) was added NBS (7.52 g, 0.0422 mol, 1.1 eq) portion wise at −10° C. and the resulting reaction mixture was stirred at room temperature for 4 h. After complete consumption of starting material (monitored by LCMS), the reaction mixture was diluted with water (500 mL) and extracted with EtOAc (2×250 mL). The combined organic layers were washed with water (500 mL) and brine (400 mL), dried over anhydrous Na$_2$SO$_4$ and concentrated under reduced pressure. The obtained crude residue was purified by column chromatography (230-400 mesh silica gel; 5% MeOH/DCM as eluent) to afford 8-bromo-1-ethyl-6-fluoro-4,4,9-trimethyl-4,5-dihydro-[1,2,4]triazolo[4,3-a]quinoxaline (7.5 g, 58%) as an off-white solid.

Synthesis of 8-bromo-6,7-difluoro-1,4,4,9-tetramethyl-4,5-dihydro-[1,2,4]triazolo[4,3-a]quinoxaline
(Intermediate B-38)

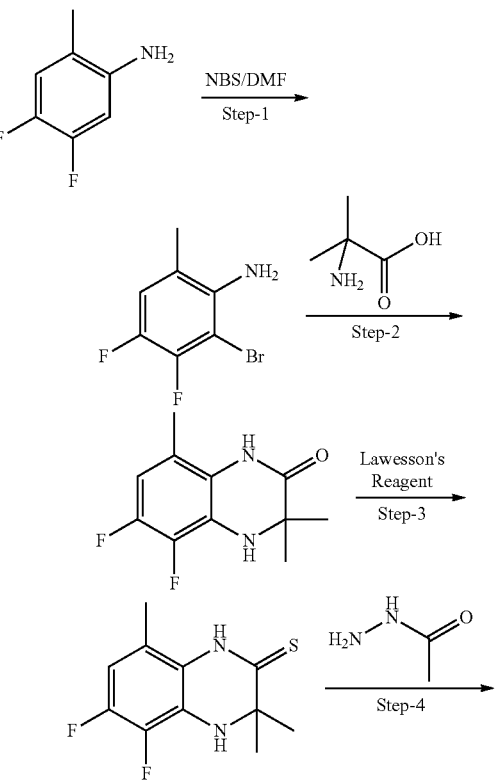

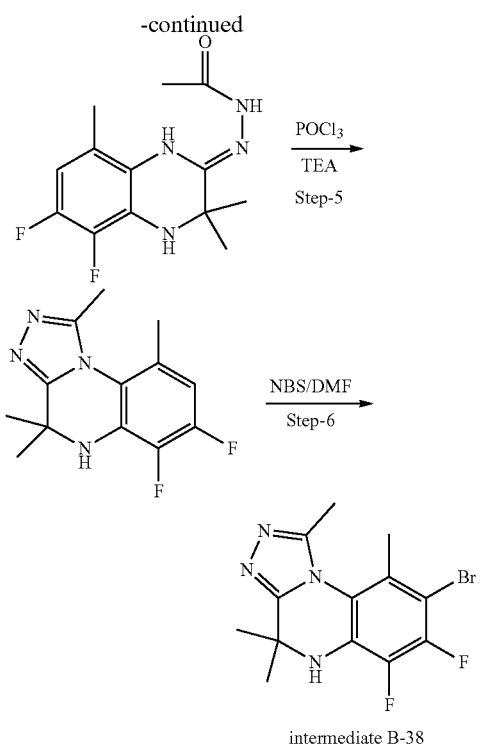

intermediate B-38

Step 1:

To a suspension of 4,5-difluoro-2-methylaniline (0.5 g, 3.49 mmol, 1 eq) in DCM (30 ml), Br$_2$ (0.55 g, 0.17 ml, 3.49 mmol, 1 eq) in DCM (20 ml) was added at 0° C. Then the reaction was stirred at RT for 2 h. After completion of starting material, the reaction mass was quenched with saturated NaHCO$_3$ solution (50 ml). The organic layer was separated and aqueous layer was extracted with DCM (50 ml). Combined organic layers was washed with water (150 ml), followed by brine (150 ml), dried over anhydrous Na$_2$SO$_4$ and the solvent was evaporated to afford crude product which was purified by column chromatography (230-400 mesh silica gel; 10% EtOAc/hexane; R$_f$-value-0.6) to afford 2-bromo-3,4-difluoro-6-methylaniline (0.4 g, 52%).

Step 2:

A suspension of 2-bromo-3,4-difluoro-6-methylaniline (0.25 g, 1.13 mmol, 1 eq), 2-aminobutyric acid (0.23 g, 2.26 mmol, 2 eq) in DMA (10 ml) in a sealed tube was deoxygenated with Ar for 20 min. DBU (0.35 ml, 2.26 mmol, 2 eq) and CuI (0.02 g, 0.113 mmol, 0.1 eq) were added and reaction mixture was stirred at 140° C. for 16 h. After completion of the reaction, it was filtered through celite bed and washed by EtOAc (100 ml). The filtrate was diluted with EtOAc (100 ml) and washed with water (3×150 ml), brine (200 ml), dried over anhydrous Na$_2$SO$_4$ and the solvent was evaporated under reduced pressure to get the crude product which was purified by column chromatography (100-200 mesh silica gel; 30% EtOAc/hexane; R$_f$-value-0.4) to afford 5,6-difluoro-3,3,8-trimethyl-3,4-dihydroquinoxalin-2(1H)-one (0.2 g, 75%).

Step 3:

To a solution of 5,6-difluoro-3,3,8-trimethyl-3,4-dihydroquinoxalin-2(1H)-one (3.66 g, 17.6 mmol, 1 eq) in toluene (75 ml) was added Lawesson's reagent (10.67 g, 26.2 mmol, 1.5 eq) at RT and the reaction mixture was heated at 120° C. for 40 min. After completion of reaction (monitored by TLC), the reaction mixture was quenched with sat. NaHCO$_3$ solution (100 ml) followed by extraction with EtOAc (2×100 ml). Combined organic layers were washed with water (100 ml), brine (100 ml), dried over anhydrous Na$_2$SO$_4$ and the solvent was evaporated to get the crude product which was purified by column chromatography (230-400 mesh silica gel; 20% EtOAc/hexane; R$_f$-value-0.4) to afford 5,6-difluoro-3,3,8-trimethyl-3,4-dihydroquinoxaline-2(1H)-thione (2.8 g, 71%) as yellow solid.

Step 4:

To a stirring solution of 5,6-difluoro-3,3,8-trimethyl-3,4-dihydroquinoxaline-2(1H)-thione (5.50 g, 24.55 mmol, 1 eq) in THF (30 ml) was drop wise added hydrazine hydrate (5.17 ml, 122.76 mmol, 5 eq) at 0° C. The reaction mixture then stirred for 16 h at RT. TEA (16.7 ml, 122.76 mmol, 5 eq) was added to the reaction mixture and stirred for another 10 min. Acetyl chloride (5.78 g, 73.65 mmol, 3 eq) was added very slowly at 0° C. and then the mixture was stirred for 2 h at RT. The reaction mixture was diluted with water (50 ml) and extracted by DCM (5×100 ml). The combined organic layers were washed by brine (100 ml). The organic layer was dried over Na$_2$SO$_4$, concentrated under reduced pressure to get the crude material which purified by washing with diethyl ether to afford N'-(5,6-difluoro-3,3,8-trimethyl-3,4-dihydroquinoxalin-2(1H)-ylidene)acetohydrazide (5.5 g, 85%) as a white solid.

Step 5:

N'-(5,6-difluoro-3,3,8-trimethyl-3,4-dihydroquinoxalin-2 (1H)-ylidene)acetohydrazide (5.5 g, 20.8 mmol, 1 eq) was taken in round bottom flax (50 ml) and then cooled to −10° C. Phosphorus oxychloride (18.4 ml, 197.6 mmol, 9.5 eq) was then added drop wise to the compound followed by drop wise addition of TEA (2.9 ml, 20.8 mmol, 1 eq). After that the reaction mixture was stirred at −10° C. for 10 min and then 10 min at RT and finally at reflux condition for 4 h. The reaction mixture was cooled to 0° C. and then drop wise added into crushed ice with constant stirring. To this aqueous part was slowly added cold ammonium solution (100 ml). The aqueous part was extracted by DCM (2×100 ml). The combined organic layer was washed by brine (100 ml). The organic layer was dried over anhydrous Na$_2$SO$_4$, concentrated under reduced pressure to get the crude product which was purified by column chromatography (230-400 mesh silica gel; 5% MeOH/DCM; R$_f$-value-0.4) to afford 6,7-difluoro-1,4,4,9-tetramethyl-4,5-dihydro-[1,2,4]triazolo [4,3-a]quinoxaline (3.0 g, 59%) as yellow solid.

Step 6:

A stirred solution of 6,7-difluoro-1,4,4,9-tetramethyl-4,5-dihydro-[1,2,4]triazolo[4,3-a]quinoxaline (4.0 g, 16.2 mmol, 1 eq) in DMF (40 ml) at −10° C. was treated portion wise over 10 min with solid N-bromosuccinimide (3.1 g, 17.1 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous Na$_2$SO$_4$ and the solvent was evaporated under reduced pressure to get the crude product which was purified by silica gel (230-400) column chromatography (5% MeOH/DCM; R$_f$-value-0.3) to afford 8-bromo-6,7-difluoro-1,4,4,9-tetramethyl-4,5-dihydro-[1,2,4]triazolo[4,3-a]quinoxaline (3.3 g, 63%) as off white solid.

Synthesis of 8-bromo-6-fluoro-1,4,4-trimethyl-4,5-dihydro-[1,2,4]triazolo[4,3-a]quinoxaline-9-carbonitrile (Intermediate B-39)

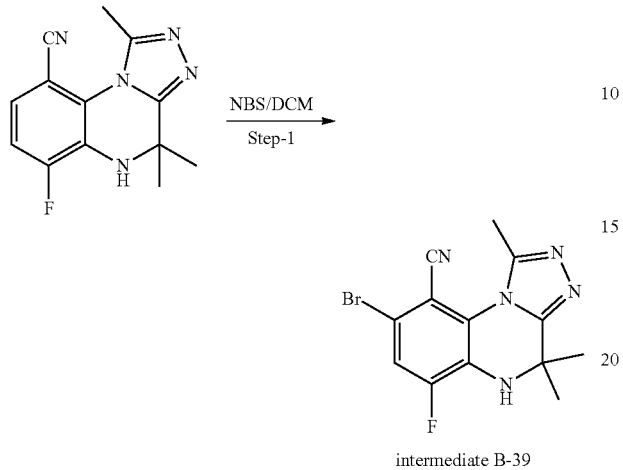

intermediate B-39

A stirred solution of 6-fluoro-1,4,4-trimethyl-4,5-dihydro-[1,2,4]triazolo[4,3-a]quinoxaline-9-carbonitrile (for synthesis see intermediate B-41) (2.0 g, 7.78 mmol, 1 eq) in DMF (20 ml) at 0° C. was treated portion wise over 10 min with solid N-bromosuccinimide (1.38 g, 7.78 mmol, 1 eq). Reaction mixture was allowed to warm to RT and stirred for 1.5 h. After completion of reaction (monitored by LCMS), reaction mixture was diluted with EtOAc (100 ml) and organic layers were washed with water (5×100 ml), brine (100 ml), dried over anhydrous $Na_2SO_4$ and the solvent was evaporated under reduced pressure to get the crude product which was purified by silica gel (230-400) column chromatography (5% MeOH/DCM; $R_f$-value-0.3) to afford 8-bromo-6-fluoro-1,4,4-trimethyl-4,5-dihydro-[1,2,4]triazolo[4,3-a]quinoxaline-9-carbonitrile (1.5 g, 58%) as off white solid.

Synthesis of (8-bromo-6-fluoro-1,4,4-trimethyl-4,5-dihydro-[1,2,4]triazolo[4,3-a]quinoxalin-9-yl)MeOH (Intermediate B-41)

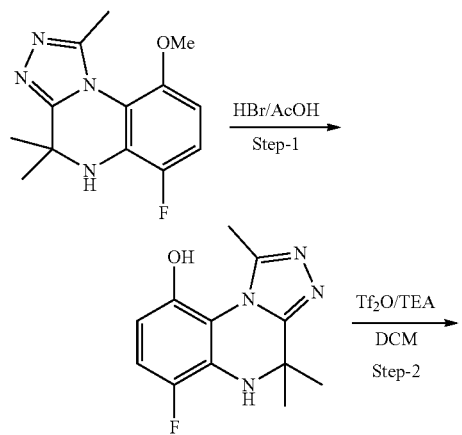

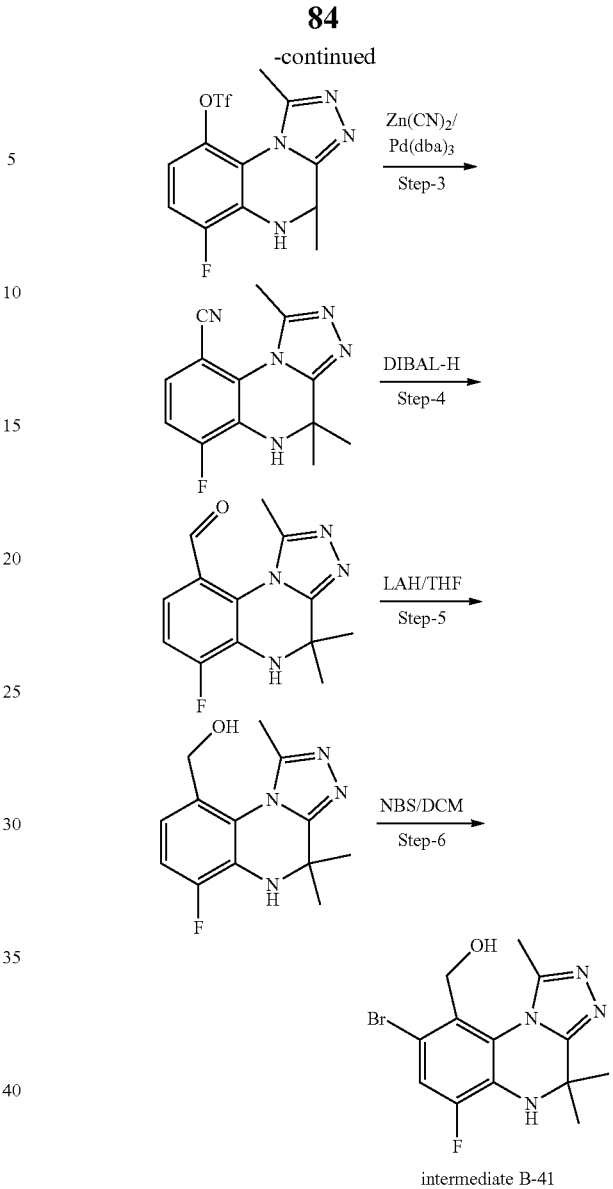

intermediate B-41

Step 1:
A solution of 6-fluoro-9-methoxy-1,4,4-trimethyl-4,5-dihydro-[1,2,4]triazolo[4,3-a]quinoxaline (for synthesis see intermediate B-10) (12 g, 45.80 mmol, 1 eq) in aqueous HBr (350 ml) was heated up to 80° C. and then acetic acid (100 ml) was added and heating was continued at 120° C. for 48 h. After completion of reaction (monitored by TLC) reaction mixture is diluted with ice cold water (1000 ml) and basified with sodium bicarbonate (pH>8). The reaction mixture was extracted with EtOAc (3×500 ml). Combined organic layers were washed with water (1000 ml), brine (1000 ml), dried over anhydrous $Na_2SO_4$ and the solvent was evaporated to get the crude product which was purified by column chromatography using 3% MeOH in DCM as an eluting solvent and 230-400 silica gel to afford 6-fluoro-1,4,4-trimethyl-4,5-dihydro-[1,2,4]triazolo[4,3-a]quinoxalin-9-ol (8 g, 70%) as off white solid (TLC system, 5% MeOH in DCM, Rf-0.2).

Step 2:
To an ice cold solution of 6-fluoro-1,4,4-trimethyl-4,5-dihydro-[1,2,4]triazolo[4,3-a]quinoxalin-9-ol (8 g, 32.25 mmol, 1 eq) in DCM, TEA (4.89 g, 48.32 mmol, 1.5 eq) and DMAP (5.91 g, 48.37 mmol, 1.5 eq) were added and the mixture was stirred at same temperature for 10 min. Then triflic anhydride (10.92 g, 38.70 mmol, 1.2 eq) was added drop wise and the mixture was stirred for 16 h. After completion of reaction (monitored by TLC) reaction mixture was diluted with ice cold water (1000 ml) and the reaction mixture was extracted with DCM (2×500 ml). Combined organic layers were washed with water (1000 ml), brine (1000 ml), dried over anhydrous $Na_2SO_4$ and the solvent was evaporated to get the crude product which was purified by column chromatography using 2% MeOH in DCM as an eluting solvent and 230-400 silica gel to afford 6-fluoro-1,4-dimethyl-4,5-dihydro-[1,2,4]triazolo[4,3-a]quinoxalin-9-yl trifluoromethanesulfonate (4 g, 33%) as liquid. (TLC system, 5% MeOH in DCM, Rf-0.5).

Step 3:

To an argon purged solution of 6-fluoro-1,4-dimethyl-4,5-dihydro-[1,2,4]triazolo[4,3-a]quinoxalin-9-yl trifluoromethanesulfonate (4 g, 10.52 mmol, 1 eq) in 1,4-dioxan, N,N'-dimethylethylenediamine (0.611 g, 37.67 mmol, 0.5 eq) and zinc cyanide (0.962 g, 10.52 mmol, 1 eq) were added and the mixture was stirred for 10 min. Then $Pd_2(dba)_3$ (1.089 g, 1.052 mmol, 0.1 eq) and xantphos (0.611 g, 1.05 mmol, 0.1 eq) were added and the reaction mixture was purged for another 5 min and the reaction mixture was heated to 100° C. for 12 h. After completion of reaction (monitored by TLC) reaction mixture was filtered through a pad of celite. The filtrate was concentrated under vacuo to get the crude product which was purified by column chromatography using 4% MeOH in DCM as an eluting solvent and 230-400 silica gel to afford 6-fluoro-1,4,4-trimethyl-4,5-dihydro-[1,2,4]triazolo[4,3-a]quinoxaline-9-carbonitrile (3 g, 37%) as liquid (TLC system, 5% MeOH in DCM, Rf-0.4).

Step 4:

To a solution of 6-fluoro-1,4,4-trimethyl-4,5-dihydro-[1,2,4]triazolo[4,3-a]quinoxaline-9-carbonitrile (0.1 g, 0.389 mmol, 1 eq) in toluene (5 ml), DIBAL-H (0.2 ml, 0.389 mmol, 1 eq) was added at 0° C. The reaction was stirred at same temperature for 3 h. After completion of reaction (monitored by TLC), reaction mixture was quenched with $NH_4Cl$ and extracted with EA. The organic layer was washed with water, brine, dried over $Na_2SO_4$, filtered and the solvent was evaporated under reduced pressure to get the crude product which was purified by column chromatography to afford 6-fluoro-1,4,4-trimethyl-4,5-dihydro-[1,2,4]triazolo[4,3-a]quinoxaline-9-carbaldehyde (0.04 g, 34%) as brown solid.

Step 5:

To a solution of 6-fluoro-1,4,4-trimethyl-4,5-dihydro-[1,2,4]triazolo[4,3-a]quinoxaline-9-carbaldehyde (0.04 g, 0.15 mmol, 1 eq) in THF (5 ml), LAH (0.005 g, 0.15 mmol, 1 eq) was added at 0° C. The reaction mixture was stirred at same temperature for 3 h. After completion of reaction (monitored by TLC), reaction mixture was quenched with saturated $Na_2SO_4$ solution and extracted with EA. The organic layer was washed with water, brine, dried over $Na_2SO_4$, filtered and the solvent was evaporated under reduced pressure to get the crude product which was purified by column chromatography to afford (6-fluoro-1,4,4-trimethyl-4,5-dihydro-[1,2,4]triazolo[4,3-a]quinoxalin-9-yl)MeOH (0.01 g, 25%) as brown gum.

Step 6:

A stirred solution of (6-fluoro-1,4,4-trimethyl-4,5-dihydro-[1,2,4]triazolo[4,3-a]quinoxalin-9-yl)MeOH (0.18 g, 0.692 mmol, 1 eq) in DMF (15 ml) at 0° C. was treated portion wise over 10 min with solid N-bromosuccinimide (0.123 g, 0.692 mmol, 1 eq). Reaction mixture was allowed to warm to RT and stirred for 1.5 It After completion of reaction (monitored by LCMS), reaction mixture was diluted with EtOAc (30 ml) and organic layers were washed with water (5×50 ml), brine (50 ml), dried over anhydrous $Na_2SO_4$ and the solvent was evaporated under reduced pressure to get the crude product which was purified by silica gel (230-400) column chromatography (5% MeOH/DCM; $R_f$-value-0.3) to afford (8-bromo-6-fluoro-1,4,4-trimethyl-4,5-dihydro-[1,2,4]triazolo[4,3-a]quinoxalin-9-yl) MeOH (0.12 g, 50%) as off white solid.

Synthesis of 8-bromo-6-chloro-1,4,4,9-tetramethyl-4,5-dihydro-[1,2,4]triazolo[4,3-a]quinoxaline (Intermediate B-42)

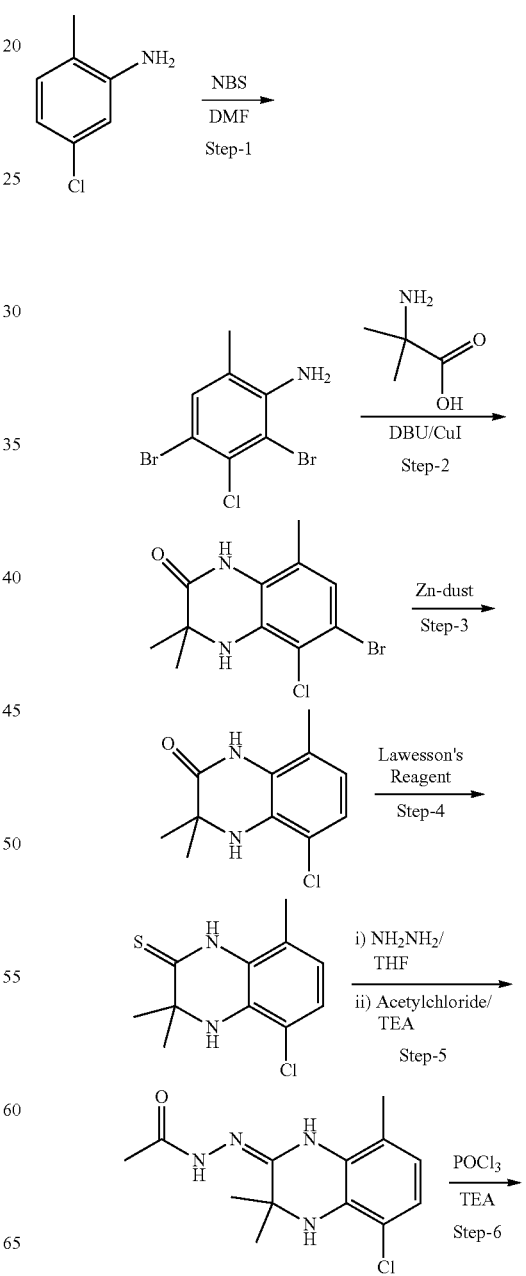

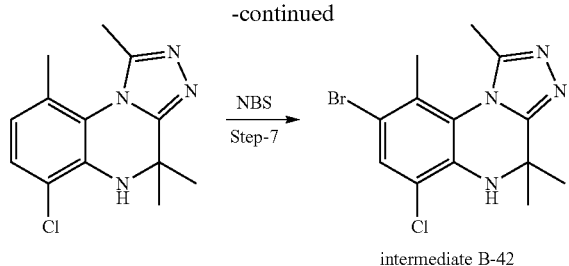

intermediate B-42

Step 1:

A stirred solution of 5-chloro-2-methylaniline (25.0 g, 176.55 mmol, 1 eq) in DMF (530 me) at −10° C. was treated portion wise over 10 min with solid N-bromosuccinimide (69.13 g, 388.4 mmol, 2.2 eq). Reaction mixture was allowed to warm to RT and stirred for 1.5 h. After completion of reaction, reaction mixture was diluted with EtOAc (3000 ml) and organic layers was washed with water (5×500 ml), brine (500 ml), dried over anhydrous $Na_2SO_4$ and the solvent was evaporated under reduced pressure to get the crude product which was purified by silica gel (230-400) column chromatography (10% EtOAc/hexane; $R_f$-value-0.6) to afford 2,4-dibromo-3-chloro-6-methylaniline (35 g, 66%2) as brown solid.

Step 2:

A solution of 2,4-dibromo-3-chloro-6-methylaniline (7.5 g, 25.08 mmol, 1 eq), 2-amino-2-methylpropanoic acid (5.16 g 50.16 mol, 2 eq) 1,4-dioxan ad DBU (9.54 g, 44.94 mmol, 2 eq) in dry DMA (112 ml) in a sealed tube were deoxygenated by Ar for 10 min. Cuprous iodide (0.479 g, 2.5 m ol, 0.1 eq) was added to the reaction mixture and again deoxygenated by Ar for 10 min. Reaction mixture was then stirred at 140° C. for 16 h. After completion of the reaction, the reaction mixture was cooled to RT and diluted with EtOAc (1000 m) and washed with water (4×150 ml), brine (200 ml), dried over anhydrous $Na_2SO_4$ and evaporated under reduced pressure to get the crude product which was purified by column chromatography (230-400 mesh silica gel; 20% EtOAc/hexane; $R_f$-value-0.4) to afford 6-bromo-5-chloro-3,3,8-trimethyl-3,4-dihydroquinoxalin-2(1H)-one (2.2 g, 29%) light brown solid.

Step 3:

To a stirring solution of 6-bromo-5-chloro-3,3,8-trimethyl-3,4-dihydroquinoxalin-2(1H)-one (3.9 g, 12.87 mmol, 1 eq) in a mixture of 1,4-dioxan and water (1:1) (100 ml), was added ammonium chloride (10.32 g, 193.06 mmol, 15 eq) and zinc dust (12.26 g 193.06 mmol, 15 eq). The reaction mixture was stirred for 16 hat reflux condition. The reaction mixture was cooled to RT and then filtered through sintered funnel. The filtrate was concentrated under reduced pressure to get the residue, which was dissolved in EtOAc (100 ml) and washed by water (2×30 ml) followed by brine (30 ml). The organic layer was dried over $Na_2SO_4$, concentrated under reduced pressure to get 5-chloro-3,3,8-trimethyl-3,4-dihydroquinoxalin-2e(1H)-one (2.3 g, 80%) as off white solid.

Step 4:

To a solution of 5-chloro-3,3,8-trimethyl-3,4-dihydroquinoxalin-2(1H)-one (2.3 g, 10.23 m mol, 1 eq) in toluene (75 ml) was added Lawesson's reagent (5.37 g, 13.3 mmol, 1.3 eq) at RT and the reaction mixture was refluxed at 120° C. for 40 min. After completion of reaction (monitored by TLC), the reaction mixture was quenched with sat. $NaHCO_3$ solution (80 ml) followed by extraction with EtOAc (2×70 ml). Combined organic layers were washed with water (80 ml), brine (80 ml), dried over anhydrous $Na_2SO_4$ and the solvent was evaporated to get the crude product which was purified by column chromatography (230-400 mesh silica gel; 20% EtOAc/hexane; Revalue-0.6) to afford 5-chloro-3,3,8-trimethyl-3,4-dihydroquinoxaline-2(1H)-thione (2.0 g, 81%) as yellow solid.

Step 5:

To a stirring solution of 5-chloro-3,3,8-trimethyl-3,4-dihydroquinoxaline-2(1H)-thione (2.0 g, 8.33 mmol, 1 eq) in THF (50 ml) was drop wise added hydrazine hydrate (2.08 ml, 41.64 mmol, 5 eq) at 0° C. The reaction mixture was stirred for 16 hat RT. TEA (5.8 ml, 41.65 mmol, 5 eq) was added and the reaction mixture was stirred for another 10 min. Acetyl chloride (1.78 ml, 24.99 mmol, 3 eq) was added to the reaction mixture very slowly at 0° C. and then stirred for 2 h at RT. The reaction mixture was diluted with water (50 ml) and extracted by DCM (3×100 ml). The combined organic layer was washed by brine (100 ml). The organic layer was dried over $Na_2SO_4$, concentrated under reduced pressure to get the crude product which was purified by washing with diethyl ether to afford N'-(5-chloro-3,3,8-trimethyl-3,4-dihydroquinoxalin-2(1H)-ylidene)acetohydrazide (2.2 g, 94%) as off white solid.

Step 6:

N'-(5-chloro-3,3,8-trimethyl-3,4-dihydroquinoxalin-2 (1H)-ylidene)acetohydrazide (5.2 g, 18.57 mmol, 1 eq) was taken in round bottom flask (100 ml) and then cooled to −10° C. Phosphorus oxychloride (17.8 ml, 185.7 mmol, 10 eq) was then added drop wise to the compound followed by drop wise addition of TEA (2.52 ml, 18.57 mmol, 1 eq). After that the reaction mixture was stirred at −10° C. for 10 min and then 10 min at RT and finally at reflux condition for 2 h. The reaction mixture was cooled to 0° C. and drop wise added into crushed ice with constant stirring. To this aqueous part was slowly added cold ammonium solution up to pH~12. The aqueous part was extract by DCM (3×100 ml). The combined organic layer was washed by brine (100 ml). The organic layer was dried over anhydrous $Na_2SO_4$, concentrated under reduced pressure to get the crude product which was purified by column chromatography (230-400 mesh silica gel; 5% MEOH/DCM; $R_f$-value-0.4) to afford 6-chloro-1,4,4,9-tetramethyl-4,5-dihydro-[1,2,4]triazolo[4,3-a]quinoxaline (3.25 g, 67%) as light yellow solid.

Step 7:

A stirred solution of 6-chloro-1,4,4,9-tetramethyl-4,5-dihydro-[1,2,4]triazolo[4,3-a]quinoxaline (3.25 g, 12.4 mmol, 1 eq) in DMF (60 ml) at −10° C. was treated portion wise over 10 min with solid N-bromosuccinimide (2.32 g, 13.02 mmol, 1.05 eq). Reaction mixture was allowed to warm to RT and stirred for 1.5 h. After completion of reaction (monitored by LCMS), reaction mixture was diluted with EtOAc (500 ml) and organic layers was washed with water (5×100 ml), brine (100 ml), dried over anhydrous $Na_2SO_4$ and the solvent was evaporated under reduced pressure to get the crude product which was purified by silica gel (230-400) column chromatography (5% MeOH/DCM; Re-value-0.4) to afford 8-bromo-6-chloro-1,4,4,9-tetramethyl-4,5-dihydro-[1,2,4]triazolo[4,3-a]quinoxaline (3.0 g, 71%) as off white solid.

Synthesis of 8-bromo-9-(difluoromethyl)-6-fluoro-1,4,4-trimethyl-4,5-dihydro-[1,2,4]triazolo[4,3-a]quinoxaline (Intermediate B-43)

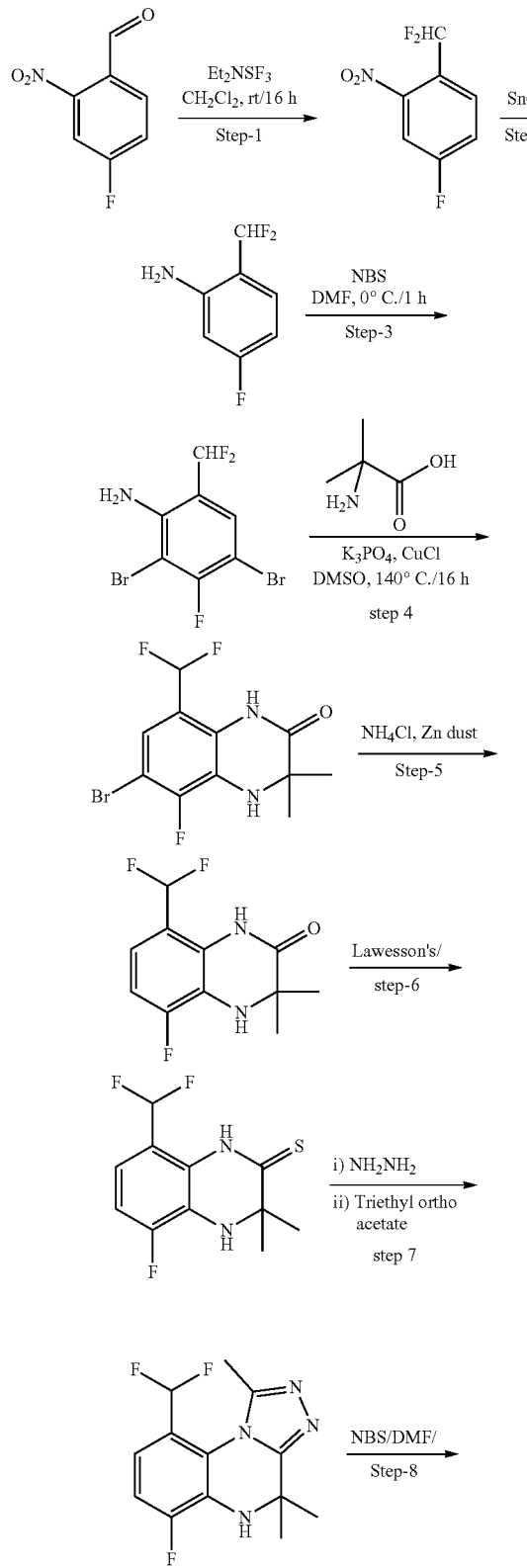

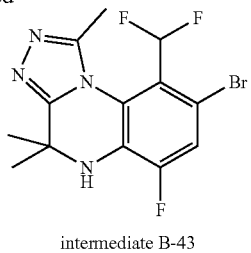

intermediate B-43

Step 1:
To a stirred solution of 4-fluoro-2-nitrobenzaldehyde (20 g, 118.27 mmol, 1 eq) in DCM (600 mL) was added DAST (23.26 ml, 177.51 mmol, 1.5 eq) at 0° C. The reaction mixture was stirred at RT for 4 h. After completion of starting material reaction mixture was quenched with sat-.NaHCO₃ solution and extracted with DCM (2×500 mL). Combined organic layers was washed with water (500 mL) followed by brine (500 mL), dried over anhydrous Na₂SO₄ and concentrated. Crude product was purified by column chromatography using 2-3% EtOAC/hexane to afford 1-(difluoromethyl)-4-fluoro-2-nitrobenzene (22 g, 88%) as yellow liquid.

Step 2:
To a stirred solution of 1-(difluoromethyl)-4-fluoro-2-nitrobenzene (10 g, 52.16 mmol, 1 eq) in EtOH (372 mL) was added SnCl₂.2H₂O (47 g, 209.46 mmol, 4 eq) followed by con. HCl (35 mL) at 0° C. The reaction mixture was stirred at RT for 2 h. After completion of starting material reaction mixture was concentrated, residue was basified with 5N NaOH solution and extracted with MTBE (2×500 mL). Combined organic layers were washed with water (500 mL) followed by brine (500 mL), dried over anhydrous Na₂SO₄ and concentrated. Crude product was purified by column chromatography using 2-3% EtOAc/hexane to afford 2-(difluoromethyl)-5-fluoroaniline (7.0 g, 83%) as yellow gummy liquid.

Step 3:
To a solution of 2-(difluoromethyl)-5-fluoroaniline (4 g, 24 mmol, 1.0 eq) in DMF (40 mL) was added NBS (13 g, 74 mmol, 3.0 eq) portion wise at −10° C. Resulting reaction mixture was stirred at 0° C. for 1 h. After completion of starting material (monitored by LCMS), reaction mixture was diluted with water (100 mL) and extracted with EtOAc (2×100 mL). Combined organic layers were washed with water (2×100 mL) and brine, dried over anhydrous Na₂SO₄ and concentrated to get crude 2,4-dibromo-6-(difluoromethyl)-3-fluoroaniline (7 g, 85%) was used for the next step without further purification.

Step 4:
A suspension of crude 2,4-dibromo-6-(difluoromethyl)-3-fluoroaniline (8 g, 25.2 mmol, 1 eq) in DMSO (80 ml), 2-aminobutyric acid (5.2 g, 50 mmol, 2 eq) was added at RT. The reaction mixture was then deoxygenated with Ar for 20 min. K₃PO₄ (10.6 g, 50 mmol, 2 eq) and CuCl (0.024 g, 2.5 mmol, 0.1 eq) were added and reaction mixture was then stirred at 140° C. for 16 h. After completion of the reaction, it was filtered through celite bed and washed by EtOAc (100 ml). The filtrate was diluted with EtOAc (100 ml) and washed with water (3×150 ml), brine (200 ml), dried over anhydrous Na₂SO₄ and the solvent was evaporated under reduced pressure to get crude product which was purified by column chromatography (100-200 mesh silica gel; 30%

EtOAc/hexane; R$_f$-value-0.4) to afford 6-bromo-8-(difluoromethyl)-5-fluoro-3,3-dimethyl-3,4-dihydroquinoxalin-2(1H)-one (1.5 g, 20%).

Step 5:

To a stirring solution of 6-bromo-8-(difluoromethyl)-5-fluoro-3,3-dimethyl-3,4-dihydroquinoxalin-2(1H)-one (3.0 g, 9.3 mmol, 1 eq) in a mixture of 1,4-dioxan and water (1:1) (100 ml), was added NH$_4$Cl (7.47 g, 139.0 mmol, 15 eq) and zinc dust (9.08 g, 139.0 mmol, 15 eq). The reaction mixture was stirred for 16 h at reflux. The reaction mixture was cooled to RT and then filtered through sintered funnel. The filtrate was concentrated under reduced pressure to get the product, which was dissolved in EtOAc (100 ml) and washed by water (2×30 ml) followed by brine (30 ml). The organic layer was dried over Na$_2$SO$_4$, concentrated under reduced pressure to get 8-(difluoromethyl)-5-fluoro-3,3-dimethyl-3,4-dihydroquinoxalin-2(1H)-one (2.0 g, 90%) as off white solid.

Step 6:

To a solution of 8-(difluoromethyl)-5-fluoro-3,3-dimethyl-3,4-dihydroquinoxalin-2(1H)-one (1 g, 4.09 mmol, 1 eq) in toluene (10 ml) was added Lawesson's reagent (2.48 g, 6.14 mmol, 1.5 eq) at RT and the reaction mixture was refluxed at 120° C. for 40 min. After completion of reaction (monitored by TLC), the reaction mixture was quenched with sat. NaHCO$_3$ solution (100 ml) followed by extraction with EtOAc (2×100 ml). Combined organic layers were washed with water (100 ml), brine (100 ml), dried over anhydrous Na$_2$SO$_4$ and the solvent was evaporated to get the crude product which was purified by column chromatography (230-400 mesh silica gel; 20% etOAc/hexane; R$_f$-value-0.4) to afford 8-(difluoromethyl)-5-fluoro-3,3-dimethyl-3,4-dihydroquinoxaline-2(1H)-thione (0.6 g, 65%) as yellow solid.

Step 7:

To a stirring solution of 8-(difluoromethyl)-5-fluoro-3,3-dimethyl-3,4-dihydroquinoxaline-2(1H)-thione (2.5 g, 9.6 mmol, 1 eq) in THF (30 ml) was drop wise added hydrazine hydrate (2.4 ml, 48 mmol, 5 eq) at 0° C. The reaction mixture then stirred for 16 h at RT. Then the reaction mixture was concentrated under reduced pressure to get the crude material. Then triethyl ortho acetate (20 ml) was added to the reaction mixture. The reaction mixture was stirred at 140° C. for 16 h. After completion of reaction (monitored by TLC), reaction mixture was diluted with water (50 ml) and extracted by DCM (5×100 ml). The combined organic layer was washed by brine (100 ml). The organic layer was dried over Na$_2$SO$_4$, concentrated under reduced pressure to get the crude product which was purified by column chromatography (230-400 mesh silica gel; 5% MeOH/DCM; R$_f$-value-0.4) to afford 9-(difluoromethyl)-6-fluoro-1,4,4-trimethyl-4,5-dihydro-[1,2,4]triazolo[4,3-a]quinoxaline (2.0 g, 74%) as a off white solid.

Step 8:

A stirred solution of 9-(difluoromethyl)-6-fluoro-1,4,4-trimethyl-4,5-dihydro-[1,2,4]triazolo[4,3-a]quinoxaline (2.0 g, 7.08 mmol, 1 eq) in DMF (30 ml) at −10° C. was treated portion wise over 10 min with solid N-bromosuccinimide (1.3 g, 7.79 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous Na$_2$SO$_4$ and the solvents were evaporated under reduced pressure to get the crude product which was purified by silica gel (230-400) column chromatography (5% MeOH/DCM; R$_f$-value-0.3) to afford 8-bromo-9-(difluoromethyl)-6-fluoro-1,4,4-trimethyl-4,5-dihydro-[1,2,4]triazolo[4,3-a]quinoxaline (1.5 g, 75%) as off white solid.

Synthesis of 8-bromo-9-cyclopropyl-6-fluoro-1,4,4-trimethyl-4,5-dihydro-[1,2,4]triazolo[4,3-a]quinoxaline (Intermediate B-45)

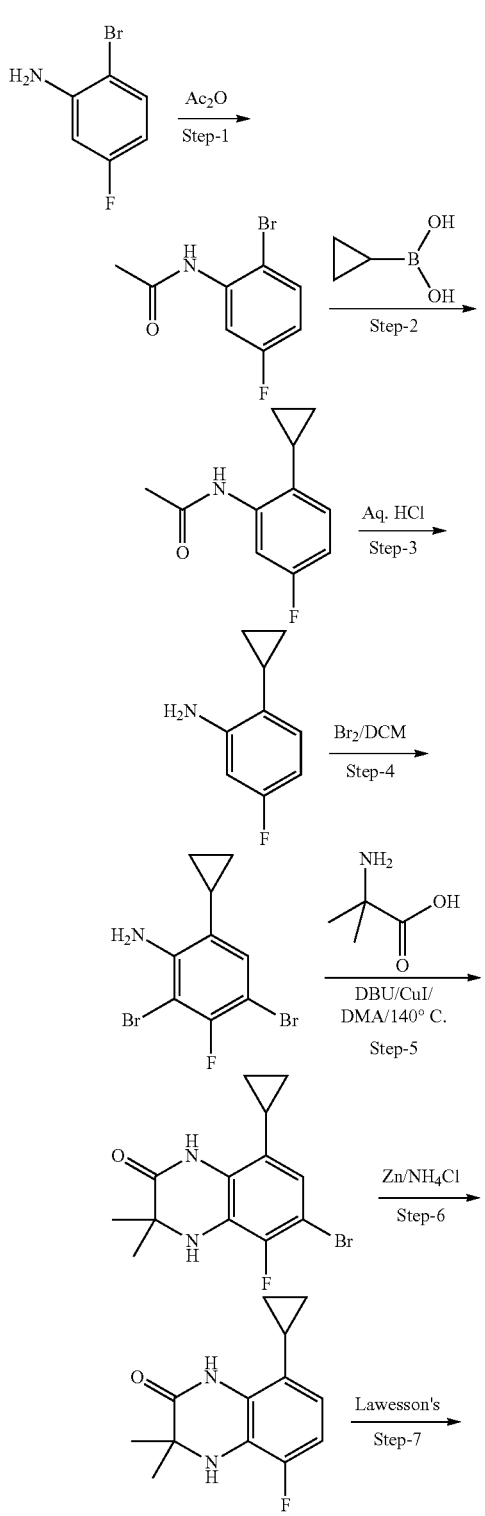

-continued

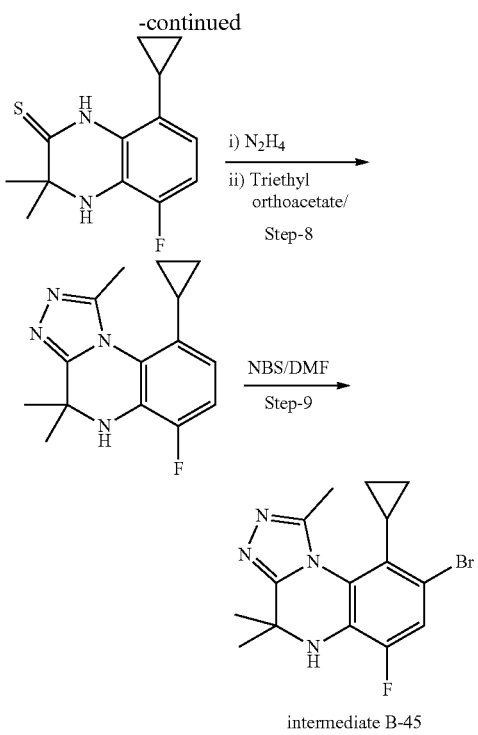

intermediate B-45

Step 1:
2-Bromo-5-fluoro-phenylamine (50 g, 0.262 mol, 1 eq) was dissolved in acetic anhydride (25 mL) at 10° C. and stirred at room temperature for 3 h. After completion of the reaction (monitored by TLC, 10% EtOAc/hexane), the thick reaction mass was diluted with n-hexane and filtered. The solid material was washed with n-hexane and dried under reduced pressure to afford N-(2-bromo-5-fluoro-phenyl)-acetamide (55 g, 90%) as an off-white solid.

Step 2:
To a stirred solution of N-(2-bromo-5-fluoro-phenyl)-acetamide (50 g, 0.259 mol, 1 eq) in a toluene:water (1:1, 1 L) mixture was added tricyclohexyl phosphine (7.26 g, 0.0259 mol, 0.1 eq), followed by $K_3PO_4$ (192 g, 0.906 mol, 3.5 eq) at room temperature and the mixture was degassed with argon for 30 minutes. Cyclopropyl boronic acid (28.98 g, 0.336 mol, 1.3 eq) and subsequently Pd(OAc)$_2$ (2.9 g, 0.0129, 0.05 eq) were added and the reaction mixture was heated at 100° C. for 16 h. After completion of the reaction (monitored by TLC, 20% EtOAc-Hexane, Rf 0.4), the reaction mixture was cooled to room temperature, diluted with EtOAc (1 L), washed with water (2×500 mL) and brine (500 mL), dried over anhydrous $Na_2SO_4$ and concentrated under reduced pressure. The obtained crude residue was purified by column chromatography (100-200 mesh silica gel; 15-20% EtOAc/hexane as eluent) to afford N-(2-cyclopropyl-4-fluoro-phenyl)-acetamide (36 g, 86%) as a brownish solid.

Step 3:
A stirred suspension of N-(2-cyclopropyl-4-fluoro-phenyl)-acetamide (54 g, 0.279 mol, 1 eq) in aqueous HCl (2.1 L, 2M) was heated at 90° C. for 16 h. After completion of the reaction (monitored by TLC, 20% EtOAc-Hexane, Rf 0.6), the reaction mixture was cooled to room temperature and basified to pH~13-14 with a NaOH solution (2M). This mixture was extracted with EtOAc (1 L), washed with water (2×500 mL) and brine (500 mL), dried over anhydrous $Na_2SO_4$ and concentrated under reduced pressure to afford 2-cyclopropyl-5-fluoro-phenylamine (48 g, crude) as a dark brown liquid.

Step 4:
To a stirred solution of 2-cyclopropyl-5-fluoro-phenylamine (27 g, 0.18 mol, 1 eq) in DMF (480 mL) was added NBS (79.5 g, 0.447 mol, 2.5 eq) portion wise at −10° C. and the resulting reaction mixture was stirred at 0° C. for 1 h. After completion of the reaction (monitored by TLC, 20% EtOAc/hexane), the reaction mixture was diluted with water (1 L) and extracted with MTBE (2×750 ml). The combined organic layers were washed with cold brine (3×500 mL), dried over anhydrous $Na_2SO_4$ and concentrated under reduced pressure. The obtained crude residue was purified by column chromatography (100-200 mesh silica gel; 5-10% EtOAc/hexane as eluent) to afford 2,4-dibromo-6-cyclopropyl-3-fluoro-phenylamine (22 g, 45% over two steps) as a brownish liquid.

Step 5:
To a stirred suspension of 2,4-dibromo-6-cyclopropyl-3-fluoro-phenylamine (20 g, 0.065 mol, 1 eq) in dry DMA (300 mL) was added 2-amino-2-methyl-propionic acid (13.35 g, 0.129 mol, 2 eq) followed by DBU (19.2 mL, 0.129 mol, 2 eq) at room temperature. The resulting reaction mixture was degassed with argon for 30 minutes, CuI (1.2 g, 0.006 mol. 0.1 eq) was added and the reaction mixture was heated at 140° C. for 16 h. After complete consumption of the starting material (monitored by TLC, 30% EtOAc-Hexane, Rf 0.4), the reaction mixture was cooled to room temperature and filtered over a bed of celite, that was then washed with EtOAc (500 mL). The organic fraction was washed with water (2×750 mL) and brine (500 mL), dried over anhydrous $Na_2SO_4$ and concentrated under reduced pressure. The obtained crude residue was purified by column chromatography (15-16% EtOAc-hexane) to afford 6-bromo-8-cyclopropyl-5-fluoro-3,3-dimethyl-3,4-dihydro-1H-quinoxalin-2-one (13 g, 64%) as a brown solid.

Step 6:
To a suspension of 6-bromo-8-cyclopropyl-5-fluoro-3,3-dimethyl-3,4-dihydro-1H-quinoxalin-2-one (10 g, 0.031 mol, 1 eq) in a dioxane:water (2:1, 200 mL) mixture was added Zn-powder (12.52 g, 0.191 mol, 6 eq), followed by ammonium chloride (10.25 g, 0.191 mol, 6 eq) at room temperature and the reaction was stirred at 100° C. for 16 h. After completion of the reaction (monitored by TLC, 30% EtOAc-Hexane, Rf 0.4), the reaction mixture was cooled to room temperature and filtered through a celite bed, that was then washed with EtOAc (500 mL). The organic fraction was washed with water (2×750 mL) and brine (500 mL), dried over anhydrous $Na_2SO_4$ and concentrated under reduced pressure. The obtained crude residue was purified by column chromatography using 15-20% EtOAc-hexane to afford 8-cyclopropyl-5-fluoro-3,3-dimethyl-3,4-dihydro-1H-quinoxalin-2-one (4.3 g, 59%) as a brown solid.

Step 7:
To a solution of 8-cyclopropyl-6-fluoro-3,3-dimethyl-3,4-dihydro-1H-quinoxalin-2-one (4.3 g, 18.376 mmol, 1 eq) in toluene (86 mL) was added Lawesson's reagent (11.16 g, 27.564 mmol, 1.5 eq) at room temperature and the reaction mixture was refluxed at 120° C. for 1 h. After completion of the reaction (monitored by TLC in 20% EtOAc-Hexane, Rf 0.6), the reaction was cooled to room temperature and quenched with a sat. $NaHCO_3$ solution. The resulting aqueous fraction was extracted with EtOAc (3×200 mL) and the combined organic layers were washed with water (200 mL) and brine (200 mL), dried over anhydrous $Na_2SO_4$ and concentrated under reduced pressure. The obtained crude residue was purified by column chromatography (100-200 mesh silica; 5-10% EtOAc/hexane) to afford 8-cyclopropyl-5-fluoro-3,3-dimethyl-3,4-dihydro-1H-quinoxaline-2-thione (4.2 g, 92%) as a yellow solid.

Step 8:

To a stirred solution of 8-cyclopropyl-5-fluoro-3,3-dimethyl-3,4-dihydro-1H-quinoxaline-2-thione (4 g, 16 mmol, 1 eq) in tetrahydrofuran (80 mL) was added hydrazine hydrate (2.35 ml, 48 mmol, 3 eq) drop wise at 0° C. and the reaction mixture was stirred at room temperature for 16 h. The solvent was then evaporated and the residue was taken up in triethyl orthoacetate and heated at 140° C. for 48 h. The reaction mixture was concentrated under reduced pressure and purified by column chromatography (100-200 mesh silica gel; 2% MeOH/DCM as eluent) to afford 9-cyclopropyl-6-fluoro-1,4,4-trimethyl-4,5-dihydro-[1,2,4]triazolo[4,3-a]quinoxaline (2.7 g, 59%) as a white solid.

Step 9:

To a stirred solution of 9-cyclopropyl-6-fluoro-4,4-dimethyl-4,5-dihydro-[1,2,4]triazolo[4,3-a]quinoxaline (2.27 g, 8.345 mmol, 1 eq) in DMF (40 mL) was added NBS (1.33 g, 7.511 mmol, 0.9 eq) portion wise at −10° C. and the resulting reaction mixture was stirred at 0° C. for 1 h. After complete consumption of starting material (monitored by LCMS), the reaction mixture was diluted with water (20 mL) and extracted with EtOAc (2×30 mL). The combined organic layers were washed with water (2×50 mL) and brine, dried over anhydrous Na₂SO₄ and concentrated. The crude residue was combined with another batch (starting from 800 mg of 9-cyclopropyl-6-fluoro-4,4-dimethyl-4,5-dihydro-[1,2,4]triazolo[4,3-a]quinoxaline and following the same procedure as described above) and the total crude amount was then purified by column chromatography (100-200 mesh silica gel; 5% MeOH/DCM as eluent) to afford 8-bromo-9-cyclopropyl-6-fluoro-1,4,4-trimethyl-4,5-dihydro-[1,2,4]triazolo[4,3-a]quinoxaline (2.2 g, 56%) as an off-white solid.

Synthesis of 8-bromo-6-fluoro-N,1,4,4-tetramethyl-4,5-dihydro-[1,2,4]triazolo[4,3-a]quinoxalin-9-amine (Intermediate B-46)

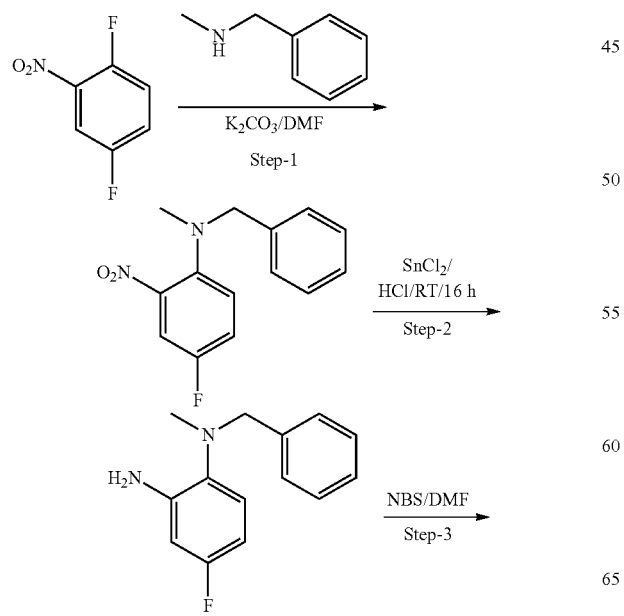

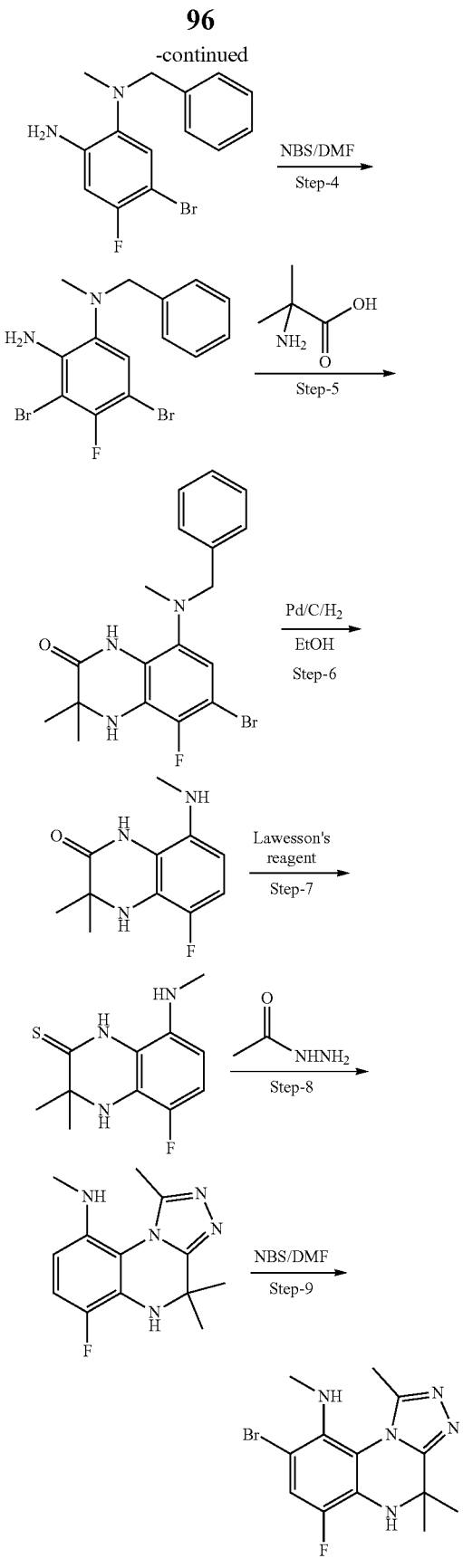

intermediate B-46

Step 1:

To a stirred solution of 1,4-difluoro-2-nitrobenzene (120 g, 754.7 mmol, 1.0 eq) in DMF was added sodium bicarbonate (82.41 g, 981.07 mmol, 1.3 eq) and the mixture was stirred for 10 min. Then N-methyl benzyl amine (109.58 g, 905.6 mmol, 1.2 eq) was added and the mixture was stirred at RT for 16 h. After completion (monitored by TLC) the reaction mixture was diluted with EtOAc and washed with water. The extracted organic layer was washed with brine, dried over anhydrous $Na_2SO_4$ and concentrated under reduced pressure. The crude product was purified by column chromatography (230-400 mesh silica gel, TLC system: EtOAc/hexane (2:8); $R_f$=0.3) to give N-benzyl-4-fluoro-N-methyl-2-nitroaniline (110 g, 56%).

Step 2:

To an ice cold solution of N-benzyl-4-fluoro-N-methyl-2-nitroaniline (110 g, 423.07 mmol, 1.0 eq) in EtOH (800 mL) was added Tin (II) chloride (381.8 g, 1692.3 mmol, 4.0 eq). The reaction mixture was stirred for 10 min at RT. Concentrated HCl (250 ml) was drop wise added at 0° C. The reaction mixture was stirred at RT for 2 h. After completion (monitored by TLC) the reaction mixture was concentrated under vacuo. The residue was dissolved in cold water and basified with NaOH pellets upto (pH~12) and the aqueous part was diluted with EtOAc. The extracted organic layer was washed with brine, dried over anhydrous $Na_2SO_4$ and concentrated under reduced pressure to get the crude product which was purified by column chromatography (230-400 mesh silica gel), (TLC system: EtOAc/hexane (2:8); $R_f$=0.4) to give N'-benzyl-4-fluoro-N1-methylbenzene-1,2-diamine (100 g, 100%).

Step 3:

A stirred solution of $N^1$-benzyl-4-fluoro-N1-methylbenzene-1,2-diamine (100 g, 434.7 mmol, 1 eq) in DMF at –10° C. was treated portion wise over 10 min with solid N-bromosuccinimide (81.26 g, 456.51 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous $Na_2SO_4$ and the solvent was evaporated under reduced pressure. Crude product was purified by silica gel (230-400) column chromatography (TLC system: EtOAc/hexane (2:8); $R_f$=0.3) to afford $N^1$-benzyl-5-bromo-4-fluoro-$N^1$-methylbenzene-1,2-diamine (60 g, 45%) as color less liquid.

Step 4:

A stirred solution of $N^1$-benzyl-5-bromo-4-fluoro-$N^1$-methylbenzene-1,2-diamine (60 g, 194.17 mmol, 1 eq) in DMF at ~10° C. was treated portion wise over 10 min with solid N-bromosuccinimide (34.56 g, 194.17 mmol, 1.05 eq). Reaction mixture was allowed to warm to RT and stirred for 1.5 h. After completion of reaction (monitored by LCMS), reaction mixture was diluted with EtOAc (300 ml) and organic layers were washed with water (5×50 ml), brine (50 ml), dried over anhydrous $Na_2SO_4$ and the solvent ws evaporated under reduced pressure to get the crude product which was purified by silica gel (230-400) column chromatography (TLC system: EtOAc/hexane (2:8); $R_f$=0.3) to afford $N^1$-benzyl-3,5-dibromo-4-fluoro-$N^1$-methylbenzene-1,2-diamine (30 g, 40%) as off white solid.

Step 5:

A suspension of $N^1$-benzyl-3,5-dibromo-4-fluoro-$N^1$-methylbenzene-1,2-diamine (30 g, 77.31 mmol, 1 eq), 2-aminoisobutaric acid (15.94 g, 154.63 mmol, 2 eq), DBU (29.42 g, 193.29 mmol, 2.5 eq) and cuprous iodide (1.47 g, 7.73 mmol, 0.1 eq) in DMA (300 ml) in a round bottom flask were deoxygenated with Ar for 20 min. Reaction mixture was then stirred at 130° C. for 16 h. After completion (monitored by TLC) the reaction mixture was diluted with EtOAc (500 ml) and water (5×100 ml), brine (100 ml), dried over anhydrous $Na_2SO_4$ and the solvent was evaporated under reduced pressure to get the crude product which was purified by column chromatography (230-400 mesh silica gel; (TLC system: EtOAc/hexane (2:8); $R_f$=0.2) to afford 8-(benzyl(methyl)amino)-6-bromo-5-fluoro-3,3-dimethyl-3,4-dihydroquinoxalin-2(1H)-one (8.0 g, 26%) as brown solid.

Step 6:

To a solution of 8-(benzyl(methyl)amino)-6-bromo-5-fluoro-3,3-dimethyl-3,4-dihydroquinoxalin-2(1H)-one (8 g, 20.40 mmol, 1 eq) in EtOH 10% Pd/C (2 g) was added. The reaction was performed in par autoclave under hydrogen atmosphere (200 psi) for 8 h. After completion of reaction the reaction mixture was filtered through a pad of celite it was washed with EtOAc. The filtrate was evaporated under reduced pressure to get the crude product which was purified by column chromatography (230-400 mesh silica gel; (TLC system: EtOAc/hexane (4:6); $R_f$=0.3) to afford 5-fluoro-3,3-dimethyl-8-(methylamino)-3,4-dihydroquinoxalin-2(1H)-one (2.0 g, 22%) as white solid.

Step 7:

To a solution of 5-fluoro-3,3-dimethyl-8-(methylamino)-3,4-dihydroquinoxalin-2(1H)-one (2 g, 8.95 mmol, 1 eq) in toluene (30 ml) was added Lawesson's reagent (5.43 g, 13.43 mmol, 1.5 eq) at RT and the reaction mixture was heated to 120° C. for 40 min. After completion (monitored by TLC), the reaction mixture was quenched with sat. $NaHCO_3$ solution (100 ml) followed by extraction with EtOAc (2×200 ml). Combined organic layers were washed with water (300 ml), brine (100 ml), dried over anhydrous $Na_2SO_4$ and the solvent was evaporated to get the crude product which was purified by column chromatography (230-400 mesh silica gel; (TLC system: EtOAc/hexane (4:6); $R_f$=0.3) to afford 5-fluoro-3,3-dimethyl-8-(methylamino)-3,4-dihydroquinoxaline-2(1H)-thione (1.85 g, 86%) as yellow solid.

Step 8:

To a stirred solution of 5-fluoro-3,3-dimethyl-8-(methylamino)-3,4-dihydroquinoxaline-2(1H)-thione (1.85 g, 7.73 mmol, 1 eq) and acetic hydrazide (2 g, 27.05 mmol, 1 eq) in n-butanol (20 ml) catalytic amount of acetic acid was added and the mixture was heated to reflux for 16 h. After completion of reaction the solvent was evaporated under reduced pressure to get the crude product which was purified by column chromatography (230-400 mesh silica gel; (TLC system: MeOH/DCM (1:9); $R_f$=0.2) to afford 6-fluoro-N,1,4,4-tetramethyl-4,5-dihydro-[1,2,4]triazolo[4,3-a]quinoxalin-9-amine (1.0 g, 50%) as liquid.

Step 9:

A stirred solution of 6-fluoro-N,1,4,4-tetramethyl-4,5-dihydro-[1,2,4]triazolo[4,3-a]quinoxalin-9-amine (1.0 g, 3.82 mmol, 1 eq) in DMF (20 ml) at –10° C. was treated portion wise over 10 min with solid N-bromosuccinimide (0.681 g, 3.82 mmol, 1.05 eq). Reaction mixture was allowed to warm to RT and stirred for 1.5 h. After completion of reaction (monitored by LCMS), reaction mixture was diluted with EtOAc (300 ml) and organic layers was washed with water (5×50 ml), brine (50 ml), dried over anhydrous $Na_2SO_4$ and the solvent was evaporated under reduced pressure to get the crude product which was purified by column chromatography (230-400 mesh silica gel; (TLC system: MeOH/DCM (1:9); $R_f$=0.4) to afford 8-bromo-6- fluoro-N,1,4,4-tetramethyl-4,5-dihydro-[1,2,4]triazolo[4,3-a]quinoxalin-9-amine (1.0 g, 77%) as liquid.

Synthesis of 8-bromo-6-chloro-9-methoxy-1,4,4-trimethyl-4,5-dihydro-[1,2,4]triazolo[4,3-a]quinoxaline (Intermediate B-47)

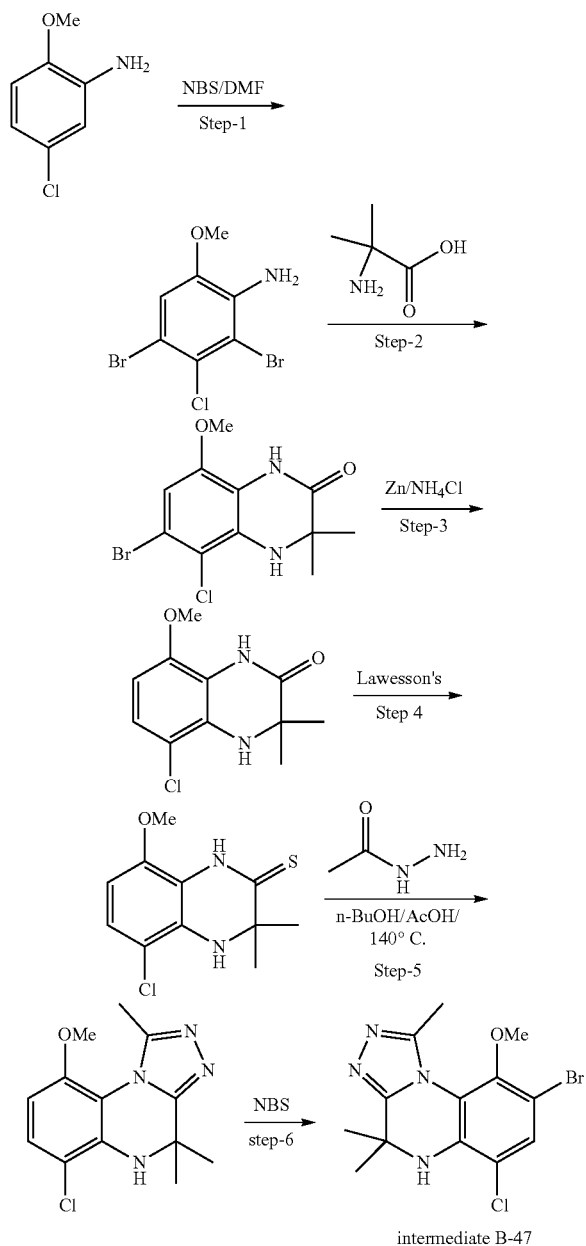

intermediate B-47

Step 1:
To an ice cold solution of 5-chloro-2-methoxyaniline (25 g, 158.62 mmol, 1.0 eq) in DMF a solution of N-bromosuccinimide (56.47 g, 317.25 mmol, 1.0 eq) was added in portion wise and the mixture was stirred at same temperature for 1 h. After completion (monitored by TLC) the reaction mixture was diluted with EtOAc and washed with water. The extracted organic layer was washed with brine, dried over anhydrous Na₂SO₄ and concentrated under reduced pressure to get the crude product which was purified by column chromatography (230-400 mesh silica gel, TLC system: EtOAc/hexane (1:9); R$_f$=0.5) to give 2,4-dibromo-3-chloro-6-methoxyaniline (30 g, 60%).

Step 2:
To a suspension of 2,4-dibromo-3-chloro-6-methoxyaniline (30 g, 95.12 mmol, 1 eq), 2-aminoisobutaric acid (24.92 g, 190.24 mmol, 2 eq), DBU (43.44 g, 285.36 mmol, 3 eq) and CuI (1.81 g, 9.51 mmol, 0.1 eq.) in DMA (300 ml) in a round bottom flask were deoxygenated with Ar for 20 min. Reaction mixture was then stirred at 130° C. for 16 h. After completion (monitored by TLC) the reaction mixture was diluted with EtOAc (500 ml) and water (5×100 ml), brine (400 ml), dried over anhydrous Na₂SO₄ and the solvent was evaporated under reduced pressure to get the crude product which was purified by column chromatography (230-400 mesh silica gel; (TLC system: EtOAc/hexane (2:8); R$_f$=0.2) to afford 6-bromo-5-chloro-8-methoxy-3,3-dimethyl-3,4-dihydroquinoxalin-2(1H)-one (3.0 g, 10%) as brown solid.

Step 3:
A stirred solution of 6-bromo-5-chloro-8-methoxy-3,3-dimethyl-3,4-dihydroquinoxalin-2(1H)-one (3 g, 9.38 mmol, 1 eq) in a mixture of water and 1,4-dioane (1:1) zinc (8.94 g, 140.78 mmol, 15 eq) and ammonium chloride (7.53 g, 140.74 mmol, 15 eq) were added and the mixture was heated to reflux for 16 h. After completion (monitored by TLC) the reaction mixture was filtered through a pad of celite. The filtrate was diluted with EtOAc (500 ml) and water (5×100 ml), brine (100 ml), dried over anhydrous Na₂SO₄ and the solvent was evaporated under reduced pressure to get the crude product which was purified by column chromatography (230-400 mesh silica gel; (TLC system: EtOAc/hexane (2:8); R$_f$=0.4) to afford 5-chloro-8-methoxy-3,3-dimethyl-3,4-dihydroquinoxalin-2(1H)-one (2 g, 88%) as white solid.

Step 4:
To a solution of 5-chloro-8-methoxy-3,3-dimethyl-3,4-dihydroquinoxalin-2(1H)-one (2.5 g, 10.38 mmol, 1 eq) in toluene (30 ml) was added Lawesson's reagent (6.30 g, 15.58 mmol, 1.5 eq.) at RT and the reaction mixture was heated to 120° C. for 40 min. After completion of reaction (monitored by TLC), the reaction mixture was quenched with sat. NaHCO₃ solution (100 ml) followed by extraction with EtOAc (2×200 ml). Combined organic layers were washed with water (300 ml), brine (100 ml), dried over anhydrous Na₂SO₄ and the solvent was evaporated to get the crude product which was purified by column chromatography (230-400 mesh silica gel; (TLC system: EtOAc/hexane (3:7); R$_f$=0.3) to afford 5-chloro-8-methoxy-3,3-dimethyl-3,4-dihydroquinoxaline-2(1H)-thione (2.1 g, 79%) as yellow solid.

Step 5:
To a stirred solution of 5-chloro-8-methoxy-3,3-dimethyl-3,4-dihydroquinoxaline-2(1H)-thione (2.1 g, 8.17 mmol, 1 eq) and acetic hydrazide (2.13 g, 28.75 mmol, 3.5 eq) were taken in n-butanol (20 ml) and catalytic amount of acetic acid was added and the mixture was heated to reflux for 16 h. After completion of reaction the solvent was evaporated under reduced pressure to get the crude product which was purified by column chromatography (230-400 mesh silica gel; (TLC system: MeOH/DCM (1:9); R$_f$=0.2) to afford 6-chloro-9-methoxy-1,4,4-trimethyl-4,5-dihydro-[1,2,4]triazolo[4,3-a]quinoxaline (1.2 g, 53%) as liquid.

Step 6:
A stirred solution of 6-chloro-9-methoxy-1,4,4-trimethyl-4,5-dihydro-[1,2,4]triazolo[4,3-a]quinoxaline (1.2 g, 4.30 mmol, 1 eq) in DMF (20 ml) at −10° C. was treated portion wise over 10 min with solid N-bromosuccinimide (0.804 g, 4.52 mmol, 1.05 eq). Reaction mixture was allowed to warm to RT and stirred for 1.5 h. After completion of reaction (monitored by LCMS), reaction mixture was diluted with EtOAc (300 ml) and organic layers was washed with water (5×50 ml), brine (50 ml), dried over anhydrous $Na_2SO_4$ and the solvent was evaporated under reduced pressure to get the crude product which was purified by column chromatography (230-400 mesh silica gel; (TLC system: MeOH/DCM (1:9); $R_f$=0.4) to afford 8-bromo-6-chloro-9-methoxy-1,4,4-trimethyl-4,5-dihydro-[1,2,4]triazolo[4,3-a]quinoxaline (0.9 g, 59%) as white solid.

Synthesis of 8-bromo-6,7-difluoro-9-methoxy-1,4,4-trimethyl-4,5-dihydro-[1,2,4]triazolo[4,3-a]quinoxaline (Intermediate B-49)

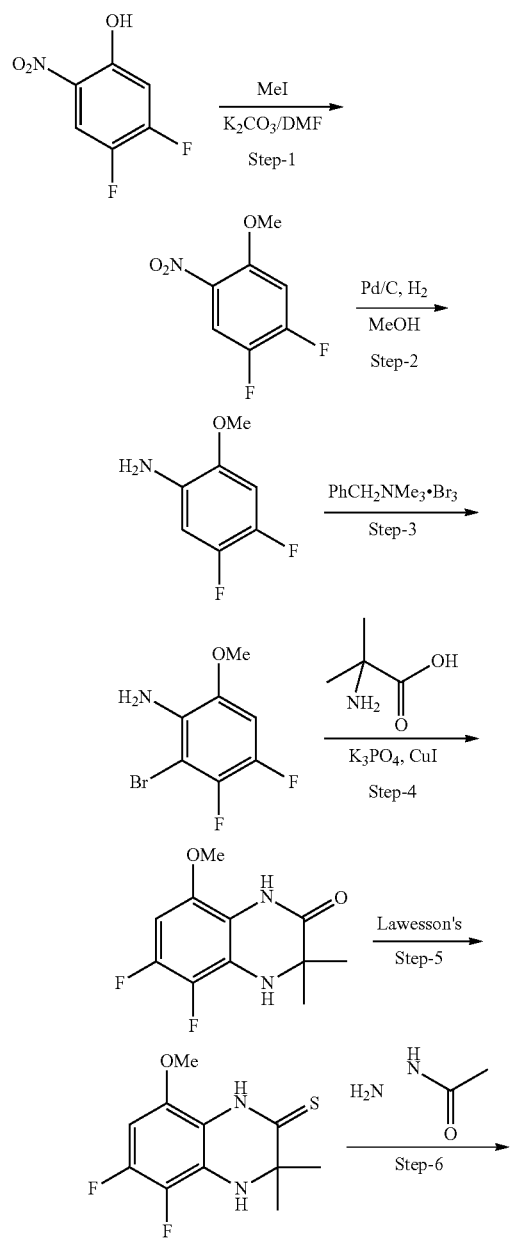

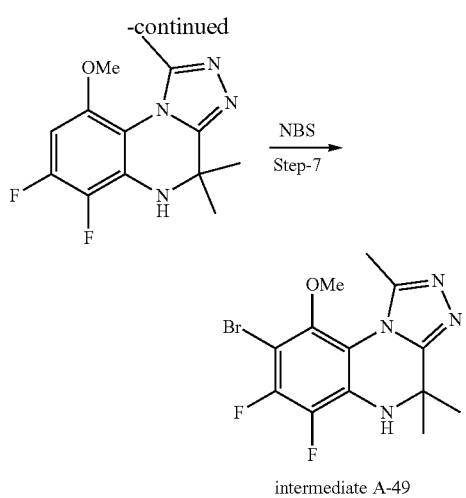

intermediate A-49

Step 1:
To a stirred solution of 4,5-difluoro-2-nitrophenol (20 g, 114.226 mmol, 1 eq) in DMF (100 ml), potassium carbonate (47.2 g, 342.68 mmol, 3 eq) and iodo methane (21.34 ml, 342.68 mmol, 3 eq) were added into the reaction mixture at RT for 4 h. After completion (monitored by TLC) the reaction mixture was diluted with EtOAc and washed with water. The extracted organic layer was washed with brine, dried over anhydrous $Na_2SO_4$ and concentrated under reduced pressure to get the crude product which was purified by column chromatography (230-400 mesh silica gel, TLC system: EtOAc/Hexane (2:8); $R_f$=0.6) to give 1,2-difluoro-4-methoxy-5-nitrobenzene (20 g, 93%).

Step 2:
To a stirred solution of 1,2-difluoro-4-methoxy-5-nitrobenzene (20.0 g, 105.75 mmol, 1 eq) in MeOH (200 ml), Pd/C (10.0 g, 10% moist) was added and the reaction mixture was stirred with hydrogen balloon for 2 h at RT. After completion (monitored by TLC, TLC system 20% EtOAc in Hexane, Rf-0.4), the reaction mixture was filtered through celite bed and washed 2-3 times with MeOH. The filtrate was concentrated to get the desired 4,5-difluoro-2-methoxyaniline (16.0 g, 95%).

Step 3:
To a stirred solution of 4,5-difluoro-2-methoxyaniline (8.0 g, 50.273 mmol, 1 eq) in MeOH:DCM (50 ml: 100 ml) was added benzyltrimethylammonium tribromide (8.82 g, 60.328 mmol, 1.2 eq) portion wise at RT. Resulting reaction mixture was stirred at RT for 12 h. After completion of starting material reaction mixture was concentrated to afford crude product which was purified by column chromatography (230-400 mesh silica gel; 15% EtOAc/Hexane; $R_f$-value-0.4) to afford 2-bromo-3,4-difluoro-6-methoxyaniline (0.5 g, 4%) as yellow solid.

Step 4:
To a stirred solution of 2-bromo-3,4-difluoro-6-methoxyaniline (0.413 g, 1.735 mmol, 1 eq) in dry DMSO (10 ml) was added 2-amino-2-methyl-propionic acid (0.536 g, 5.205 mmol, 3.0 eq) followed by $K_3PO_4$ (0.919 g, 4.337 mmol, 2.5 eq) at RT. Resulting reaction mixture was degassed with Ar for 10 min, then CuI (0.033 g, 0.1735 mmol, 0.1 eq) was added and reaction mixture was heated at 140° C. for 12 h. After completion of the starting material reaction mixture was cooled to RT and filtered through celite. Celite bed was washed with EtOAc (500 ml). Resulting filtrate was washed with water (2×50 ml), followed by brine (50 ml), dried over anhydrous Na₂SO₄ and the solvent was evaporated under reduced pressure to afford crude product which was purified by column chromatography (100-200 mesh silica gel; 20% EtOAc/hexane; R$_f$-value-0.2) to afford 5,6-difluoro-8-methoxy-3,3-dimethyl-3,4-dihydroquinoxalin-2(1H)-one (0.3 g, 71%) as brown solid.

Step 5:
To a solution of 5,6-difluoro-8-methoxy-3,3-dimethyl-3,4-dihydroquinoxalin-2(1H)-one (0.3 g, 1.238 mmol, 1 eq) in toluene (50 ml) was added Lawesson's reagent (0.65 g, 1.61 mmol, 1.5 eq) at RT and the reaction mixture was heated to 120° C. for 1 h. After completion of starting material, the reaction mass was cooled to RT and quenched with saturated NaHCO₃ solution (50 ml). The organic layer was separated and aqueous layer was extracted with EtOAc (50 ml). Combined organic layers were washed with water (50 ml), followed by brine (50 ml), dried over anhydrous Na₂SO₄ and the solvent was evaporated to afford crude product which was purified by column chromatography (230-400 mesh silica gel; 20% EtOAc/hexane; R$_f$-value-0.6) to afford 5,6-difluoro-8-methoxy-3,3-dimethyl-3,4-dihydroquinoxaline-2(1H)-thione (0.3 g, 94%) as yellow solid.

Step 6:
To a solution of 5,6-difluoro-8-methoxy-3,3-dimethyl-3,4-dihydroquinoxaline-2(1H)-thione (0.1 g, 0.3871 mmol, 1 eq) in n-BuOH (10 ml) was added acetic hydrazide (0.094 g, 1.277 mmol, 3.3 eq) followed by addition of acetic acid (1 ml) and then the reaction mixture was stirred at 140° C. for 12 h. After completion of reaction (monitored by TLC) reaction mixture was diluted with water (10 ml) and extracted with EtOAc (2×20 ml). Combined organic layer was washed with water (20 ml), brine (20 ml), dried over anhydrous Na₂SO₄ and the solvent was evaporated to get the crude product which was purified by column chromatography using 5% MeOH in DCM as an eluting solvent and 230-400 silica gel to afford 6,7-difluoro-9-methoxy-1,4,4-trimethyl-4,5-dihydro-[1,2,4]triazolo[4,3-a]quinoxaline (0.05 g, 46%) as off white solid.

Step 7:
To a stirred solution of 6,7-difluoro-9-methoxy-1,4,4-trimethyl-4,5-dihydro-[1,2,4]triazolo[4,3-a]quinoxaline (0.8 g, 2.854 mmol, 1 eq) in DMF (20 ml) at 0° C. was treated portion wise over 10 min with solid N-bromosuccinamide (0.6 g, 3.425 mmol, 1.2 eq). Reaction mixture was allowed to warm to RT and stirred for 30 min. After completion of reaction (monitored by LCMS), reaction mixture was diluted with EtOAc (50 ml) and organic layers were washed with water (3×50 ml), brine (100 ml), dried over anhydrous Na₂SO₄ and the solvents were evaporated under reduced pressure to get crude product which was purified by column chromatography using 1.5% MeOH in DCM as an eluting solvent and 230-400 silica gel to afford 8-bromo-6,7-difluoro-9-methoxy-1,4,4-trimethyl-4,5-dihydro-[1,2,4]triazolo[4,3-a]quinoxaline (0.25 g, 42%) as off white solid.

Synthesis of 8-bromo-6,7-difluoro-1,4,4-trimethyl-9-(trifluoromethyl)-4,5-dihydro-[1,2,4]triazolo[4,3-a]quinoxaline (Intermediate B-50)

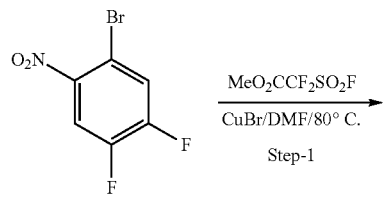

Step-1

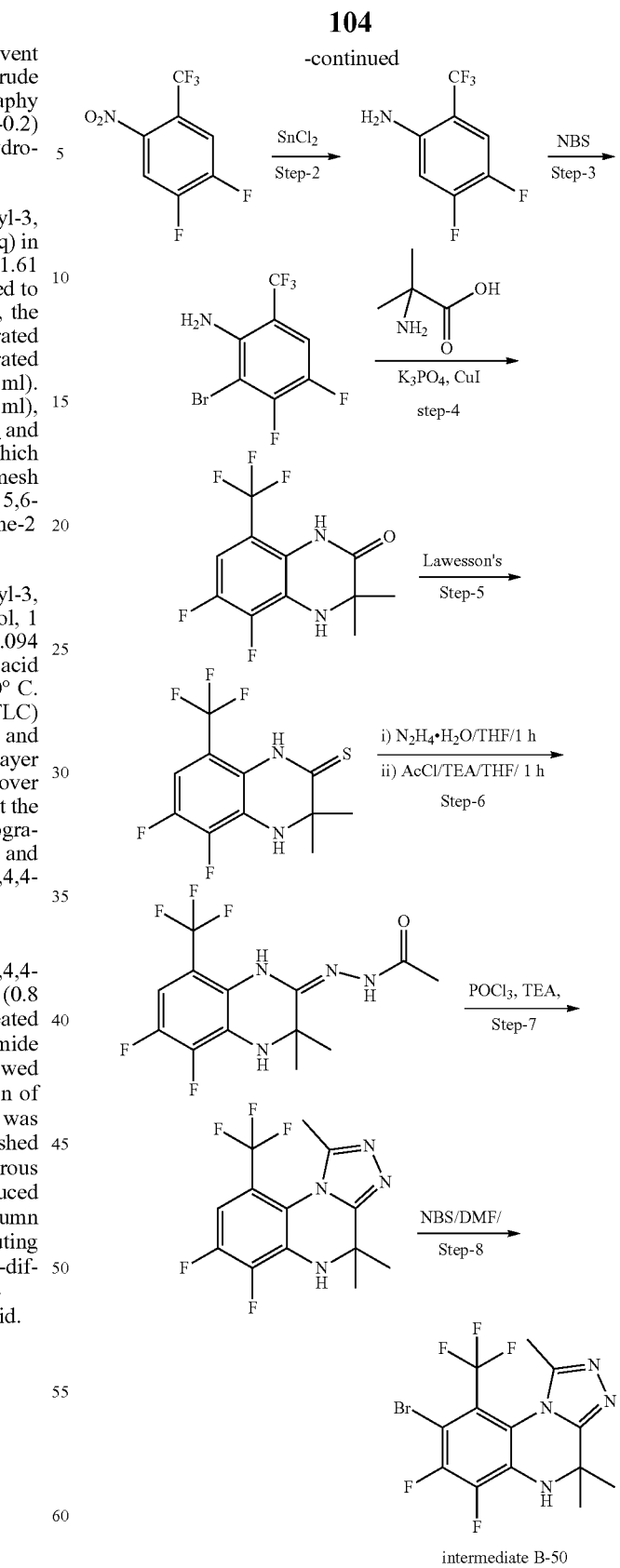

intermediate B-50

Step 1:
A solution of 1-bromo-4,5-difluoro-2-nitrobenzene (1.0 g, 4.2 mmol, 1 eq) in DMF (15 ml) was degassed with Ar for 20 min followed by addition of CuBr (0.06 g, 0.42 mmol, 0.1 eq) and methyl 2,2-difluoro-2-(fluorosulfonyl)acetate (0.88 ml, 6.93 mmol, 1.65 eq). The reaction mixture was stirred at 80° C. for 16 h. After completion of reaction (monitored by TLC), reaction mixture was diluted with diethyl ether and washed with ice cold water (2-3 times). Combined organic layer was evaporated to get the crude product, which was purified by column chromatography using 100-200 silica gel and hexane as eluting solvent to afford 1,2-difluoro-4-nitro-5-(trifluoromethyl)benzene (0.6 g, 45%) as light yellow liquid.

Step 2:

A solution of 1,2-difluoro-4-nitro-5-(trifluoromethyl)benzene (0.25 g, 1.1 mmol, 1 eq.) in EtOH (10 ml) was cooled to 0° C. $SnCl_2 \cdot 2H_2O$ was added portionwise (0.994 g, 4.4 mmol, 4.0 eq.) followed by drop wise addition of conc. HCl (2.5 ml). The reaction mixture was stirred at RT for 2 h. After completion of reaction (monitored by TLC), reaction mixture was basified with 6N NaOH solution and diluted with DCM. The organic layer was washed with water (2-3 times). Combined organic layer was evaporated to get the desired 4,5-difluoro-2-(trifluoromethyl)aniline (0.21 g, 93%) as light yellow liquid compound.

Step 3:

A solution of 4,5-difluoro-2-(trifluoromethyl)aniline (0.20 g, 1.01 mmol, 1 eq.) in DMF (10 ml) was cooled to 0° C. NBS was added portionwise (0.217 g, 1.21 mmol, 1.2 eq.). The reaction mixture was gradually allowed to RT for 5 h. After completion of reaction (monitored by TLC), reaction mixture was diluted with diethylether. The organic layer was washed with ice cold water (2-3 times). Combined organic layer was evaporated to get the crude product which was purified by column chromatography using 100-200 silica gel and hexane as eluting solvent to afford 2-bromo-3,4-difluoro-6-(trifluoromethyl)aniline (0.19 g, 63%) as light yellow liquid compound.

Step 4:

A solution of 2-bromo-3,4-difluoro-6-(trifluoromethyl)aniline (5.0 g, 18.11 mmol, 1 eq.), 2-aminoisobutyric acid (3.76 g, 36.23 mmol, 2 eq.), $K_3PO_4$ (9.6 g, 45.28 mmol, 2.5 eq.) in dry DMSO (86 ml) taken in a sealed tube were deoxygenated with Ar. CuI (0.34 g, 1.8 mmol, 0.1 eq.) was added and again deoxygenated for 5 min. Reaction mixture was then stirred at 120° C. for 6 h. After completion of the reaction, (monitored by TLC, 20% EtOAc in hexane, Rf-0.2), it was filtered through celite bed and washed by EtOAc (100 ml), washed with water (3×100 ml), brine (100 ml), dried over anhydrous $Na_2SO_4$ and evaporated under reduced pressure to get the crude product which was purified by column chromatography (230-400 mesh silica gel; 20% EtOAc/hexane; $R_f$-value-0.2) to afford 5,6-difluoro-3,3-dimethyl-8-(trifluoromethyl)-3,4-dihydroquinoxalin-2(1H)-one (0.7 g, 14%) as brown solid.

Step 5:

To a solution of 5,6-difluoro-3,3-dimethyl-8-(trifluoromethyl)-3,4-dihydroquinoxalin-2(1H)-one (0.7 g, 2.5 mmol, 1 eq.) in toluene (15 ml) was added Lawesson's reagent (1.5 g, 3.75 mmol, 1.5 eq.) at RT and the reaction mixture was refluxed at 120° C. for 1.5 h. After completion of reaction (monitored by TLC, 20% EtOAc in hexane, Rf-0.5), the reaction mixture was quenched with sat. $NaHCO_3$ solution (100 ml) followed by extraction with EtOAc (2×100 ml). Combined organic layers were washed with water (100 ml), brine (100 ml), dried over anhydrous $Na_2SO_4$ and the solvent was evaporated to get the crude product which was purified by column chromatography using 230-400 mesh silica gel and 10% EtOAc in hexane as an eluting solvent to afford 5,6-difluoro-3,3-dimethyl-8-(trifluoromethyl)-3,4-dihydroquinoxaline-2(1H)-thione (0.7 g, 94%) as yellow solid.

Step 6:

To a solution of 5,6-difluoro-3,3-dimethyl-8-(trifluoromethyl)-3,4-dihydroquinoxaline-2(1H)-thione (0.7 g, 2.36 mmol, 1 eq.) in THF (30 ml) was added hydrazine hydrate (0.59 g, 11.82 mmol, 5.0 eq.) at RT and the reaction mixture was stirred at RT for 1 h. After completion of reaction (monitored by TLC, 5% MeOH-DCM, Rf-0.5), the reaction mixture was concentrated. Reaction mixture was dissolved in THF and cooled to 0° C. TEA (1.6 ml, 11.82 mmol, 5.0 eq.) and acetyl chloride (0.5 ml, 7.09 mmol, 3.0 eq.) was added and stirred at RT for 1 h. After completion of reaction (monitored by TLC, 5% MeOH-DCM, Rf-0.5), reaction mixture was diluted with EtOAc. Combined organic layers were washed with water, brine, dried over anhydrous $Na_2SO_4$ and the solvent was evaporated to get the crude N'-(5,6-difluoro-3,3-dimethyl-8-(trifluoromethyl)-3,4-dihydroquinoxalin-2(1H)-ylidene)acetohydrazide which was taken to the next step without further purification.

Step 7:

A solution of N'-(5,6-difluoro-3,3-dimethyl-8-(trifluoromethyl)-3,4-dihydroquinoxalin-2(1H)-ylidene)acetohydrazide (2.36 mmol, 1 eq) in $POCl_3$ (15 ml) was cooled to 0° C. TEA (0.33 ml, 2.36 mmol, 1.0 eq) was added and the mixture was stirred at the same temperature for 10 min and then at reflux for 6 h. After completion of reaction (monitored by TLC, 50% Acetone-Hexane, Rf-0.5), the reaction mixture was concentrated. Reaction mixture was cooled to 0° C. and basified using aqueous ammonia solution and diluted with EtOAc. Combined organic layers were washed with water, brine, dried over anhydrous $Na_2SO_4$ and the solvent was evaporated to get the crude product which was purified by column chromatography using 230-400 mesh silica gel and 50% acetone in hexane as an eluting solvent to afford 6,7-difluoro-1,4,4-trimethyl-9-(trifluoromethyl)-4,5-dihydro-[1,2,4]triazolo[4,3-a]quinoxaline (0.5 g, 66%) as brown solid.

Step 8:

A solution of 6,7-difluoro-1,4,4-trimethyl-9-(trifluoromethyl)-4,5-dihydro-[1,2,4]triazolo[4,3-a]quinoxaline (0.5 g, 1.57 mmol, 1 eq) in DMF (15 ml) was cooled to 0° C. NBS (0.559 g, 6.28 mmol, 2.0 eq.) was added and the mixture was stirred at RT for 10 min and then at reflux for 2 h. After completion of reaction (monitored by TLC, 50% Acetone-Hexane, Rf-0.5), the reaction mixture was diluted with EtOAc. Combined organic layers were washed with ice cold water, brine, dried over anhydrous $Na_2SO_4$ and the solvent was evaporated to get the crude product which was purified by column chromatography using 230-400 mesh silica gel and 50% acetone in hexane as an eluting solvent to afford 8-bromo-6,7-difluoro-1,4,4-trimethyl-9-(trifluoromethyl)-4,5-dihydro-[1,2,4]triazolo[4,3-a]quinoxaline (0.45 g, 72%) as brown solid.

Synthesis of 8-bromo-6-chloro-7-fluoro-1,4,4,9-tetramethyl-4,5-dihydro-[1,2,4]triazolo[4,3-a]quinoxaline (Intermediate B-51)

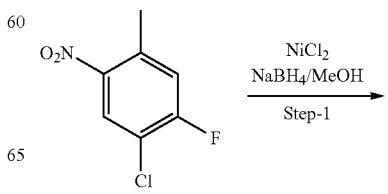

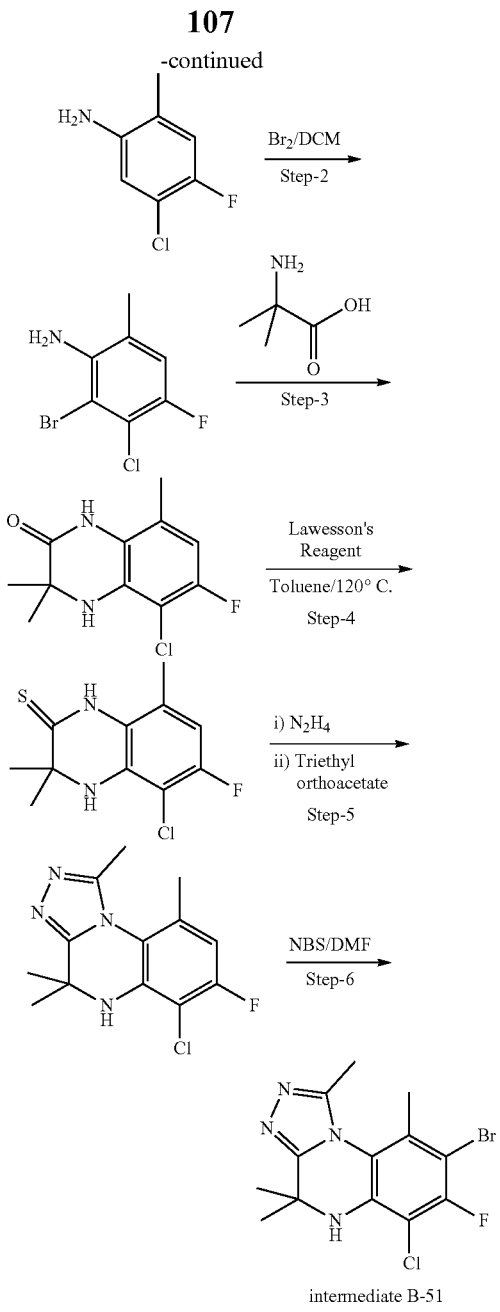

intermediate B-51

Step 1:

To a stirred solution of NiCl$_2$.6H$_2$O (12.54 g, 0.0527 mol, 1 eq) in MeOH (526 mL) was added NaBH$_4$ (5.97 g, 0.158 mol, 3 eq) portion wise at 0° C. and the resulting suspension was stirred at 0° C. for 1 h. Then, 1-chloro-2-fluoro-4-methyl-5-nitro-benzene (20 g, 0.1055 mol, 2 eq) was added, followed by further addition of NaBH$_4$ (13.95 g, 0.369 mol, 7 eq) portion wise and the reaction mixture was stirred at 0° C. for 2 h. After complete consumption of starting material (monitored by TLC), the reaction mixture was concentrated and the obtained residue was diluted with 1N HCl (150 mL) followed by aqueous ammonia (150 mL) and EtOAc (200 mL). This mixture was stirred at room temperature for 15 min, filtered over a celite bed, and the obtained aqueous filtrate was extracted with EtOAc (2×250 mL). The combined organic fractions were washed with water (350 mL) and brine (250 mL), dried over anhydrous Na$_2$SO$_4$ and concentrated to afford 5-chloro-4-fluoro-2-methyl-phenylamine (14 g, 83%) as an off-white solid.

Step 2:

To a solution of 5-chloro-4-fluoro-2-methyl-phenylamine (14 g, 0.087 mol, 1 eq) in DCM (280 mL) was added a solution of Br$_2$ (4.97 mL, 0.098 mol, 1.1 eq) in DCM (70 mL) drop-wise at 0° C. and the resulting reaction mixture was stirred at 0° C. for 2 h. After complete consumption of starting material (monitored by TLC in 10% EtOAc-Hexane), the reaction mixture was diluted with water (300 mL) and extracted with DCM (2×150 mL). The combined organic layers were washed with water (2×250 mL), a saturated sodium thiosulfate solution (2×250 mL) and brine (250 mL), dried over anhydrous Na$_2$SO$_4$ and concentrated under reduced pressure. The obtained crude residue was purified by column chromatography (100-200 mesh silica gel; 5% EtOAc/hexane as eluent) to yield 2-bromo-3-chloro-4-fluoro-6-methyl-phenylamine (11.2 g, 53%) as a brown solid.

Step 3:

To a stirred suspension of 2-bromo-3-chloro-4-fluoro-6-methyl-phenylamine (18 g, 0.075 mol, 1 eq) in dry DMAc (270 mL) was added 2-amino-2-methyl-propionic acid (15.56 g, 0.15 mol, 2 eq), followed by DBU (22.57 mL, 0.15 mol, 2 eq) at room temperature and the resulting reaction mixture was degassed with nitrogen for 30 minutes. Then, CuI (1.43 g, 0.0075 mol, 0.1 eq) was added and the reaction mixture was heated at 140° C. for 16 h. After complete consumption of the starting material (monitored by TLC, 20% EtOAc-Hexane, Rf 0.4), the reaction mixture was cooled to room temperature and poured into ice-cold water (1 L). The resulting aqueous mixture was extracted with EtOAc (2×400 mL) and the combined organic fractions were washed with water (2×500 mL) and brine (400 mL), dried over anhydrous Na$_2$SO$_4$ and evaporated under reduced pressure. The obtained crude residue was triturated with hexane to afford 5-chloro-6-fluoro-3,3,8-trimethyl-3,4-dihydro-1H-quinoxalin-2-one (8 g, 44%) as a brown liquid.

Step 4:

To a solution of 5-chloro-6-fluoro-3,3,8-trimethyl-3,4-dihydro-1H-quinoxalin-2-one (12 g, 0.049 mol, 1 eq) in toluene (150 mL) was added Lawesson's reagent (29.97 g, 0.074 mol, 1.5 eq) at room temperature and the reaction mixture was refluxed at 120° C. for 2 h. After complete consumption of starting material (monitored by TLC in 20% EtOAc-Hexane, Rf 0.6), the reaction mixture was quenched with a sat. NaHCO$_3$ solution (200 mL) and the resulting aqueous mixture was extracted with EtOAc (2×350 mL). The combined organic layers were washed with water (200 mL) and brine (200 mL), dried over anhydrous Na$_2$SO$_4$ and evaporated under reduced pressure. The obtained crude residue was purified by column chromatography (100-200 mesh silica gel; 10% EtOAc/hexane as eluent) to afford 5-chloro-6-fluoro-3,3,8-trimethyl-3,4-dihydro-1H-quinoxaline-2-thione (128 g, 93%) as a yellow solid.

Step 5:

To a stirring solution of 5-chloro-6-fluoro-3,3,8-trimethyl-3,4-dihydro-1H-quinoxaline-2-thione (11 g, 0.042 mol, 1 eq) in tetrahydrofuran (275 mL) was added hydrazine hydrate (6.38 g, 0.127 mol, 3 eq) drop wise at 0° C. and the resulting reaction mixture was stirred at room temperature for 16 h. After formation of imine intermediate, the reaction mixture was concentrated and azeotroped with toluene twice. The obtained residue was dissolved in triethyl-orthoacetate (120 mL) and heated to reflux for 24 h. After complete consumption of starting material (monitored by LCMS), the reaction mixture was concentrated and the obtained crude residue was purified by column chromatography (230-400 mesh silica gel; 5% MeOH/DCM as eluent) to afford 6-chloro-7-fluoro-1,4,4,9-tetramethyl-4,5-dihydro-[1,2,4]triazolo[4,3-a]quinoxaline (8.5 g, 71%) as an off-white solid.

Step 6:

To a solution of 6-chloro-7-fluoro-1,4,4,9-tetramethyl-4,5-dihydro-[1,2,4]triazolo[4,3-a]quinoxaline (8 g, 0.028 mol, 1 eq) in DMF (160 mL) was added NBS (5.07 g, 0.028 mol, 1 eq) portion wise at 0° C. and the resulting reaction mixture was stirred at room temperature for 3 h. After complete consumption of starting material (monitored by LCMS), the reaction mixture was diluted with water (500 mL) and extracted with EtOAc (2×250 mL). The combined organic layers were washed with water (2×250 mL) and brine (250 mL), dried over anhydrous $Na_2SO_4$ and concentrated under reduced pressure. The obtained crude residue was purified by column chromatography (230-400 mesh silica gel; 5% MeOH/DCM as eluent) to afford 8-bromo-6-chloro-7-fluoro-1,4,4,9-tetramethyl-4,5-dihydro-[1,2,4]triazolo[4,3-a]quinoxaline (6.2 g, 60%) as an off-white solid.

Synthesis of 8-bromo-7-chloro-6-fluoro-1,4,4,9-tetramethyl-4,5-dihydro-[1,2,4]triazolo[4,3-a]quinoxaline (Intermediate B-53)

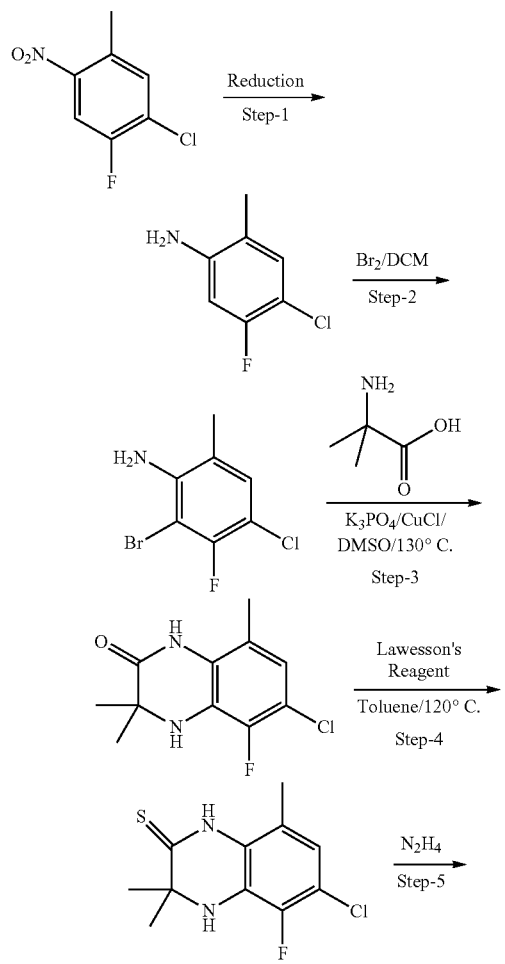

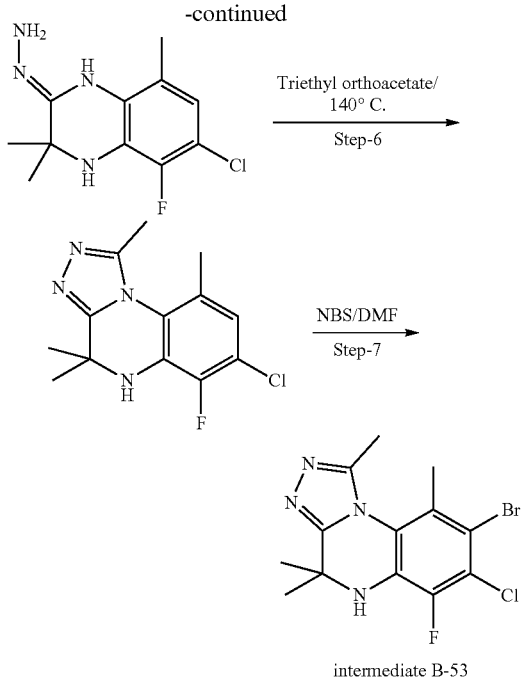

intermediate B-53

Step 1:

To a stirred solution of 1-chloro-2-fluoro-5-methyl-4-nitro-benzene (10.0 g, 52.91 mmol, 1 eq) in an EtOH-water (1:1, 120 mL) mixture was added a conc. aqueous HCl solution (6 mL), followed by addition of iron powder (10.3 g, 185.18 mmol, 3.5 eq) at room temperature and the reaction mixture was stirred for 16 h at 110° C. After completion of the reaction (monitored by TLC, 20% EtOAc/hexane, Rf 0.3), the reaction mixture was filtered through a celite bed and washed with EtOAc (200 mL×3). The combined organic fractions were concentrated under reduced pressure, diluted with EtOAc (500 mL), washed with water (100 mL×2) and brine (200 mL), dried over anhydrous $Na_2SO_4$ and concentrated under reduced pressure. The obtained crude residue was purified by column chromatography (100-200 mesh silica gel; 20% EtOAc/hexane as eluent) to afford 4-chloro-5-fluoro-2-methyl-phenylamine (7.5 g, 89%) as a light brown solid.

Step 2:

To a stirred solution of 4-chloro-5-fluoro-2-methyl-phenylamine (5.5 g, 34.81 mmol, 1 eq) in DCM (150 mL) was added a solution of $Br_2$ (1.79 mL, 34.81 mmol, 1 eq) in DCM (60 mL) drop wise at 0° C. and the resulting reaction mixture was stirred at 0° C. for 2 h. After complete consumption of starting material (monitored by TLC in 20% EtOAc-Hexane, Rf 0.6), the reaction mixture was quenched with a saturated $NaHCO_3$ solution (400 mL) and the organic layer was separated. The aqueous fraction was extracted and the combined organic layers were washed with water (2×300 mL) and brine (200 mL), dried over anhydrous $Na_2SO_4$ and concentrated under reduced pressure. The obtained crude residue was purified by column chromatography (100-200 mesh silica gel; 10% EtOAc/hexane as eluent) to afford 2-bromo-4-chloro-3-fluoro-6-methylaniline (4.5 g, 54%) as a brown solid.

Step 3:

To a stirred solution of 2-bromo-4-chloro-3-fluoro-6-methylaniline (5 g, 21.008 mmol, 1 eq) in dry DMAc (100 mL) were added 2-amino-2-methyl-propionic acid (4.4 g, 42.016 mmol, 2 eq) and DBU (5.46 mL, 42.016 mmol, 2 eq) at room temperature and the resulting reaction mixture was degassed with nitrogen for 30 minutes. CuI (400 mg, 2.1006 mmol, 0.1 eq) was added to this reaction mixture, which was heated at 140° C. for 16 h. After complete consumption of the starting material (monitored by TLC, 20% EtOAc-Hexane, Rf 0.3), the reaction mixture was cooled to room temperature and filtered over a celite bed, that was then washed with EtOAc (2×300 mL). The resulting filtrate was poured into ice-cold water (200 mL) and extracted with EtOAc (2×400 mL). The combined organic fractions were washed with cold water (3×100 mL) and brine (100 mL), dried over anhydrous $Na_2SO_4$ and evaporated under reduced pressure. The crude residue was purified by chromatography (100-200 mesh silica gel; 20% EtOAc/hexane as eluent) to afford 6-chloro-5-fluoro-3,3,8-trimethyl-3,4-dihydroquinoxalin-2(1H)-one (28 g, 69%) as an off-white solid.

Step 4:

To a stirred solution of 6-chloro-5-fluoro-3,3,8-trimethyl-3,4-dihydroquinoxalin-2(1H)-one (12 g, 49.58 mmol, 1 eq) in toluene (240 mL) was added Lawesson's reagent (30.08 g, 74.38 mmol, 1.5 eq) at room temperature and the reaction mixture was refluxed at 120° C. for 2 h. After consumption of starting material (monitored by TLC in 20% EtOAc-Hexane, Rf 0.6), the reaction mixture was concentrated under reduced pressure. The obtained solid residue was quenched with sat. $NaHCO_3$ solution (500 mL) and the resulting aqueous phase was extracted with EtOAc (3×300 mL), after which the combined organic layers were washed with water (400 mL) and brine (200 mL), dried over anhydrous $Na_2SO_4$ and evaporated under reduced pressure. The obtained crude residue was purified by column chromatography (100-200 mesh silica gel; 10% EtOAc/hexane as eluent) to afford 6-chloro-5-fluoro-3,3,8-trimethyl-3,4-dihydro-1H-quinoxaline-2-thione (11.5 g, 90%) as a yellow solid.

Step 5:

To a stirred solution of 6-chloro-5-fluoro-3,3,8-trimethyl-3,4-dihydro-1H-quinoxaline-2-thione (8 g, 31.007 mmol, 1 eq) in tetrahydrofuran (200 mL) was drop wise added hydrazine hydrate (6.209 g, 124 mmol, 4 eq) at 0° C. and the reaction mixture was stirred at room temperature for 16 h. After complete consumption of starting material (monitored by TLC in 5% MeOH-DCM, Rf 0.4), the reaction mixture was concentrated to afford crude 7-chloro-8-fluoro-3-hydrazinylidene-2,2,5-trimethyl-1,2,3,4-tetrahydroquinoxaline (8 g), which was used in the next step without purification.

Step 6:

To crude 7-chloro-8-fluoro-3-hydrazinylidene-2,2,5-trimethyl-1,2,3,4-tetrahydroquinoxaline (8 g, 34.06 mmol, 1 eq), triethyl orthoacetate (240 mL) was added at room temperature, and the solution was stirred at 140° C. for 48 t After consumption of starting material (monitored by LCMS), the reaction mixture was concentrated and purified by column chromatography (100-200 mesh silica gel; 2% MeOH/DCM as eluent) to afford 7-chloro-6-fluoro-1,4,4,9-tetramethyl-4,5-dihydro-[1,2,4]triazolo[4,3-a]quinoxaline (6 g, 69% over two steps) as a white solid.

Step 7:

To a stirred solution of 7-chloro-6-fluoro-1,4,4,9-tetramethyl-4,5-dihydro-[1,2,4]triazolo[4,3-a]quinoxaline (3 g, 10.686 mmol, 1 eq) in DMF (90 mL) was added NBS (1.99 g, 11.22 mmol, 1.05 eq) portion wise at 0° C. and the resulting reaction mixture was stirred at 0° C. for 1 h. After consumption of starting material (monitored by LCMS), the reaction mixture was diluted with water (60 mL) and extracted with EtOAc (2×100 mL). The combined organic layers were washed with water (2×60 mL) and brine, dried over anhydrous $Na_2SO_4$ and concentrated under reduced pressure. Three batches (3×3 g) were done in parallel and the combined crude material was purified by column chromatography (100-200 mesh silica gel; 5% MeOH/DCM as eluent) to afford 8-bromo-7-chloro-6-fluoro-1,4,4,9-tetramethyl-4,5-dihydro-[1,2,4]triazolo[4,3-a]quinoxaline (7.6 g, 66%) as a yellow solid.

Any of intermediates-A can be coupled to any of intermediates-B in standard chemical reactions which are known to the person skilled in the art, e.g. those as described herein below.

Example 38: 8-(3-cyclopropyl-5-fluoro-1H-indol-7-yl)-6-fluoro-1,4,4,9-tetramethyl-4,5-dihydro-[1,2,4]triazolo[4,3-a]quinoxaline

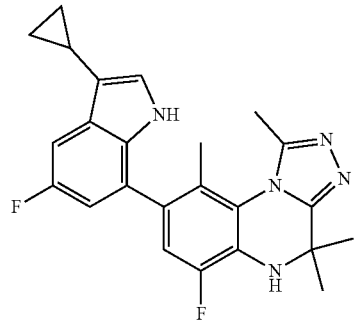 [SMILES: Cc1c(-c2cc(F)cc3c(C4CC4)c[nH]c23)cc(F)c2c1-n1c(C)nnc1C(C)(C)N2]

To a solution of intermediate B-7 (0.30 g, 0.923 mmol, 1 eq) in toluene:EtOH (2:1) (9 ml) were added 10% $Na_2CO_3$ (1.0 ml) solution and 3-cyclopropyl-5-fluoro-7-(4,4,5,5-tetramethyl-1,3,2-dioxaborolan-2-yl)-1H-indole (Intermediate A-16) (0.361 g, 1.2 mmol, 1.3 eq) in a sealed tube. The solution was degassed with Ar for 20 min followed by addition of $Pd(PPh_3)_4$ (0.053 g, 0.0461 mmol, 0.05 eq) The reaction mixture was refluxed at 110° C. for 16 h. After completion of reaction, the reaction mixture was evaporated to dryness and the residue was diluted with EtOAc (50 ml). The organic layer was washed with water (2×30 ml), brine (30 ml), dried over anhydrous $Na_2SO_4$ and the solvents were evaporated to get the crude product which was purified by silica gel (230-400) column chromatography (5% MeOH/DCM; $R_f$-value-0.4) to afford 8-(3-cyclopropyl-5-fluoro-1H-indol-7-yl)-6-fluoro-1,4,4,9-tetramethyl-4,5-dihydro-[1,2,4]triazolo[4,3-a]quinoxaline (0.140 g, 36%) as off white solid.

$^1$H NMR (400 MHz, DMSO-$d_6$): δ 10.64 (s, 1H), 7.36 (d, 1H), 7.17 (d, 1H), 7.08 (s, 1H), 6.9 (d, 1H), 6.49 (s, 1H), 2.5 (s, 3H), 1.98 (s, 3H), 1.93-1.9 (m, 1H), 1.53-1.48 (m, 6H), 0.85 (d, 2H), 0.60 (d, 2H).

Example 49: 9-ethyl-6-fluoro-1,4,4-trimethyl-8-(1-(methylsulfonyl)-1H-indol-4-yl)-4,5-dihydro-[1,2,4]triazolo[4,3-a]quinoxaline

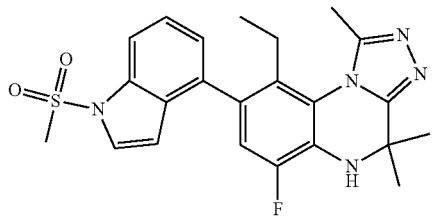 [SMILES: CCc1c(-c2cccc3c2ccn3S(C)(=O)=O)cc(F)c2c1-n1c(C)nnc1C(C)(C)N2]

To a solution of intermediate B-9 (0.25 g, 0.737 mmol, 1 eq) in 1,4-dioxan and water (15 ml and 1.5 ml) were added CsF (0.336 g, 2.21 mmol, 3 eq) and intermediate A-2 (0.344 g, 1.1 mmol, 1.5 eq) in a sealed tube. The solution was degassed with Ar for 20 min followed by addition of Pd(PPh$_3$)$_4$ (0.043 g, 0.0368 mmol, 0.05 eq). The reaction mixture was stirred at 90° C. for 16 h. After completion of reaction (monitored by LCMS), the solvents were evaporated to dryness and the residue was diluted with EtOAc (50 ml). The organic layer was washed with water (2×20 ml), brine (20 ml), dried over anhydrous Na$_2$SO$_4$ and the solvent was evaporated to get the crude product which was purified by silica gel (230-400) column chromatography (5% MeOH/DCM; R$_f$-value-0.4) to afford 9-ethyl-6-fluoro-1,4,4-trimethyl-8-(1-(methylsulfonyl)-1H-indol-4-yl)-4,5-dihydro-[1,2,4]triazolo[4,3-a]quinoxaline (0.08 g, 24%) as off white solid. 1H NMR (400 MHz, DMSO-d$_6$, at 100° C.): 7.92 (d, 1H), 7.62 (s, 1H), 7.48 (t, 1H), 7.34 (d, 1H), 7.08 (d, 1H), 6.58 (s, 1H), 6.21 (s, 1H), 3.43 (s, 3H), 2.68-2.66 (m, 2H), 2.53 (s, 3H), 1.57 (s, 6H), 0.51 (t).

Example 58: 8-(1-(2,2-difluoroethyl)-6-fluoro-1H-indol-4-yl)-6-fluoro-9-methoxy-1,4,4-trimethyl-4,5-dihydro-[1,2,4]triazolo[4,3-a]quinoxaline

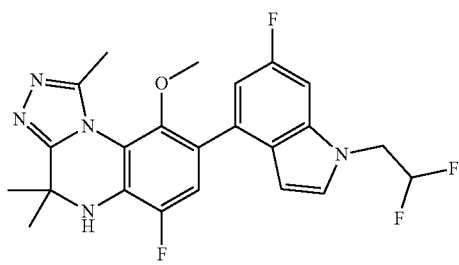 [SMILES: COc1c(-c2cc(F)cc3c2ccn3CC(F)F)cc(F)c2c1-n1c(C)nnc1C(C)(C)N2]

To a solution of intermediate B-10 (0.1 g, 0.294 mmol, 1 eq) and intermediate A-25 (0.115 g, 0.353 mmol, 1.2 eq) in t-amyl alcohol (3 ml)/dioxane (3 ml)/water (0.3 ml) mixture was added K$_2$CO$_3$ (0.122 g, 0.882 mmol, 3 eq). The solution was then degassed (N$_2$) for 10 min followed by addition of Attaphos catalyst (0.011 g, 0.0147 mmol, 0.05 eq). The reaction mixture was then heated at 100° C. for 16 h. After completion (LCMS), reaction mixture was filtered through celite pad. The filtrate was concentrated under reduced pressure to get crude product which was purified by preparative HPLC to afford 8-(1-(2,2-difluoroethyl)-6-fluoro-1H-indol-4-yl)-6-fluoro-9-methoxy-1,4,4-trimethyl-4,5-dihydro-[1,2,4]triazolo[4,3-a]quinoxaline (0.071 g, 50%).

1H-NMR (400 MHz; DMSO-d$_6$): δ 7.51 (dd, 1H), 7.41 (d, 1H), 7.25 (d, 1H), 7.05 (dd, 1H), 6.67 (s, 1H), 6.54-6.27 (m, 2H), 4.71 (td, 1H), 3.16 (s, 3H), 2.55 (d, 3H), 1.55 (s, 3H).

Example 446: 8-(1-(ethylsulfonyl)-6-fluoro-1H-indol-4-yl)-6,7-difluoro-1,4,4,9-tetramethyl-4,5-dihydro-[1,2,4]triazolo[4,3-a]quinoxaline

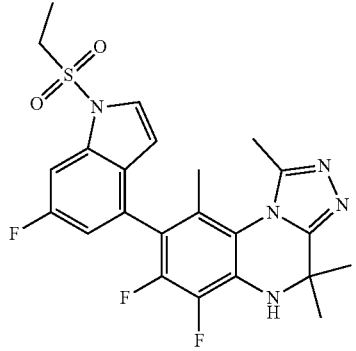 [SMILES: CCS(=O)(=O)n1ccc2c(-c3c(C)c4c(c(F)c3F)NC(C)(C)c3nnc(C)n3-4)cc(F)cc21]

To a solution of 8-bromo-6,7-difluoro-1,4,4,9-tetramethyl-4,5-dihydro-[1,2,4]triazolo[4,3-a]quinoxaline (Intermediate B-38) (0.6 g, 1.75 mmol, 1.0 eq) in t-amyl alcohol: 1,4-dioxane:H$_2$O (3:2:1) (100 ml), K$_2$CO$_3$ (0.725 g, 5.25 mmol, 3 eq) was added at RT. The solution was degassed with Ar for 20 min followed by addition of 1-(ethylsulfonyl)-6-fluoro-4-(4,4,5,5-tetramethyl-1,3,2-dioxaborolan-2-yl)-1H-indole (Intermediate A-8) (0.930 g, 2.63 mmol, 1.2 eq) and Attaphos (0.062 g, 0.0875 mmol, 0.05 eq). The reaction mixture was then placed to pre-heated oil bath at 90° C. for 2 h. After completion of reaction (monitored by TLC & LCMS), reaction mixture was diluted with water (100 mL) and extracted with EtOAc (2×250 mL). The organic layer was washed with brine (75 mL), dried over Na$_2$SO$_4$, filtered and the solvent was evaporated under reduced pressure to get the crude product which was initially purified by column chromatography using MeOH-DCM as eluent. After that it was again repurified in combiflash column chromatography using acetone-hexane as eluent. The product was then washed with ether to afford pure 8-(1-(ethylsulfonyl)-6-fluoro-1H-indol-4-yl)-6,7-difluoro-1,4,4,9-tetramethyl-4,5-dihydro-[1,2,4]triazolo[4,3-a]quinoxaline (0.32 g, 38%) as white solid.

$^1$H NMR (400 MHz, DMSO-d$_6$): δ 7.71 (d, 1H), 7.66 (d, 1H), 7.37 (d, 1H), 6.93 (s, 1H), 6.59 (d, 1H), 3.75 (q, 2H), 2.45 (s, 3H), 1.97 (s, 3H), 1.57 (s, 3H), 1.51 (s, 3H), 1.11 (t, 3H).

Example 448: 6,7-difluoro-1,4,4,9-tetramethyl-8-(1-(methylsulfonyl)-1H-indol-4-yl)-4,5-dihydro-[1,2,4]triazolo[4,3-a]quinoxaline

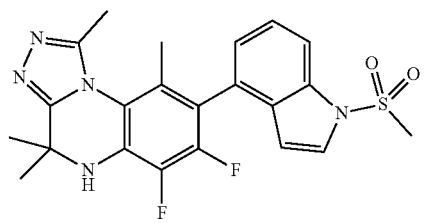 [SMILES: Cc1c(-c2cccc3c2ccn3S(C)(=O)=O)c(F)c(F)c2c1-n1c(C)nnc1C(C)(C)N2]

To a solution of 8-bromo-6,7-difluoro-1,4,4,9-tetramethyl-4,5-dihydro-[1,2,4]triazolo[4,3-a]quinoxaline (Intermediate B-38) (0.05 g, 0.146 mmol, 1 eq) in 1,4-dioxan (9 ml) were added CsF (0.067 g, 0.438 mmol, 3 eq) and 1-(methylsulfonyl)-4-(4,4,5,5-tetramethyl-1,3,2-dioxaborolan-2-yl)-1H-indole (Intermediate A-12) (0.07 g, 0.219 mmol, 1.5 eq) in a sealed tube. The solution was degassed with Ar for 20 min followed by addition of Pd(PPh$_3$)$_4$ (0.013 g, 0.0073 mmol, 0.05 eq) The reaction mixture was refluxed at 110° C. for 16 h. After completion of reaction (monitored by LCMS), reaction mixture was evaporated to dryness and the residue was diluted with EtOAc (50 ml). The organic layer was washed with water (2×20 ml), brine (20 ml), dried over anhydrous Na$_2$SO$_4$ and the solvent was evaporated to get the crude product, which was purified by preparative HPLC (5% MeOH/DCM; R$_f$-value-0.4) to afford 6,7-difluoro-1,4,4,9-tetramethyl-8-(1-(methylsulfonyl)-1H-indol-4-yl)-4,5-dihydro-[1,2,4]triazolo[4,3-a]quinoxaline (0.04 g, 61%) as a white solid.

$^1$H NMR (DMSO-d$_6$) δ=7.94 (d, 1H), 7.65 (d, 1H), 7.51 (t, 1H), 7.35 (d, 1H), 6.88 (s, 1H), 6.57 (d, 1H), 3.53 (s, 3H), 2.44 (s, 3H), 1.95 (s, 3H), 1.58 (s, 3H), 1.49 (s, 3H).

Example 450: 8-(1-cyclopropyl-1H-indol-4-yl)-6-fluoro-1,4,4-trimethyl-4,5-dihydro-[1,2,4]triazolo[4,3-a]quinoxaline-9-carbonitrile

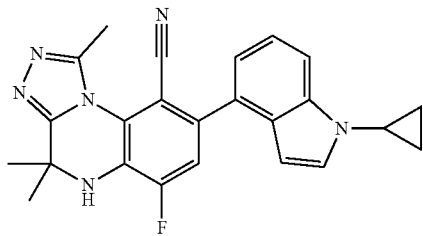 [SMILES: Cc1nnc2n1-c1c(C#N)c(-c3cccc4c3ccn4C3CC3)cc(F)c1NC2(C)C]

To a solution of 8-bromo-6-fluoro-1,4,4-trimethyl-4,5-dihydro-[1,2,4]triazolo[4,3-a]quinoxaline-9-carbonitrile (Intermediate B-39) (0.130 g, 0.388 mmol, 1.00 eq) in dioxane:water (10:1, 10 ml) were added added CsF (0.176 g, 1.164 mmol, 3.00 eq) and 1-cyclopropyl-4-(4,4,5,5-tetramethyl-1,3,2-dioxaborolan-2-yl)-1H-indole (Intermediate A-44) (0.219 g, 0.776 mmol, 2.00 eq). The solution was degassed with Ar for 20 min followed by the addition of Pd(PPh$_3$)$_4$(0.022 g, 0.019 mmol, 0.05 eq). The reaction mixture was then heated to 90° C. for 16 h. After completion of the reaction (monitored by TLC) the reaction mixture was filtered through a celite pad and the celite pad was washed with EtOAc. The combined organic layers were evaporated under reduced pressure to get the crude compound, which was purified by prep. HPLC to afford 8-(1-cyclopropyl-1H-indol-4-yl)-6-fluoro-1,4,4-trimethyl-4,5-dihydro-[1,2,4]triazolo[4,3-a]quinoxaline-9-carbonitrile (0.045 g, 28.3%) as a white solid.

$^1$H NMR (DMSO-d$_6$) δ=δ 7.71 (d, 1H), 7.52-7.50 (m, 1H), 7.47 (d, 1H), 7.34-7.30 (m, 1H), 7.26-7.25 (m, 1H), 7.13 (s, 1H), 6.42-6.41 (m, 1H), 3.52-3.49 (m, 1H), 2.75 (s, 3H), 1.57 (s, 6H), 1.11-1.08 (m, 2H), 1.02-1.00 (m, 2H).

Example 455: 9-(difluoromethyl)-6-fluoro-8-(6-fluoro-1-(methylsulfonyl)-1H-indol-4-yl)-1,4,4-trimethyl-4,5-dihydro-[1,2,4]triazolo[4,3-a]quinoxaline

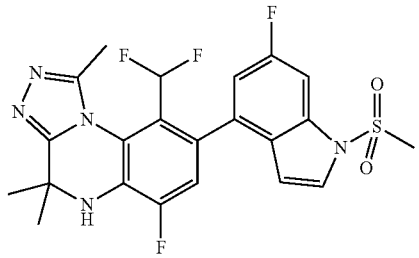

To a solution of 8-bromo-9-(difluoromethyl)-6-fluoro-1,4,4-trimethyl-4,5-dihydro-[1,2,4]triazolo[4,3-a]quinoxaline (Intermediate B-43) (0.470 g, 1.388 mmol, 1.50 eq) in t-amyl alcohol:dioxane:water (3:2:1, 30 ml) was added K$_2$CO$_3$ (0.287 g, 2.082 mmol, 3.00 eq) at ambient temperature. The solution was degassed with Ar for 20 minutes followed by the addition of 6-fluoro-1-(methylsulfonyl)-4-(4,4,5,5-tetramethyl-1,3,2-dioxaborolan-2-yl)-1H-indole (Intermediate A-2) (0.250 g, 0.694 mmol, 1.00 eq) and Attaphos (0.025 g, 0.035 mmol, 0.05 eq). The reaction mixture was then heated to 90° C. for 2 h. After completion of the reaction (monitored by TLC & LCMS) the reaction mixture was diluted with water and was extracted with EtOAc. The organic layer was washed with brine, dried over Na$_2$SO$_4$ and evaporated under reduced pressure to get the crude compound. This crude material was then purified via column chromatography using MeOH-DCM as eluent and again purified via column chromatography using acetone-hexane as eluent. The resulting material was then washed with ether to afford 9-(difluoromethyl)-6-fluoro-8-(6-fluoro-1-(methylsulfonyl)-1H-indol-4-yl)-1,4,4-trimethyl-4,5-dihydro-[1,2,4]triazolo[4,3-a]quinoxaline (0.150 g, 42%) as a white solid.

$^1$H NMR (DMSO-d$_6$) δ=7.68-7.65 (m, 1H), 7.61 (d, 1H), 7.29-7.26 (m, 2H), 7.18-6.92 (m, 2H), 6.56-6.55 (m, 1H), 3.56 (s, 3H), 1.54 (bs, 6H); (CH$_3$— omitted by DMSO).

Example 465: 6-fluoro-8-(6-fluoro-1H-indol-4-yl)-1,4,4,9-tetramethyl-4,5-dihydro-[1,2,4]triazolo[4,3-a]quinoxaline

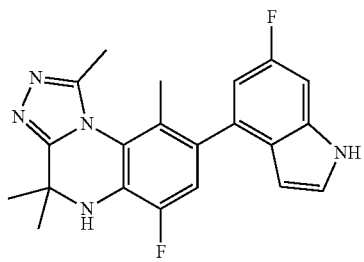 [SMILES: Cc1c(-c2cc(F)cc3[nH]ccc23)cc(F)c2c1-n1c(C)nnc1C(C)(C)N2]

Into a microwave vial were weighed out 6-fluoro-4-(4,4,5,5-tetramethyl-1,3,2-dioxaborolan-2-yl)-1H-indole (Intermediate A-1) (144.5 mg, 0.554 mmol, 2.0 eq), 8-bromo-6-fluoro-1,4,4,9-tetramethyl-5H-[1,2,4]triazolo[4,3-a]quinoxaline (Intermediate B-7) (90.0 mg, 0.277 mmol, 1.0 eq) and bis(tri-tert-butylphosphine)palladium(0) (14.2 mg, 0.028 mmol, 0.1 eq). A stir bar was added, the vial was sealed and the vial was purged with nitrogen for 5 minutes under stirring. Then, THF (1.8 mL) and 2 M $Na_2CO_3$ (0.6 mL) solution were added and the mixture was heated to 60° C. for 16 hours. The mixture was then cooled back to ambient temperature, followed by the addition of DCM and water. The mixture was filtered through a hydrophobic frit, and the organic layer was evaporated under reduced pressure. The crude remains were then purified using silica gel column chromatography to yield 84.0 mg (80%) of 6-fluoro-8-(6-fluoro-1H-indol-4-yl)-1,4,4,9-tetramethyl-4,5-dihydro-[1,2,4]triazolo[4,3-a]quinoxaline (example 465) as a white solid.

$^1$H NMR (DMSO-$d_6$) δ: 11.30 (s, 1H), 7.40 (t, 1H), 7.22 (dd, 1H), 7.18 (d, 1H), 6.91 (dd, 1H), 6.46 (d, 1H), 6.19 (t, 1H), 2.50 (s, 3H), 2.05 (s, 3H), 1.53 (s, 6H).

Example 466: 9-(difluoromethyl)-6-fluoro-1,4,4-trimethyl-8-(3-methyl-1H-indazol-7-yl)-4,5-dihydro-[1,2,4]triazolo[4,3-a]quinoxaline

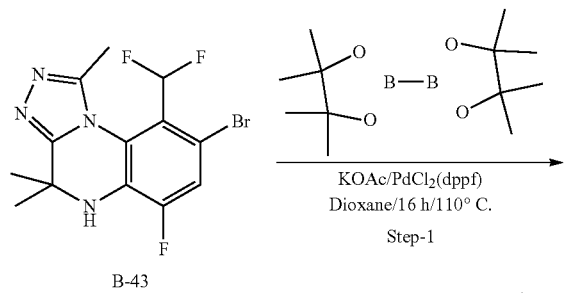

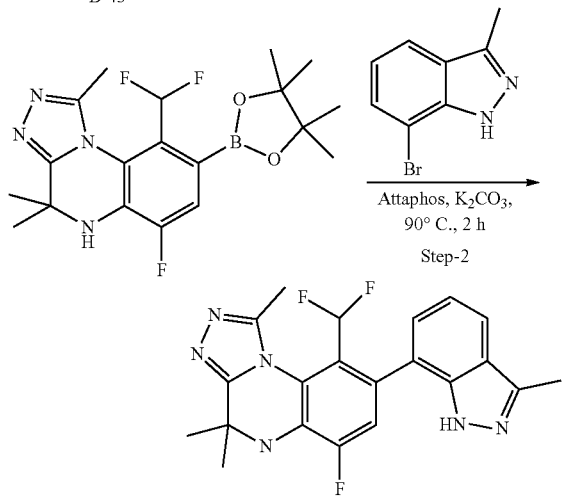

Step 1:
To a solution of 8-bromo-9-(difluoromethyl)-6-fluoro-1,4,4-trimethyl-4,5-dihydro[1,2,4]triazolo[4,3-a]quinoxaline (Intermediate B-43) (0.05 g, 0.138 mmol, 1 eq) in dioxane (10.0 ml) were added KOAc (0.041 g, 0.414 mmol, 3 eq) and bispincolatediborane (0.42 g, 0.166 mmol, 1.2 eq) The solution was degassed with Ar for 20 min followed by addition of $PdCl_2$(dppf).DCM (0.011 g, 0.0138 mmol, 0.01 eq). The reaction mixture was refluxed for 16 h. After completion of reaction (monitored by TLC), solvent was evaporated under reduced pressure to get the crude product which was purified by column chromatography to afford 9-(difluoromethyl)-6-fluoro-1,4,4-trimethyl-8-(4,4,5,5-tetramethyl-1,3,2-dioxaborolan-2-yl)-4,5-dihydro-[1,2,4]triazolo[4,3-a]quinoxaline (0.05 g, 89%), as brown solid.

Step 2:
To a solution of 7-bromo-3-methyl-1H-indazole (0.10 g, 0.473 mmol, 1.0 eq) in t-amyl alcohol:dioxane:$H_2O$ (3:2:1) (30 ml), $K_2CO_3$ (0.196 g, 1.419 mmol, 3 eq) was added at RT. The solution was degassed with Ar for 20 min followed by addition of 9-(difluoromethyl)-6-fluoro-1,4,4-trimethyl-8-(4,4,5,5-tetramethyl-1,3,2-dioxaborolan-2-yl)-4,5-dihydro-[1,2,4]triazolo[4,3-a]quinoxaline (0.231 g, 0.568 mmol, 1.2 eq) and Attaphos (0.017 g, 0.023 mmol, 0.05 eq). The reaction mixture was then placed to pre-heated oil bath at 90° C. for 2 h. After completion of reaction (monitored by TLC & LCMS), reaction mixture was diluted with water and extracted with EA. The organic layer was washed with brine, dried over $Na_2SO_4$, filtered and the solvent was evaporated under reduced pressure to get the crude product which was initially purified by column chromatography using MeOH-DCM as eluent. After that it was again repurified in combiflash column chromatography using acetone-hexane as eluent. The product was then washed with ether to afford pure 9-(difluoromethyl)-6-fluoro-1,4,4-trimethyl-8-(3-methyl-1H-indazol-7-yl)-4,5-dihydro-[1,2,4]triazolo[4,3-a]quinoxaline (0.08 g, 40%) as white solid. 1H NMR (400 MHz, dmso-d6): δ 12.55 (s, 1H), 7.72 (d, 1H), 7.26-7.22 (m, 2H), 7.14-7.12 (m, 1H), 7.11-6.82 (m, 2H), 2.51 (s, 3H), 1.54-1.51 (m, 6H).

Example 481: 8-(1-cyclopropyl-1H-indol-4-yl)-6-fluoro-N,1,4,4-tetramethyl-4,5-dihydro-[1,2,4]triazolo[4,3-a]quinoxalin-9-amine

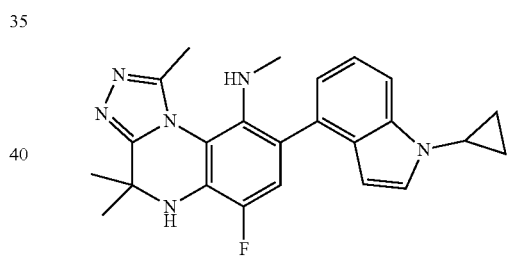

To a solution of 8-bromo-6-fluoro-N,1,4,4-tetramethyl-4,5-dihydro-[1,2,4]triazolo[4,3-a]quinoxalin-9-amine (Intermediate B-46) (0.15 g, 0.44 mmol, 1 eq.) in t-amyl alcohol: dioxane (2:1) (5.0-2.5 ml) were added 2 M $K_2CO_3$ (1.0 ml) solution and 1-cyclopropyl-4-(4,4,5,5-tetramethyl-1,3,2-dioxaborolan-2-yl)-1H-indole (Intermediate A-44) (0.15 g, 0.53 mmol, 1.2 eq). The solution was degassed with Ar for 20 min followed by addition of Attaphos (0.016 g, 0.02 mmol, 0.05 eq.). The reaction mixture was heated to 90° C. for 16 h. After completion of reaction (monitored by TLC), reaction mixture was filtered through celite pad and washed with EtOAc. Combined organic layer was evaporated to get the crude product which was purified by prep-HPLC ($R_f$-value-0.3:5% MeOH/DCM) to afford 8-(1-cyclopropyl-1H-indol-4-yl)-6-fluoro-N,1,4,4-tetramethyl-4,5-dihydro-[1,2,4]triazolo[4,3-a]quinoxalin-9-amine (0.09 g, 49%) as white solid.

1H NMR (400 MHz, dmso-d6): δ 7.63-7.61 (m, 1H), 7.40 (d, 1H), 7.31-7.27 (m, 1H), 7.08 (d, 1H), 7.00-6.98 (m, 1H), 6.46 (s, 1H), 6.20 (d, 1H), 4.07-4.05 (m, 1H), 3.48-3.47 (m, 1H), 2.53 (s, 3H), 2.16-2.14 (m, 3H), 1.58-1.49 (m, 6H), 1.10-1.08 (m, 2H), 0.99-0.98 (m, 2H).

Example 483: 6-chloro-8-(6-fluoro-1-(methylsulfo-nyl)-1H-indol-4-yl)-9-methoxy-1,4,4-trimethyl-4,5-dihydro-[1,2,4]triazolo[4,3-a]quinoxaline

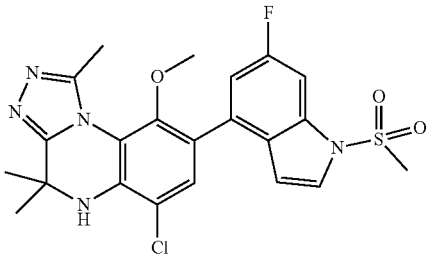 [SMILES: COc1c(-c2cc(F)cc3c2ccn3S(C)(=O)=O)cc(Cl)c2c1-n1c(C)nnc1C(C)(C)N2]

To a solution of 8-bromo-6-chloro-9-methoxy-1,4,4-trimethyl-4,5-dihydro-[1,2,4]triazolo[4,3-a]quinoxaline (Intermediate B-47) (0.150 g, 0.42 mmol, 1 eq) in t-amyl alcohol:dioxane:H$_2$O (3:2:1) (10 ml) were added K$_2$CO$_3$ (0.174 g, 1.26 mmol, 3 eq) and 6-fluoro-1-(methylsulfonyl)-4-(4,4,5,5-tetramethyl-1,3,2-dioxaborolan-2-yl)-1H-indole (Intermediate A-2) (0.171 g, 0.50 mmol, 1.2 eq). The solution was degassed with Ar for 20 min followed by addition of Attaphos (0.015 g, 0.021 mmol, 0.05 eq.). The reaction mixture was heated to 90° C. for 30 min. After completion of reaction (monitored by TLC), reaction mixture is filtered through celite pad and celite pad was washed with EtOAc. Combined organic layer was evaporated to get the crude product which was purified by prep-HPLC (R$_f$-value-0.3: 50% acetone/hexane) to afford 6-chloro-8-(6-fluoro-1-(methylsulfonyl)-1H-indol-4-yl)-9-methoxy-1,4,4-trimethyl-4,5-dihydro-[1,2,4]triazolo[4,3-a]quinoxaline (0.05 g, 24%) as white solid.
1H NMR (400 MHz, dmso-d6): δ 7.68-7.65 (m, 1H), 7.64-7.63 (m, 1H), 7.40 (s, 1H), 7.33-7.30 (m, 1H), 6.68-6.67 (m, 1H), 6.33 (s, 1H), 3.56 (s, 3H), 3.21 (s, 3H), 2.55 (s, 3H), 1.57 (s, 6H).

Example 490: 6-fluoro-8-(7-fluoro-1H-indol-4-yl)-1,4,4,9-tetramethyl-4,5-dihydro-[1,24]triazolo[4,3-a]quinoxaline

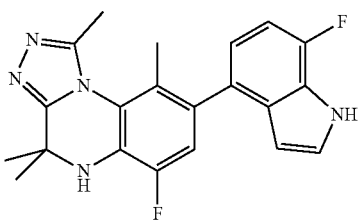 [SMILES: Cc1c(-c2ccc(F)c3[nH]ccc23)cc(F)c2c1-n1c(C)nnc1C(C)(C)N2]

Into a microwave vial were weighed out 7-fluoro-4-(4,4,5,5-tetramethyl-1,3,2-dioxaborolan-2-yl)-1H-indole (128.5 mg, 0.492 mmol, 2.0 eq), 8-bromo-6-fluoro-1,4,4,9-tetramethyl-5H-[1,2,4]triazolo[4,3-a]quinoxaline (Intermediate B-7) (80.0 mg, 0.246 mmol, 1.0 eq) and Pd(PPh$_3$)$_4$. A stir bar was added, the vial was sealed and the vial was purged with nitrogen under stirring for 5 minutes. Then, toluene (2.1 mL), EtOH (0.6 mL) and 2M Na$_2$CO$_3$ solution (0.5 mL) were added successively. The reaction mixture was then heated to 90° C. for 16 hours. The mixture was allowed to cool to ambient temperature, diluted with water and DCM and was filtered through a hydrophobic frit. The organic layer was evaporated under reduced pressure to obtain the crude material, which was then purified via silica gel column chromatography and HPLC to obtain 6-fluoro-8-(7-fluoro-1H-indol-4-yl)-1,4,4,9-tetramethyl-4,5-dihydro-[1,2,4]triazolo[4,3-a]quinoxaline (example 490) in 71% (66.0 mg) yield as a white solid.
$^1$H NMR (DMSO-d$_6$) δ: 11.76 (t, 1H), 7.47 (t, 1H), 7.13 (d, 1H), 7.01 (dd, 1H), 6.96 (dd, 1H), 6.42 (d, 1H), 6.27 (m, 1H), 2.49 (s, 3H), 2.02 (s, 3H), 1.52 (s, 6H).

Example 500: 6,7-difluoro-1,4,4-trimethyl-8-(1-(methylsulfonyl)-1H-indol-4-yl)-9-(trifluoromethyl)-4,5-dihydro-[1,2,4]triazolo[4,3-a]quinoxaline To a solution of 8-bromo-6,7-difluoro-1,4,4-trimethyl-9-(trifluoromethyl)-4,5-dihydro-[1,2,4]triazolo[4,3-a]quinoxaline (Intermediate B-50) (0.07 g, 0.17 mmol, 1 eq) in t-amyl alcohol:dioxane:H$_2$O (3:2:1) (3.0 ml:2.0 ml:1 ml) were added K$_2$CO$_3$ (0.073 g, 0.53 mmol, 3 eq) and 1-(methylsulfonyl)-4-(4,4,5,5-tetramethyl-1,3,2-dioxaborolan-2-yl)-1H-indole (Intermediate A-12) (0.085 g, 0.26 mmol, 1.5 eq). The solution was degassed with Ar for 20 min followed by addition of Attaphos (0.006 g, 0.008 mmol, 0.05 eq). The reaction mixture was heated to 90° C. for 16 h. After completion of reaction (monitored by TLC), reaction mixture was filtered through celite pad and washed with EtOAc. Combined organic layer was evaporated to get the crude product which was purified by prep-HPLC(R$_f$-value-0.3: 50% acetone/hexane) to afford 6,7-difluoro-1,4,4-trimethyl-8-(1-(methylsulfonyl)-1H-indol-4-yl)-9-(trifluoromethyl)-4,5-dihydro-[1,2,4]triazolo[4,3-a]quinoxaline (0.037 g, 39%) as white solid. 1H NMR (400 MHz, dmso-d6): δ 8.00-7.98 (m, 1H), 7.61 (s, 1H), 7.51-7.47 (m, 1H), 7.38 (s, 1H), 7.25 (s, 1H), 6.63 (s, 1H), 3.46 (s, 3H), 2.49 (s, 3H), 1.85 (s, 3H), 1.40 (s, 3H).

Example 518: 6,7-difluoro-8-(6-fluoro-1-(methylsulfonyl)-1H-indol-4-yl)-1,4,4-trimethyl-9-(trifluoromethyl)-4,5-dihydro-[1,2,4]triazolo[4,3-a]quinoxaline

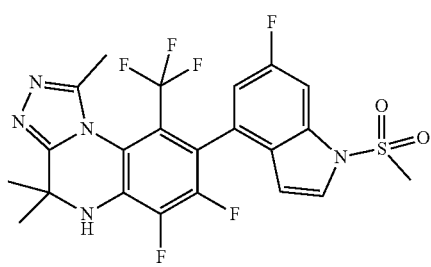 [SMILES: Cc1nnc2n1-c1c(c(F)c(F)c(-c3cc(F)cc4c3ccn4S(C)(=O)=O)c1C(F)(F)F)NC2(C)C]

To a solution of 8-bromo-6,7-difluoro-1,4,4-trimethyl-9-(trifluoromethyl)-4,5-dihydro-[1,2,4]triazolo[4,3-a]quinoxaline (Intermediate B-50) (0.07 g, 0.17 mmol, 1 eq) in t-amyl alcohol:dioxane (1:1) (2.5 ml-2.5 ml) were added K$_2$CO$_3$ (0.073 g, 0.53 mmol, 3 eq) and 6-fluoro-1-(methylsulfonyl)-4-(4,4,5,5-tetramethyl-1,3,2-dioxaborolan-2-yl)-1H-indole (Intermediate A-2) (0.09 g, 0.26 mmol, 1.5 eq). The solution was degassed with Ar for 20 min followed by addition of X-phos (0.017 g, 0.035 mmol, 0.2 eq.) and Pd$_2$(dba)$_3$ (0.016 g, 0.017 mmol, 0.1 eq.). The reaction mixture was refluxed at 90° C. for 16 h. After completion of reaction (monitored by TLC), reaction mixture was filtered through celite pad and washed with EtOAc. Combined organic layer was evaporated to get the crude product which was purified by prep-HPLC (R$_f$-value-0.3:50% acetone/hexane) to afford 6,7-difluoro-8-(6-fluoro-1-(methylsulfonyl)-1H-indol-4-yl)-1,4,4-trimethyl-9-(trifluoromethyl)-4,5-dihydro-[1,2,4]triazolo[4,3-a]quinoxaline (0.037 g, 37%) as white solid.

$^1$H NMR (400 MHz, DMSO-d$_6$): δ 7.77 (d, 1H), 7.63 (d, 1H), 7.28-7.34 (m, 2H), 6.64 (s, 1H), 3.51 (s, 3H), 2.47 (s, 3H), 1.77 (s, 3H), 1.38 (S, 3H).

Example 520: 4-(6,7-difluoro-1,4,4,9-tetramethyl-4,5-dihydro-[1,2,4]triazolo[4,3-a]quinoxalin-8-y)-1H-indole-7-carbonitrile

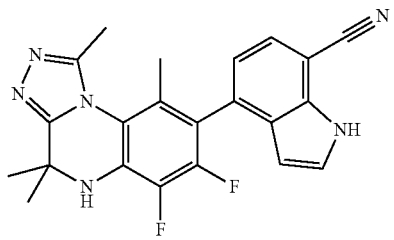 [SMILES: Cc1c(-c2ccc(C#N)c3[nH]ccc23)c(F)c(F)c2c1-n1c(C)nnc1C(C)(C)N2]

Into a microwave vial were weighed out 8-bromo-6,7-difluoro-1,4,4,9-tetramethyl-5H-[1,2,4]triazolo[4,3-a]quinoxaline (Intermediate B-38) (60.0 mg, 0.175 mmol, 1.0 eq), 4-(4,4,5,5-tetramethyl-1,3,2-dioxaborolan-2-yl)-1H-indole-7-carbonitrile (Intermediate A-75) (93.8 mg, 0.350 mmol, 2.0 eq), Pd$_2$dba$_3$ (16.0 mg, 0.018 mmol, 0.1 eq) and X-Phos (16.9 mg, 0.036 mmol, 0.2 eq). A stir bar was then added and the vial was sealed. The vial was then evacuated and backfilled with nitrogen three times, followed by the addition of 1,4-dioxane (1.3 mL), tert-amyl alcohol (1.3 mL) and 2M K$_2$CO$_3$ (0.4 mL). The reaction mixture was then sparged with nitrogen under ultra sonication, followed by heating to 60° C. for four hours. The mixture was allowed to cool to ambient temperature, diluted with water and DCM and was filtered through a hydrophobic frit. The organic layer was evaporated under reduced pressure to obtain the crude material, which was then purified via silica gel column chromatography and HPLC to obtain 4-(6,7-difluoro-1,4,4,9-tetramethyl-4,5-dihydro-[1,2,4]triazolo[4,3-a]quinoxalin-8-yl)-1H-indole-7-carbonitrile (example 520) in 76% (54.0 mg) yield as a white solid.

$^1$H NMR (DMSO-d$_6$) δ: 12.20 (s, 1H), 7.72 (d, 1H), 7.57 (t, 1H), 7.22 (d, 1H), 6.90 (d, 1H), 6.36 (dd, 1H), 2.45 (s, 3H), 1.95 (s, 3H), 1.59 (s, 3H), 1.50 (s, 3H)

In the following Tables 3, 4 and 5 it is summarized how the remaining examples have been obtained.

TABLE 3

| Ex. # | Intermediates | Synthesis in analogy to | yield (mol-%) | $^1$H-NMR |
|---|---|---|---|---|
| 48 | Int-A-2 + Int-B-9 | Ex. 49 | 31% | 1H NMR (400 MHz, DMSO-d$_6$, at 100° C.): 7.68 (d, 1H), 7.63 (s, 1H), 7.24 (d, 1H, J = 10.16 Hz), 7.11 (d, 1H), 6.57 (s, 1H), 6.26 (s, 1H), 3.48 (s, 3H), 2.69-2.67 (m, 2H), 2.53 (s, 3H), 1.57 (s, 6H), 0.54 (t, 3H). |
| 53 | Int-A-23 + Int-B-9 | Ex. 49 | 15% | 1H NMR (400 MHz, DMSO-d$_6$, at 100° C.): 8.33 (s, 1H), 7.73 (d, 1H, J = 9.0 Hz), 7.4 (d, 1H), 7.2 (d, 1H), 6.36 (s, 1H), 3.53 (s, 3H), 2.74-2.66 (m, 2H), 2.56 (s, 3H), 1.58 (s, 6H), 0.56 (t, 3H). |
| 54 | Int-A-24 + Int-B-10 | Ex. 49 | 40% | $^1$H NMR (400 MHz, DMSO-d$_6$): δ 7.44-7.38 (m, 2H), 7.24 (d, 1H), 7.0 (dd,, 1H), 6.67 (s, 1H), 6.33 (d, 1H), 4.33 (t, 2H), 3.67 (t,, 2H), 3.24 (s, 3H), 3.16 (s, 3H), 2.55 (s, 3H), 1.55 (s, 6H). |
| 55 | Int-A-20 + Int-B-10 | Ex. 49 | 63% | $^1$H NMR (400 MHz, DMSO-d$_6$): δ 7.40-7.39 (m, 2H), 7.23 (d, 1H), 7.0 (dd,, 1H), 6.67 (s, 1H), 6.33 (d, 1H), 4.9 (t, 1H), 4.22 (t, 2H), 3.74 (q, 2H), 3.17 (s, 3H), 2.56 (s, 3H), 1.55 (s, 6H). |
| 56 | Int-A-2 + Int-B-10 | Ex. 49 | 34% | $^1$H NMR (400 MHz, DMSO-d$_6$): δ 7.68-7.62 (m, 2H), 7.33-7.26 (m, 2H), 6.66 (s, 1H), 6.69 (d, 1H), 3.56 (s, 3H), 3.18 (s, 3H), 2.57 (s, 3H), 1.55 (s, 6H). |
| 57 | Int-A-12 + Int-B-10 | Ex. 49 | 33% | $^1$H NMR (400 MHz, DMSO-d$_6$): δ 7.89 (d, 1H), 7.62 (d, 1H), 7.48 (d, 1H), 7.38 (d, 1H), 7.23 (d, 1H), 6.69 (d, 1H), 3.5 (s, 3H), 3.14 (s, 3H), 2.57 (s, 3H), 1.55 (s, 6H). |
| 59 | Int-A-2 + Int-B-11 | Ex. 49 | 20% | $^1$H NMR (400 MHz, DMSO-d$_6$): δ 7.66 (dd, 1H), 7.63 (d, 1H), 7.31-7.36 (m, 1H), 7.19 (d, 1H), 6.55-6.56 (m, 2H), 3.56 (s, 3H), 2.18 (s, 3H), 1.95 (m, 1H), 1.50 (bs, 6H), 1.08 (bs, 4H). |
| 60 | Int-A-12 + Int-B11 | Ex. 49 | 26% | $^1$H NMR (400 MHz, DMSO-d$_6$): δ 7.88 (d, 1H), 7.62 (d, 1H), 7.46 (t, 1H), 7.33-7.35 (m, 1H), 7.16 (d, J = 10.4 Hz, 1H), 6.55 (d, 1H), 6.50 (s, 1H), 3.50 (s, 3H), 2.15 (s, 3H), 1.90 (m, 1H), 1.50 (bs, 6H), 1.07-1.11 (m, 4H). |
| 61 | Int-A-20 + Int-B-11 | Ex. 49 | 27% | $^1$H NMR (400 MHz, DMSO-d$_6$): δ 7.38-7.40 (m, 2H), 7.15 (d, 1H), 6.96 (d, 1H), 6.46 (s, 1H), 6.16 (d, 1H), 4.90 (t, J = 5.2 Hz, 1H), |

TABLE 3-continued

| Ex. # | Intermediates | Synthesis in analogy to | yield (mol-%) | $^1$H-NMR |
|---|---|---|---|---|
| | | | | 4.21 (t, 2H), 3.73 (q, 2H), 2.19 (s, 3H), 1.92 (m, 1H), 1.50 (bs, 6H), 1.07-1.12 (m, 4H). |
| 62 | Int-A-15 + Int-B-11 | Ex. 49 | 29% | $^1$H NMR (400 MHz, DMSO-d$_6$): δ 10.61 (s, 1H), 7.26 (dd, 1H), 7.15-7.18 (m, 2H), 6.93 (d, 1H), 6.46 (s, 1H), 2.25 (s, 3H), 2.07-2.08 (m, 4H), 1.51 (bs, 6H), 1.09 (bs, 4H). |
| 63 | Int-A-2 + Int-B-12 | Ex. 49 | 20% | $^1$H NMR (400 MHz, DMSO-d$_6$): δ 10.61 (s, 1H), 7.26 (dd, 1H), 7.15-7.18 (m, 2H), 6.93 (d, 1H), 6.46 (s, 1H), 2.25 (s, 3H), 2.07-2.08 (m, 4H), 1.51 (bs, 6H), 1.09 (bs, 4H). |
| 64 | Int-A-22 + Int-B-12 | Ex. 49 | 26% | $^1$H NMR (400 MHz, DMSO-d$_6$): δ 7.88 (d, 1H), 7.62 (d, 1H), 7.46 (t, J = 8.0 Hz, 1H), 7.33-7.35 (m, 1H), 7.16 (d, J = 10.4 Hz, 1H), 6.55 (d, 1H), 6.50 (s, 1H), 3.50 (s, 3H), 2.15 (s, 3H), 1.90 (m, 1H), 1.50 (bs, 6H), 1.07-1.11 (m, 4H). |
| 65 | Int-A-20 + Int-B-12 | Ex. 49 | 27% | $^1$H NMR (400 MHz, DMSO-d$_6$): δ 7.38-7.40 (m, 2H), 7.15 (d, 1H), 6.96 (d, J = 10.0 Hz, 1H), 6.46 (s, 1H), 6.16 (d, 1H), 4.90 (t, 1H), 4.21 (t, 2H), 3.73 (q, 2H), 2.19 (s, 3H), 1.92 (m, 1H), 1.50 (bs, 6H), 1.07-1.12 (m, 4H). |
| 66 | Int-A-15 + Int-B-12 | Ex. 49 | 29% | $^1$H NMR (400 MHz, DMSO-d$_6$): δ 10.61 (s, 1H), 7.26 (dd, 1H), 7.15-7.18 (m, 2H), 6.93 (d, 1H), 6.46 (s, 1H), 2.25 (s, 3H), 2.07-2.08 (m, 4H), 1.51 (bs, 6H), 1.09 (bs, 4H). |

TABLE 4

| Ex. # | Intermediates | Synthesis in analogy to | yield (mol-%) | m/z [M + 1] | $^1$H-NMR |
|---|---|---|---|---|---|
| 300 | Int-B-7 + Int-A-43 | Exp. 465 | 22% | | $^1$H NMR (DMSO-d$_6$) δ: 7.54 (m$_c$, 1H), 7.41 (d, 1H), 7.23 (dd, 1H), 7.13 (d, 1H), 7.02 (d, 1H), 6.44-6.40 (m, 1H), 6.21-6.17 (m, 1H), 4.38 (t, 2H), 3.70 (t, 2H), 3.25 (d, 3H), 2.50 (s, 3H), 2.03 (s, 3H), 1.55-1.51 (m, 6H) |
| 304 | Int-B-7 + 1-methyl-4-(4,4,5,5-tetramethyl-[1,3,2]dioxaborolan-2-yl)-1H-indazole | Exp. 490 | 57% | | $^1$H NMR (DMSO-d$_6$) δ: 7.86 (s, 1H), 7.68 (d, 1H), 7.49 (dd, 1H), 7.20 (d, 1H), 7.16 (d, 1H), 6.51 (s, 1H), 4.10 (s, 3H), 2.52 (s, 3H), 2.04 (s, 3H), 1.53 (s, 6H) |
| 305 | Int-B-7 + Int-A-44 | Exp. 465 | 88% | | $^1$H NMR (DMSO-d$_6$) δ: 7.61 (dd, 1H), 7.38 (d, 1H), 7.27 (dd, 1H), 7.11 (d, 1H), 7.08-7.03 (m, 1H), 6.42 (d, 1H), 6.15 (dd, 1H), 2.49 (s, 3H), 2.02 (s, 3H), 1.52 (s, 6H), 1.34-1.25 (m, 1H), 1.13-1.05 (m, 2H), 1.02-0.96 (m, 2H) |
| 308 | Int-B-30 + Int-A-12 | Exp. 465 | 70% | | $^1$H NMR (DMSO-d$_6$) δ: 7.91 (d, 1H), 7.66 (d, 1H), 7.48 (dd, 1H), 7.31 (d, 1H), 7.15 (d, 1H), 6.55 (dd, 1H), 6.50 (d, 1H), 3.51 (s, 3H), 2.84 (s, 2H), 2.01 (s, 3H), 1.75-1.34 (m, 6H), 1.29 (t, 3H) |
| 316 | Int-B-30 + Int-A-15 | Exp. 465 | 80% | | $^1$H NMR (DMSO-d$_6$) δ: 10.59 (d, 1H), 7.27 (dd, 1H), 7.21-7.12 (m, 2H), 6.90 (d, 1H), 6.45 (d, 1H), 2.86 (s, 2H), 2.27 (d, 3H), 1.98 (s, 3H), 1.69-1.39 (m, 6H), 1.29 (t, 3H) |
| 322 | Int-B-30 + Int-A-43 | Exp. 465 | 66% | | $^1$H NMR (DMSO-d$_6$) δ: 7.53 (dd, 1H), 7.41 (d, 1H), 7.22 (dd, 1H), 7.12 (d, 1H), 7.01 (d, 1H), 6.41 (d, 1H), 6.16 (m$_c$, 1H), 4.37 (t, 2H), 3.70 (t, 2H), 3.25 (d, 3H), 2.84 (s, 2H), 2.02 (s, 3H), 1.52 (s, 6H), 1.28 (t, 3H) |
| 323 | Int-B-30 + Int-A-2 | Exp. 465 | 82% | | $^1$H NMR (DMSO-d$_6$) δ: 7.69-7.67 (m, 1H), 7.66 (d, 1H), 7.27 (d, 1H), 7.19 (d, 1H), 6.54 (d, 1H), 6.53 (dd, 1H), 3.56 (s, 3H), 2.83 (s, 2H), 2.03 (s, 3H), 1.74-1.33 (m, 6H), 1.28 (t, 3H) |
| 326 | Int-B-7 + Int-A-42 | Exp. 490 | 62% | | $^1$H NMR (DMSO-d$_6$) δ: 7.60 (d, 1H), 7.44 (d, 1H), 7.27 (dd, 1H), 7.14 (d, 1H), 7.08-7.04 (m, 1H), 6.51-6.30 (m, 2H), 6.27 (dd, 1H), 4.73 (td, 2H), 2.50 (s, 3H), 2.02 (s, 3H), 1.52 (s, 6H) |
| 340 | Int-B-7 + Int-A-23 | Exp. 465 | 77% | | $^1$H NMR (DMSO-d$_6$) δ: 8.47-8.43 (m, 1H), 7.72 (dd, 1H), 7.47 (dd, 1H), 7.29 (dd, 1H), 6.63 (d, 1H), 3.57 (d, 3H), 2.54 (d, 3H), 2.08 (s, 3H), 1.53 (s, 6H) |
| 349 | Int-B-7 + Int-A-45 | Exp. 465 | 57% | | $^1$H NMR (DMSO-d$_6$) δ: 7.89 (d, 1H), 7.65 (d, 1H), 7.54-7.46 (m, 1H), 7.35 (d, 1H), 7.17 (d, 1H), 6.66 (d, 1H), 6.51 (d, 1H), 6.07 (d, 2H), 2.50 (s, 3H), 2.01 (s, 3H), 1.58 (s, 3H), 1.48 (s, 6H) |
| 350 | Int-B-7 + Int-A-47 | Exp. 465 | 56% | | $^1$H NMR (DMSO-d$_6$) δ: 7.90 (m$_c$, 1H), 7.65 (m$_c$, 1H), 7.47 (m$_c$, 1H), 7.31 (m$_c$, 1H), 7.17 (m$_c$, 1H), 6.58 (m$_c$, 1H), 6.50 (t, 1H), 3.66 (m$_c$, 2H), 2.50-2.49 (m, 3H), 2.00 (s, 3H), 1.45 (s, 6H), 1.10 (m$_c$, 3H) |

TABLE 4-continued

| Ex. # | Intermediates | Synthesis in analogy to | yield (mol-%) | m/z [M + 1] | ¹H-NMR |
|---|---|---|---|---|---|
| 352 | Int-B-7 + 3-Methyl-1H-indazole-7-boronic acid | Exp. 465 | 20% | | ¹H NMR (DMSO-d₆) δ: 12.56 (s, 1H), 7.74 (dd, 1H), 7.26 (dd, 1H), 7.20-7.12 (m, 2H), 6.47 (d, 1H), 2.55 (s, 3H), 2.53 (s, 3H), 1.97 (s, 3H), 1.53 (s, 6H) |
| 355 | Int-B-30 + 3-methyl-7-(4,4,5,5-tetramethyl-1,3,2-dioxaborolan-2-yl)-1H-indole | Exp. 465 | 81% | | ¹H NMR (DMSO-d₆) δ: 10.47 (d, 1H), 7.51 (d, 1H), 7.14-7.06 (m, 3H), 6.99 (d, 1H), 6.40 (d, 1H), 2.93-2.78 (m, 2H), 2.29 (d, 3H), 1.96 (s, 3H), 1.67-1.43 (m, 6H), 1.28 (t, 3H) |
| 366 | Int-B-7 + Int-A-30 | Exp. 465 | 97% | | ¹H NMR (DMSO-d₆) δ: 7.90 (d, 1H), 7.64 (d, 1H), 7.47 (dd, 1H), 7.31 (d, 1H), 7.18 (d, 1H), 6.58 (d, 1H), 6.50 (d, 1H), 3.84 (m_c, 1H), 2.50 (s, 3H), 2.00 (s, 3H), 1.64-1.42 (m, 6H), 1.23 (s, 3H), 1.22 (s, 3H) |
| 374 | Int-B-30 + Int-A-23 | Exp. 465 | 85% | | ¹H NMR (DMSO-d₆) δ: 8.42 (d, 1H), 7.75-7.70 (m, 1H), 7.49-7.44 (m, 1H), 7.29 (d, 1H), 6.62 (d, 1H), 3.57 (s, 3H), 2.94-2.80 (m, 2H), 2.10-2.06 (m, 3H), 1.67-1.42 (m, 6H), 1.30 (t, 3H) |
| 375 | Int-B-7 + Int-A-46 | Exp. 465 | 67% | | ¹H NMR (DMSO-d₆) δ: 7.52 (d, 1H), 7.45 (d, 1H), 7.23 (dd, 1H), 7.13 (d, 1H), 7.02 (d, 1H), 6.42 (d, 1H), 6.20-6.13 (m, 1H), 4.30 (t, 2H), 2.65 (t, 2H), 2.49 (d, 3H), 2.21 (d, 6H), 2.03 (s, 3H), 1.57-1.48 (m, 6H) |
| 378 | Int-B-7 + Int-A-22 | Exp. 465 | 99% | | ¹H NMR (DMSO-d₆) δ: 8.45 (s, 1H), 8.03 (d, 1H), 7.73 (dd, 1H), 7.46 (d, 1H), 7.25 (d, 1H), 6.58 (d, 1H), 3.53 (s, 3H), 2.52 (d, 3H), 2.05 (s, 3H), 1.54 (s, 6H) |
| 389 | Int-B-30 + Int-A-22 | Exp. 465 | 96% | | ¹H NMR (DMSO-d₆) δ: 8.41 (d, 1H), 8.02 (d, 1H), 7.73 (ddd, 1H), 7.46 (d, 1H), 7.24 (d, 1H), 6.57 (d, 1H), 3.53 (d, 3H), 2.86 (s, 2H), 2.04 (s, 3H), 1.72-1.38 (m, 6H), 1.30 (t, 3H) |
| 391 | Int-B-7 + Int-A-48 | Exp. 465 | 86% | | ¹H NMR (DMSO-d₆) δ: 7.95 (dd, 1H), 7.66 (dd, 1H), 7.50-7.44 (m, 1H), 7.31 (d, 1H), 7.18 (dd, 1H), 6.58 (dd, 1H), 6.50 (d, 1H), 3.15 (m_c, 1H), 2.53-2.47 (m, 3H), 2.01 (s, 3H), 1.53 (m, 6H), 1.33-1.25 (m, 2H), 1.15-1.07 (m, 2H) |
| 464 | Int-B-9 + Int-A-20 | Exp. 465 | 43% | | ¹H NMR (DMSO-d₆) δ: 7.43 (d, 1H), 7.42-7.38 (m, 1H), 7.13 (d, 1H), 6.55 (d, 1H), 6.28-6.18 (m, 1H), 4.23 (t, 2H), 3.76 (m_c, 2H), 2.67 (s, 2H), 2.54 (s, 3H), 1.78-1.35 (m, 6H), 0.49 (t, 3H) |
| 467 | Int-B-45 + Int-A-23 | Exp. 465 | 50% | | ¹H NMR (DMSO-d₆) δ: 8.52 (s, 1H), 7.72 (dd, 1H), 7.52 (s, 1H), 7.29 (d, 1H), 6.64 (d, 1H), 3.57 (s, 3H), 2.65 (s, 3H), 2.02 (s, 1H), 1.80 (s, 3H), 1.19 (s, 3H), 0.65 (s, 1H), 0.25 (s, 1H), −0.20 (d, 2H) |
| 468 | Int-B-7 + indole-4-boronic acid | Exp. 465 | 99% | | ¹H NMR (DMSO-d₆) δ: 11.24 (s, 1H), 7.44 (d, 1H), 7.40 (t, 1H), 7.18 (t, 1H), 7.14 (d, 1H), 6.99 (d, 1H), 6.40 (d, 1H), 6.19 (dd, 1H), 2.50 (d, 3H), 2.03 (s, 3H), 1.53 (s, 6H) |
| 469 | Int-B-10 + indole-4-boronic acid | Exp. 465 | 71% | | ¹H NMR (DMSO-d₆) δ: 11.19 (s, 1H), 7.44 (d, 1H), 7.37 (t, 1H), 7.23-7.15 (m, 2H), 7.10 (d, 1H), 6.57 (d, 1H), 6.35 (t, 1H), 3.13 (s, 3H), 2.57 (s, 3H), 1.56 (s, 6H) |
| 470 | Int-B-10 + Int-A-1 | Exp. 465 | 75% | | ¹H NMR (DMSO-d₆) δ: 11.26 (s, 1H), 7.38 (t, 1H), 7.25 (d, 1H), 7.22 (dd, 1H), 6.99 (dd, 1H), 6.64 (d, 1H), 6.35 (t, 1H), 3.16 (s, 3H), 2.57 (s, 3H), 1.56 (s, 6H) |
| 471 | Int-B-45 + Int-A-2 | Exp. 465 | 67% | | ¹H NMR (DMSO-d₆) δ: 7.69-7.63 (m, 2H), 7.47-7.23 (m, 1H), 7.19 (d, 1H), 6.69-6.64 (m, 1H), 6.56 (d, 1H), 3.54 (s, 3H), 2.61 (s, 3H), 2.08-1.82 (m, 1H), 1.79 (s, 3H), 1.18 (s, 3H), 0.62 (s, 1H), 0.21 (s, 1H), −0.19 (d, 2H) |
| 472 | Int-B-45 + 3-methyl-7-(4,4,5,5-tetramethyl-1,3,2-dioxaborolan-2-yl)-1H-indole | Exp. 465 | 63% | | ¹H NMR (DMSO-d₆) δ: 10.49 (s, 1H), 7.50 (d, 1H), 7.27-6.70 (m, 4H), 6.42 (d, 1H), 2.64 (s, 3H), 2.30 (s, 3H), 2.04-1.86 (m, 1H), 1.79 (s, 3H), 1.19 (s, 3H), 0.55 (s, 1H), 0.06 (s, 1H), −0.14-−0.34 (m, 2H) |
| 473 | Int-B-10 + 4-(tetramethyl-1,3,2-dioxaborolan-2-yl)-6-(trifluoromethyl)-1H-indole | Exp. 465 | 68% | | ¹H NMR (DMSO-d₆) δ: 11.64 (s, 1H), 7.78 (d, 1H), 7.64 (t, 1H), 7.36 (d, 1H), 7.28 (d, 1H), 6.67 (d, 1H), 6.47 (t, 1H), 3.15 (s, 3H), 2.57 (s, 3H), 1.57 (s, 6H) |
| 474 | Int-B-45 + Int-A-12 | Exp. 465 | 45% | | ¹H NMR (DMSO-d₆) δ: 7.89 (d, 1H), 7.64 (d, 1H), 7.48 (t, 1H), 7.36 (s, 1H), 7.15 (d, 1H), 6.67 (d, 1H), 6.51 (d, 1H), 3.49 (s, 3H), 3.35 (s, 1H), 2.61 (s, 3H), 1.79 (s, 3H), 1.18 (s, 3H), 0.60 (s, 1H), 0.13 (s, 1H), −0.20 (s, 2H) |
| 475 | Int-B-7 + Int-A-54 | Exp. 465 | 91% | | ¹H NMR (DMSO-d₆) δ: 7.16 (d, 1H), 7.15 (d, 1H), 6.48 (d, 1H), 7.72 (d, 1H), 7.55 (d, 1H), 6.52 (dd, 1H), |

TABLE 4-continued

| Ex. # | Intermediates | Synthesis in analogy to | yield (mol-%) | m/z [M + 1] | $^1$H-NMR |
|---|---|---|---|---|---|
| 476 | Int-B-10 + Int-A-54 | Exp. 465 | 63% | | 3.48 (s, 3H), 2.52 (s, 3H), 2.50 (s, 3H), 2.01 (s, 3H), 1.73-1.17 (m, 6H) $^1$H NMR (DMSO-d$_6$) δ: 7.72 (m$_c$, 1H), 7.53 (d, 1H), 7.23 (t, 1H), 7.21 (d, 1H), 6.66 (d, 1H), 6.63 (dd, 1H), 3.47 (s, 3H), 3.16 (s, 3H), 2.58 (s, 3H), 2.53 (s, 3H), 1.56 (s, 6H) |
| 477 | Int-B-7 + 4-(4,4,5,5-Tetramethyl-1,3,2-dioxaborolan-2-yl)-1H-indole-6-carbonitrile | Exp. 465 | 67% | | $^1$H NMR (DMSO-d$_6$) δ: 11.84-11.80 (m, 1H), 7.95 (d, 1H), 7.71 (t, 1H), 7.38 (d, 1H), 7.20 (d, 1H), 6.50 (d, 1H), 6.34 (t, 1H), 2.51 (s, 3H), 2.02 (s, 3H), 1.55-1.49 (m, 6H) |
| 478 | Int-B-10 + Int-A-16 | Exp. 465 | 48% | | $^1$H NMR (DMSO-d$_6$) δ: 10.56 (d, 1H), 7.36 (dd, 1H), 7.22 (d, 1H), 7.08 (d, 1H), 6.98 (dd, 1H), 6.64 (d, 1H), 3.18 (d, 3H), 2.57 (s, 3H), 1.92 (m$_c$, 1H), 1.56 (s, 6H), 0.86 (m$_c$, 2H), 0.66-0.55 (m, 2H) |
| 484 | Int-B-7 + Int-A-59 | Exp. 465 | 24% | | $^1$H NMR (DMSO-d$_6$) δ: 7.48 (dd, 1H), 7.38 (d, 1H), 7.25 (dd, 1H), 7.12 (d, 1H), 7.06-7.00 (m, 1H), 6.42 (d, 1H), 6.18 (dd, 1H), 3.84 (s, 3H), 2.49 (s, 3H), 2.02 (s, 3H), 1.52 (s, 6H) |
| 485 | Int-B-10 + Int-A-59 | Exp. 465 | 52% | | $^1$H NMR (DMSO-d$_6$) δ: 7.47 (d, 1H), 7.35 (d, 1H), 7.25 (dd, 1H), 7.19 (d, 1H), 7.14 (dd, 1H), 6.58 (d, 1H), 6.33 (dd, 1H), 3.83 (s, 3H), 3.12 (s, 3H), 2.57 (s, 3H), 1.56 (s, 6H) |
| 489 | Int-B-10 + 7-fluoro-4-(4,4,5,5-tetramethyl-1,3,2-dioxaborolan-2-yl)-1H-indazole | Exp. 465 | 36% | | $^1$H NMR (DMSO-d$_6$) δ: 8.06 (dd, 1H), 7.30 (d, 1H), 7.28 (d, 1H), 7.19 (dd, 1H), 6.69 (s, 1H), 3.13 (s, 3H), 2.61 (s, 3H), 1.56 (s, 6H) |
| 491 | Int-B-25 + Int-A-53 | Exp. 465 | 57% | | $^1$H NMR (DMSO-d$_6$) δ: 7.90 (d, 1H), 7.62 (d, 1H), 7.46 (t, 1H), 7.30 (d, 1H), 7.17 (d, 1H), 6.58 (d, 1H), 6.50 (d, 1H), 3.61 (d, 2H), 2.50 (s, 3H), 2.01 (s, 3H), 1.77-1.33 (m, 6H), 0.90-0.76 (m, 1H), 0.42-0.27 (m, 2H), −0.00--0.11 (m, 2H) |
| 492 | Int-B-10 + Int-A-66 | Exp. 465 | 59% | | $^1$H NMR (DMSO-d$_6$) δ: 8.22-8.18 (m, 1H), 7.88 (d, 1H), 7.69 (d, 1H), 7.32 (d, 1H), 6.82 (dd, 1H), 6.77 (d, 1H), 3.64 (s, 3H), 3.18 (s, 3H), 2.58 (s, 3H), 1.57 (s, 6H) |
| 494 | Int-B-10 7-fluoro-4-(4,4,5,5-tetramethyl-1,3,2-dioxaborolan-2-yl)-1H-indole | Exp. 490 | 50% | | $^1$H NMR (DMSO-d$_6$) δ: 11.69 (t, 1H), 7.44 (t, 1H), 7.20 (d, 1H), 7.09-6.98 (m, 2H), 6.59 (d, 1H), 6.41 (m, 1H), 3.12 (s, 3H), 2.57 (s, 3H), 1.56 (s, 6H) |
| 495 | Int-B-10 + 6-fluoro-4-(4,4,5,5-tetramethyl-1,3,2-dioxaborolan-2-yl)-1H-indazole | Exp. 465 | 22% | | $^1$H NMR (DMSO-d$_6$) δ: 13.21 (s, 1H), 7.99 (s, 1H), 7.39-7.32 (m, 2H), 7.14 (dd, 1H), 6.78-6.73 (m, 1H), 3.17 (s, 3H), 2.61 (s, 3H), 1.56 (s, 6H) |
| 496 | Int-B-7 + 6-fluoro-4-(4,4,5,5-tetramethyl-1,3,2-dioxaborolan-2-yl)-1H-indazole | Exp. 465 | 51% | | $^1$H NMR (DMSO-d$_6$) δ: 13.28 (s, 1H), 7.89 (d, 1H), 7.41-7.34 (m, 1H), 7.26 (d, 1H), 7.09 (dd, 1H), 6.55 (d, 1H), 2.53 (s, 3H), 2.07 (s, 3H), 1.53 (s, 6H) |
| 497 | Int-B-7 + Int-A-68 | Exp. 465 | 20% | | $^1$H NMR (DMSO-d$_6$) δ: 7.66 (dd, 1H), 7.63 (dd, 1H), 7.29-7.23 (m, 1H), 7.21 (d, 1H), 6.58 (d, 1H), 6.55 (d, 1H), 3.68 (d, 2H), 2.51-2.50 (m, 3H), 2.03 (s, 3H), 1.53 (s, 6H), 0.86 (tt, 1H), 0.36 (d, 2H), −0.01--0.06 (m, 2H) |
| 502 | Int-B-51 + Int-A-12 | Exp. 465 | 37% | | $^1$H NMR (DMSO-d$_6$) δ: 7.95 (m, 1H), 7.65 (d, 1H), 7.51 (dd, 1H), 7.34 (d, 1H), 6.55 (d, 1H), 6.45 (s, 1H), 3.52 (s, 3H), 2.44 (s, 3H), 1.98 (s, 3H), 1.63 (s, 3H), 1.52 (s, 3H) |
| 503 | Int-B-51 + Int-A-2 | Exp. 465 | 70% | | $^1$H NMR (DMSO-d$_6$) δ: 7.73 (m, 1H), 7.66 (d, 1H), 7.35 (dd, 1H), 6.56 (d, 1H), 6.50 (s, 1H), 3.59 (s, 3H), 2.45 (s, 3H), 2.01 (s, 3H), 1.64-1.60 (m, 3H), 1.53 (s, 3H), |
| 504 | Int-B-7 + 4-(4,4,5,5-tetramethyl-1,3,2-dioxaborolan-2-yl)-1H-indazole | Exp. 465 | 13% | | $^1$H NMR (DMSO-d$_6$) δ: 7.88 (s, 1H), 7.58 (d, 1H), 7.45 (dd, 1H), 7.21 (d, 1H), 7.12 (d, 1H), 6.50 (d, 1H), 2.52 (s, 3H), 2.05 (s, 3H), 1.53 (s, 6H) |
| 505 | Int-B-10 + Int-A-48 | Exp. 465 | 62% | | $^1$H NMR (DMSO-d$_6$) δ: 7.94 (dt, 1H), 7.64 (d, 1H), 7.47 (dd, 1H), 7.38 (dd, 1H), 7.24 (d, 1H), 6.72-6.64 (m, 2H), 3.17-3.09 (m, 4H), 2.58 (s, 3H), 1.56 (s, 6H), 1.28 (dd, 2H), 1.11 (dd, 2H) |

TABLE 4-continued

| Ex. # | Intermediates | Synthesis in analogy to | yield (mol-%) | m/z [M + 1] | ¹H-NMR |
|---|---|---|---|---|---|
| 506 | Int-B-7 + Int-A-69 | Exp. 465 | 90% | | ¹H NMR (DMSO-$d_6$) δ: 11.37 (t, 1H), 7.49 (dd, 1H), 7.45 (t, 1H), 7.17 (d, 1H), 7.03 (d, 1H), 6.47 (d, 1H), 6.20 (ddd, 1H), 2.49 (s, 3H), 2.03 (s, 3H), 1.52 (s, 6H) |
| 507 | Int-B-7 + 4-(4,4,5,5-tetramethyl-1,3,2-dioxaborolan-2-yl)-6-(trifluoromethyl)-1H-indazole | Exp. 465 | 35% | | ¹H NMR (DMSO-$d_6$) δ: 8.06 (s, 1H), 7.98 (s, 1H), 7.41 (s, 1H), 7.29 (d, 1H), 6.57 (d, 1H), 2.54 (s, 3H), 2.04 (s, 3H), 1.53 (s, 6H) |
| 508 | Int-B-51 + Int-A-15 | Exp. 465 | 67% | | ¹H NMR (DMSO-$d_6$) δ: 10.70 (d, 1H), 7.33 (dd, 1H), 7.18 (dd, 1H), 6.97 (dd, 1H), 6.41 (s, 1H), 2.45 (s, 3H), 2.27 (s, 3H), 1.96 (s, 3H), 1.61 (s, 3H), 1.55 (s, 3H) |
| 509 | Int-B-51 + Int-A-22 | Exp. 465 | 39% | | ¹H NMR (DMSO-$d_6$) δ: 8.46 (s, 1H), 8.08 (d, 1H), 7.77 (dd, 1H), 7.49 (d, 1H), 6.52 (s, 1H), 3.56 (s, 3H), 2.47 (s, 3H), 2.01 (s, 3H), 1.64 (s, 3H), 1.53 (s, 3H) |
| 510 | Int-B-51 + Int-A-23 | Exp. 465 | 4% | | ¹H NMR (DMSO-$d_6$) δ: 8.47 (s, 1H), 7.81-7.75 (m, 1H), 7.54 (dd, 1H), 6.58 (s, 1H), 3.60 (s, 3H), 2.48 (s, 3H), 2.04 (s, 3H), 1.58 (d, 6H) |
| 511 | Int-B-10 + Int-A-44 | Exp. 465 | 20% | | ¹H NMR (DMSO-$d_6$) δ: 7.60 (dd, 1H), 7.35 (d, 1H), 7.27 (dd, 1H), 7.21-7.13 (m, 2H), 6.59 (d, 1H), 6.29 (dd, 1H), 3.48 (tt, 1H), 3.13 (s, 3H), 2.56 (s, 3H), 1.55 (s, 6H), 1.09 (td, 2H), 1.02-0.96 (m, 2H) |
| 512 | Int-B-38 + indole-4-boronic acid | Exp. 465 | 52% | | ¹H NMR (DMSO-$d_6$) δ: 11.27 (s, 1H), 7.49 (d, 1H), 7.40 (t, 1H), 7.21 (t, 1H), 7.01 (d, 1H), 6.77 (s, 1H), 6.14 (t, 1H), 2.45 (s, 3H), 1.97 (s, 3H), 1.60 (s, 3H), 1.49 (s, 3H) |
| 513 | Int-B-38 + Int-3-methyl-7-(4,4,5,5-tetramethyl-1,3,2-dioxaborolan-2-yl)-1H-indole | Exp. 465 | 73% | | ¹H NMR (DMSO-$d_6$) δ: 10.59 (d, 1H), 7.57 (d, 1H), 7.17-7.08 (m, 2H), 7.05 (dd, 1H), 6.78 (d, 1H), 2.47 (s, 3H), 2.30 (d, 3H), 1.93 (s, 3H), 1.56 (d, 6H) |
| 514 | Int-B-38 + Int-A-15 | Exp. 465 | 55% | | ¹H NMR (DMSO-$d_6$) δ: 7.33 (dd, 1H), 7.19 (s, 1H), 6.99 (dd, 1H), 6.84 (d, 1H), 2.47 (s, 3H), 2.27 (d, 3H), 1.95 (s, 3H), 1.57 (s, 3H), 1.55 (s, 3H) |
| 515 | Int-B-10 + Int-A-71 | Exp. 465 | 4% | 396.1 | |
| 517 | Int-B-7 7-fluoro-4-(4,4,5,5-tetramethyl-1,3,2-dioxaborolan-2-yl)-1H-indazole | Exp. 465 | 46% | | ¹H NMR (DMSO-$d_6$) δ: 7.99 (d, 1H), 7.28 (dd, 1H), 7.20 (d, 1H), 7.09 (dd, 1H), 6.50 (d, 1H), 2.52 (s, 3H), 2.03 (s, 3H), 1.53 (s, 6H) |
| 521 | Int-B-38 + Int-A-73 | Exp. 465 | 59% | | ¹H NMR (DMSO-$d_6$) δ: 7.42 (dt, 1H), 7.38 (d, 1H), 6.99 (dd, 1H), 6.84 (d, 1H), 6.14 (d, 1H), 3.82 (d, 3H), 2.44 (s, 3H), 1.97 (s, 3H), 1.59 (s, 3H), 1.50 (s, 3H), |
| 522 | Int-B-38 + Int-A-77 | Exp. 520 | 55% | | ¹H NMR (DMSO-$d_6$) δ: 7.49 (d, 1H), 7.46-7.42 (m, 1H), 7.01 (d, 1H), 6.87 (d, 1H), 6.46 (d, 1H), 3.88 (s, 3H), 2.45 (s, 3H), 1.97 (s, 3H), 1.58 (s, 3H), 1.49 (s, 3H) (MeO-ommited by water) |
| 523 | Int-B-7 + Int-A-77 | Exp. 520 | 87% | | ¹H NMR (DMSO-$d_6$) δ: 7.49 (d, 1H), 7.42-7.38 (m, 1H), 7.16 (d, 1H), 6.96 (d, 1H), 6.51 (d, 1H), 6.50-6.45 (m, 1H), 3.89 (s, 3H), 3.48 (s, 3H), 2.50 (s, 3H), 2.02 (s, 3H), 1.52 (s, 6H) |
| 524 | Int-B-10 + Int-A-77 | Exp. 465 | 86% | | ¹H NMR (DMSO-$d_6$) δ: 7.47 (d, 1H), 7.42-7.38 (m, 1H), 7.24 (d, 1H), 7.03 (d, 1H), 6.69 (d, 1H), 6.60 (dd, 1H), 3.89 (s, 3H), 3.46 (s, 3H), 3.18 (s, 3H), 2.57 (s, 3H), 1.55 (s, 6H) |
| 525 | Int-B-53 + Int-A-23 | Exp. 465 | 41% | | ¹H NMR (DMSO-$d_6$) δ: 8.48 (s, 1H), 7.78 (d, 1H), 7.54 (d, 1H), 6.58 (s, 1H), 3.60 (s, 3H), 2.48 (d, 3H), 2.05 (s, 3H), 1.62 (s, 3H), 1.55 (s, 3H) |
| 526 | Int-B-53 + Int-A-15 | Exp. 465 | 61% | | ¹H NMR (DMSO-$d_6$) δ: 10.72-10.68 (m, 1H), 7.33 (dd, 1H), 7.21-7.12 (m, 1H), 6.97 (dd, 1H), 6.41 (s, 1H), 2.45 (s, 3H), 2.27 (d, 3H), 1.96 (s, 3H), 1.61 (s, 3H), 1.55 (s, 3H) |
| 527 | Int-B-53 + Int-A-22 | Exp. 465 | 73% | | ¹H NMR (DMSO-$d_6$) δ: 8.46 (s, 1H), 8.08 (d, 1H), 7.81-7.75 (m, 1H), 7.49 (d, 1H), 6.53 (s, 1H), 3.56 (s, 3H), 2.47 (s, 3H), 2.01 (s, 3H), 1.65 (s, 3H), 1.53 (s, 3H) |

TABLE 5

| Ex. # | Intermediates | Synthesis in analogy to | yield (mol-%) | $^1$H NMR |
|---|---|---|---|---|
| 447 | Int-A2 + Int-B-38 | Ex. 446 | 56% | $^1$H NMR (400 MHz, DMSO-d$_6$): δ 7.72 (dd, 1H), 7.66 (d, 1H), 7.36 (dd, 1H), 6.93 (s, 1H), 6.58 (d, 1H), 3.59 (s, 3H), 2.45 (s, 3H), 1.97 (s, 3H), 1.57 (s, 3H), 1.50 (s, 3H). |
| 449 | Int-A-20 + Int-B-38 | Ex. 448 | 59% | $^1$H NMR (DMSO-d$_6$) δ = 7.46 (d, 1H), 7.41 (m, 1H), 6.98 (d, 1H), 6.85 (m, 1H), 6.13 (s, 1H), 4.92 (s, 1H), 4.22 (s, 2H), 3.74 (s, 2H), 2.44 (s, 3H), 1.97 (s, 3H), 1.58 (s, 3H), 1.48 (s, 3H). |
| 451 | Int-A-22 + Int-B-38 | Ex. 448 | 54% | $^1$H NMR (DMSO-d$_6$) δ = 8.49 (s, 1H), 8.07 (d, 1H), 7.77 (t, 1H), 7.51 (d, 1H), 6.95 (s, 1H), 3.55 (s, 3H), 2.48 (s, 3H), 1.98 (s, 3H), 1.52-1.58 (m, 6H). |
| 452 | Int-A-23 + Int-B-38 | Ex. 448 | 58% | $^1$H NMR (DMSO-d$_6$) δ = 8.51 (S, 1H), 7.77 (d, 1H), 7.57 (d, 1H), 7.02 (s, 1H), 3.59 (s, 3H), 2.02 (s, 3H), 1.53-1.56 (m, 6H). (CH$_3$-ommited by DMSO) |
| 453 | Int-A-2 + Int-B-41 | Ex. 450 | 28% | $^1$H NMR (DMSO-d$_6$) δ = 7.66-7.64 (m, 2H), 7.29-7.26 (m, 1H), 7.18-7.16 (m, 1H), 6.58-6.56 (m, 2H), 4.84 (s, 1H), 4.55 (s, 2H), 3.56 (s, 3H), 1.52 (s, 6H). (CH$_3$-ommited by DMSO) |
| 454 | Int-A-15 + Int-B-42 | Ex. 450 | 54% | $^1$H NMR (DMSO-d$_6$) δ = 10.62 (s, 1H), 7.28-7.25 (m, 2H), 7.17 (s, 1H), 6.90-6.88 (m, 1H), 6.06 (s, 1H), 2.25 (s, 3H), 1.97 (s, 3H), 1.62-1.48 (m, 6H). (CH$_3$-ommited by DMSO) |
| 456 | Int-A-12 + Int-B-42 | Ex. 450 | 55% | $^1$H NMR (DMSO-d$_6$) δ = 7.91 (d, 1H), 7.65-7.64 (m, 1H), 7.49 (t, 1H), 7.31-7.29 (m, 1H), 7.27 (s, 1H), 6.57-6.56 (m, 1H), 6.10 (s, 1H), 3.50 (s, 3H), 2.47 (s, 3H), 2.01 (s, 3H), 1.62-1.47 (m, 6H). |
| 457 | Int-A-2 + Int-B-42 | Ex. 450 | 52% | $^1$H NMR (DMSO-d$_6$) δ = 7.68-7.65 (m, 2H), 7.31-7.27 (m, 2H), 6.56-6.55 (m, 1H), 6.15 (s, 1H), 3.56 (s, 3H), 2.03 (s, 3H), 1.59-1.48 (m, 6H). (CH$_3$-ommited by DMSO) |
| 458 | Int-A-22 + Int-B-42 | Ex. 450 | 57% | $^1$H NMR (DMSO-d$_6$) δ = 8.43 (s, 1H), 8.03 (d, 1H), 7.74 (t, 1H), 7.45 (d, 1H), 7.35 (m, 1H), 6.17 (s, 1H), 3.53 (s, 3H), 2.04 (s, 3H), 1.55 (s, 6H). (CH$_3$-ommited by DMSO) |
| 459 | Int-A-12 + Int-B-43 | Ex. 455 | 40% | 1H NMR (400 MHz, dmso-d6): δ 7.90-7.88 (m, 1H), 7.59 (d, 1H), 7.45-7.41 (m, 1H), 7.33-7.31 (m, 1H), 7.24-7.21 (m, 1H), 7.12-6.86 (m, 2H), 6.56-6.55 (m, 1H), 3.50 (s, 3H), 1.54 (bs, 6H). (CH$_3$-ommited by DMSO) |
| 460 | Int-A-8 + Int-B-43 | Ex. 455 | 40% | 1H NMR (400 MHz, dmso-d6): δ 7.67-7.65 (m, 1H), 7.61 (d, 1H), 7.31-7.25 (m, 2H), 7.17-6.91 (m, 2H), 6.56-6.55 (m, 1H), 3.75-3.69 (m, 2H), 1.61-1.54 (m, 6H), 1.14-1.07 (m, 3H). (CH$_3$-ommited by DMSO) |
| 461 | Int-A-47 + Int-B-43 | Ex. 455 | 40% | 1H NMR (400 MHz, dmso-d6): δ 7.89 (d, 1H), 7.60 (d, 1H), 7.44-7.40 (m, 1H), 7.33-7.31 (m, 1H), 7.26-7.23 (m, 1H), 7.11-6.85 (m, 2H), 6.56-6.55 (m, 1H), 3.69-3.63 (m, 2H), 1.54-1.50 (m, 6H), 1.14-1.05 (m, 3H). (CH$_3$-ommited by DMSO) |
| 462 | Int-A-15 + Int-B-43 | Ex. 455 | 40% | 1H NMR (400 MHz, dmso-d6): δ 10.57 (s, 1H), 7.28-7.22 (m, 2H), 7.14 (s, 1H), 7.08-6.82 (m, 3H), 2.25 (s, 3H), 1.55-1.48 (m, 6H). (CH$_3$-ommited by DMSO) |
| 463 | Int-A-20 + Int-B-42 | Ex. 450 | 43% | 1H NMR (400 MHz, dmso-d6): δ 7.42-7.39 (m, 2H), 7.28 (s, 1H), 6.93-6.91 (m, 1H), 6.16-6.15 (m, 1H), 6.07 (m, 1H), 4.91 (t, 1H), 4.23 (t, 2H), 3.75-3.71 (m, 2H), 2.47 (s, 3H), 2.05 (s, 3H), 1.54 (s, 6H). |
| 479 | Int-A-8 + Int-B-46 | Ex. 481 | 37% | 1H NMR (400 MHz, dmso-d6): δ 7.66-7.64 (m, 2H), 7.24-7.21 (m, 1H), 7.06-7.03 (m, 1H), 6.57-6.55 (m, 2H), 4.45-4.44 (m, 1H), 3.73-3.68 (m, 2H), 2.54 (s, 3H), 2.17-2.15 (m, 3H), 1.60-1.47 (m, 6H), 1.14 (t, 3H). (CH$_3$-ommited by DMSO) |
| 480 | Int-A-20 + Int-B-46 | Ex. 481 | 52% | 1H NMR (400 MHz, dmso-d6): δ 7.43-7.41 (m, 2H), 7.04-7.02 (m, 1H), 6.92-6.89 (m, 1H), 6.51 (s, 1H), 6.23 (d, 1H), 4.89-4.86 (m, 1H), 4.23-4.21 (m, 2H), 4.17-4.16 (m, 1H), 3.75-3.71 (m, 2H), 2.56 (s, 3H), 2.17-2.16 (m, 3H), 1.54 (bs, 6H). |
| 482 | Int-A-12 + Int-B-47 | Ex. 455 | 20% | 1H NMR (400 MHz, dmso-d6): δ 7.90-7.88 (m, 1H), 7.62 (d, 1H), 7.47-7.45 (m, 1H), 7.39-7.35 (m, 2H), 6.68 (d, 1H), 6.27 (s, 1H), 3.50 (s, 3H), 3.17 (s, 3H), 2.55 (s, 3H), 1.57 (s, 6H). |
| 486 | Int-A-2 + Int-B-46 | Ex. 481 | 43% | 1H NMR (400 MHz, dmso-d6): δ 7.67-7.63 (m, 2H), 7.24-7.21 (m, 1H), 7.05-7.02 (m, 1H), 6.56-6.55 (m, 2H), 4.41-4.39 (m, 1H), 3.53 (s, 3H), 2.54 (s, 3H), 2.17-2.16 (m, 3H), 1.61-1.47 (m, 6H). |
| 487 | Int-A-15 + Int-B-46 | Ex. 481 | 50% | 1H NMR (400 MHz, dmso-d6, 100° C.): δ 10.29 (s, 1H), 7.27-7.25 (m, 1H), 7.14 (s, 1H), 7.00-6.97 (m, 1H), 6.86-6.84 (m, 1H), 6.16 (s, 1H), 3.86-3.85 (m, 1H), 2.56 (s, 3H), 2.28-2.23 (m, 6H), 1.60 (s, 6H). |
| 488 | Int-A-1 + Int-B-47 | Ex. 483 | 29% | 1H NMR (400 MHz, dmso-d6): δ 11.28 (s, 1H), 7.38-7.37 (m, 2H), 7.22-7.19 (m, 1H), 6.99-6.96 (m, 1H), 6.31 (s, 1H), 6.23 (s, 1H), 3.19 (s, 3H), 2.54 (s, 3H), 1.57 (s, 6H). |

TABLE 5-continued

| Ex. # | Intermediates | Synthesis in analogy to | yield (mol-%) | $^1$H NMR |
|---|---|---|---|---|
| 493 | Int-A-43 + Int-B-47 | Ex. 483 | 29% | 1H NMR (400 MHz, dmso-d6): δ 8.46 (s, 1H), 7.72-7.70 (m, 1H), 7.53 (s, 1H), 7.49-7.46 (m, 1H), 6.43 (s, 1H), 3.57 (s, 3H), 3.22 (s, 3H), 2.60 (s, 3H), 1.58 (s, 6H). |
| 498 | Int-A-2 + Int-B-49 | Ex. 455 | 29% | 1H NMR (400 MHz, dmso-d6): δ 7.73-7.71 (m, 1H), 7.65-7.64 (m, 1H), 7.38-7.35 (m, 1H), 7.12 (s, 1H), 6.67-6.66 (m, 1H), 3.59 (s, 3H), 3.22 (s, 3H), 1.65 (s, 3H), 1.49 (s, 3H). (CH$_3$-ommited by DMSO) |
| 499 | Int-A-12 + Int-B-49 | Ex. 455 | 36% | 1H NMR (400 MHz, dmso-d6): δ 7.94-7.92 (m, 1H), 7.63 (d, 1H), 7.52-7.48 (m, 1H), 7.40-7.38 (m, 1H), 7.05 (s, 1H), 6.66-6.65 (m, 1H), 3.53 (s, 3H), 3.18 (s, 3H), 1.65 (s, 3H), 1.49 (s, 3H). |
| 501 | Int-A-23 + Int-B-49 | Ex. 500 | 39% | 1H NMR (400 MHz, dmso-d6): δ 8.53 (s, 1H), 7.78 (d, 1H), 7.55 (d, 1H), 7.23 (s, 1H), 3.60 (s, 3H), 3.22 (s, 3H), 2.54 (s, 3H), 1.68 (s, 3H), 1.48 (s, 3H). |
| 516 | Int-A-1 + Int-B-50 | Ex. 500 | 44% | $^1$H NMR (400 MHz, DMSO-d$_6$): δ 11.33 (d, 1H), 7.51 (d, 1H), 7.36-7.39 (m, 1H), 7.28-32 (m, 1H), 7.02 (dd, 1H), 6.23 (d, 1H), 2.41 (s, 2H), 1.82 (s, 3H), 1.35 (s, 3H). (CH$_3$-ommited by DMSO) |
| 519 | Int-A-23 + Int-B-50 | Ex. 518 | 17% | $^1$H NMR (400 MHz, DMSO-d$_6$): δ 8.65 (d, 1H), 7.83 (d, 1H), 7.59-7.67 (m, 2H), 3.62 (d, 3H), 2.49 (s, 3H), 1.83 (s, 3H), 1.37 (d,, 3H). |

The example in Table 6 (below) was synthesized in standard chemical reactions which are known to the person skilled in the art:

| Ex. # | Intermediates | Yield (%) | $^1$H NMR |
|---|---|---|---|
| 301 | Demethylation of Ex. 300 (DL-Methionin) | 19% | $^1$H NMR (DMSO-d$_6$) δ: 7.53 (d, 1H), 7.42 (d, 1H), 7.22 (dd, 1H), 7.12 (d, 1H), 7.01 (d, 1H), 6.42 (d, 1H), 6.20-6.16 (m, 1H), 4.91 (t, 1H), 4.27 (t, 2H), 3.77 (q, 2H), 2.50 (s, 3H), 2.04 (s, 3H), 1.55-1.51 (m, 6H) |

The molecular structures and chemical names of the Examples summarized in Tables 3, 4, 5 and 6 are given in Table 7 below:

| Ex. # | Structure | Name |
|---|---|---|
| 48 | 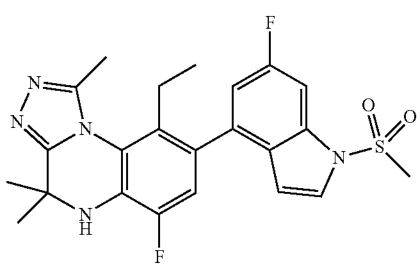 [SMILES: CCc1c(-c2cc(F)cc3c2ccn3S(C)(=O)=O)cc(F)c2c1-n1c(C)nnc1C(C)(C)N2] | 9-Ethyl-6-fluoro-8-(6-fluoro-1-methylsulfonyl-1H-indol-4-yl)-1,4,4-trimethyl-5H-[1,2,4]triazolo[4,3-a]quinoxaline |
| 53 | 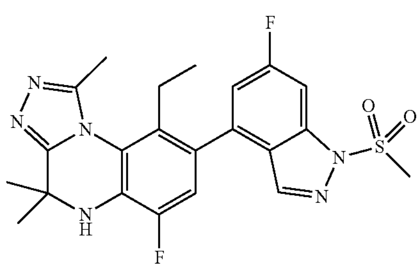 [SMILES: CCc1c(-c2cc(F)cc3c2cnn3S(C)(=O)=O)cc(F)c2c1-n1c(C)nnc1C(C)(C)N2] | 9-Ethyl-6-fluoro-8-(6-fluoro-1-methylsulfonyl-1H-indazol-4-yl)-1,4,4-trimethyl-5H-[1,2,4]triazolo[4,3-a]quinoxaline |

| Ex. # | Structure | Name |
|---|---|---|
| 54 | 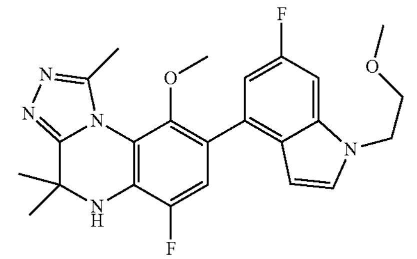 [SMILES: COCCn1ccc2c(-c3cc(F)c4c(c3OC)-n3c(C)nnc3C(C)(C)N4)cc(F)cc21] | 6-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline |
| 55 | 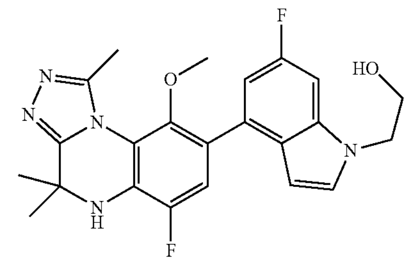 [SMILES: COc1c(-c2cc(F)cc3c2ccn3CCO)cc(F)c2c1-n1c(C)nnc1C(C)(C)N2] | 2-[6-Fluoro-4-(6-fluoro-9-methoxy-1,4,4-trimethyl-5H-[1,2,4]triazolo[4,3-a]quinoxalin-8-yl)-1H-indol-1-yl]-EtOH |
| 56 | 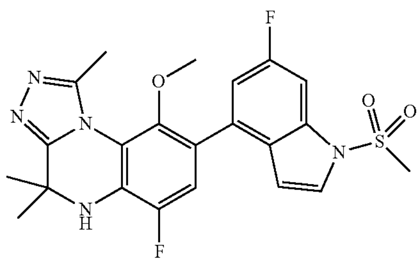 [SMILES: COc1c(-c2cc(F)cc3c2ccn3S(C)(=O)=O)cc(F)c2c1-n1c(C)nnc1C(C)(C)N2] | 6-Fluoro-8-(6-fluoro-1-methylsulfonyl-1H-indol-4-yl)-9-methoxy-1,4,4-trimethyl-5H-[1,2,4]triazolo[4,3-a]quinoxaline |
| 57 | 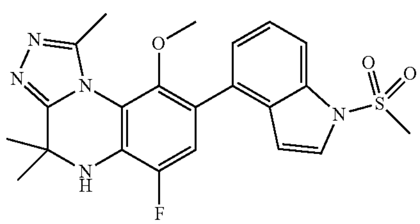 [SMILES: COc1c(-c2cccc3c2ccn3S(C)(=O)=O)cc(F)c2c1-n1c(C)nnc1C(C)(C)N2] | 6-Fluoro-9-methoxy-1,4,4-trimethyl-8-(1-methylsulfonyl-1H-indol-4-yl)-5H-[1,2,4]triazolo[4,3-a]quinoxaline |
| 59 | 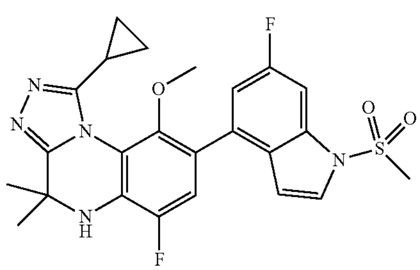 [SMILES: COc1c(-c2cc(F)cc3c2ccn3S(C)(=O)=O)cc(F)c2c1-n1c(C3CC3)nnc1C(C)(C)N2] | 1-Cyclopropyl-6-fluoro-8-(6-fluoro-1-methylsulfonyl-1H-indol-4-yl)-9-methoxy-4,4-dimethyl-5H-[1,2,4]triazolo[4,3-a]quinoxaline |
| 60 | 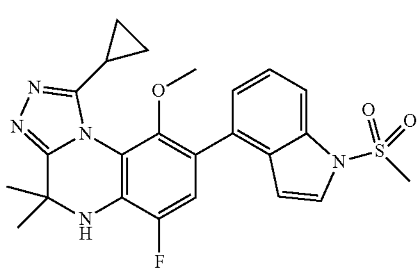 [SMILES: COc1c(-c2cccc3c2ccn3S(C)(=O)=O)cc(F)c2c1-n1c(C3CC3)nnc1C(C)(C)N2] | 1-Cyclopropyl-6-fluoro-9-methoxy-4,4-dimethyl-8-(1-methylsulfonyl-1H-indol-4-yl)-5H-[1,2,4]triazolo[4,3-a]quinoxaline |

-continued

| Ex. # | Structure | Name |
|---|---|---|
| 61 | 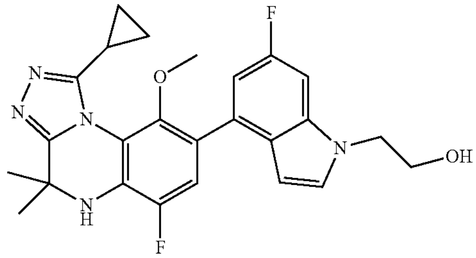 [SMILES: COc1c(-c2cc(F)cc3c2ccn3CCO)cc(F)c2c1-n1c(C3CC3)nnc1C(C)(C)N2] | 2-[4-(1-Cyclopropyl-6-fluoro-9-methoxy-4,4-dimethyl-5H-[1,2,4]triazolo[4,3-a]quinoxalin-8-yl)-6-fluoro-1H-indol-1-yl]-EtOH |
| 62 | 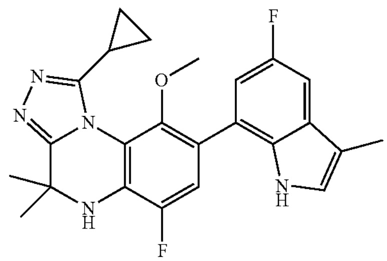 | 1-Cyclopropyl-6-fluoro-8-(5-fluoro-3-methyl-1H-indol-7-yl)-9-methoxy-4,4-dimethyl-5H-[1,2,4]triazolo[4,3-a]quinoxaline |
| 63 | 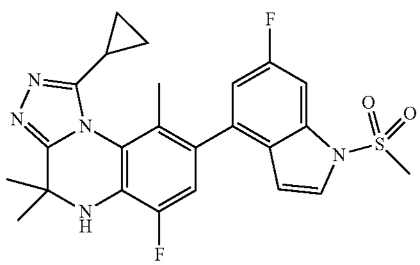 [SMILES: Cc1c(-c2cc(F)cc3c2ccn3S(C)(=O)=O)cc(F)c2c1-n1c(C3CC3)nnc1C(C)(C)N2] | 1-Cyclopropyl-6-fluoro-8-(6-fluoro-1-methylsulfonyl-1H-indol-4-yl)-4,4,9-trimethyl-5H-[1,2,4]triazolo[4,3-a]quinoxaline |
| 64 | 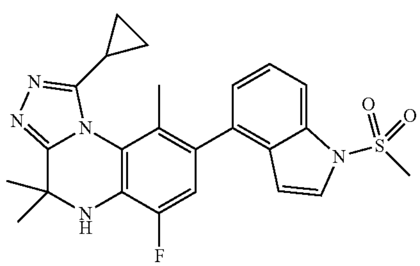 [SMILES: Cc1c(-c2cccc3c2ccn3S(C)(=O)=O)cc(F)c2c1-n1c(C3CC3)nnc1C(C)(C)N2] | 1-Cyclopropyl-6-fluoro-4,4,9-trimethyl-8-(1-methylsulfonyl-1H-indol-4-yl)-5H-[1,2,4]triazolo[4,3-a]quinoxaline |
| 65 | 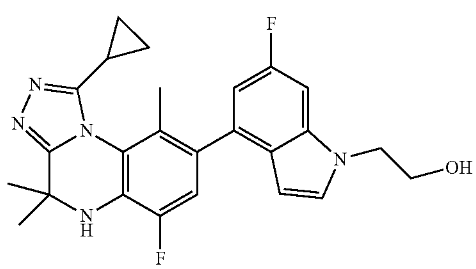 [SMILES: Cc1c(-c2cc(F)cc3c2ccn3CCO)cc(F)c2c1-n1c(C3CC3)nnc1C(C)(C)N2] | 2-[4-(1-Cyclopropyl-6-fluoro-4,4,9-trimethyl-5H-[1,2,4]triazolo[4,3-a]quinoxalin-8-yl)-6-fluoro-1H-indol-1-yl]-EtOH |
| 66 | 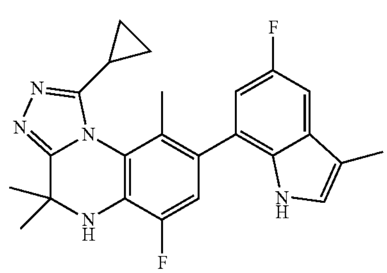 | 1-Cyclopropyl-6-fluoro-8-(5-fluoro-3-methyl-1H-indol-7-yl)-4,4,9-trimethyl-5H-[1,2,4]triazolo[4,3-a]quinoxaline |

| Ex. # | Structure | Name |
|---|---|---|
| 300 | 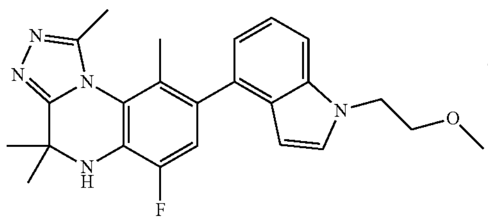 | 6-Fluoro-8-[1-(2-methoxy-ethyl)-1H-indol-4-yl]-1,4,4,9-tetramethyl-5H-[1,2,4]triazolo[4,3-a]quinoxaline |
| 301 | 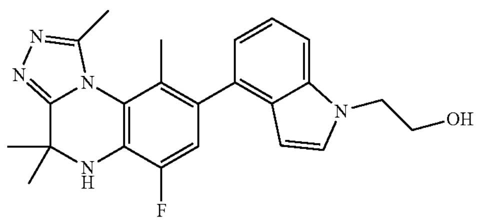 [SMILES: Cc1c(-c2cccc3c2ccn3CCO)cc(F)c2c1-n1c(C)nnc1C(C)(C)N2] | 2-[4-(6-Fluoro-1,4,4,9-tetramethyl-5H-[1,2,4]triazolo[4,3-a]quinoxalin-8-yl)-1H-indol-1-yl]-EtOH |
| 304 | 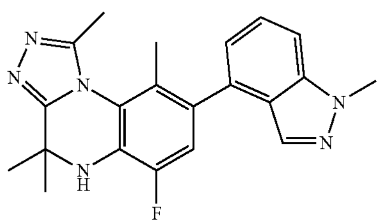 | 6-Fluoro-1,4,4,9-tetramethyl-8-(1-methyl-1H-indazol-4-yl)-5H-[1,2,4]triazolo[4,3-a]quinoxaline |
| 305 | 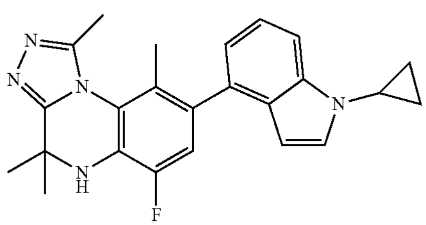 [SMILES: Cc1c(-c2cccc3c2ccn3C2CC2)cc(F)c2c1-n1c(C)nnc1C(C)(C)N2] | 8-(1-Cyclopropyl-1H-indol-4-yl)-6-fluoro-1,4,4,9-tetramethyl-5H-[1,2,4]triazolo[4,3-a]quinoxaline |
| 308 | 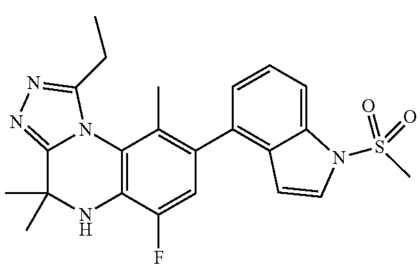 [SMILES: CCc1nnc2n1-c1c(C)c(-c3cccc4c3ccn4S(C)(=O)=O)cc(F)c1NC2(C)C] | 1-Ethyl-6-fluoro-4,4,9-trimethyl-8-(1-methylsulfonyl-1H-indol-4-yl)-5H-[1,2,4]triazolo[4,3-a]quinoxaline |
| 316 | 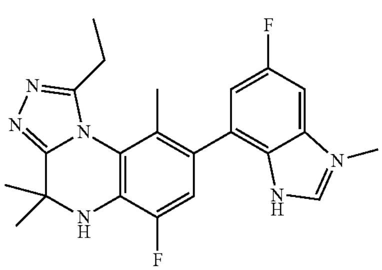 | 1-Ethyl-6-fluoro-8-(5-fluoro-3-methyl-1H-indol-7-yl)-4,4,9-trimethyl-5H-[1,2,4]triazolo[4,3-a]quinoxaline |

-continued

| Ex. # | Structure | Name |
|---|---|---|
| 322 | 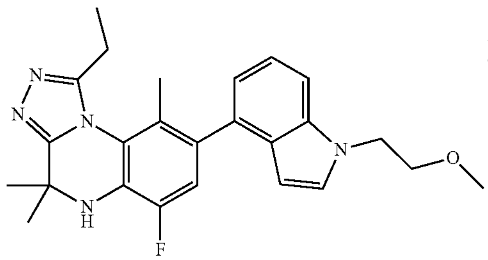 | 1-Ethyl-6-fluoro-8-[1-(2-methoxy-ethyl)-1H-indol-4-yl]-4,4,9-trimethyl-5H-[1,2,4]triazolo[4,3-a]quinoxaline |
| 323 | 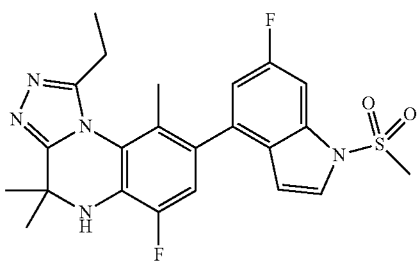 | 1-Ethyl-6-fluoro-8-(6-fluoro-1-methylsulfonyl-1H-indol-4-yl)-4,4,9-trimethyl-5H-[1,2,4]triazolo[4,3-a]quinoxaline |
| 326 | 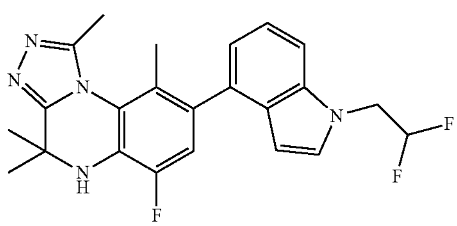 [SMILES: Cc1c(-c2cccc3c2ccn3CC(F)F)cc(F)c2c1-n1c(C)nnc1C(C)(C)N2] | 8-[1-(2,2-Difluoro-ethyl)-1H-indol-4-yl]-6-fluoro-1,4,4,9-tetramethyl-5H-[1,2,4]triazolo[4,3-a]quinoxaline |
| 340 | 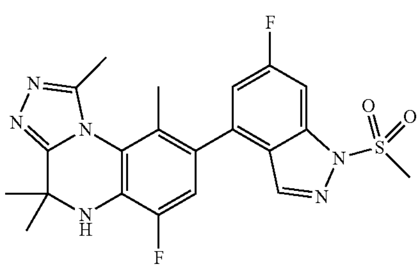 [SMILES: Cc1c(-c2cc(F)cc3c2cnn3S(C)(=O)=O)cc(F)c2c1-n1c(C)nnc1C(C)(C)N2] | 6-Fluoro-8-(6-fluoro-1-methylsulfonyl-1H-indazol-4-yl)-1,4,4,9-tetramethyl-5H-[1,2,4]triazolo[4,3-a]quinoxaline |
| 349 | 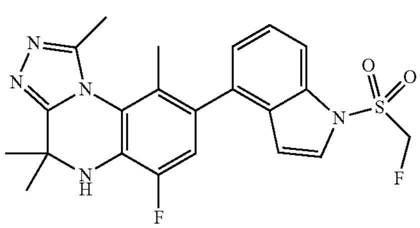 [SMILES: Cc1c(-c2cccc3c2ccn3S(=O)(=O)CF)cc(F)c2c1-n1c(C)nnc1C(C)(C)N2] | 6-Fluoro-8-[1-(fluoro-methylsulfonyl)-1H-indol-4-yl]-1,4,4,9-tetramethyl-5H-[1,2,4]triazolo[4,3-a]quinoxaline |
| 350 | 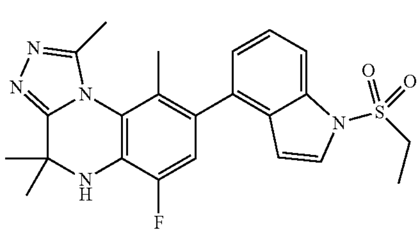 | 8-[1-(Ethylsulfonyl)-1H-indol-4-yl]-6-fluoro-1,4,4,9-tetramethyl-5H-[1,2,4]triazolo[4,3-a]quinoxaline |

-continued

| Ex. # | Structure | Name |
|---|---|---|
| 352 | 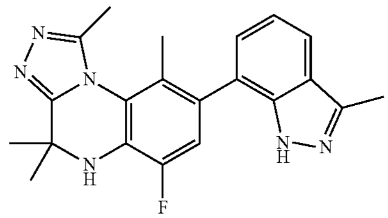 | 6-Fluoro-1,4,4,9-tetramethyl-8-(3-methyl-1H-indazol-7-yl)-5H-[1,2,4]triazolo[4,3-a]quinoxaline |
| 355 | 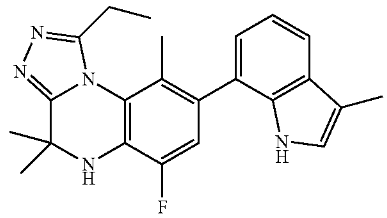 | 1-Ethyl-6-fluoro-4,4,9-trimethyl-8-(3-methyl-1H-indol-7-yl)-5H-[1,2,4]triazolo[4,3-a]quinoxaline |
| 366 | 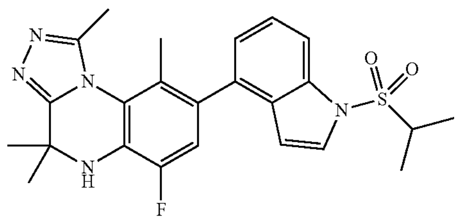 [SMILES: Cc1c(-c2cccc3c2ccn3S(=O)(=O)C(C)C)cc(F)c2c1-n1c(C)nnc1C(C)(C)N2] | 6-Fluoro-8-[1-(isopropylsulfonyl)-1H-indol-4-yl]-1,4,4,9-tetramethyl-5H-[1,2,4]triazolo[4,3-a]quinoxaline |
| 374 | 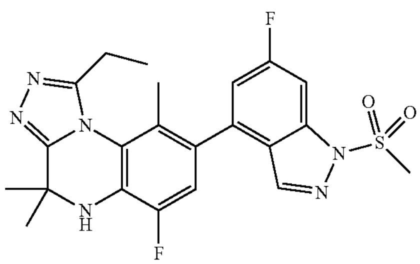 [SMILES: CCc1nnc2n1-c1c(C)c(-c3cc(F)cc4c3cnn4S(C)(=O)=O)cc(F)c1NC2(C)C] | 1-Ethyl-6-fluoro-8-(6-fluoro-1-methylsulfonyl-1H-indazol-4-yl)-4,4,9-trimethyl-5H-[1,2,4]triazolo[4,3-a]quinoxaline |
| 375 | 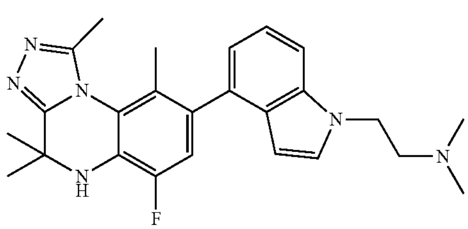 | [2-[4-(6-Fluoro-1,4,4,9-tetramethyl-5H-[1,2,4]triazolo[4,3-a]quinoxalin-8-yl)-1H-indol-1-yl]-ethyl]-dimethyl-amine |
| 378 | 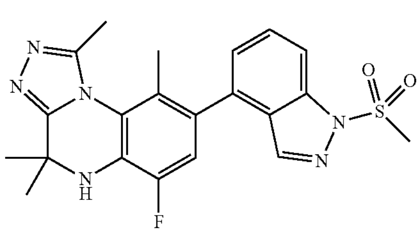 [SMILES: Cc1c(-c2cccc3c2cnn3S(C)(=O)=O)cc(F)c2c1-n1c(C)nnc1C(C)(C)N2] | 6-Fluoro-1,4,4,9-tetramethyl-8-(1-methylsulfonyl-1H-indazol-4-yl)-5H-[1,2,4]triazolo[4,3-a]quinoxaline |

-continued

| Ex. # | Structure | Name |
|---|---|---|
| 389 | 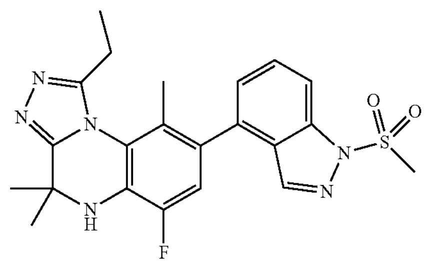 | 1-Ethyl-6-fluoro-4,4,9-trimethyl-8-(1-methylsulfonyl-1H-indazol-4-yl)-5H-[1,2,4]triazolo[4,3-a]quinoxaline |
| 391 | 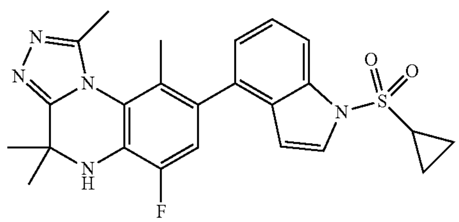 [SMILES: Cc1c(-c2cccc3c2ccn3S(=O)(=O)C2CC2)cc(F)c2c1-n1c(C)nnc1C(C)(C)N2] | 8-[1-(Cyclopropylsulfonyl)-1H-indol-4-yl]-6-fluoro-1,4,4,9-tetramethyl-5H-[1,2,4]triazolo[4,3-a]quinoxaline |
| 447 | 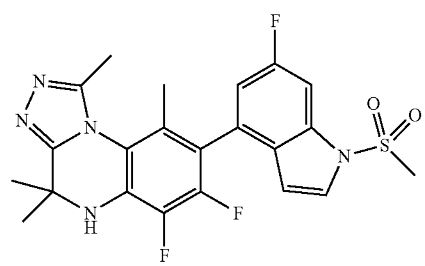 [SMILES: Cc1c(-c2cc(F)cc3c2ccn3S(C)(=O)=O)c(F)c(F)c2c1-n1c(C)nnc1C(C)(C)N2] | 6,7-Difluoro-8-(6-fluoro-1-methylsulfonyl-1H-indol-4-yl)-1,4,4,9-tetramethyl-5H-[1,2,4]triazolo[4,3-a]quinoxaline |
| 449 | 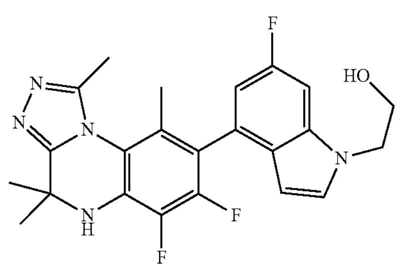 [SMILES: Cc1c(-c2cc(F)cc3c2ccn3CCO)c(F)c(F)c2c1-n1c(C)nnc1C(C)(C)N2] | 2-[4-(6,7-Difluoro-1,4,4,9-tetramethyl-5H-[1,2,4]triazolo[4,3-a]quinoxalin-8-yl)-6-fluoro-1H-indol-1-yl]-EtOH |
| 451 | 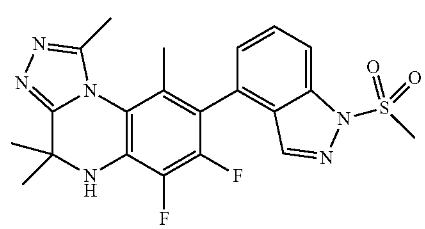 [SMILES: Cc1c(-c2cccc3c2cnn3S(C)(=O)=O)c(F)c(F)c2c1-n1c(C)nnc1C(C)(C)N2] | 6,7-Difluoro-1,4,4,9-tetramethyl-8-(1-methylsulfonyl-1H-indazol-4-yl)-5H-[1,2,4]triazolo[4,3-a]quinoxaline |
| 452 | 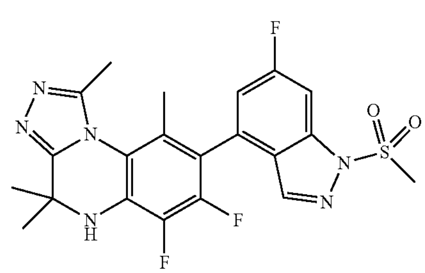 [SMILES: Cc1c(-c2cc(F)cc3c2cnn3S(C)(=O)=O)c(F)c(F)c2c1-n1c(C)nnc1C(C)(C)N2] | 6,7-Difluoro-8-(6-fluoro-1-methylsulfonyl-1H-indazol-4-yl)-1,4,4,9-tetramethyl-5H-[1,2,4]triazolo[4,3-a]quinoxaline |

| Ex. # | Structure | Name |
|---|---|---|
| 453 | 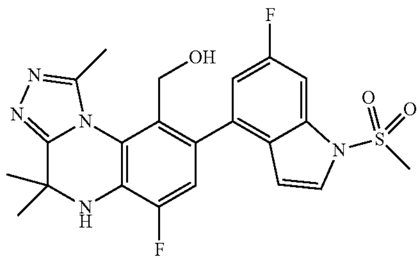 [SMILES: Cc1nnc2n1-c1c(CO)c(-c3cc(F)cc4c3ccn4S(C)(=O)=O)cc(F)c1NC2(C)C] | [6-Fluoro-8-(6-fluoro-1-methylsulfonyl-1H-indol-4-yl)-1,4,4-trimethyl-5H-[1,2,4]triazolo[4,3-a]quinoxalin-9-yl]-MeOH |
| 454 | 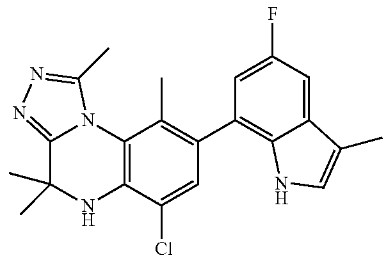 | 6-Chloro-8-(5-fluoro-3-methyl-1H-indol-7-yl)-1,4,4,9-tetramethyl-5H-[1,2,4]triazolo[4,3-a]quinoxaline |
| 456 | 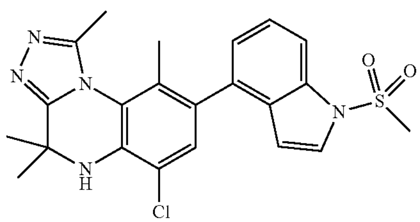 [SMILES: Cc1c(-c2cccc3c2ccn3S(C)(=O)=O)cc(Cl)c2c1-n1c(C)nnc1C(C)(C)N2] | 6-Chloro-1,4,4,9-tetramethyl-8-(1-methylsulfonyl-1H-indol-4-yl)-5H-[1,2,4]triazolo[4,3-a]quinoxaline |
| 457 | 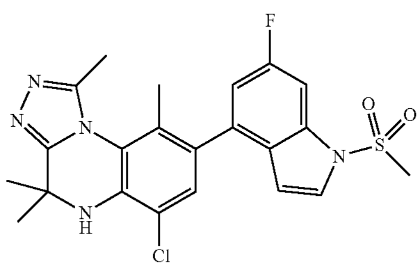 [SMILES: Cc1c(-c2cc(F)cc3c2ccn3S(C)(=O)=O)cc(Cl)c2c1-n1c(C)nnc1C(C)(C)N2] | 6-Chloro-8-(6-fluoro-1-methylsulfonyl-1H-indol-4-yl)-1,4,4,9-tetramethyl-5H-[1,2,4]triazolo[4,3-a]quinoxaline |
| 458 | 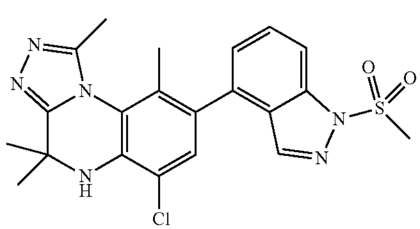 [SMILES: Cc1c(-c2cccc3c2cnn3S(C)(=O)=O)cc(Cl)c2c1-n1c(C)nnc1C(C)(C)N2] | 6-Chloro-1,4,4,9-tetramethyl-8-(1-methylsulfonyl-1H-indazol-4-yl)-5H-[1,2,4]triazolo[4,3-a]quinoxaline |
| 459 | 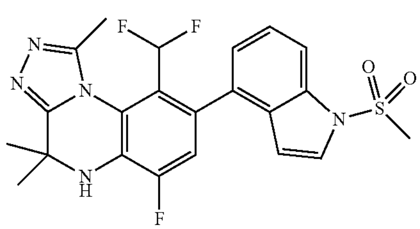 [SMILES: Cc1nnc2n1-c1c(c(F)cc(-c3cccc4c3ccn4S(C)(=O)=O)c1C(F)F)NC2(C)C] | 9-(Difluoro-methyl)-6-fluoro-1,4,4-trimethyl-8-(1-methylsulfonyl-1H-indol-4-yl)-5H-[1,2,4]triazolo[4,3-a]quinoxaline |

| Ex. # | Structure | Name |
|---|---|---|
| 460 | 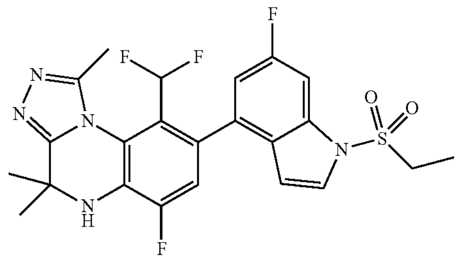 [SMILES: CCS(=O)(=O)n1ccc2c(-c3cc(F)c4c(c3C(F)F)-n3c(C)nnc3C(C)(C)N4)cc(F)cc21] | 9-(Difluoro-methyl)-8-[1-(ethylsulfonyl)-6-fluoro-1H-indol-4-yl]-6-fluoro-1,4,4-trimethyl-5H-[1,2,4]triazolo[4,3-a]quinoxaline |
| 461 | 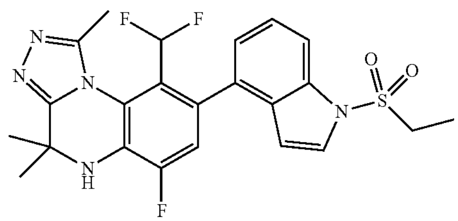 [SMILES: CCS(=O)(=O)n1ccc2c(-c3cc(F)c4c(c3C(F)F)-n3c(C)nnc3C(C)(C)N4)cccc21] | 9-(Difluoro-methyl)-8-[1-(ethylsulfonyl)-1H-indol-4-yl]-6-fluoro-1,4,4-trimethyl-5H-[1,2,4]triazolo[4,3-a]quinoxaline |
| 462 | 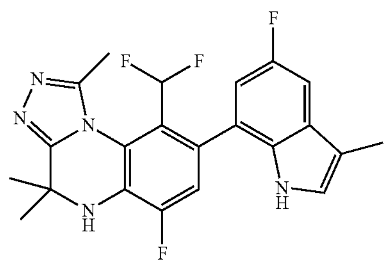 | 9-(Difluoro-methyl)-6-fluoro-8-(5-fluoro-3-methyl-1H-indol-7-yl)-1,4,4-trimethyl-5H-[1,2,4]triazolo[4,3-a]quinoxaline |
| 463 | 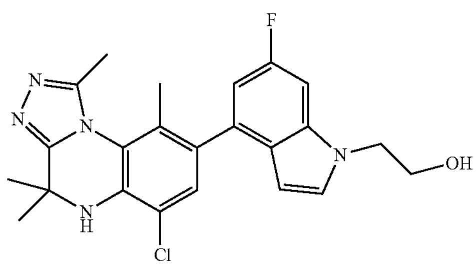 [SMILES: Cc1c(-c2cc(F)cc3c2ccn3CCO)cc(Cl)c2c1-n1c(C)nnc1C(C)(C)N2] | 2-[4-(6-Chloro-1,4,4,9-tetramethyl-5H-[1,2,4]triazolo[4,3-a]quinoxalin-8-yl)-6-fluoro-1H-indol-1-yl]-EtOH |
| 464 | 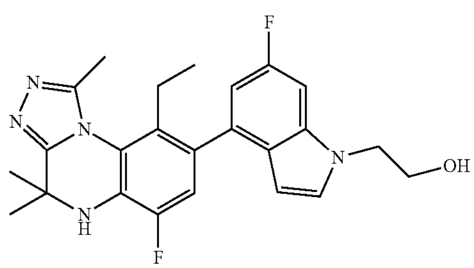 [SMILES: CCc1c(-c2cc(F)cc3c2ccn3CCO)cc(F)c2c1-n1c(C)nnc1C(C)(C)N2] | 2-[4-(9-Ethyl-6-fluoro-1,4,4-trimethyl-5H-[1,2,4]triazolo[4,3-a]quinoxalin-8-yl)-6-fluoro-1H-indol-1-yl]-EtOH |
| 467 | 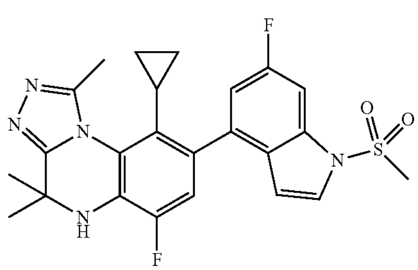 [SMILES: Cc1nnc2n1-c1c(c(F)cc(-c3cc(F)cc4c3ccn4S(C)(=O)=O)c1C1CC1)NC2(C)C] | 9-Cyclopropyl-6-fluoro-8-(6-fluoro-1-methylsulfonyl-1H-indazol-4-yl)-1,4,4-trimethyl-5H-[1,2,4]triazolo[4,3-a]quinoxaline |

| Ex. # | Structure | Name |
|---|---|---|
| 468 | 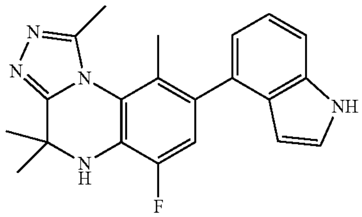 [SMILES: Cc1c(-c2cccc3[nH]ccc23)cc(F)c2c1-n1c(C)nnc1C(C)(C)N2] | 6-Fluoro-8-(1H-indol-4-yl)-1,4,4,9-tetramethyl-5H-[1,2,4]triazolo[4,3-a]quinoxaline |
| 469 | 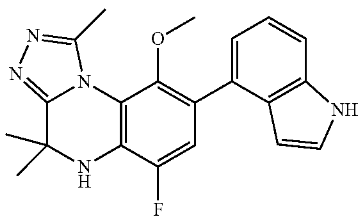 [SMILES: COc1c(-c2cccc3[nH]ccc23)cc(F)c2c1-n1c(C)nnc1C(C)(C)N2] | 6-Fluoro-8-(1H-indol-4-yl)-9-methoxy-1,4,4-trimethyl-5H-[1,2,4]triazolo[4,3-a]quinoxaline |
| 470 | 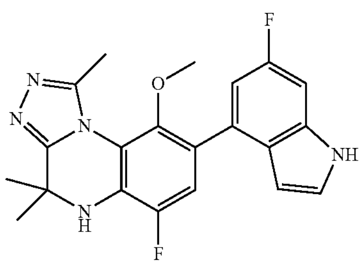 [SMILES: COc1c(-c2cc(F)cc3[nH]ccc23)cc(F)c2c1-n1c(C)nnc1C(C)(C)N2] | 6-Fluoro-8-(6-fluoro-1H-indol-4-yl)-9-methoxy-1,4,4-trimethyl-5H-[1,2,4]triazolo[4,3-a]quinoxaline |
| 471 | 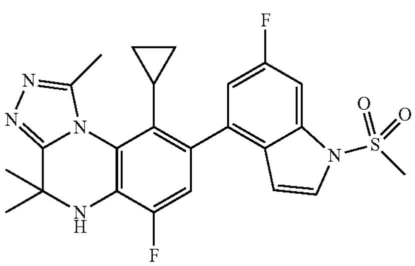 [SMILES: Cc1nnc2n1-c1c(c(F)cc(-c3cc(F)cc4c3ccn4S(C)(=O)=O)c1C1CC1)NC2(C)C] | 9-Cyclopropyl-6-fluoro-8-(6-fluoro-1-methylsulfonyl-1H-indol-4-yl)-1,4,4-trimethyl-5H-[1,2,4]triazolo[4,3-a]quinoxaline |
| 472 | 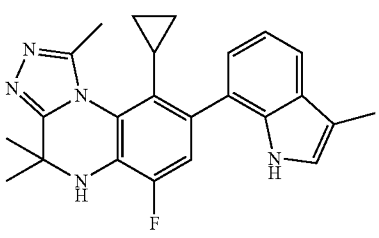 | 9-Cyclopropyl-6-fluoro-1,4,4-trimethyl-8-(3-methyl-1H-indol-7-yl)-5H-[1,2,4]triazolo[4,3-a]quinoxaline |
| 473 | 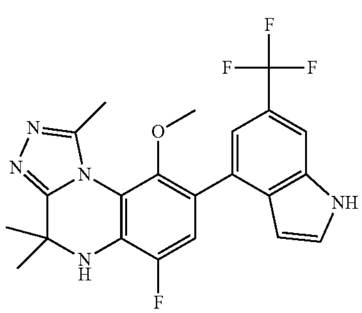 [SMILES: COc1c(-c2cc(C(F)(F)F)cc3[nH]ccc23)cc(F)c2c1-n1c(C)nnc1C(C)(C)N2] | 6-Fluoro-9-methoxy-1,4,4-trimethyl-8-[6-(trifluoromethyl)-1H-indol-4-yl]-5H-[1,2,4]triazolo[4,3-a]quinoxaline |

| Ex. # | Structure | Name |
|---|---|---|
| 474 | 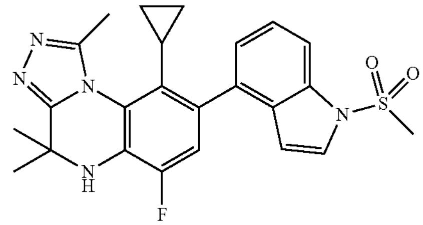 [SMILES: Cc1nnc2n1-c1c(c(F)cc(-c3cccc4c3ccn4S(C)(=O)=O)c1C1CC1)NC2(C)C] | 9-Cyclopropyl-6-fluoro-1,4,4-trimethyl-8-(1-methylsulfonyl-1H-indol-4-yl)-5H-[1,2,4]triazolo[4,3-a]quinoxaline |
| 475 | 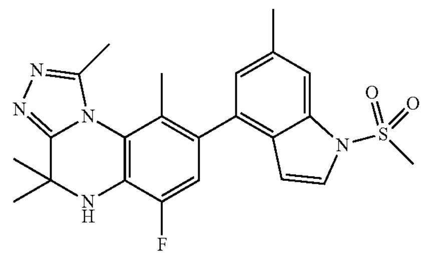 [SMILES: Cc1cc(-c2cc(F)c3c(c2C)-n2c(C)nnc2C(C)(C)N3)c2ccn(S(C)(=O)=O)c2c1] | 6-Fluoro-1,4,4,9-tetramethyl-8-(6-methyl-1-methylsulfonyl-1H-indol-4-yl)-5H-[1,2,4]triazolo[4,3-a]quinoxaline |
| 476 | 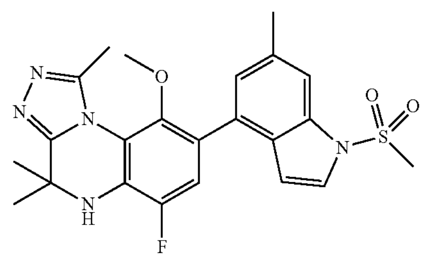 [SMILES: COc1c(-c2cc(C)cc3c2ccn3S(C)(=O)=O)cc(F)c2c1-n1c(C)nnc1C(C)(C)N2] | 6-Fluoro-9-methoxy-1,4,4-trimethyl-8-(6-methyl-1-methylsulfonyl-1H-indol-4-yl)-5H-[1,2,4]triazolo[4,3-a]quinoxaline |
| 477 | 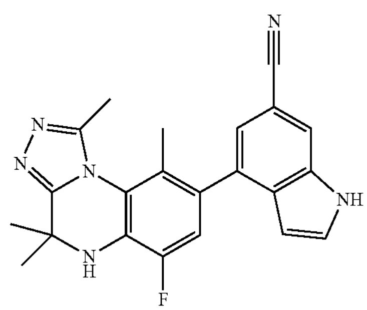 [SMILES: Cc1c(-c2cc(C#N)cc3[nH]ccc23)cc(F)c2c1-n1c(C)nnc1C(C)(C)N2] | 4-(6-Fluoro-1,4,4,9-tetramethyl-5H-[1,2,4]triazolo[4,3-a]quinoxalin-8-yl)-1H-indole-6-carbonitrile |
| 478 | 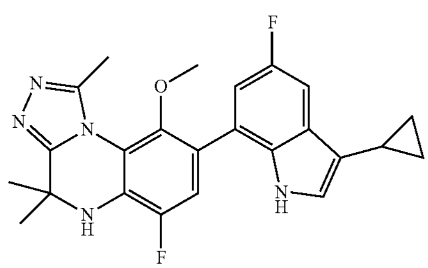 [SMILES: COc1c(-c2cc(F)cc3c(C4CC4)c[nH]c23)cc(F)c2c1-n1c(C)nnc1C(C)(C)N2] | 8-(3-Cyclopropyl-5-fluoro-1H-indol-7-yl)-6-fluoro-9-methoxy-1,4,4-trimethyl-5H-[1,2,4]triazolo[4,3-a]quinoxaline |
| 479 | 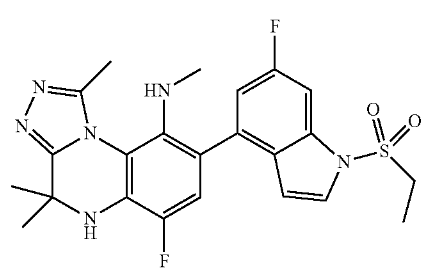 [SMILES: CCS(=O)(=O)n1ccc2c(-c3cc(F)c4c(c3NC)-n3c(C)nnc3C(C)(C)N4)cc(F)cc21] | [8-[1-(Ethylsulfonyl)-6-fluoro-1H-indol-4-yl]-6-fluoro-1,4,4-trimethyl-5H-[1,2,4]triazolo[4,3-a]quinoxalin-9-yl]-methyl-amine |

-continued

| Ex. # | Structure | Name |
|---|---|---|
| 480 | 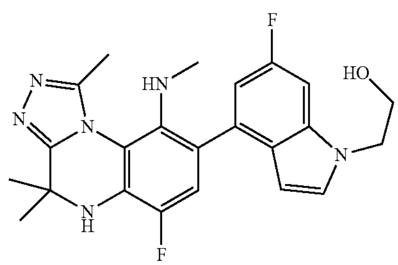 [SMILES: CNc1c(-c2cc(F)cc3c2ccn3CCO)cc(F)c2c1-n1c(C)nnc1C(C)(C)N2] | 2-[6-Fluoro-4-(6-fluoro-1,4,4-trimethyl-9-methylamino-5H-[1,2,4]triazolo[4,3-a]quinoxalin-8-yl)-1H-indol-1-yl]-EtOH |
| 482 | 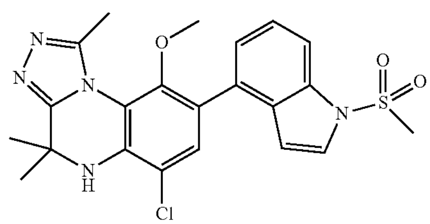 [SMILES: COc1c(-c2cccc3c2ccn3S(C)(=O)=O)cc(Cl)c2c1-n1c(C)nnc1C(C)(C)N2] | 6-Chloro-9-methoxy-1,4,4-trimethyl-8-(1-methylsulfonyl-1H-indol-4-yl)-5H-[1,2,4]triazolo[4,3-a]quinoxaline |
| 484 | 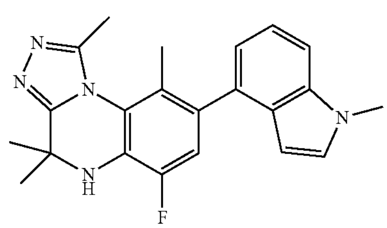 | 6-Fluoro-1,4,4,9-tetramethyl-8-(1-methyl-1H-indol-4-yl)-5H-[1,2,4]triazolo[4,3-a]quinoxaline |
| 485 | 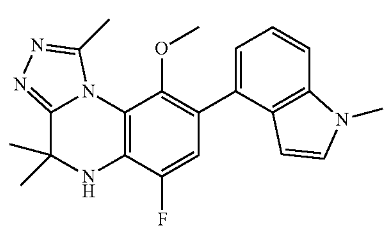 | 6-Fluoro-9-methoxy-1,4,4-trimethyl-8-(1-methyl-1H-indol-4-yl)-5H-[1,2,4]triazolo[4,3-a]quinoxaline |
| 486 | 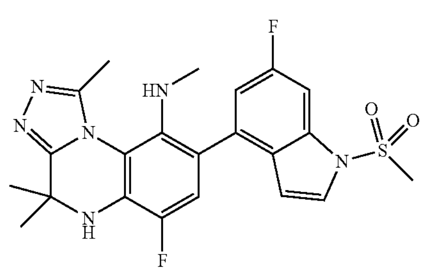 [SMILES: CNc1c(-c2cc(F)cc3c2ccn3S(C)(=O)=O)cc(F)c2c1-n1c(C)nnc1C(C)(C)N2] | [6-Fluoro-8-(6-fluoro-1-methylsulfonyl-1H-indol-4-yl)-1,4,4-trimethyl-5H-[1,2,4]triazolo[4,3-a]quinoxalin-9-yl]-methyl-amine |
| 487 | 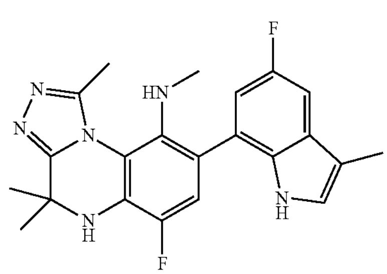 | [6-Fluoro-8-(5-fluoro-3-methyl-1H-indol-7-yl)-1,4,4-trimethyl-5H-[1,2,4]triazolo[4,3-a]quinoxalin-9-yl]-methyl-amine |

-continued

| Ex. # | Structure | Name |
|---|---|---|
| 488 | 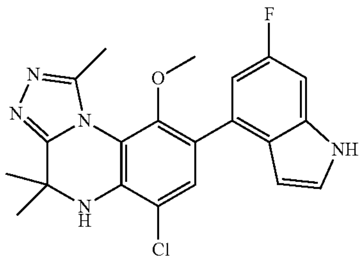 [SMILES: COc1c(-c2cc(F)cc3[nH]ccc23)cc(Cl)c2c1-n1c(C)nnc1C(C)(C)N2] | 6-Chloro-8-(6-fluoro-1H-indol-4-yl)-9-methoxy-1,4,4-trimethyl-5H-[1,2,4]triazolo[4,3-a]quinoxaline |
| 489 | 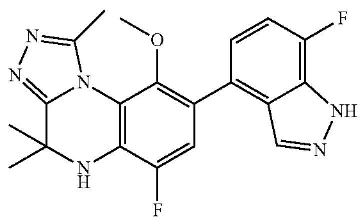 [SMILES: COc1c(-c2ccc(F)c3[nH]ncc23)cc(F)c2c1-n1c(C)nnc1C(C)(C)N2] | 6-Fluoro-8-(7-fluoro-1H-indazol-4-yl)-9-methoxy-1,4,4-trimethyl-5H-[1,2,4]triazolo[4,3-a]quinoxaline |
| 491 | 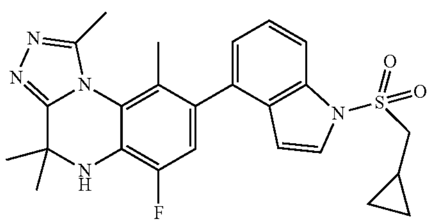 [SMILES: Cc1c(-c2cccc3c2ccn3S(=O)(=O)CC2CC2)cc(F)c2c1-n1c(C)nnc1C(C)(C)N2] | 8-[1-(Cyclopropyl-methylsulfonyl)-1H-indol-4-yl]-6-fluoro-1,4,4,9-tetramethyl-5H-[1,2,4]triazolo[4,3-a]quinoxaline |
| 492 | 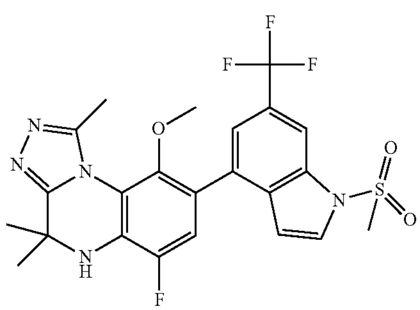 [SMILES: COc1c(-c2cc(C(F)(F)F)cc3c2ccn3S(C)(=O)=O)cc(F)c2c1-n1c(C)nnc1C(C)(C)N2] | 6-Fluoro-9-methoxy-1,4,4-trimethyl-8-[1-methylsulfonyl-6-(trifluoromethyl)-1H-indol-4-yl]-5H-[1,2,4]triazolo[4,3-a]quinoxaline |
| 493 | 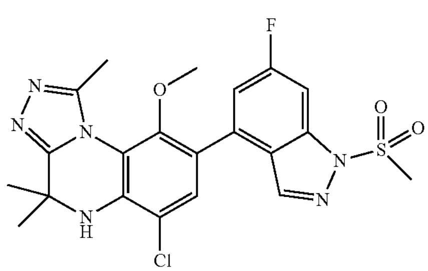 [SMILES: COc1c(-c2cc(F)cc3c2cnn3S(C)(=O)=O)cc(Cl)c2c1-n1c(C)nnc1C(C)(C)N2] | 6-Chloro-8-(6-fluoro-1-methylsulfonyl-1H-indazol-4-yl)-9-methoxy-1,4,4-trimethyl-5H-[1,2,4]triazolo[4,3-a]quinoxaline |
| 494 | 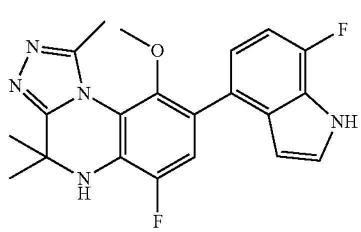 [SMILES: COc1c(-c2ccc(F)c3[nH]ccc23)cc(F)c2c1-n1c(C)nnc1C(C)(C)N2] | 6-Fluoro-8-(7-fluoro-1H-indol-4-yl)-9-methoxy-1,4,4-trimethyl-5H-[1,2,4]triazolo[4,3-a]quinoxaline |

-continued

| Ex. # | Structure | Name |
|---|---|---|
| 495 | 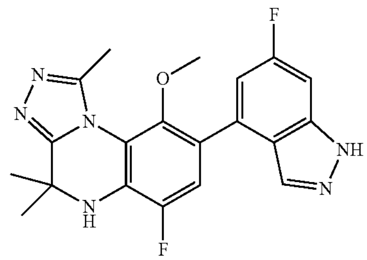 [SMILES: COc1c(-c2cc(F)cc3[nH]ncc23)cc(F)c2c1-n1c(C)nnc1C(C)(C)N2] | 6-Fluoro-8-(6-fluoro-1H-indazol-4-yl)-9-methoxy-1,4,4-trimethyl-5H-[1,2,4]triazolo[4,3-a]quinoxaline |
| 496 | 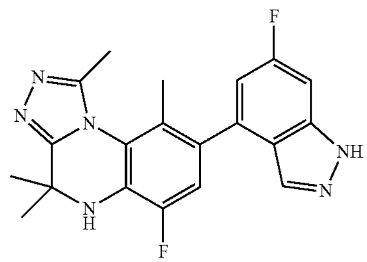 [SMILES: Cc1c(-c2cc(F)cc3[nH]ncc23)cc(F)c2c1-n1c(C)nnc1C(C)(C)N2] | 6-Fluoro-8-(6-fluoro-1H-indazol-4-yl)-1,4,4,9-tetramethyl-5H-[1,2,4]triazolo[4,3-a]quinoxaline |
| 497 | 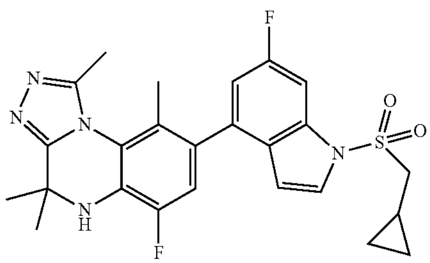 [SMILES: Cc1c(-c2cc(F)cc3c2ccn3S(=O)(=O)CC2CC2)cc(F)c2c1-n1c(C)nnc1C(C)(C)N2] | 8-[1-(Cyclopropyl-methylsulfonyl)-6-fluoro-1H-indol-4-yl]-6-fluoro-1,4,4,9-tetramethyl-5H-[1,2,4]triazolo[4,3-a]quinoxaline |
| 498 | 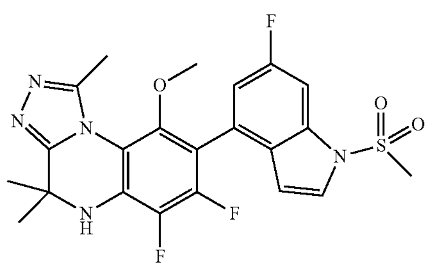 [SMILES: COc1c(-c2cc(F)cc3c2ccn3S(C)(=O)=O)c(F)c(F)c2c1-n1c(C)nnc1C(C)(C)N2] | 6,7-Difluoro-8-(6-fluoro-1-methylsulfonyl-1H-indol-4-yl)-9-methoxy-1,4,4-trimethyl-5H-[1,2,4]triazolo[4,3-a]quinoxaline |
| 499 | 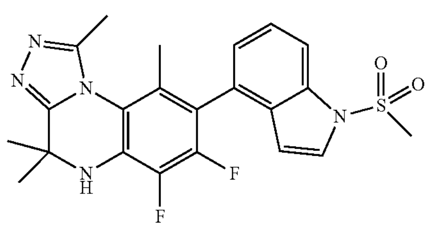 [SMILES: Cc1c(-c2cccc3c2ccn3S(C)(=O)=O)c(F)c(F)c2c1-n1c(C)nnc1C(C)(C)N2] | 6,7-Difluoro-9-methoxy-1,4,4-trimethyl-8-(1-methylsulfonyl-1H-indol-4-yl)-5H-[1,2,4]triazolo[4,3-a]quinoxaline |
| 501 | 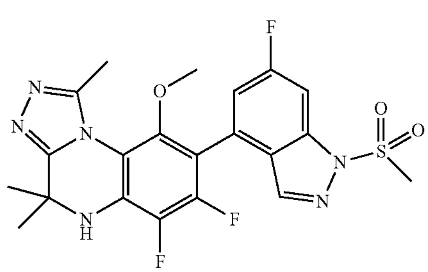 [SMILES: COc1c(-c2cc(F)cc3c2cnn3S(C)(=O)=O)c(F)c(F)c2c1-n1c(C)nnc1C(C)(C)N2] | 6,7-Difluoro-8-(6-fluoro-1-methylsulfonyl-1H-indazol-4-yl)-9-methoxy-1,4,4-trimethyl-5H-[1,2,4]triazolo[4,3-a]quinoxaline |

| Ex. # | Structure | Name |
|---|---|---|
| 502 | 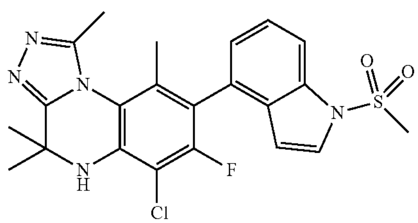 [SMILES: Cc1c(-c2cccc3c2ccn3S(C)(=O)=O)c(F)c(Cl)c2c1-n1c(C)nnc1C(C)(C)N2] | 6-Chloro-7-fluoro-1,4,4,9-tetramethyl-8-(1-methylsulfonyl-1H-indol-4-yl)-5H-[1,2,4]triazolo[4,3-a]quinoxaline |
| 503 | 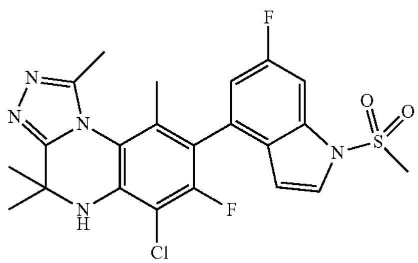 [SMILES: Cc1c(-c2cc(F)cc3c2ccn3S(C)(=O)=O)c(F)c(Cl)c2c1-n1c(C)nnc1C(C)(C)N2] | 6-Chloro-7-fluoro-8-(6-fluoro-1-methylsulfonyl-1H-indol-4-yl)-1,4,4,9-tetramethyl-5H-[1,2,4]triazolo[4,3-a]quinoxaline |
| 504 | 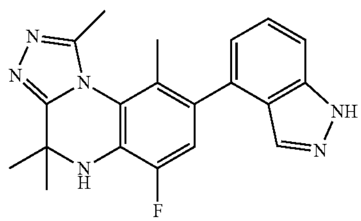 [SMILES: Cc1c(-c2cccc3[nH]ncc23)cc(F)c2c1-n1c(C)nnc1C(C)(C)N2] | 6-Fluoro-8-(1H-indazol-4-yl)-1,4,4,9-tetramethyl-5H-[1,2,4]triazolo[4,3-a]quinoxaline |
| 505 | 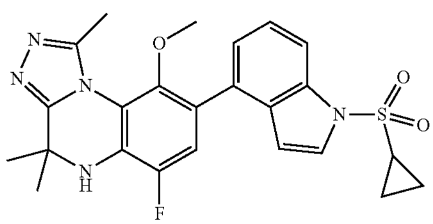 [SMILES: COc1c(-c2cccc3c2ccn3S(=O)(=O)C2CC2)cc(F)c2c1-n1c(C)nnc1C(C)(C)N2] | 8-[1-(Cyclopropylsulfonyl)-1H-indol-4-yl]-6-fluoro-9-methoxy-1,4,4-trimethyl-5H-[1,2,4]triazolo[4,3-a]quinoxaline |
| 506 | 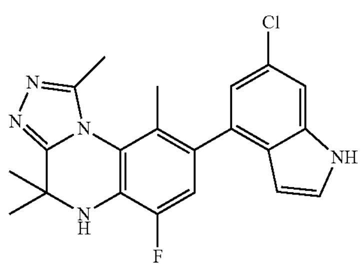 [SMILES: Cc1c(-c2cc(Cl)cc3[nH]ccc23)cc(F)c2c1-n1c(C)nnc1C(C)(C)N2] | 8-(6-Chloro-1H-indol-4-yl)-6-fluoro-1,4,4,9-tetramethyl-5H-[1,2,4]triazolo[4,3-a]quinoxaline |
| 507 | 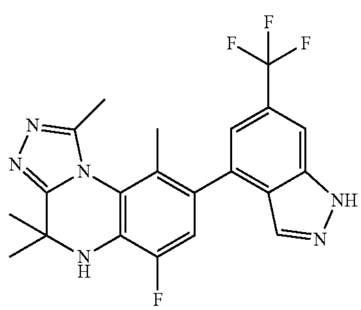 [SMILES: Cc1c(-c2cc(C(F)(F)F)cc3[nH]ncc23)cc(F)c2c1-n1c(C)nnc1C(C)(C)N2] | 6-Fluoro-1,4,4,9-tetramethyl-8-[6-(trifluoromethyl)-1H-indazol-4-yl]-5H-[1,2,4]triazolo[4,3-a]quinoxaline |

| Ex. # | Structure | Name |
|---|---|---|
| 508 | 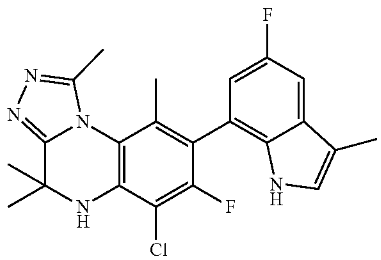 | 6-Chloro-7-fluoro-8-(5-fluoro-3-methyl-1H-indol-7-yl)-1,4,4,9-tetramethyl-5H-[1,2,4]triazolo[4,3-a]quinoxaline |
| 509 | 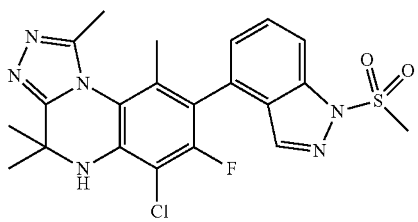 [SMILES: Cc1c(-c2cccc3c2cnn3S(C)(=O)=O)c(F)c(Cl)c2c1-n1c(C)nnc1C(C)(C)N2] | 6-Chloro-7-fluoro-1,4,4,9-tetramethyl-8-(1-methylsulfonyl-1H-indazol-4-yl)-5H-[1,2,4]triazolo[4,3-a]quinoxaline |
| 510 | 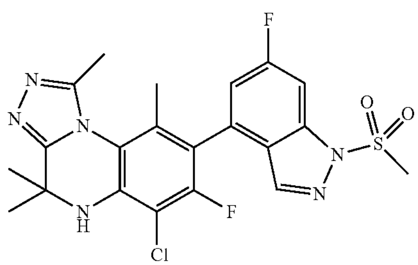 [SMILES: Cc1c(-c2cc(F)cc3c2cnn3S(C)(=O)=O)c(F)c(Cl)c2c1-n1c(C)nnc1C(C)(C)N2] | 6-Chloro-7-fluoro-8-(6-fluoro-1-methylsulfonyl-1H-indazol-4-yl)-1,4,4,9-tetramethyl-5H-[1,2,4]triazolo[4,3-a]quinoxaline |
| 511 | 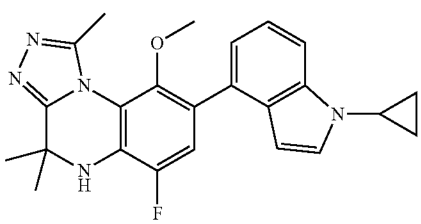 [SMILES: COc1c(-c2cccc3c2ccn3C2CC2)cc(F)c2c1-n1c(C)nnc1C(C)(C)N2] | 8-(1-Cyclopropyl-1H-indol-4-yl)-6-fluoro-9-methoxy-1,4,4-trimethyl-5H-[1,2,4]triazolo[4,3-a]quinoxaline |
| 512 | 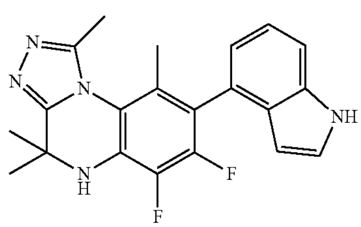 [SMILES: Cc1c(-c2cccc3[nH]ccc23)c(F)c(F)c2c1-n1c(C)nnc1C(C)(C)N2] | 6,7-Difluoro-8-(1H-indol-4-yl)-1,4,4,9-tetramethyl-5H-[1,2,4]triazolo[4,3-a]quinoxaline |
| 513 | 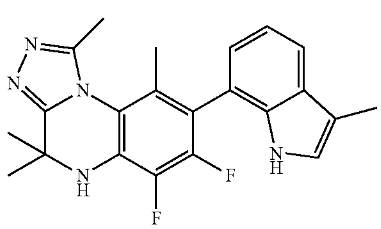 | 6,7-Difluoro-1,4,4,9-tetramethyl-8-(3-methyl-1H-indol-7-yl)-5H-[1,2,4]triazolo[4,3-a]quinoxaline |

| Ex. # | Structure | Name |
|---|---|---|
| 514 | 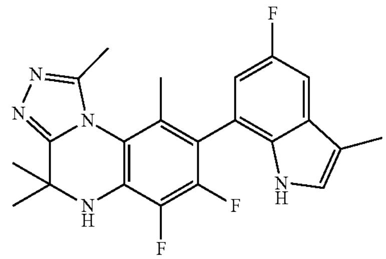 | 6,7-Difluoro-8-(5-fluoro-3-methyl-1H-indol-7-yl)-1,4,4,9-tetramethyl-5H-[1,2,4]triazolo[4,3-a]quinoxaline |
| 515 | 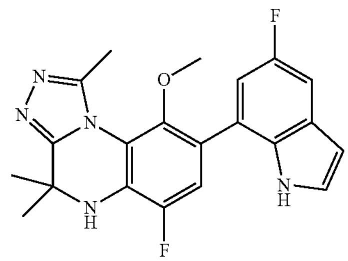 [SMILES: COc1c(-c2cc(F)cc3cc[nH]c23)cc(F)c2c1-n1c(C)nnc1C(C)(C)N2] | 6-Fluoro-8-(5-fluoro-1H-indol-7-yl)-9-methoxy-1,4,4-trimethyl-5H-[1,2,4]triazolo[4,3-a]quinoxaline |
| 516 | 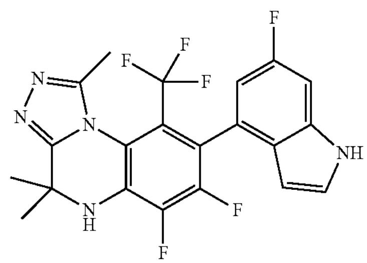 [SMILES: Cc1nnc2n1-c1c(c(F)c(F)c(-c3cc(F)cc4[nH]ccc34)c1C(F)(F)F)NC2(C)C] | 6,7-Difluoro-8-(6-fluoro-1H-indol-4-yl)-1,4,4-trimethyl-9-(trifluoromethyl)-5H-[1,2,4]triazolo[4,3-a]quinoxaline |
| 517 | 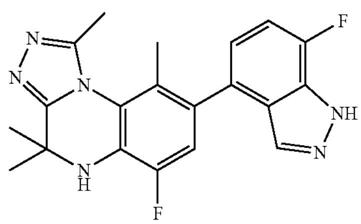 [SMILES: Cc1c(-c2ccc(F)c3[nH]ncc23)cc(F)c2c1-n1c(C)nnc1C(C)(C)N2] | 6-Fluoro-8-(7-fluoro-1H-indazol-4-yl)-1,4,4,9-tetramethyl-5H-[1,2,4]triazolo[4,3-a]quinoxaline |
| 519 | 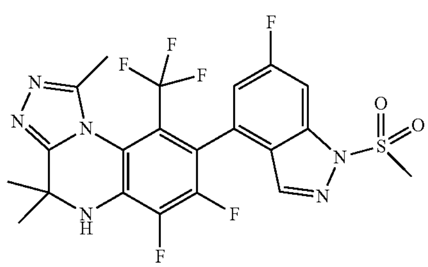 [SMILES: Cc1nnc2n1-c1c(c(F)c(F)c(-c3cc(F)cc4c3cnn4S(C)(=O)=O)c1C(F)(F)F)NC2(C)C] | 6,7-Difluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline |
| 521 | 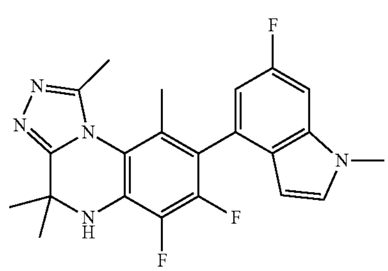 | 6,7-Difluoro-8-(6-fluoro-1-methyl-1H-indol-4-yl)-1,4,4,9-tetramethyl-5H-[1,2,4]triazolo[4,3-a]quinoxaline |

| Ex. # | Structure | Name |
|---|---|---|
| 522 | 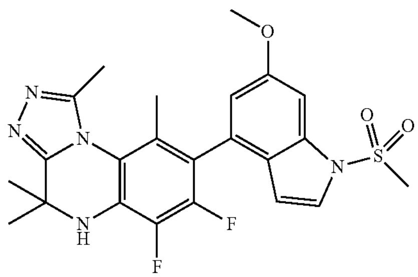 [SMILES: COc1cc(-c2c(C)c3c(c(F)c2F)NC(C)(C)c2nnc(C)n2-3)c2ccn(S(C)(=O)=O)c2c1] | 6,7-Difluoro-8-(6-methoxy-1-methylsulfonyl-1H-indol-4-yl)-1,4,4,9-tetramethyl-5H-[1,2,4]triazolo[4,3-a]quinoxaline |
| 523 | 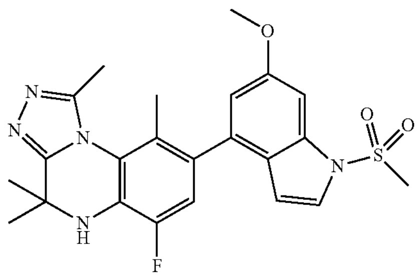 [SMILES: COc1cc(-c2cc(F)c3c(c2C)-n2c(C)nnc2C(C)(C)N3)c2ccn(S(C)(=O)=O)c2c1] | 6-Fluoro-8-(6-methoxy-1-methylsulfonyl-1H-indol-4-yl)-1,4,4,9-tetramethyl-5H-[1,2,4]triazolo[4,3-a]quinoxaline |
| 524 | 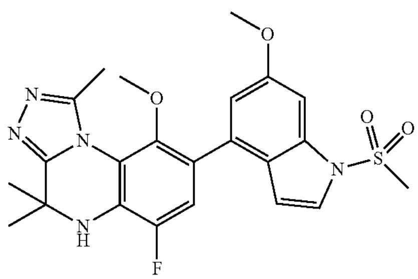 [SMILES: COc1cc(-c2cc(F)c3c(c2OC)-n2c(C)nnc2C(C)(C)N3)c2ccn(S(C)(=O)=O)c2c1] | 6-Fluoro-9-methoxy-8-(6-methoxy-1-methylsulfonyl-1H-indol-4-yl)-1,4,4-trimethyl-5H-[1,2,4]triazolo[4,3-a]quinoxaline |
| 525 | 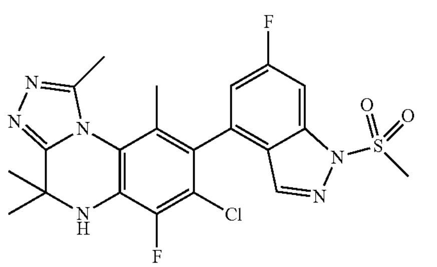 [SMILES: Cc1c(-c2cc(F)cc3c2cnn3S(C)(=O)=O)c(Cl)c(F)c2c1-n1c(C)nnc1C(C)(C)N2] | 7-Chloro-6-fluoro-8-(6-fluoro-1-methylsulfonyl-1H-indazol-4-yl)-1,4,4,9-tetramethyl-5H-[1,2,4]triazolo[4,3-a]quinoxaline |
| 526 | 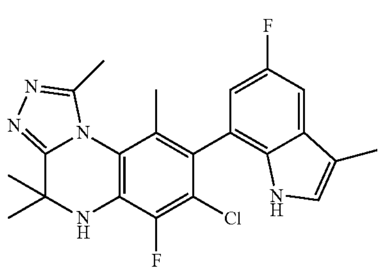 | 7-Chloro-6-fluoro-8-(5-fluoro-3-methyl-1H-indol-7-yl)-1,4,4,9-tetramethyl-5H-[1,2,4]triazolo[4,3-a]quinoxaline |

| Ex. # | Structure | Name |
|---|---|---|
| 527 | 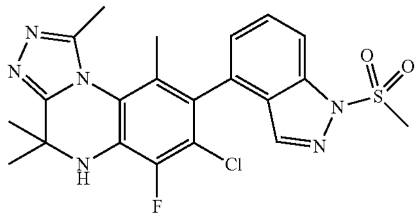 [SMILES: Cc1c(-c2cccc3c2cnn3S(C)(=O)=O)c(Cl)c(F)c2c1-n1c(C)nnc1C(C)(C)N2] | 7-Chloro-6-fluoro-1,4,4,9-tetramethyl-8-(1-methylsulfonyl-1H-indazol-4-yl)-5H-[1,2,4]triazolo[4,3-a]quinoxaline |

Biological Assays

Agonistic Mode of Action on the Glucocorticoid Receptor

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)
25 mL of 7.5% Sodium Bicarbonate (LONZA cat. No. BE17-613E)
6.5 mL of 1 M Hepes (LONZA cat. No: BE17-737E)
5 mL of 100× Penicillin/Streptomycin (LONZA cat. No. DE17-602E)
50 mL of Fetal Bovine Serum (Euroclone cat. No. ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 μl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 30 μl Opti-MEM (GIBCO, cat. #31985062) as assay buffer. To test the compounds an 8-point half-log compound dilution curve was generated in 100% DMSO starting from a 2 mM stock and compounds were then diluted 1:50 in Opti-MEM. 10 μl of compounds were then added to the wells containing 30 μl Opti-MEM resulting in a final assay concentration range from 10 μM to 0.003 μM in 0.5% DMSO. Compounds were tested at 8 concentrations in quadruplicate data points. Cells were incubated for 6 hour with compounds and beclometasone (Sigma, cat. #Y0000351) as control compound at 37° C., 5% $CO_2$ and 95% humidity in a total volume of 40 μl. Finally, cells were lysed with 20 μl of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:

% effect=((compound−min)/(max−min))×100

[min=Opti-MEM only, max=beclometasone]

To calculate $EC_{50}$, max, min and slope factor for each compound a concentration response curve was fitted by plotting % effect versus compound concentration using a 4 parameter logistic equation:

$y=A+(B−A)/(1+((10C)/x)D)$

[$A$=min $y$, $B$=max $y$, $C$=log $EC_{50}$, $D$=slope]

Antagonistic Mode of Action on the Glucocorticoid Receptor

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)
25 mL of 7.5% Sodium Bicarbonate (LONZA cat. No. BE17-613E)
6.5 mL of 1 M Hepes (LONZA cat. No: BE17-737E)
5 mL of 100× Penicillin/Streptomycin (LONZA cat. No. DE17-602E)

50 mL of Fetal Bovine Serum (Euroclone cat. No. ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 20 µl Opti-MEM (GIBCO, cat. #31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 µl of compounds were then added to the wells containing 20 µl Opti-MEM and incubated for 10 min. After this pre-incubation 10 µl of the reference agonist beclometasone (Sigma, cat. #Y0000351) at an EC50 of 2.5 nM were added resulting in a final assay concentration range from 10 µM to 0.003 µM in 0.5% DMSO in a total volume of 40 µl. Compounds were tested at 8 concentrations in quadruplicate data points. Cells were incubated for 6 hour with compound and mifepristone as control compound (Sigma, cat. #M8046) at 37° C., 5% $CO_2$ and 95% humidity. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:

% effect=((compound−min)/(max−min))x−100

[min=Opti-MEM only, max=mifepristone]

To calculate $IC_{50}$, max, min and slope factor for each compound a concentration response curve was fitted by plotting % effect versus compound concentration using a 4 parameter logistic equation:

$y=A+(B-A)/(1+((10C)/x)D)$

[A=min y, B=max y, C=log $IC_{50}$, D=slope]

In Table 7 below, the IC50 or EC50 ranges of the Examples are summarized which were observed in the agonistic assay or the antagonistic assay described above.

TABLE 7

(A <100 nM; B = 100 nM-1 µM; C = 1 µM-15 µM; n.d. = not determined):

| | |
|---|---|
| 38 | A |
| 48 | A |
| 49 | B |
| 53 | B |
| 54 | B |
| 55 | B |
| 56 | B |
| 57 | B |
| 58 | B |
| 59 | C |
| 60 | n.d. |
| 61 | C |
| 62 | B |
| 63 | B |
| 64 | C |
| 65 | C |
| 66 | B |
| 300 | B |
| 301 | B |
| 304 | B |
| 305 | A |
| 308 | A |
| 316 | B |
| 322 | n.d. |
| 323 | B |
| 326 | B |
| 340 | B |
| 349 | B |
| 350 | A |
| 352 | B |
| 355 | B |
| 366 | C |
| 374 | n.d. |
| 375 | B |
| 378 | C |
| 389 | n.d. |
| 391 | A |
| 446 | A |
| 447 | A |
| 448 | A |
| 449 | B |
| 450 | A |
| 451 | B |
| 452 | A |
| 453 | A |
| 454 | A |
| 455 | A |
| 456 | A |
| 457 | A |
| 458 | B |
| 459 | A |
| 460 | A |
| 461 | B |
| 462 | A |
| 463 | A |
| 464 | B |
| 465 | A |
| 466 | B |
| 467 | B |
| 468 | A |
| 469 | B |
| 470 | B |
| 471 | A |
| 472 | B |
| 473 | B |
| 474 | B |
| 475 | B |
| 476 | B |
| 477 | B |
| 478 | A |
| 479 | B |
| 480 | B |
| 481 | B |
| 482 | B |
| 483 | A |
| 484 | A |
| 485 | B |
| 486 | B |
| 487 | A |
| 488 | A |
| 489 | B |
| 490 | B |
| 491 | A |
| 492 | A |
| 493 | B |
| 494 | B |
| 495 | B |
| 496 | B |
| 497 | A |
| 498 | A |
| 499 | B |
| 500 | B |
| 501 | B |
| 502 | A |
| 503 | C |
| 504 | B |

173

TABLE 7-continued (A <100 nM; B = 100 nM-1 µM; C = 1 µM-15 µM;
n.d. = not determined):

| | | |
|---|---|---|
| 505 | B | |
| 506 | B | |
| 507 | B | |
| 508 | B | |
| 509 | B | |
| 510 | A | |
| 511 | B | |
| 512 | A | |
| 513 | B | |
| 514 | A | |
| 515 | B | |
| 516 | A | |
| 517 | B | |
| 518 | B | |
| 519 | B | |
| 520 | B | |
| 521 | A | |
| 522 | B | |
| 523 | B | |
| 524 | B | |
| 525 | A | |
| 526 | A | |
| 527 | B | |

The invention claimed is:
1. A compound according to general formula (I),

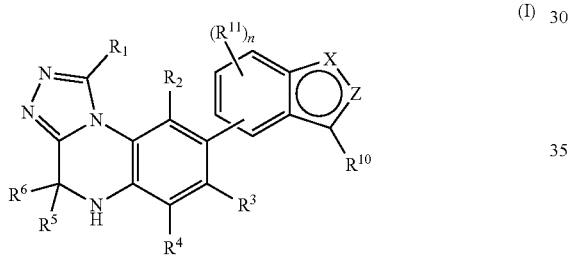

(I)

wherein
$R^1$ represents H; $C_{1-10}$-alkyl; $C_{3-10}$-cycloalkyl; 3 to 7 membered heterocycloalkyl; aryl; or 5 or 6-membered heteroaryl;
wherein $C_{3-10}$-cycloalkyl, 3 to 7 membered heterocycloalkyl, aryl and 5 or 6-membered heteroaryl can optionally be bridged via $C_{1-6}$-alkylene;
$R^2$ represents H; F; Cl; Br; I; CN; $C_{1-10}$-alkyl; $C_{3-10}$-cycloalkyl; O—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);
wherein $C_{3-10}$-cycloalkyl can optionally be bridged via $C_{1-6}$-alkylene;
$R^3$ represents H; F; Cl; Br; I; CN; $C_{1-10}$-alkyl; $C_{3-10}$-cycloalkyl; O—$C_{1-10}$-alkyl; N(H)($C_{1-10}$-alkyl); N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl) or C(O)—N($C_{1-10}$-alkyl)($C_{3-10}$-cycloalkyl);

174 wherein $C_{3-10}$-cycloalkyl can optionally be bridged via $C_{1-6}$-alkylene;
$R^4$ represents F or Cl;
$R^5$ and $R^6$ represent independently from one another H or unsubstituted $C_{1-4}$-alkyl;
X represents N or NR';
Z represents N, NR' or $CR^9$;
with the proviso that
when X represents NR', Z represents N or $CR^9$;
when X represents N, Z represents NR';
$R^7$ represents H or L-$R^8$; wherein
L represents a bond; S(O); S(O)$_2$; $C_{1-6}$-alkylene; C(O); $C_{1-6}$-alkylene-C(O); C(O)—O; $C_{1-6}$-alkylene-C(O)—O; $C_{1-6}$-alkylene-N(H)—C(O); $C_{1-6}$-alkylene-N($C_{1-10}$-alkyl)-C(O); $C_{1-6}$-alkylene-N(H)—C(O)—O; $C_{1-6}$-alkylene-N($C_{1-10}$-alkyl)-C(O)—O; O; NH or N($C_{1-10}$-alkyl);
$R^8$ represents $C_{1-10}$-alkyl; $C_{3-10}$-cycloalkyl or 3 to 7 membered heterocycloalkyl; wherein $C_{3-10}$-cycloalkyl and 3 to 7 membered heterocycloalkyl can optionally be bridged via $C_{1-6}$-alkylene;
$R^9$ and $R^{10}$ represent independently from one another H; F; Cl; Br; I; CN; $C_{1-10}$-alkyl; $C_{3-10}$-cycloalkyl; 3 to 7 membered heterocycloalkyl; S(O)—($C_{1-10}$-alkyl); S(O)—($C_{3-10}$-cycloalkyl); S(O)-(3 to 7-membered heterocycloalkyl); S(O)$_2$—($C_{1-10}$-alkyl); S(O)$_2$—($C_{3-10}$-cycloalkyl); S(O)$_2$-(3 to 7-membered heterocycloalkyl); P(O)—($C_{1-10}$-alkyl)$_2$; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)$_2$; P(O)(O—$C_{1-10}$-alkyl)(O—$C_{3-10}$-cycloalkyl); P(O)(O—$C_{1-10}$-alkyl)(O-(3 to 7-membered heterocycloalkyl)); O—$C_{1-10}$-alkyl; S—$C_{1-10}$-alkyl; N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)($C_{3-10}$-cycloalkyl); O-3 to 7-membered heterocycloalkyl; N(H)(3 to 7-membered heterocycloalkyl), N($C_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N($C_{1-10}$-alkyl)(3 to 7-membered heterocycloalkyl); wherein $C_{3-10}$-cycloalkyl and 3 to 7 membered heterocycloalkyl can optionally be bridged via $C_{1-6}$-alkylene;
$R^{11}$ represents F; Cl; Br; I; CN; $C_{1-10}$-alkyl; O—$C_{1-10}$-alkyl; NO$_2$; OH; NH$_2$; $C_{3-10}$-cycloalkyl; 3 to 7-membered heterocycloalkyl; S(O)—($C_{1-10}$-alkyl); S(O)—($C_{3-10}$-cycloalkyl); S(O)-(3 to 7-membered heterocycloalkyl); S(O)$_2$—($C_{1-10}$-alkyl); S(O)$_2$—($C_{3-10}$-cycloalkyl); S(O)$_2$-(3 to 7-membered heterocycloalkyl); P(O)—($C_{1-10}$-alkyl)$_2$; P(O)($C_{1-10}$-alkyl)($C_{3-10}$-cycloalkyl); P(O)($C_{1-10}$-alkyl)(3 to 7-membered heterocycloalkyl); P(O)—(O—$C_{1-10}$-alkyl)$_2$; P(O)(O—$C_{1-10}$-alkyl)(O—$C_{3-10}$-cycloalkyl); P(O)(O—$C_{1-10}$-alkyl)(O-(3 to 7-membered heterocycloalkyl)); N(H)($C_{1-10}$-alkyl), N($C_{1-10}$-alkyl)$_2$; C(O)—$C_{1-10}$-alkyl; C(O)—O—$C_{1-10}$-alkyl; C(O)—NH$_2$; C(O)—N(H)($C_{1-10}$-alkyl); C(O)—N($C_{1-10}$-alkyl)$_2$; O—$C_{3-10}$-cycloalkyl; N(H)($C_{3-10}$-cycloalkyl), N($C_{1-10}$-alkyl)($C_{3-10}$-cycloalkyl); C(O)—$C_{3-10}$-cycloalkyl; C(O)—O—$C_{3-10}$-cycloalkyl; C(O)—N(H)($C_{3-10}$-cycloalkyl); C(O)—N($C_{1-10}$-alkyl)(C$_{3-10}$-cycloalkyl); O-3 to 7-membered heterocycloalkyl; N(H)(3 to 7-membered heterocycloalkyl), N(C$_{1-10}$-alkyl)(3 to 7-membered heterocycloalkyl); C(O)-3 to 7-membered heterocycloalkyl; C(O)—O-(3 to 7-membered heterocycloalkyl); C(O)—N(H)(3 to 7-membered heterocycloalkyl) or C(O)—N(C$_{1-10}$-alkyl)(3 to 7-membered heterocycloalkyl); wherein C$_{3-10}$-cycloalkyl and 3 to 7 membered heterocycloalkyl can optionally be bridged via C$_{1-6}$-alkylene;

n represents 0, 1, 2 or 3;

wherein C$_{1-10}$-alkyl, C$_{1-4}$-alkyl and C$_{1-6}$-alkylene in each case independently from one another is linear or branched, saturated or unsaturated;

wherein C$_{1-10}$-alkyl, C$_{1-6}$-alkylene, C$_{3-10}$-cycloalkyl and 3 to 7 membered heterocycloalkyl in each case independently from one another are unsubstituted or mono- or polysubstituted with one or more substituents selected from F; Cl; Br; I; CN; C$_{1-6}$-alkyl; CF$_3$; CF$_2$H; CFH$_2$; CF$_2$Cl; CFCl$_2$; C(O)—C$_{1-6}$-alkyl; C(O)—OH; C(O)—OC$_{1-6}$-alkyl; C(O)—NH$_2$; C(O)—N(H)(C$_{1-6}$-alkyl); C(O)—N(C$_{1-6}$-alkyl)$_2$; OH; =O; OCF$_3$; OCF$_2$H; OCFH$_2$; OCF$_2$Cl; OCFCl$_2$; O—C$_{1-6}$-alkyl; O—C(O)—C$_{1-6}$-alkyl; O—C(O)—O—C$_{1-6}$-alkyl; O—(CO)—N(H)(C$_{1-6}$-alkyl); O—C(O)—N(C$_{1-6}$-alkyl)$_2$; O—S(O)$_2$—NH$_2$; O—S(O)$_2$—N(H)(C$_{1-6}$-alkyl); O—S(O)$_2$—N(C$_{1-6}$-alkyl)$_2$; NH$_2$; N(H)(C$_{1-6}$-alkyl); N(C$_{1-6}$-alkyl)$_2$; N(H)—C(O)—C$_{1-6}$-alkyl; N(H)—C(O)—O—C$_{1-6}$-alkyl; N(H)—C(O)—NH$_2$; N(H)—C(O)—N(H)(C$_{1-6}$-alkyl); N(H)—C(O)—N(C$_{1-6}$-alkyl)$_2$; N(C$_{1-6}$-alkyl)-C(O)—C$_{1-6}$-alkyl; N(C$_{1-6}$-alkyl)-C(O)—O—C$_{1-6}$-alkyl; N(C$_{1-6}$-alkyl)-C(O)—NH$_2$; N(C$_{1-6}$-alkyl)-C(O)—N(H)(C$_{1-6}$-alkyl); N(C$_{1-6}$-alkyl)-C(O)—N(C$_{1-6}$-alkyl)$_2$; N(H)—S(O)$_2$OH; N(H)—S(O)$_2$—C$_{1-6}$-alkyl; N(H)—S(O)$_2$—O—C$_{1-6}$-alkyl; N(H)—S(O)$_2$—NH$_2$; N(H)—S(O)$_2$—N(H)(C$_{1-6}$-alkyl); N(H)—S(O)$_2$N(C$_{1-6}$-alkyl)$_2$; N(C$_{1-6}$-alkyl)-S(O)$_{2-0}$H; N(C$_{1-6}$-alkyl)-S(O)$_2$—C$_{1-6}$-alkyl; N(C$_{1-6}$-alkyl)-S(O)$_2$—O—C$_{1-6}$-alkyl; N(C$_{1-6}$-alkyl)-S(O)$_2$—NH$_2$; N(C$_{1-6}$-alkyl)-S(O)$_2$—N(H)(C$_{1-6}$-alkyl); N(C$_{1-6}$-alkyl)-S(O)$_2$—N(C$_{1-6}$-alkyl)$_2$; SCF$_3$; SCF$_2$H; SCFH$_2$; S—C$_{1-6}$-alkyl; S(O)—C$_{1-6}$-alkyl; S(O)$_2$—C$_{1-6}$-alkyl; S(O)$_2$—OH; S(O)$_2$—O—C$_{1-6}$-alkyl; S(O)$_2$—NH$_2$; S(O)$_2$—N(H)(C$_{1-6}$-alkyl); S(O)$_2$—N(C$_{1-6}$-alkyl)$_2$; C$_{3-6}$-cycloalkyl; 3 to 6-membered heterocycloalkyl; phenyl; 5 or 6-membered heteroaryl; O—C$_{3-6}$-cycloalkyl; O-(3 to 6-membered heterocycloalkyl); O-phenyl; O-(5 or 6-membered heteroaryl); C(O)—C$_{3-6}$-cycloalkyl; C(O)-(3 to 6-membered heterocycloalkyl); C(O)-phenyl; C(O)-(5 or 6-membered heteroaryl); S(O)$_2$—(C$_{3-6}$-cycloalkyl); S(O)$_2$-(3 to 6-membered heterocycloalkyl); S(O)$_2$-phenyl or S(O)$_2$-(5 or 6-membered heteroaryl);

wherein aryl and 5 or 6-membered heteroaryl in each case independently from one another are unsubstituted or mono- or polysubstituted with one or more substituents selected from F; Cl; Br; I; CN; C$_{1-6}$-alkyl; CF$_3$; CF$_2$H; CFH$_2$; CF$_2$Cl; CFCl$_2$; C$_{1-4}$-alkylene-CF$_3$; C$_{1-4}$-alkylene-CF$_2$H; C$_{1-4}$-alkylene-CFH$_2$; C(O)—C$_{1-6}$-alkyl; C(O)—OH; C(O)—OC$_{1-6}$-alkyl; C(O)—N(H)(OH); C(O)—NH$_2$; C(O)—N(H)(C$_{1-6}$-alkyl); C(O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; O—C$_{3-6}$-cycloalkyl; O-(3 to 6-membered heterocycloalkyl); NH$_2$; N(H)(C$_{1-6}$-alkyl); N(C$_{1-6}$-alkyl)$_2$; N(H)—C(O)—C$_{1-6}$-alkyl; N(C$_{1-6}$-alkyl)-C(O)—C$_{1-6}$-alkyl; N(H)—C(O)—NH$_2$; N(H)—C(O)—N(H)(C$_{1-6}$-alkyl); N(H)—C(O)—N(C$_{1-6}$-alkyl)$_2$; N(C$_{1-6}$-alkyl)-C(O)—N(H)(C$_{1-6}$-alkyl); N(C$_{1-6}$-alkyl)-C(O)—N(C$_{1-6}$-alkyl)$_2$; N(H)—S(O)$_2$—C$_{1-6}$-alkyl; SCF$_3$; S—C$_{1-6}$-alkyl; S(O)—C$_{1-6}$-alkyl; S(O)$_2$—C$_{1-6}$-alkyl; S(O)$_2$—NH$_2$; S(O)$_2$—N(H)(C$_{1-6}$-alkyl); S(O)$_2$—N(C$_{1-6}$-alkyl)$_2$; C$_{3-6}$-cycloalkyl; C$_{1-4}$-alkylene-C$_{3-6}$-cycloalkyl; 3 to 6-membered heterocycloalkyl; C$_{1-4}$-alkylene-(3 to 6-membered heterocycloalkyl); phenyl or 5 or 6-membered heteroaryl;

in the form of the free compound or a physiologically acceptable salt thereof.

2. The compound according to claim 1, wherein $R^5$ and $R^6$ both represent CH$_3$.

3. The compound according to claim 1, which is according to general formula (II) or (III):

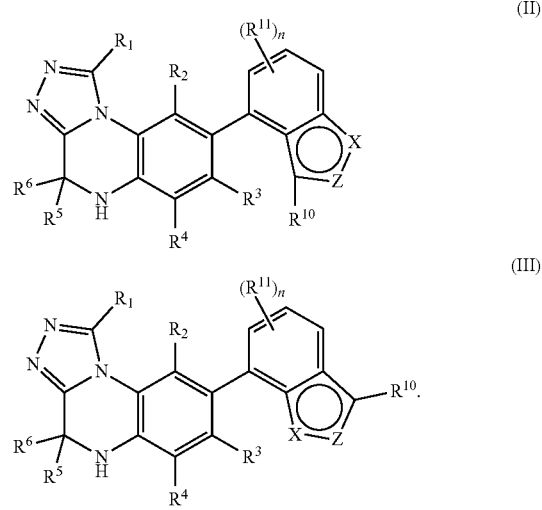

4. The compound according to claim 1, wherein X represents NR$^7$ and Z represents N or CR$^9$.

5. The compound according to claim 1, wherein
$R^1$ represents H; C$_{1-6}$-alkyl; C$_{3-6}$-cycloalkyl; 3 to 6-membered heterocycloalkyl; phenyl; or 5 or 6-membered heteroaryl;
wherein C$_{3-6}$-cycloalkyl, 3 to 6-membered heterocycloalkyl, phenyl and 5 or 6-membered heteroaryl can optionally be bridged via C$_{1-4}$-alkylene.

6. The compound according to claim 1, wherein
$R^2$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
wherein C$_{3-6}$-cycloalkyl can optionally be bridged via C$_{1-4}$-alkylene; and/or
$R^3$ represents H; F; Cl; Br; CN; C$_{1-6}$-alkyl; C$_{3-6}$-cycloalkyl; O—C$_{1-6}$-alkyl; C(O)—NH$_2$; C(O)—N(H)(C$_{1-6}$-alkyl); C(O)—N(C$_{1-6}$-alkyl)$_2$; C(O)—N(H)(C$_{3-6}$-cycloalkyl) or C(O)—N(C$_{1-6}$-alkyl)(C$_{3-6}$-cycloalkyl);
wherein C$_{3-6}$-cycloalkyl can optionally be bridged via C$_{1-4}$-alkylene.

7. The compound according to claim 1, wherein $R^7$ represents H.

8. The compound according to claim 1, wherein $R^7$ represents L-R$^8$;
wherein
L represents a bond; S(O); S(O)$_2$; C$_{1-4}$-alkylene; C(O); C$_{1-4}$-alkylene-C(O); C(O)—O; C$_{1-4}$-alkylene-C (O)—O; C$_{1-4}$-alkylene-N(H)—C(O) or C$_{1-4}$-alkylene-N(H)—C(O)—O; and R$^8$ represents C$_{1-6}$-alkyl; C$_{3-6}$-cycloalkyl or 3 to 6-membered heterocycloalkyl; wherein C$_{3-6}$-cycloalkyl and 3 to 6-membered heterocycloalkyl can optionally be bridged via C$_{1-4}$-alkylene.

9. The compound according to claim 1, wherein

R$^9$ represents H; F; CN; methyl; ethyl; n-propyl; 2-propyl; CF$_3$; CH$_2$CF$_3$; CHF$_2$; CH$_2$CHF$_2$; CH$_2$F; CH$_2$CH$_2$F; S(O)—CH$_3$; S(O)—CH$_2$CH$_3$; S(O)—CH$_2$CH$_2$CH$_3$; S(O)—CH(CH$_3$)$_2$; S(O)$_2$—CH$_3$; S(O)$_2$—CH$_2$CH$_3$; S(O)$_2$—CH$_2$CH$_2$CH$_3$ or S(O)$_2$—CH(CH$_3$)$_2$.

10. The compound according to claim 1, wherein
R$^{10}$ represents H; F; Cl; Br; CN; C$_{1-6}$-alkyl; C$_{3-6}$-cycloalkyl; 3 to 6-membered heterocycloalkyl; P(O)—(C$_{1-6}$-alkyl)$_2$; P(O)(C$_{1-6}$-alkyl)(C$_{3-6}$-cycloalkyl); P(O)(C$_{1-6}$-alkyl)(3 to 6-membered heterocycloalkyl) P(O)—(O—C$_{1-6}$-alkyl)$_2$; P(O)(O—C$_{1-6}$-alkyl)(O—C$_{3-6}$-cycloalkyl); or P(O)(O—C$_{1-6}$-alkyl)(O-(3 to 6-membered heterocycloalkyl)).

11. The compound according to claim 1, wherein
R$^{11}$ represents F; Cl; Br; I; CN; C$_{1-6}$-alkyl or O—C$_{1-6}$-alkyl;

and/or n represents 0, 1 or 2.

12. The compound according to claim 1, wherein the compound is selected from the group consisting of:

| | |
|---|---|
| 38 | 8-(3-Cyclopropyl-5-fluoro-1H-indol-7-yl)-6-fluoro-1,4,4,9-tetramethyl-5H-[1,2,4]triazolo[4,3-a]quinoxaline |
| 48 | 9-Ethyl-6-fluoro-8-(6-fluoro-1-methylsulfonyl-1H-indol-4-yl)-1,4,4-trimethyl-5H-[1,2,4]triazolo[4,3-a]quinoxaline |
| 49 | 9-Ethyl-6-fluoro-1,4,4-trimethyl-8-(1-methylsulfonyl-1H-indol-4-yl)-5H-[1,2,4]triazolo[4,3-a]quinoxaline |
| 53 | 9-Ethyl-6-fluoro-8-(6-fluoro-1-methylsulfonyl-1H-indazol-4-yl)-1,4,4-trimethyl-5H-[1,2,4]triazolo[4,3-a]quinoxaline |
| 54 | 6-Fluoro-8-[6-fluoro-1-(2-methoxy-ethyl)-1H-indol-4-yl]-9-methoxy-1,4,4-trimethyl-5H-[1,2,4]triazolo[4,3-a]quinoxaline |
| 55 | 2-[6-Fluoro-4-(6-fluoro-9-methoxy-1,4,4-trimethyl-5H-[1,2,4]triazolo[4,3-a]quinoxalin-8-yl)-1H-indol-1-yl]-EtOH |
| 56 | 6-Fluoro-8-(6-fluoro-1-methylsulfonyl-1H-indol-4-yl)-9-methoxy-1,4,4-trimethyl-5H-[1,2,4]triazolo[4,3-a]quinoxaline |
| 57 | 6-Fluoro-9-methoxy-1,4,4-trimethyl-8-(1-methylsulfonyl-1H-indol-4-yl)-5H-[1,2,4]triazolo[4,3-a]quinoxaline |
| 58 | 8-[1-(2,2-Difluoro-ethyl)-6-fluoro-1H-indol-4-yl]-6-fluoro-9-methoxy-1,4,4-trimethyl-5H-[1,2,4]triazolo[4,3-a]quinoxaline |
| 59 | 1-Cyclopropyl-6-fluoro-8-(6-fluoro-1-methylsulfonyl-1H-indol-4-yl)-9-methoxy-4,4-dimethyl-5H-[1,2,4]triazolo[4,3-a]quinoxaline |
| 60 | 1-Cyclopropyl-6-fluoro-9-methoxy-4,4-dimethyl-8-(1-methylsulfonyl-1H-indol-4-yl)-5H-[1,2,4]triazolo[4,3-a]quinoxaline |
| 61 | 2-[4-(1-Cyclopropyl-6-fluoro-9-methoxy-4,4-dimethyl-5H-[1,2,4]triazolo[4,3-a]quinoxalin-8-yl)-6-fluoro-1H-indol-1-yl]-EtOH |
| 62 | 1-Cyclopropyl-6-fluoro-8-(5-fluoro-3-methyl-1H-indol-7-yl)-9-methoxy-4,4-dimethyl-5H-[1,2,4]triazolo[4,3-a]quinoxaline |
| 63 | 1-Cyclopropyl-6-fluoro-8-(6-fluoro-1-methylsulfonyl-1H-indol-4-yl)-4,4,9-trimethyl-5H-[1,2,4]triazolo[4,3-a]quinoxaline |
| 64 | 1-Cyclopropyl-6-fluoro-4,4,9-trimethyl-8-(1-methylsulfonyl-1H-indol-4-yl)-5H-[1,2,4]triazolo[4,3-a]quinoxaline |
| 65 | 2-[4-(1-Cyclopropyl-6-fluoro-4,4,9-trimethyl-5H-[1,2,4]triazolo[4,3-a]quinoxalin-8-yl)-6-fluoro-1H-indol-1-yl]-EtOH |
| 66 | 1-Cyclopropyl-6-fluoro-8-(5-fluoro-3-methyl-1H-indol-7-yl)-4,4,9-trimethyl-5H-[1,2,4]triazolo[4,3-a]quinoxaline |
| 300 | 6-Fluoro-8-[1-(2-methoxy-ethyl)-1H-indol-4-yl]-1,4,4,9-tetramethyl-5H-[1,2,4]triazolo[4,3-a]quinoxaline |
| 301 | 2-[4-(6-Fluoro-1,4,4,9-tetramethyl-5H-[1,2,4]triazolo[4,3-a]quinoxalin-8-yl)-1H-indol-1-yl]-EtOH |
| 304 | 6-Fluoro-1,4,4,9-tetramethyl-8-(1-methyl-1H-indazol-4-yl)-5H-[1,2,4]triazolo[4,3-a]quinoxaline |
| 305 | 8-(1-Cyclopropyl-1H-indol-4-yl)-6-fluoro-1,4,4,9-tetramethyl-5H-[1,2,4]triazolo[4,3-a]quinoxaline |
| 308 | 1-Ethyl-6-fluoro-4,4,9-trimethyl-8-(1-methylsulfonyl-1H-indol-4-yl)-5H-[1,2,4]triazolo[4,3-a]quinoxaline |
| 316 | 1-Ethyl-6-fluoro-8-(5-fluoro-3-methyl-1H-indol-7-yl)-4,4,9-trimethyl-5H-[1,2,4]triazolo[4,3-a]quinoxaline |
| 322 | 1-Ethyl-6-fluoro-8-[1-(2-methoxy-ethyl)-1H-indol-4-yl]-4,4,9-trimethyl-5H-[1,2,4]triazolo[4,3-a]quinoxaline |
| 323 | 1-Ethyl-6-fluoro-8-(6-fluoro-1-methylsulfonyl-1H-indol-4-yl)-4,4,9-trimethyl-5H-[1,2,4]triazolo[4,3-a]quinoxaline |
| 326 | 8-[1-(2,2-Difluoro-ethyl)-1H-indol-4-yl]-6-fluoro-1,4,4,9-tetramethyl-5H-[1,2,4]triazolo[4,3-a]quinoxaline |
| 340 | 6-Fluoro-8-(6-fluoro-1-methylsulfonyl-1H-indazol-4-yl)-1,4,4,9-tetramethyl-5H-[1,2,4]triazolo[4,3-a]quinoxaline |
| 349 | 6-Fluoro-8-[1-(fluoro-methylsulfonyl)-1H-indol-4-yl]-1,4,4,9-tetramethyl-5H-[1,2,4]triazolo[4,3-a]quinoxaline |
| 350 | 8-[1-(Ethylsulfonyl)-1H-indol-4-yl]-6-fluoro-1,4,4,9-tetramethyl-5H-[1,2,4]triazolo[4,3-a]quinoxaline |
| 352 | 6-Fluoro-1,4,4,9-tetramethyl-8-(3-methyl-1H-indazol-7-yl)-5H-[1,2,4]triazolo[4,3-a]quinoxaline |
| 355 | 1-Ethyl-6-fluoro-4,4,9-trimethyl-8-(3-methyl-1H-indol-7-yl)-5H-[1,2,4]triazolo[4,3-a]quinoxaline |
| 366 | 6-Fluoro-8-[1-(isopropylsulfonyl)-1H-indol-4-yl]-1,4,4,9-tetramethyl-5H-[1,2,4]triazolo[4,3-a]quinoxaline |
| 374 | 1-Ethyl-6-fluoro-8-(6-fluoro-1-methylsulfonyl-1H-indazol-4-yl)-4,4,9-trimethyl-5H-[1,2,4]triazolo[4,3-a]quinoxaline |

| | -continued |
|---|---|
| 375 | [2-[4-(6-Fluoro-1,4,4,9-tetramethyl-5H-[1,2,4]triazolo[4,3-a]quinoxalin-8-yl)-1H-indol-1-yl]-ethyl]-dimethyl-amine |
| 378 | 6-Fluoro-1,4,4,9-tetramethyl-8-(1-methylsulfonyl-1H-indazol-4-yl)-5H-[1,2,4]triazolo[4,3-a]quinoxaline |
| 389 | 1-Ethyl-6-fluoro-4,4,9-trimethyl-8-(1-methylsulfonyl-1H-indazol-4-yl)-5H-[1,2,4]triazolo[4,3-a]quinoxaline |
| 391 | 8-[1-(Cyclopropylsulfonyl)-1H-indol-4-yl]-6-fluoro-1,4,4,9-tetramethyl-5H-[1,2,4]triazolo[4,3-a]quinoxaline |
| 446 | 8-[1-(Ethylsulfonyl)-6-fluoro-1H-indol-4-yl]-6,7-difluoro-1,4,4,9-tetramethyl-5H-[1,2,4]triazolo[4,3-a]quinoxaline |
| 447 | 6,7-Difluoro-8-(6-fluoro-1-methylsulfonyl-1H-indol-4-yl)-1,4,4,9-tetramethyl-5H-[1,2,4]triazolo[4,3-a]quinoxaline |
| 448 | 6,7-Difluoro-1,4,4,9-tetramethyl-8-(1-methylsulfonyl-1H-indol-4-yl)-5H-[1,2,4]triazolo[4,3-a]quinoxaline |
| 449 | 2-[4-(6,7-Difluoro-1,4,4,9-tetramethyl-5H-[1,2,4]triazolo[4,3-a]quinoxalin-8-yl)-6-fluoro-1H-indol-1-yl]-EtOH |
| 450 | 8-(1-Cyclopropyl-1H-indol-4-yl)-6-fluoro-1,4,4-trimethyl-5H-[1,2,4]triazolo[4,3-a]quinoxaline-9-carbonitrile |
| 451 | 6,7-Difluoro-1,4,4,9-tetramethyl-8-(1-methylsulfonyl-1H-indazol-4-yl)-5H-[1,2,4]triazolo[4,3-a]quinoxaline |
| 452 | 6,7-Difluoro-8-(6-fluoro-1-methylsulfonyl-1H-indazol-4-yl)-1,4,4,9-tetramethyl-5H-[1,2,4]triazolo[4,3-a]quinoxaline |
| 453 | [6-Fluoro-8-(6-fluoro-1-methylsulfonyl-1H-indol-4-yl)-1,4,4-trimethyl-5H-[1,2,4]triazolo[4,3-a]quinoxalin-9-yl]-MeOH |
| 454 | 6-Chloro-8-(5-fluoro-3-methyl-1H-indol-7-yl)-1,4,4,9-tetramethyl-5H-[1,2,4]triazolo[4,3-a]quinoxaline |
| 455 | 9-(Difluoro-methyl)-6-fluoro-8-(6-fluoro-1-methylsulfonyl-1H-indol-4-yl)-1,4,4-trimethyl-5H-[1,2,4]triazolo[4,3-a]quinoxaline |
| 456 | 6-Chloro-1,4,4,9-tetramethyl-8-(1-methylsulfonyl-1H-indol-4-yl)-5H-[1,2,4]triazolo[4,3-a]quinoxaline |
| 457 | 6-Chloro-8-(6-fluoro-1-methylsulfonyl-1H-indol-4-yl)-1,4,4,9-tetramethyl-5H-[1,2,4]triazolo[4,3-a]quinoxaline |
| 458 | 6-Chloro-1,4,4,9-tetramethyl-8-(1-methylsulfonyl-1H-indazol-4-yl)-5H-[1,2,4]triazolo[4,3-a]quinoxaline |
| 459 | 9-(Difluoro-methyl)-6-fluoro-1,4,4-trimethyl-8-(1-methylsulfonyl-1H-indol-4-yl)-5H-[1,2,4]triazolo[4,3-a]quinoxaline |
| 460 | 9-(Difluoro-methyl)-8-[1-(ethylsulfonyl)-6-fluoro-1H-indol-4-yl]-6-fluoro-1,4,4-trimethyl-5H-[1,2,4]triazolo[4,3-a]quinoxaline |
| 461 | 9-(Difluoro-methyl)-8-[1-(ethylsulfonyl)-1H-indol-4-yl]-6-fluoro-1,4,4-trimethyl-5H-[1,2,4]triazolo[4,3-a]quinoxaline |
| 462 | 9-(Difluoro-methyl)-6-fluoro-8-(5-fluoro-3-methyl-1H-indol-7-yl)-1,4,4-trimethyl-5H-[1,2,4]triazolo[4,3-a]quinoxaline |
| 463 | 2-[4-(6-Chloro-1,4,4,9-tetramethyl-5H-[1,2,4]triazolo[4,3-a]quinoxalin-8-yl)-6-fluoro-1H-indol-1-yl]-EtOH |
| 464 | 2-[4-(9-Ethyl-6-fluoro-1,4,4-trimethyl-5H-[1,2,4]triazolo[4,3-a]quinoxalin-8-yl)-6-fluoro-1H-indol-1-yl]-EtOH |
| 465 | 6-Fluoro-8-(6-fluoro-1H-indol-4-yl)-1,4,4,9-tetramethyl-5H-[1,2,4]triazolo[4,3-a]quinoxaline |
| 466 | 9-(Difluoro-methyl)-6-fluoro-1,4,4-trimethyl-8-(3-methyl-1H-indazol-7-yl)-5H-[1,2,4]triazolo[4,3-a]quinoxaline |
| 467 | 9-Cyclopropyl-6-fluoro-8-(6-fluoro-1-methylsulfonyl-1H-indazol-4-yl)-1,4,4-trimethyl-5H-[1,2,4]triazolo[4,3-a]quinoxaline |
| 468 | 6-Fluoro-8-(1H-indol-4-yl)-1,4,4,9-tetramethyl-5H-[1,2,4]triazolo[4,3-a]quinoxaline |
| 469 | 6-Fluoro-8-(1H-indol-4-yl)-9-methoxy-1,4,4-trimethyl-5H-[1,2,4]triazolo[4,3-a]quinoxaline |
| 470 | 6-Fluoro-8-(6-fluoro-1H-indol-4-yl)-9-methoxy-1,4,4-trimethyl-5H-[1,2,4]triazolo[4,3-a]quinoxaline |
| 471 | 9-Cyclopropyl-6-fluoro-8-(6-fluoro-1-methylsulfonyl-1H-indol-4-yl)-1,4,4-trimethyl-5H-[1,2,4]triazolo[4,3-a]quinoxaline |
| 472 | 9-Cyclopropyl-6-fluoro-1,4,4-trimethyl-8-(3-methyl-1H-indol-7-yl)-5H-[1,2,4]triazolo[4,3-a]quinoxaline |
| 473 | 6-Fluoro-9-methoxy-1,4,4-trimethyl-8-[6-(trifluoromethyl)-1H-indol-4-yl]-5H-[1,2,4]triazolo[4,3-a]quinoxaline |
| 474 | 9-Cyclopropyl-6-fluoro-1,4,4-trimethyl-8-(1-methylsulfonyl-1H-indol-4-yl)-5H-[1,2,4]triazolo[4,3-a]quinoxaline |
| 475 | 6-Fluoro-1,4,4,9-tetramethyl-8-(6-methyl-1-methylsulfonyl-1H-indol-4-yl)-5H-[1,2,4]triazolo[4,3-a]quinoxaline |
| 476 | 6-Fluoro-9-methoxy-1,4,4-trimethyl-8-(6-methyl-1-methylsulfonyl-1H-indol-4-yl)-5H-[1,2,4]triazolo[4,3-a]quinoxaline |
| 477 | 4-(6-Fluoro-1,4,4,9-tetramethyl-5H-[1,2,4]triazolo[4,3-a]quinoxalin-8-yl)-1H-indole-6-carbonitrile |
| 478 | 8-(3-Cyclopropyl-5-fluoro-1H-indol-7-yl)-6-fluoro-9-methoxy-1,4,4-trimethyl-5H-[1,2,4]triazolo[4,3-a]quinoxaline |
| 479 | [8-[1-(Ethylsulfonyl)-6-fluoro-1H-indol-4-yl]-6-fluoro-1,4,4-trimethyl-5H-[1,2,4]triazolo[4,3-a]quinoxalin-9-yl]-methyl-amine |
| 480 | 2-[6-Fluoro-4-(6-fluoro-1,4,4-trimethyl-9-methylamino-5H-[1,2,4]triazolo[4,3-a]quinoxalin-8-yl)-1H-indol-1-yl]-EtOH |
| 481 | [8-(1-Cyclopropyl-1H-indol-4-yl)-6-fluoro-1,4,4-trimethyl-5H-[1,2,4]triazolo[4,3-a]quinoxalin-9-yl]-methyl-amine |
| 482 | 6-Chloro-9-methoxy-1,4,4-trimethyl-8-(1-methylsulfonyl-1H-indol-4-yl)-5H-[1,2,4]triazolo[4,3-a]quinoxaline |

| | |
|---|---|
| 483 | 6-Chloro-8-(6-fluoro-1-methylsulfonyl-1H-indol-4-yl)-9-methoxy-1,4,4-trimethyl-5H-[1,2,4]triazolo[4,3-a]quinoxaline |
| 484 | 6-Fluoro-1,4,4,9-tetramethyl-8-(1-methyl-1H-indol-4-yl)-5H-[1,2,4]triazolo[4,3-a]quinoxaline |
| 485 | 6-Fluoro-9-methoxy-1,4,4-trimethyl-8-(1-methyl-1H-indol-4-yl)-5H-[1,2,4]triazolo[4,3-a]quinoxaline |
| 486 | [6-Fluoro-8-(6-fluoro-1-methylsulfonyl-1H-indol-4-yl)-1,4,4-trimethyl-5H-[1,2,4]triazolo[4,3-a]quinoxalin-9-yl]-methyl-amine |
| 487 | [6-Fluoro-8-(5-fluoro-3-methyl-1H-indol-7-yl)-1,4,4-trimethyl-5H-[1,2,4]triazolo[4,3-a]quinoxalin-9-yl]-methyl-amine |
| 488 | 6-Chloro-8-(6-fluoro-1H-indol-4-yl)-9-methoxy-1,4,4-trimethyl-5H-[1,2,4]triazolo[4,3-a]quinoxaline |
| 489 | 6-Fluoro-8-(7-fluoro-1H-indazol-4-yl)-9-methoxy-1,4,4-trimethyl-5H-[1,2,4]triazolo[4,3-a]quinoxaline |
| 490 | 6-Fluoro-8-(7-fluoro-1H-indol-4-yl)-1,4,4,9-tetramethyl-5H-[1,2,4]triazolo[4,3-a]quinoxaline |
| 491 | 8-[1-(Cyclopropyl-methylsulfonyl)-1H-indol-4-yl]-6-fluoro-1,4,4,9-tetramethyl-5H-[1,2,4]triazolo[4,3-a]quinoxaline |
| 492 | 6-Fluoro-9-methoxy-1,4,4-trimethyl-8-[1-methylsulfonyl-6-(trifluoromethyl)-1H-indol-4-yl]-5H-[1,2,4]triazolo[4,3-a]quinoxaline |
| 493 | 6-Chloro-8-(6-fluoro-1-methylsulfonyl-1H-indazol-4-yl)-9-methoxy-1,4,4-trimethyl-5H-[1,2,4]triazolo[4,3-a]quinoxaline |
| 494 | 6-Fluoro-8-(7-fluoro-1H-indol-4-yl)-9-methoxy-1,4,4-trimethyl-5H-[1,2,4]triazolo[4,3-a]quinoxaline |
| 495 | 6-Fluoro-8-(6-fluoro-1H-indazol-4-yl)-9-methoxy-1,4,4-trimethyl-5H-[1,2,4]triazolo[4,3-a]quinoxaline |
| 496 | 6-Fluoro-8-(6-fluoro-1H-indazol-4-yl)-1,4,4,9-tetramethyl-5H-[1,2,4]triazolo[4,3-a]quinoxaline |
| 497 | 8-[1-(Cyclopropyl-methylsulfonyl)-6-fluoro-1H-indol-4-yl]-6-fluoro-1,4,4,9-tetramethyl-5H-[1,2,4]triazolo[4,3-a]quinoxaline |
| 498 | 6,7-Difluoro-8-(6-fluoro-1-methylsulfonyl-1H-indol-4-yl)-9-methoxy-1,4,4-trimethyl-5H-[1,2,4]triazolo[4,3-a]quinoxaline |
| 499 | 6,7-Difluoro-9-methoxy-1,4,4-trimethyl-8-(1-methylsulfonyl-1H-indol-4-yl)-5H-[1,2,4]triazolo[4,3-a]quinoxaline |
| 500 | 6,7-Difluoro-1,4,4-trimethyl-8-(1-methylsulfonyl-1H-indol-4-yl)-9-(trifluoromethyl)-5H-[1,2,4]triazolo[4,3-a]quinoxaline |
| 501 | 6,7-Difluoro-8-(6-fluoro-1-methylsulfonyl-1H-indazol-4-yl)-9-methoxy-1,4,4-trimethyl-5H-[1,2,4]triazolo[4,3-a]quinoxaline |
| 502 | 6-Chloro-7-fluoro-1,4,4,9-tetramethyl-8-(1-methylsulfonyl-1H-indol-4-yl)-5H-[1,2,4]triazolo[4,3-a]quinoxaline |
| 503 | 6-Chloro-7-fluoro-8-(6-fluoro-1-methylsulfonyl-1H-indol-4-yl)-1,4,4,9-tetramethyl-5H-[1,2,4]triazolo[4,3-a]quinoxaline |
| 504 | 6-Fluoro-8-(1H-indazol-4-yl)-1,4,4,9-tetramethyl-5H-[1,2,4]triazolo[4,3-a]quinoxaline |
| 505 | 8-[1-(Cyclopropylsulfonyl)-1H-indol-4-yl]-6-fluoro-9-methoxy-1,4,4-trimethyl-5H-[1,2,4]triazolo[4,3-a]quinoxaline |
| 506 | 8-(6-Chloro-1H-indol-4-yl)-6-fluoro-1,4,4,9-tetramethyl-5H-[1,2,4]triazolo[4,3-a]quinoxaline |
| 507 | 6-Fluoro-1,4,4,9-tetramethyl-8-[6-(trifluoromethyl)-1H-indazol-4-yl]-5H-[1,2,4]triazolo[4,3-a]quinoxaline |
| 508 | 6-Chloro-7-fluoro-8-(5-fluoro-3-methyl-1H-indol-7-yl)-1,4,4,9-tetramethyl-5H-[1,2,4]triazolo[4,3-a]quinoxaline |
| 509 | 6-Chloro-7-fluoro-1,4,4,9-tetramethyl-8-(1-methylsulfonyl-1H-indazol-4-yl)-5H-[1,2,4]triazolo[4,3-a]quinoxaline |
| 510 | 6-Chloro-7-fluoro-8-(6-fluoro-1-methylsulfonyl-1H-indazol-4-yl)-1,4,4,9-tetramethyl-5H-[1,2,4]triazolo[4,3-a]quinoxaline |
| 511 | 8-(1-Cyclopropyl-1H-indol-4-yl)-6-fluoro-9-methoxy-1,4,4-trimethyl-5H-[1,2,4]triazolo[4,3-a]quinoxaline |
| 512 | 6,7-Difluoro-8-(1H-indol-4-yl)-1,4,4,9-tetramethyl-5H-[1,2,4]triazolo[4,3-a]quinoxaline |
| 513 | 6,7-Difluoro-1,4,4,9-tetramethyl-8-(3-methyl-1H-indol-7-yl)-5H-[1,2,4]triazolo[4,3-a]quinoxaline |
| 514 | 6,7-Difluoro-8-(5-fluoro-3-methyl-1H-indol-7-yl)-1,4,4,9-tetramethyl-5H-[1,2,4]triazolo[4,3-a]quinoxaline |
| 515 | 6-Fluoro-8-(5-fluoro-1H-indol-7-yl)-9-methoxy-1,4,4-trimethyl-5H-[1,2,4]triazolo[4,3-a]quinoxaline |
| 516 | 6,7-Difluoro-8-(6-fluoro-1H-indol-4-yl)-1,4,4-trimethyl-9-(trifluoromethyl)-5H-[1,2,4]triazolo[4,3-a]quinoxaline |
| 517 | 6-Fluoro-8-(7-fluoro-1H-indazol-4-yl)-1,4,4,9-tetramethyl-5H-[1,2,4]triazolo[4,3-a]quinoxaline |
| 518 | 6,7-Difluoro-8-(6-fluoro-1-methylsulfonyl-1H-indol-4-yl)-1,4,4-trimethyl-9-(trifluoromethyl)-5H-[1,2,4]triazolo[4,3-a]quinoxaline |
| 519 | 6,7-Difluoro-8-(6-fluoro-1-methylsulfonyl-1H-indazol-4-yl)-1,4,4-trimethyl-9-(trifluoromethyl)-5H-[1,2,4]triazolo[4,3-a]quinoxaline |
| 520 | 4-(6,7-Difluoro-1,4,4,9-tetramethyl-5H-[1,2,4]triazolo[4,3-a]quinoxalin-8-yl)-1H-indole-7-carbonitrile |
| 521 | 6,7-Difluoro-8-(6-fluoro-1-methyl-1H-indol-4-yl)-1,4,4,9-tetramethyl-5H-[1,2,4]triazolo[4,3-a]quinoxaline |
| 522 | 6,7-Difluoro-8-(6-methoxy-1-methylsulfonyl-1H-indol-4-yl)-1,4,4,9-tetramethyl-5H-[1,2,4]triazolo[4,3-a]quinoxaline |
| 523 | 6-Fluoro-8-(6-methoxy-1-methylsulfonyl-1H-indol-4-yl)-1,4,4,9-tetramethyl-5H-[1,2,4]triazolo[4,3-a]quinoxaline |
| 524 | 6-Fluoro-9-methoxy-8-(6-methoxy-1-methylsulfonyl-1H-indol-4-yl)-1,4,4-trimethyl-5H-[1,2,4]triazolo[4,3-a]quinoxaline |
| 525 | 7-Chloro-6-fluoro-8-(6-fluoro-1-methylsulfonyl-1H-indazol-4-yl)-1,4,4,9-tetramethyl-5H-[1,2,4]triazolo[4,3-a]quinoxaline |

| | |
|---|---|
| 526 | 7-Chloro-6-fluoro-8-(5-fluoro-3-methyl-1H-indol-7-yl)-1,4,4,9-tetramethyl-5H-[1,2,4]triazolo[4,3-a]quinoxaline |
| 527 | 7-Chloro-6-fluoro-1,4,4,9-tetramethyl-8-(1-methylsulfonyl-1H-indazol-4-yl)-5H-[1,2,4]triazolo[4,3-a]quinoxaline | in the form of the free compound or a physiologically acceptable salt thereof.

13. A pharmaceutical dosage form comprising a compound according to claim 1.

14. A method for treating pain and/or inflammation, comprising administering a therapeutically effective amount of a compound according to claim 1 to a patient in need thereof.

15. The method according to claim 14, wherein the pain is inflammatory pain.

* * * * *